US008865885B2

(12) United States Patent
Croce et al.

(10) Patent No.: US 8,865,885 B2
(45) Date of Patent: Oct. 21, 2014

(54) MICRORNA FINGERPRINTS DURING HUMAN MEGAKARYOCYTOPOIESIS

(71) Applicant: The Ohio State University Research Foundation, Columbus, OH (US)

(72) Inventors: Carlo M. Croce, Columbus, OH (US); Ramiro Garzon, Columbus, OH (US); George A. Calin, Pearland, TX (US)

(73) Assignee: The Ohio State University Research Foundation, Columbus, OH (US)

( * ) Notice: Subject to any disclaimer, the term of this patent is extended or adjusted under 35 U.S.C. 154(b) by 0 days.

(21) Appl. No.: 13/925,954

(22) Filed: Jun. 25, 2013

(65) Prior Publication Data

US 2013/0273151 A1 Oct. 17, 2013

Related U.S. Application Data

(62) Division of application No. 13/595,204, filed on Aug. 27, 2012, now Pat. No. 8,486,913, which is a division of application No. 13/169,184, filed on Jun. 27, 2011, now Pat. No. 8,354,224, which is a division of application No. 12/293,471, filed as application No. PCT/US2007/006824 on Mar. 19, 2007, now Pat. No. 7,985,584.

(60) Provisional application No. 60/743,585, filed on Mar. 20, 2006.

(51) Int. Cl.

| | |
|---|---|
| ***C07H 21/04*** | (2006.01) |
| ***C12N 15/113*** | (2010.01) |
| ***C12Q 1/68*** | (2006.01) |
| ***A61K 45/06*** | (2006.01) |
| ***A61K 31/7105*** | (2006.01) |

(52) U.S. Cl.

CPC ...... *C12N 15/1135* (2013.01); *C12Q 2600/178* (2013.01); *C12Q 2600/106* (2013.01); *C12Q 1/6883* (2013.01); *A61K 45/06* (2013.01); *C12Q 1/6886* (2013.01); *A61K 31/7105* (2013.01); *C12N 15/113* (2013.01)

USPC .......................................... 536/24.5; 514/44

(58) Field of Classification Search

None

See application file for complete search history.

(56) References Cited

U.S. PATENT DOCUMENTS

| | | | | |
|---|---|---|---|---|
| 7,455,995 | B2 | 11/2008 | Tanner et al. | |
| 7,811,759 | B2 | 10/2010 | Han | |
| 7,888,010 | B2 | 2/2011 | Brown et al. | |
| 7,919,245 | B2 | 4/2011 | Brown et al. | |
| 8,084,199 | B2 | 12/2011 | Croce et al. | |
| 8,361,710 | B2 | 1/2013 | Croce et al. | |
| 2003/0143646 | A1 | 7/2003 | Laskey et al. | |
| 2005/0013247 | A1 | 1/2005 | Sipola et al. | |
| 2006/0105360 | A1* | 5/2006 | Croce et al. | 435/6 |
| 2006/0116321 | A1 | 6/2006 | Robbins et al. | |
| 2006/0134639 | A1 | 6/2006 | Huffel et al. | |
| 2006/0199233 | A1 | 9/2006 | Dahlberg et al. | |
| 2007/0092882 | A1 | 4/2007 | Wang et al. | |
| 2007/0213292 | A1 | 9/2007 | Stoffel et al. | |
| 2008/0050744 | A1* | 2/2008 | Brown et al. | 435/6 |
| 2008/0171715 | A1* | 7/2008 | Brown et al. | 514/44 |
| 2009/0023149 | A1 | 1/2009 | Knudsen | |
| 2009/0131356 | A1 | 5/2009 | Bader et al. | |
| 2009/0192102 | A1 | 7/2009 | Bader et al. | |
| 2009/0220589 | A1 | 9/2009 | Trieu et al. | |
| 2009/0239818 | A1 | 9/2009 | Cheng | |
| 2010/0004320 | A1 | 1/2010 | Elmen et al. | |
| 2010/0021734 | A1 | 1/2010 | Uemoto et al. | |
| 2010/0099200 | A1 | 4/2010 | Nazabal et al. | |
| 2010/0104662 | A1 | 4/2010 | Oren et al. | |
| 2010/0151480 | A1 | 6/2010 | Taylor et al. | |
| 2010/0179213 | A1 | 7/2010 | Patrawala et al. | |
| 2010/0196426 | A1 | 8/2010 | Skog et al. | |
| 2010/0285471 | A1 | 11/2010 | Croce et al. | |
| 2010/0298410 | A1 | 11/2010 | Obad et al. | |
| 2010/0305188 | A1 | 12/2010 | Nakanoe et al. | |
| 2011/0003704 | A1 | 1/2011 | Skog et al. | |
| 2011/0021601 | A1 | 1/2011 | Park et al. | |
| 2011/0054006 | A1 | 3/2011 | Slack et al. | |
| 2011/0054009 | A1 | 3/2011 | Croce et al. | |
| 2011/0107440 | A1 | 5/2011 | Pivaresi et al. | |
| 2011/0136124 | A1 | 6/2011 | Roa et al. | |
| 2011/0166200 | A1 | 7/2011 | Zhang | |
| 2011/0251150 | A2 | 10/2011 | Bennett et al. | |
| 2011/0275534 | A1 | 11/2011 | Cohn et al. | |

FOREIGN PATENT DOCUMENTS

| | | | |
|---|---|---|---|
| AU | 2007-243475 | B2 | 5/2013 |
| CA | 2533701 | A1 | 2/2005 |
| CN | 1282422 | A | 1/2011 |
| EP | 1662259 | A1 | 5/2006 |
| EP | 1676914 | A1 | 7/2006 |

(Continued)

OTHER PUBLICATIONS

Brummelkamp. Science 2002, vol. 296: 550-553.*

Australian Exam Rpt. No. 3, 2007205257, dated Jan. 9, 2013.

Australian Examination Report No. 2, 2007227423, dated Mar. 1, 2013.

(Continued)

*Primary Examiner* — Kimberly Chong

(74) *Attorney, Agent, or Firm* — MacMillan, Sobanski & Todd, LLC

(57) ABSTRACT

Described herein is a pharmaceutical composition for treating a subject having a cancer and/or myeloproliferative disorder associated with overexpression of a HOXA1 gene product where an effective amount of at least one miR-10a gene product or an isolated variant or biologically-active fragment thereof is administered to the subject sufficient to decrease expression of the HOXA1 gene product in the subject.

14 Claims, 13 Drawing Sheets
(10 of 13 Drawing Sheet(s) Filed in Color)

(56) References Cited

FOREIGN PATENT DOCUMENTS

| | | | |
|---|---|---|---|
| EP | 2354246 | A1 | 8/2011 |
| EP | 2487240 | A1 | 8/2012 |
| FR | 2877350 | A1 | 5/2006 |
| JP | 2005-503827 | A | 2/2005 |
| JP | 2005-517452 | A | 6/2005 |
| JP | 2005-192484 | A | 7/2005 |
| JP | 2005-296014 | A | 10/2005 |
| JP | 2008-086201 | A | 4/2008 |
| WO | 2005/013901 | A3 | 2/2005 |
| WO | 2005/079397 | A2 | 9/2005 |
| WO | 2005/094263 | A2 | 10/2005 |
| WO | 2005/103298 | A2 | 11/2005 |
| WO | 2005/111211 | A2 | 11/2005 |
| WO | 2007/112754 | A2 | 10/2007 |
| WO | 2008/029295 | A2 | 3/2008 |
| WO | 2008/036168 | A2 | 3/2008 |
| WO | 2008/064519 | A1 | 6/2008 |
| WO | 2008/073915 | A2 | 6/2008 |
| WO | 2009/036236 | A1 | 3/2009 |
| WO | 2011/057304 | A2 | 5/2011 |
| WO | 2011/063382 | A1 | 5/2011 |
| WO | 2011/119553 | A2 | 9/2011 |
| WO | 2011/163116 | A3 | 12/2011 |
| WO | 2012/019053 | A2 | 2/2012 |
| WO | 2012/065049 | A2 | 5/2012 |
| WO | 2012/097047 | A1 | 7/2012 |
| WO | 2012/122239 | A1 | 9/2012 |

OTHER PUBLICATIONS

Australian Office Action, Application No. 2007314212 dated Aug. 28, 2012.
Australian Office Action, Application No. 2007272947 dated May 21, 2012.
Australian Office Action, Application No. 2006291165 dated Feb. 13, 2012.
Australian Office Action, Application No. 2007227423 dated Apr. 13, 2012.
Australian Office Action, Application No. 2007346101 dated Jun. 21, 2012.
Australian Office Action, Application No. 2007205257 dated Jul. 16, 2012.
Australian Office Action, Application No. 2006291165 dated Jan. 7, 2013.
Australian Office Action, Application No. 2007205163 dated Nov. 15, 2012.
Australian Office Action, Application No. 2006291165 dated Sep. 12, 2012.
Australian Office Action, Application No. 2008262252 dated Feb. 15, 2013.
Australian Office Action, Application No. 2008266014 dated Jul. 6, 2012.
Australian Office Action, Application No. 2007314212 dated Apr. 29, 2013.
Australian Office Action, Report No. 2, Application No. 2008248319 dated Apr. 9, 2013.
Australian Office Action, Application No. 2007205257 dated Dec. 22, 2011.
Australian Office Action Application No. 2008282318 dated Feb. 7, 2013.
Australian Office Action, Application No. 2007205234 dated Jun. 17, 2011.
Australian Office Action, Application No. 2008248319 dated Jul. 12, 2012.
Australian Office Action Application No. 2007205257 dated Feb. 26, 2013.
Australian Office Action, Application No. 2007205163 dated Mar. 28, 2013.
Australian Patent Examination Report No. 1, Appln. No. 2008283997 Dated Aug. 20, 2007.
Australian Patent Examination Report No. 2, Application No. 2008282318 , dated Nov. 19, 2013.
Australian Patent Examination Rpt., No. 1., 2008316577 dated Feb. 11, 2013.
Australian Patent Examination Report No. 1, Appln. No. 2008310704, Dated Jun. 24, 2013.
Australian Patent Examination Report No. 2, Appln. No. 2007346101, Dated May 24, 2013.
Australian Patent Examination Report No. 1, Appln. No. 2009219197, Dated Sep. 19, 2013.
Canadian Intellectual Property Office, Requisition by the Examiner, Application 2,621,441 dated Apr. 8, 2013.
Canadian Intellectual Property Office, Requisition by the Examiner, Application No. 2,646,051, dated Feb. 25, 2011.
Canadian Office Action, Application No. 2,635,616, dated Feb. 27, 2012.
Canadian Office Action, Application No. 2,617,581, dated Apr. 2, 2012.
Chinese 1st Office Action, Appln. No. 200880025276.8, dated Nov. 23, 2011.
Chinese 1st Office Action, Appln. No. 200980113258, dated Mar. 13, 2013.
Chinese 1st Office Action, Appln. No. 201110319534.7, dated Jun. 8, 2013.
Chinese 1st Office Action, Appln. No. 200880112581.0, Aug. 13, 2012.
Chinese 1st Office Action, Appln. No. 200980126520.4, dated Dec. 4, 2012.
Chinese 1st Office Action, Appln. No. 200980155340.9 dated Jan. 21, 2013.
Chinese 1st Office Action, Appln. No. 200980135456.6, dated Nov. 13, 2012.
Chinese 1st Office Action, Appln. No. 200980112966.1, dated Sep. 20, 2012.
Chinese 1st Office Action, Appln. No. 200880108689.2, dated Feb. 13, 2012.
Chinese 1st Office Action, Appln. No. 200780005791.5, dated Mar. 24, 2011.
Chinese 1st Office Action, Application No. 200780023093.8 dated Dec. 27, 2010.
Chinese 1st Office Action, Application No. 200780018496.3 dated Mar. 22, 2011.
Chinese 1st Office Action Appln. No. 201080059339.9 dated Aug. 26, 2013.
Chinese 1st Office Action, Appln. No. 201210312507.1, dated Jul. 29, 2013.
Chinese 2nd OA—EnglishTrans, Appln. No. 200880112581.0, dated May 10, 2013.
Chinese 2nd Office Action, Appln. No. 200980112966.1, dated May 9, 2013.
Chinese 2nd Office Action, Appln. No. 200980135456.6 dated Aug. 1, 2013.
Chinese 2nd Office Action, Application No. 200780040146.7 dated Dec. 31, 2011.
Chinese 2nd Office Action Application No. 200980111708.1 dated May 20, 2013.
Chinese 2nd Office Action, Appln. No. 200780005791.5, dated May 3, 2012.
Chinese 2nd Office Action, Appln. No. 200880003736.7 dated Nov. 5, 2012.
Chinese 2nd Office Action, Application No. 200780018496.3 dated Mar. 1, 2012.
Chinese 2nd Office Action, Appln. No. 200880119206.9, dated Feb. 1, 2013.
Chinese 2nd Office Action, Appln. No. 200980155340.9, dated Aug. 26, 2013.
Chinese 2nd Office Action, Appln. No. 200880103023.8 dated Jun. 20, 2013.
Chinese 2nd Office Action Appln. No. 200980126520.4 dated Aug. 14, 2013.
Chinese 2nd Office Action, Application No. 200780023093.8 dated Dec. 9, 2011.

(56) References Cited

OTHER PUBLICATIONS

Chinese 2nd Office Action Appln. No. 200880025276.8 dated Aug. 1, 2012.
Chinese 2nd Office Action, Application No. 200780005821.2 dated Apr. 1, 2012.
Chinese 3rd Office Action, Appln. No. 200880119206.9 dated Aug. 12, 2013.
Chinese 3rd Office Action, Application No. 200880003736.7 dated Apr. 12, 2013.
Chinese 3rd Office Action, Application No. 200780040146.7 dated Apr. 25, 2012.
Chinese 3rd Office Action, Appln. No. 200880108689.2, dated Apr. 1, 2013.
Chinese 3rd Office Action, Application No. 200780005821.2 dated Nov. 5, 2012.
Chinese 3rd Office Action, Application No. 200880116343.7 dated Apr. 8, 2013.
Chinese 3rd Office Action, Application No. 200780023093.8 dated Jul. 2, 2012.
Chinese 3rd OfficeAction, Appln. No. 200780005791.5, dated Dec. 5, 2012.
Chinese 3rd OfficeAction, Application No. 200980111708.1, dated Nov. 4, 2013.
Chinese 4th Office Action, Application No. 200780023093.8 dated Jan. 14, 2013.
Chinese 4th Office Action Application No. 200780005821.2 dated May 13, 2013.
Chinese 4th Office Action Appln. No. 200880116343.7 dated Jul. 10, 2013.
Chinese 4th Office Action, Application No. 200780040146.7 dated Nov. 23, 2012.
Chinese 5th Office Action, Application No. 200780040146.7 dated Apr. 16, 2013.
Chinese Fourth Office Action, dated Nov. 19, 2013, Appln. No. 20880022612.3.
Chinese Notification of the First Office Action, Appln. No. 201210380806.9, dated Nov. 5, 2013.
Chinese Office Action, Application No. 200780033066.9 dated Jun. 26, 2012.
Chinese Office Action, Application No. 200780018496.3 dated Sep. 5, 2012.
Chinese Office Action, Application No. 200880116343.7 dated Jan. 31, 2012.
Chinese Office Action, Application No. 200880116343.7 dated Oct. 22, 2012.
Chinese Office Action, Application No. 200980111708.1 dated Aug. 27, 2012.
Chinese Office Action Application No. 200880108625.2 dated Feb. 13, 2012.
Chinese Office Action, Application No. 200880022612.3 dated Oct. 29, 2012.
Chinese Office Action, Application No. 200880112585.9 dated Jan. 21, 2013.
Chinese Office Action, Application No. 200980112966.1 dated Sep. 20, 2012.
Chinese Office Action, Application No. 200880108689.2 dated Sep. 12, 2012.
Chinese Office Action, Application No. 200880108625.2 dated Jan. 5, 2013.
Chinese Office Action 3rd Application No. 200780033066.9 dated Dec. 17, 2012.
Chinese Office Action, Application No. 200680039776.8 dated Jun. 30, 2011.
Chinese Office Action Application No. 200880022612.3 dated May 17, 2013.
Chinese Office Action, 1st Application No. 200880022612.3 dated Apr. 24, 2012.
Chinese Office Action, Application No. 200880103023.8 dated Oct. 9, 2012.
Chinese Office Action, Application No. 200880112585.9 dated May 24, 2012.
Chinese Office Action 1st Application No. 200780033066.9 dated Sep. 18, 2011.
Chinese Office Action, Application No. 200880119206 dated May 3, 2012.
Chinese Office Action, Application No. 200880108625.2 dated Aug. 21, 2012.
Chinese Rejection Decision Appln. No. 200780033066.9 dated Jun. 13, 2013.
Communication Concerning Office Action Received from Japanese Patent Office dated Jan. 30, 2012, Japanese Patent Application No. 2008-531200.
Communication Concerning Office Action Received from Japanese Patent Office dated Dec. 12, 2012, Japanese Patent Application No. 2008-549555.
EP Communication Appln, No. 12154343.3 dated Jul. 10, 2012.
EP Communication Appln. No. 11170608.1 dated May 3, 2012.
EP Communication Appln. No. 12154350.8 dated Jan. 25, 2013.
EP Communication Appn. No. 08782609.5 dated May 24, 2012.
EP Communication Appln. No. 08796821.0 dated Jul. 19, 2013.
EP Communication Appln. No. 09715356.3 dated Jul. 10, 2013.
EP Communication Appln. No. 08782609.5 dated Jun. 24, 2011.
EP Communication Pursuant to Article 94-3, Appln. No. 13175161.2, dated Sep. 24, 2013.
EP Communication Pursuant to Article 94-3, Appln. No. 11151769.4, dated Jan. 3, 2013.
EP Communication Pursuant to Article 94-3, Appln. No. 12165748.0, dated Sep. 17, 2013.
EP Communication Pursuant to Article 94-3, Appln. No. 12165734.0 dated Aug. 14, 2013.
EP Communication Pursuant to Article 94-3, Appln. No. 12185438.4 dated Sep. 18, 2013.
EP Communication Pursuant to Article 94-3, Appln. No. 12154350.8 dated Aug. 21, 2013.
EP Communication Pursuant to Article 94-3, Appln. No. 12154307.8 dated Feb. 20, 2013.
EP Communication Pursuant to Article 94-3, Appln. No. 11151771.0, dated Jan. 3, 2013.
EP Communication, 09713926.5 dated Jul. 30, 2012.
EP Communication, Application No. 13159600.9, dated Sep. 19, 2013.
EP Communication, Application No. 12154246.8, dated Nov. 22, 2013.
EP Communication, Application No. 12154347.4 dated Oct. 9, 2013.
EP Communication, Appln. No. 07867402.5 dated Dec. 11, 2009.
EP Communication, Appln. No. 12154304.5, dated Feb. 25, 2013.
EP Communication, Appln. No. 08768266.2 dated Jul. 29, 2010.
EP Communication, Application No. 12154298.9, dated Nov. 22, 2013.
EP Examination Report 08770974.7 dated Feb. 25, 2013.
EP Examination Report, Application No. 09715064.3 dated Nov. 5, 2012.
EP Examination Report, Application No. 12154346.6 dated Jun. 27, 2013.
EP Extended Srch Rpt., 12185446.7 dated Mar. 28, 2013.
EP Invitation Pursuant to Article 94(3) and Rule 71(1) EPC, Appln. No. 12154354.0, dated Oct. 23, 2013.
EP Search Report Appln, No. 12154307.8, dated Jun. 26, 2012.
EP Search Report, 12154300.3, dated Jan. 7, 2013.
EP Search Report, Application No. 12154345.8 dated Sep. 19, 2012.
EP Search Report, Application No. 12154298.9 dated Jun. 4, 2012.
EP Search Report, Application No. 11196253.6 dated Apr. 24, 2012.
EP Search Report, Application No. 12154342.5 dated Jul. 6, 2012.
EP Search Report, Application No. 11196250.2 dated Apr. 24, 2012.
EP Search Report, Application No. 12154301.1 dated Aug. 22, 2012.
EP Search Report, Application No. 12154327.6 dated Sep. 19, 2012.
EP Search Report, Application No. 09830750.7 dated Aug. 27, 2012.
EP Search Report, Application No. 11196190.0 dated Apr. 24, 2012.
EP Search Report, Application No. 12154300.3 dated Aug. 20, 2012.
EP Search Report, Application No. 12154348.2 dated Oct. 9, 2012.
EP Search Report, Application No. 09715356.3 dated Jul. 12, 2012.
EP Search Report, Application No. 12154341.7 dated Aug. 9, 2013.

(56) References Cited

OTHER PUBLICATIONS

EP Search Report, Application No. 12154347.4 dated Sep. 27, 2012.
EP Search Report, Application No. 12154326.8 dated Sep. 6, 2012.
EP Search Report, Application No. 12154337.5 dated Oct. 9, 2012.
EP Search Report, Application No. 12154350.8 dated Sep. 27, 2012.
EP Search Report, Application No. 12165748.0 dated Aug. 23, 2012.
EP Search Report, Application No. 12154339.1 dated Oct. 9, 2012.
EP Search Report, Application No. 12154344.1 dated Sep. 19, 2012.
EP Search Report, Application No. 12165740.7 dated Aug. 27, 2012.
EP Search Report, Application No. 12165734.0 dated Aug. 27, 2012.
EP Search Report, Application No. 11196254.4 dated Feb. 28, 2012.
EP Search Report, Application No. 12154352.4 dated Oct. 12, 2012.
EP Search Report, Application No. 11196261.9 dated Feb. 28, 2012.
EP Search Report, Application No. 11196264-3 dated Feb. 28, 2012.
EP Search Report, Application No. 12154322.7 dated Aug. 29, 2012.
EP Search Report, Application No. 11196256.9 dated Feb. 28, 2012.
EP Search Report, Application No. 12154329.2 dated Sep. 19, 2012.
EP Search Report, Application No. 11196262.7 dated Feb. 28, 2012.
EP Search Report, Application No. 12154353.2 dated Oct. 15, 2012.
EP Search Report, Application No. 11196265.0 dated Mar. 5, 2012.
EP Search Report, Application No. 12154354.0 dated Oct. 12, 2012.
EP Search Report, Application No. 12165636.7 dated Sep. 25, 2012.
EP Search Report, Application No. 12154334.2 dated Sep. 21, 2012.
EP Search Report, Application No. 12154321.9 dated Jul. 20, 2012.
EP Search Report, Application No. 12154349.0 dated Sep. 27, 2012.
EP Search Report, Application No. 12165638.3 dated Jun. 12, 2012.
EP Search Report, Application No. 12154346.6 dated Oct. 23, 2012.
EP Search Report, Application No. 12165636.7 dated Jun. 8, 2012.
EP Search Report, Application No. 12154332.6 dated Sep. 21, 2012.
EP Search Report, Application No. 09807241.6 dated Dec. 6, 2012.
EP Search Report, Application No. 12154304.5 dated Jun. 26, 2012.
EP Search Report, Application No. 12154351.6 dated Oct. 15, 2012.
European Communication Pursuant to Article 94(3) EPC, Application No. 06800599.0 dated Nov. 25, 2011.
European Communication Pursuant to Article 94(3) EPC, Application No. 08767439.6, dated Feb. 12, 2011.
European Communication Pursuant to Article 94(3) EPC, Application No. 08796821.0, dated Jan. 7, 2013.
European Communication Pursuant to Article 94(3) EPC, Application No. 07717903.4 dated Aug. 16, 2011.
European Communication Pursuant to Article 94(3) EPC, Application No. 07717903.4 dated Jan. 29, 2010.
European Communication Pursuant to Article 94(3) EPC, Application No. 09830750.7, dated Apr. 18, 2013.
European Communication Pursuant to Article 94(3) EPC, Application No. 08841700.1, dated Jun. 1, 2012.
European Communication Pursuant to Article 94(3) EPC, Application No. 07716208.9 dated Sep. 13, 2012.
European Communication, Application No. 07776079.1, dated Sep. 6, 2011.
European Communication Pursuant to Article 94(3) EPC, Application No. 07717903.4, dated Apr. 25, 2012.
European Communication Pursuant to Article 94(3) EPC, Application No. 07716208.9, dated Sep. 13, 2011.
European Communication Pursuant to Article 94(3) EPC, Application No. 07867402.5, dated Apr. 10, 2012.
European Communication Pursuant to Article 94(3)EPC, Application No. 06814375.9 dated Oct. 14, 2011.
European Communication Pursuant to Article 94(3) EPC, Application No. 08799295.4, dated Nov. 18, 2011.
European Communication Pursuant to Article 94(3) EPC, Application No. 07716208.9 dated Apr. 20, 2010.
European Communication Pursuant to Article 94-3 Appln. No. 08799295.4 dated Dec. 10, 2012.
European Communication Pursuant to Article 94(3) EPC, Application No. 07716208.9 dated Sep. 27, 2010.
European Examination Rpt., 11196265.0, dated Feb. 22, 2013.
European Seach Report, Application No. 09714868.8 dated Aug. 1, 2011.
European Search Report, Application No. 08713330.2, dated Jul. 22, 2011.
European Search Report, Application No. 08770974.4, dated Oct. 21, 2011.
European Search Report, Application No. 09713926.5 dated Jul. 21, 2011.
European Search Report, Application No. 12185440.0 dated Apr. 12, 2013.
European Srch Rpt. 08838376.5 dated Mar. 4, 2011.
European Srch Rpt., 09763590.8 dated Aug. 29, 2011.
Ext. Srch Rpt., Appln. No. 12154246.8 dated Jun. 4, 2012.
Extended EP Search Report Appl. No. 12185438.4 dated Mar. 28, 2013.
Extended EP Search Report Appl. No. 12179595.9 dated Jan. 23, 2013.
Extended EP Search Rpt., Appln. No. 12154353.2 dated Jan. 31, 2013.
Extended EP Search Report 12179592.6 dated Jan. 21, 2013.
Extended EP Srch Rpt., Appln. No. 12154301.1, dated Jan. 11, 2013.
Extended EP Srch Rpt., Appln. No. 12154351.6 dated Jan. 31, 2013.
Extended EP Srch Rpt., Appln. No. 12154352.4, dated Jan. 28, 2013.
Extended EP Srch Rpt., Appln. No. 12154354.0 dated Jan. 28, 2013.
Extended EP Srch Rpt., Appln. No. 12165740.7 dated Jan. 11, 2013.
Extended EP Srch Rpt., Appln. No. 12165734.0 dated Jan. 11, 2013.
Extended EP Srch Rpt., Appln. No. 12165748.0.
Extended European Search Report, Appln. No. 12154300.3.
Extented EP Search Rpt., Appln. No. 12154349.0 dated Jan. 25, 2013.
Japanese Notification of ReasonsFor Rejection 2010-524221 dated Jun. 19, 2013.
Japanese Notification Reason for Rejection—EnglishTrans, 2010-512377 dated Jun. 4, 2013.
Japanese Notification of Reasons for Rejection, dated Sep. 27, 2013, Appl. No. 2008-549532.
Japanese Notification of Reasons for Rejection 2010529072 dated Jul. 30, 2013.
Japanese Notification Reasons for Rejection 2010-519269 dated Jul. 12, 2013.
Japanese Notification Reasons for Rejection 2009-529212 dated Jul. 19, 2013.
Japanese Notification of Reasons for Rejection 2009-519525 dated Nov. 1, 2012.
Japanese Notification of Reasons for Rejection, 2010548907 dated Sep. 2, 2013.
Japanese Notification of Reasons for Rejection, 2009-519525 dated Jul. 9, 2012.
Japanese Notification of Reasons for Rejection 2010522058 dated Aug. 13, 2013.
Japanese Notification of Reasons for Rejection 2009548281 dated Sep. 3, 2013.
Japanese Notification of Reasons for Rejection, Appln. No. 2010-548899, dated Oct. 8, 2013.
Japanese Notification of Reasons for Rejection, 2010548904, dated Sep. 2, 2013.
Japanese Office Action 2008-525107 dated Jan. 4, 2011.
Japanese Office Action, Application No. 2009-529212 dated Oct. 17, 2012.
Japanese Office Action dated Feb. 24, 2012, Japanese Patent Application No. 2008-549532.
Japanese Office Action, Application No. 2008-525107 dated Oct. 19, 2012.
Japanese Office Action, Application No. 2010-506300 dated Apr. 16, 2013.
Japanese Office Action dated Feb. 22, 2012, Japanese Patent Application No. 2008-549549.
Japanese Office Action dated Jan. 4, 2012, Japanese Patent Application No. 2008-5251070.
Japanese Office Action, Application No. 2010-511218 dated Jun. 3, 2013.
Japanese Office Action dated Feb. 24, 2012, Japanese Patent Application No. 2008-549555.
Japanese Office Action, Application No. 2009-501495 dated Jul. 27, 2012.

(56) References Cited

OTHER PUBLICATIONS

Japanese Office Action, Application No. 2009-535366 dated Dec. 21, 2012.
JP Notification of Reasons for Rejection, Appln. No. 2011539528, dated Oct. 25, 2013.
PCT International Preliminary Report on Patentability, PCT/US2010/057758 filed Nov. 23, 2010, dated Jun. 7, 2012.
PCT International Preliminary Report on Patentability, PCT/US2011/034451 filed Apr. 29, 2011, dated Nov. 15, 2012.
PCT International Preliminary Report on Patentability, PCT/US2010/025173 filed Feb. 24, 2010, dated Sep. 9, 2011.
PCT International Search Report and the Written Opinion, PCT/US2012/020911 filed Jan. 11, 2012, dated Apr. 25, 2012.
PCT International Search Report and the Written Opinion, PCT/US2012/060225 filed Oct. 15, 2012, dated Jan. 7, 2013.
PCT International Search Report and the Written Opinion, PCT/US2012/28016 filed Mar. 7, 2012, dated Aug. 3, 2012.
PCT Intr Srch Rpt., Written Opinion, PCT/US12/62853, dated Mar. 14, 2013.
PCT Invitation to Pay Additional Fees, PCT/US2012/028016 filed Mar. 7, 2012, dated May 29, 2012.
PCT Search Report and Written Opinion, PCT/US13/22492, dated May 20, 2013.
PCT Search Report and Written Opinion PCT/US2012/67651, dated May 13, 2013.
PCT Search Report and Written Opinion PCT/US2012/68736, dated Apr. 8, 2013.
PCT Srch Rpt. Wrtn. Opin, PCT-US12-69484, dated Apr. 29, 2013.
PCT Srch Rpt., Written Opinion, PCT/US11/29348, dated Jun. 3, 2011.
PCT Srch Rpt., Wrtn Opin, PCT/US11/41046, dated Mar. 5, 2012.
PCT Srch Rpt., Wrtn Opin PCT/US12/62853 dated Mar. 14, 2013.
PCT Srch Rpt., Wrtn Opin PCT/US13/538930 dated Feb. 10, 2012.
PCT Written Opinion PCT/US13/538930 dated May 23, 2013.
Ahmad, A. et al., "Distant Metastases of Nasopharyngeal Carcinoma: A Study of 256 Male Patients," Journal of Surgical Oncology, 1986, pp. 194-197, vol. 33.
Aiba, M. "Pathology of the Breast Carcinoma from the Viewpoint of the Proliferative Activity and Grade of Malignancy," JP J Cancer Clin, 2000, pp. 475-181, vol. 46, No. 5.
Alberts, B. et al., Molecular Biology of the Cell, 3rd Edition, 1994, p. 465.
Ambros, MicroRNA Pathways in Flies and Worms: Growth, Death, Fat, Stress, and Timing, Nature, 2004, vol. 431, pp. 350-355.
Andriani, Increased Sensitivity to Cisplatin-Neoplasia, vol. 8, No. 1, pp. 9-17, 2006.
Arata, et al., Cdk2-dependent and -independent Pathways in E2F-mediated S Phase Induction, J. Biol. Chem, 2000.
Asangani, IA,, et al., MicroRNA-21 (miR-21) post-transcriptionally downregulates tumor suppressor Pdcd4 and stimulates invasion, intravasation and metastasis in colorectal cancer, Oncogene, 2008, vol. 27, pp. 2128-2136.
Attwooll, et al., The E2F family: specific functions and overlapping interests, EMBO, 2004.
Bakkus, M. et al., "MicroRNA Expression Analysis in Multiple Myeloma Plasma Cells and Cell Lines by a Quantitative Real-Time PCR Approach," Blood, 2007, p. 729A, vol. 110, No. 11, Abstract.
Bao, B. et al. Anti-Tumor Activity of a Novel Compound, PLOS One, 2011, vol. 6, Issue 3, pp. 1-12.
Barad, O. et al., "MicroRNA Exrpession Detected by Oligonucleotide Microarrays: System Establishment and Expression Profiling in Human Tissues," Genome Research, 2004, pp. 2846-2494, vol. 14.
Bartel, MicroRNAs: Genomics, Biogenesis, Mechanism, and Function, Cell, vol. 116, 2004, pp. 281-297.
Basu, et al., MicroRNA-375 and MicroRNA-221:Potential Noncoding RNAs Associated with Antiproliferative Activity of Benzyl Isothiocyanate in Pancreatic Cancer, Croce, Genes & Cancer, 2011, pp. 108-119.

Bejerano, Computational Screening of Conserved Genomic DNA-Nature Methods, 2005, vol. 2, No. 7, pp. 535-545.
Belinsky, et al., Inhibition of DNA Methylation and Histone Deacetylation Prevents Murine Lung Cancer, Cancer Research 63, 2004, pp. 7089-7093.
Bendoraite, et al, Regulation of miR-200 family microRNAs and ZEB transcription factors in ovarian cancer: evidence supporting a mesothelial-toepithelial transition, Gyneol Oncol, 2010, vol. 116, pp. 117-125.
Bloomston, et al., Identification of Molecular Markers Specific for Pancreatic Neuroendocrine Tumors by Genetic Profiling of Core Biopsies, Ann. Surg. Oncol. 2004, vol. 11, 4, pp. 413-419.
Blow, Replication licensing—defining the proliferative state, Cell Biol, 2002.
Boominathan, L., The Tumor Suppressors p53-p63 and p72, PLOS ONE, May 2010, vol. 5, Issue 5, pp. 1-13.
Braun et al., "p53-Responsive MicroRNAs 192 and 215 are Capable of Inducing Cell Cycle Arrest," Cancer Research, 2008, pp. 10094-10104, vol. 68.
Budhu, et al., Prediction of venous metastases, recurrence, and prognosis in hepatocellular carcinoma based on a unique immune response signature of the liver microenvironment, Cancer Cell, 2006, vol. 10, 2, pp. 99-111.
Butz, H. et al., "Down-Regulation of Wee1 Kinase by a Specific Subset of MicroRNA Sporadic Pituitary Adenomas," Journal of Clinical Endocrinol Metab, Oct. 2010, pp. E181-E191, vol. 95, No. 10.
Chambers, et al., Dissemination and Growth of Cancer Cells in Metastatic Sites, Nat. Rev. Cancer, 2002, vol. 2, pp. 563-572.
Chan, et al., Concordant and Discordant Regulation of Target Genes by miR-31 and Its Isoforms, PLOS ONE, 2013, vol. 8, pp. 1-11.
Chang, T. C., et al., Transactivation of miR-34a by p53, Molecular Cell 26, pp. 745-752, 2007.
Chen, et al., Expanded Polyglutamine-Binding Peptoid as a Novel Therapeutic Agent for Treatment of Huntington's Disease, Chemistry Biology, 2011, vol. 18, pp. 1113-1125.
Chen, et al., Real-time quantification of microRNAs by stem-loop RT-PCR, Nucleic Acids, 2005, e179.
Chen,et al., Downregulation of miR-221/222 sensitizes glioma cells to tempzolomide by regulating apoptosis independently of p53 status, Onocolgy Reports, 2012, vol. 27, pp. 854-860.
Chun-Zhi, et al., MicroRNA-221 and microRNA-222 regulate gastric carcinoma cell proliferation and radioresistance by targeting PTEN, BMC Cancer, 2010, gastric, vol. 10, pp. 1-10.
Cillo, et al., The critical issue of hepatocellular carcinoma prognostic classification: which is the best tool available, J. Hepatol., 2004, vol. 40, 1, pp. 124-131.
Cowgill, The genetics of pancreatic cancer Am. J. Surg, 2003, vol. 186, 3, pp. 279-286.
Dahiya, N. et al., "MicroRNA Expression and Identification of Putative miRNA Targets in Ovarian Cancer," PLOS ONE, Jan. 2008, pp. 1-11, vol. 3, No. 6.
Debernardi, S. et al., "MicroRNA miR-181a Correlates with Morphological Sub-Class of Acute Myeloid Leukemia and the Expression of its Target Genes in Global Genome-Wide Analysis," Leukemia, 2007, pp. 912-916, vol. 21.
Delott, et al., CDX2 Is a Useful Marker of Intestinal-Type Differentiation Arch. Pathol. Lab, Med, 2005 vol. 129, 9, pp. 1100-1105.
Dignam, et al., Accurate transcription initiation by RNA polymerase D in a soluble extract from isolated mammalian nuclei, Nucleic Acids Res., 11, 1983, pp. 1475-1489.
Ehrich, et al., Quantitative High-Throughput Analysis of DNA Methylation Patterns by Base-Specific Cleavage and Mass Spectrometry, vol. 102, 2005, pp. 15785-15790.
Eiriksdottir, G. et al., "Mapping Loss of Heterozygosity at Chromosome 13q: Loss at 13q12-q13 is Associated with Breast Tumour Progression and Poor Prognosis," European Journal of Cancer, 1998, pp. 2076-2081, vol. 34, No. 13.
Eychene, A. et al., "A New MAFia in Cancer," Nature Reviews Cancer, Sep. 2008, pp. 683-693, vol. 8.
Farazi, et al., MicroRNA Sequence and Expression Analysis in Breast Tumors by Deep Sequencing, AACR, 71(13), Jul. 1, 2011, pp. 4443-4453.

(56) References Cited

OTHER PUBLICATIONS

Fornari, et al., MiR-221 controls CDKNIC/p57 and CDKNIB/p27 expression in human hepatocellular carcinoma, Oncogene 2008, vol. 27, pp. 5651-5661.
Fujuta, S. et al., "miR-21 Gene Expression Triggered by AP-1 is Sustained Through a Double-Negative Feedback Mechanism," J. Mol. Biol., Abstract, 2008, pp. 492-504, vol. 378.
Fulci, et al., Quantitative Technologies Establish a Novel MicroRNA Profile of Chronic Lymphocytic Leukemia, Blood, Jun. 1, 2007, vol. 109, pp. 4944-4951.
Gailiun, M., "Single MicroRNA Causes Cancer in Transgenic Mice," Research Communications, The Ohio State University, Apr. 2006, pp. 1-3.
Gang, M. et al., "Expression of Programmed Cell Death 4 and Its Clinicopathological Significance in Human Pancreatic Cancer," Abstract, 2005, pp. 597-600, vol. 27.
Garcea, et al., Molecular prognostic markers in pancreatic cancer, A systematic review, Eur. J. Cancer, 2005, vol. 4, 15, pp. 2213-2236.
Garofalo, M. et al., "MicroRNA Signatures of TRAIL Resistance in Human Non-Small Cell Lung Cancer," Oncogene, 2008, pp. 3854-3855, vol. 27.
Garzon et al., MicroRNA signatures associated with cytogenetics and prognosis in acute myeloid leukemia; Blood, Mar. 15, 2008, vol. 111, No. 6.
Garzon et al., MicroRNA expression and function in cancer, Trend Mol Med, vol. 12, 2006, pp. 580-587.
Ghaneh, et al., Molecular prognostic markers in pancreatic cancer, J. Hepatobiliary, Pancreat. Surg., 2002, vol. 9, pp. 1-11.
Goel, A., et al., A Novel Mechanism for Aspirin Mediated Growth Inhibition, Clin Cancer Res, 2003, vol. 9, pp. 383-390.
Greenbaum, D. et al., "Comparing Protein Abundance and mRNA Expression Levels on a Genomic Scale," Genome Biology, 2003, pp. 117.1-117.8, vol. 4, Issue 9.
Gregory, et al., MicroRNA Biogenesis and Cancer, Cancer Res, 2005, vol. 65, 9, pp. 3509-3512.
Gregory, et al., The Microprocessor complex mediates the genesis of microRNAs, Nature, 432, 2004, pp. 235-240.
Grier, D.G. et al., "The Pathophysiology of HIX Genes and Their Role in Cancer," Journal of Pathology, 2005, pp. 154-171, vol. 205.
Gu, et al., The t(4;II) Chromosome Translocation of Human Acute Leukemias Fuses the ALL-7 Gene, Related to *Drosphila trithorax*, to the AF-4 Gene, Cell 71, 1992, pp. 701-709.
Guenther, et al., Global and Hox-specific roles for the MLL1 methyltransferase, Proc. Natl. Acad. Sci., 102, 2005, pp. 8603-8608.
Habbe, et al., MicroRNA miR-155 is a biomarker of early pancreatic neoplasia, Cancer Biol Therapy, 2009, pp. 340-346.
He, H. et al., "The Role of MicroRNA Genes in Papillary Thyroid Carcinoma," PNAS, Dec. 2005, pp. 19075-19080, vol. 102, No. 52.
Hezel, et al., Genetics and biology of pancreatic ductal adenocarcinoma, Genes Dev., 2006, vol. 20, pp. 1218-1249.
Hu, et al., A miR-200 microRNA cluster as prognostic marker in advanced ovarian cancer, Gynecol Oncol, 2009, vol. 114, pp. 457-464.
Huang, et al., Evaluation of predictive value of CLIP, Okuda, TNM and JIS staging systems for hepatocellular carcinoma patients undergoing surgery, J. Gastroenterol Hepatol, 2005, vol. 20, 5, pp. 765-771.
Hudlebusch, H. et al., "Expression of HOXA Genes in Patients with Multiple Myeloma," Leukemia & Lymphoma, Jun. 2004, pp. 1215-1217, vol. 45, No. 6.
Hutvagner, et al., A MicroRNA in a Multiple Turnover RNAi Enzyme Complex, Science, 2002, vol. 297, 5589, pp. 2056-2060.
Iizuka, et al., Oligonucleotide microarray for prediction of early intrahepatic, Lancet, 2003, vol. 361, 9361, pp. 923-929.
Iorio et al., MicroRNAs in Cancer: Small Molecules With a Hugh Impact, Journal of Clinical Oncology, vol. 27, Dec. 1, 2009, pp. 5848-5856.
Iorio, et al., Causes and consequences of microRNA Dysregulation, Cancer Journal, 2012, vol. 18, pp. 215-222.
Izzotti, A. et al., Relationships of MicroRNA Expression in Mouse, FASEB Journal, vol. 23, Sep. 2009, pp. 3243-3250.
Jazbutyte, V. et al., "MicroNRA-21: From Cancer to Cardiovascular Disease," Current Drug Targets, Abstract, 2010, pp. 926-935, vol. 11.
Jemal, et al., Cancer Statistics, Cancer Stats vol. 57, 2007, pp. 43-66.
Johansson, et al., Hematologic malignancies with t(4;11)(q21;q23) a cytogenetic, morphologic, immunophenotypic and clinical study of 183 cases, Leukemia, 12, 1998, pp. 779-787.
Joost, et al., BIC and miR-155 are highly expressed in Hodgkin, primary mediastinal and diffuse large B cell lymphomas , J. Pathol, 2005, 207, pp. 243-249.
Kan, et al., Elevated Levels of Circulating MicroRNA, BMC, Cancer, 2012, vol. 12, pp. 2-9.
Kim, et al., FHIT Protein Enhances Paclitaxel-Induced Apoptosis, Int. J. Cancer, vol. 118, pp. 1692-1698, 2006.
Kim, MicroRNA Biogenesis: Coordinated Cropping and Dicing , Nature Rev. Mol. Cell Bio, vol. 6, 2005, pp. 376-385.
Kim, Processing of intronic microRNAs, EMBO, 2007, vol. 26, 3, pp. 775-783.
Kluiver, et al., BIC and miR-155 are highly expressed in Hodgkin, primary mediastinal and diffuse large B cell lymphomas, J. Pathol., 2005, 207, 2, pp. 243-249.
Kluiver, et al., Lack of BIC and MicroRNA miR-155 Expression in Primary Cases of Burkitt Lymphoma, Cancer, 2006, vol. 45, 2, pp. 147-153.
Kudo, et al., Prognostic staging system for hepatocellular carcinoma (CLIP score): its value and limitations, and a proposal for a new staging system, the Japan Integrated Staging Score (JIS score), J. Gastroenterol, 2003, vol. 38, 3, pp. 207-215.
Kulshreshtha, et al., A MicroRNA Signature of Hypoxia, Mol. Cell Biol., 2006, pp. 1395-1306.
Lagos-Quintana, et al., Identification of Novel Genes Coding for Small Expressed RNA's, Science, 2001, vol. 294, 5543, pp. 853-858.
Lall, et al., A Genome-Wide Map of Conserved MicroRNA Targets in *C. elegans*, Curr Biol 16, 2006, pp. 460-471.
Landthaler, et al., The Human DiGeorge Syndrome Critical Region Gene 8 and Its *D. melanogaster* Homolog Are Required for miRNA Biogenesis, CB, 14, 2004, pp. 2162-2167.
Lau, et al., An Abundant Class of Tiny RNA's with Probable Regulatory Roles in *Caenorhabditis elegans*, Science 2001, vol. 294, 5543, pp. 858-862.
Lawrie, C. H. "MicroRNAs and Haematology: Small Molecules, Big Function," British Journal of Haematology, Jun. 2007, pp. 503-512, vol. 137, No. 6.
Lawrie, C.H., "MicroRNA, Expression in Lymphoma," Expert Opinoin on Biological Therapy, Sep. 2007, pp. 1363-1374, vol. 7, No. 9.
Lecellier, et al., A Cellular MicroRNA mediates Antiviral, Science, 2005, vol. 308, pp. 557-560.
Lee, et al., An Extensive Class of Small RNA's in *Caenorhabditis elegans*, Science, 2001, vol. 294, 5543, pp. 862-864.
Lee, et al., MicroRNA maturation: stepwise processing and subcellular localization, EMBO, J. 2002, vol. 21, 17, pp. 4663-4670.
Lee, et al., MicroRNA maturation: stepwise processing and subcellular localization, EMBO, J., 2004, vol. 40, 3, pp. 667-676.
Lee, Y.S. et al., "MicroRNAs: Small but Potent Onogenes or Tumor Suppressors," Current Opinion in Investigational Drugs, Jun. 2006, pp. 560-564, vol. 7, No. 6.
Levy, et al., Staging of hepatocellular carcinoma: assessment of the CLIP, Okuda, and Child-Pugh staging systems in a cohort of 257 patients in Toronto, Gut, 2002, vol. 50, 6, pp. 881-885.
Lewis, et al., Conserved Seed Pairing, Often Flanked by Adenosines, Indicates that Thousands of Human Genes are MicroRNA Targets, Cell, 2005, vol. 120, 1, pp. 15-20.
Li et al., miR-181a Is an Intrinsic Modulator of T Cell Sensitivity and Selection, Cell 2007, pp. 147-161.
Li, et al., DNA mismatch repair (MMR)-dependent 5-fluorouracil cytotoxicity and the potential for new therapeutic targets, British Journal of Pharmacology, 2008, vol. 158, pp. 679-692.
Li, et al., Expression of serum miR-221 in human heptocellular carcinoma and its prognostic significance, Biochemical Biophys Res Commun, 2011, Vol, 406, pp. 70-73.

(56) References Cited

OTHER PUBLICATIONS

Li, Z. et al., "Inhibition of PRL-3 Gene Expression in Gastric Cancer Cell Line SGC7901 via MicroRNA Suppressed Reduces Peritoneal Metastasis," Biochemical and Biophysical Research, Sep. 2006, pp. 229-237, vol. 348, No. 1.
Lin, et al., Alteration of DNA methyltransferases contributes to 5 CpG methylation and poor prognosis in lung cancer, LungCancer, vol. 55, 2007, pp. 205-213.
Liu, et al., Characterization of in vitro and in vivo hypomethylating effects of decitabine in acute myeloid leukemia by a rapid, specific and sensitive LC-MS/MS method, Nucleic Acids, vol. 35, 2007, e31.
Liu, et al., Increased Expression of MicroRNA-221 in Gastric Cancer and Its Clinical Significance, Journal of International Medical Research, 2012, vol. 40, pp. 467-474.
Loffler, D. et al., "Interleukin-6-Dependent Survival of Multiple Myeloma Cells Involves the Stat3-Mediated Induction of MicroRNA-21 Through a Highly Conserved Enhancer," Blood, 2007, pp. 1330-1333, vol. 110, No. 4.
Ma, X., et al., MicroRNAs in NF-kB signaling, Journal of Molecular Cell Biology, 2011, vol. 3, pp. 159-166.
Marsit, et al., MicroRNA Responses to Cellular Stress, Cancer Research, 2006, vol. 66, pp. 10843-10848.
Martin, M. et al., "MicroRNA-155 Regulates Human Angiotensin II Type 1 Receptor Expression in Fibroblasts," The Journal of Biological Chemistry, Jul. 2006, pp. 18277-18284, vol. 281, No. 27.
Mascellani, N. et al., "Using miRNA Expression Data for the Study of Human Cancer," Minerva Biotec, 2008, pp. 23-30, vol. 20.
Masri, A. et al., "MicroRNA Expression Analysis in Multiple Myeloma," Blood, Nov. 2005, p. 446A, vol. 106, No. 11, Abstract.
Mazurek, N. et al., "Phosphorylated Galectin-3 Mediates Tumor Necrosis Factor-Related Apoptosis-Inducing Ligand Signaling by Regulating Phosphatase and Tensin Homologue Deleted on Chromosome 10 in Human Breast Carcinoma Cells," The Journal of Biological C, 2006.
Medina, et al., MicroRNA's 221 and 222 Bypass Quiescence and Compromise Cell Survival Cancer Research, 2008, vol. 68, pp. 2773-2780.
Mercatelli, et al., The Inhibition of the Highly Expressed Mir-221 and Mir-222 Impairs the Growth of Prostate Carcinoma Xenografts in Mice, PLOS ONE, 2008, vol. 3, No. 12, pp. 21337-21348.
Metzler, et al., High Expression of Precursor MicroRNA-155/BIC RNA in Children with Burkitt Lymphoma, Genes, Chromosomes, Cancer, 2004, vol. 39, 2, pp. 167-169.
Mizusawa, et al., Differentiation phenotypes of pancreatic islet h- and a-cells are closely related with homeotic genes and a group of differentially expressed genes, Gene 2004, vol. 331, pp. 53, 63.
Nakajima, G. et al., "Non-Coding Micro-RNAs HAS-LET-7G and HAS-MIR-181b are Associated with Chemoresponse to S-1 in Colon Cancer," Cancer Genomics & Proteonmics, Sep. 2006, pp. 317-324, vol. 3, No. 5.
Nakamura, et al., ALL-1 Is a Histone Methyltransferase that Assembles a Supercomplex of Proteins Involved in Transcriptional Regulation, Mol. Cell, 10, 2002, pp. 1119-1128.
Nana-Sinkam, et al., Clinical applications for microRNA's in cancer, Nature, 2013, vol. 93.
NIPPON—Journal of The Japanese Society, 1993, vol. 82, pp. 1053-1057.
O'Connell, R. et al., "Inositol Phosphatase SHIP1 is a Primary Target of miR-155," PNAS, Apr. 2009, pp. 7113-7118, vol. 106, No. 17.
O'Donnell, c-Myc-regulated microRNAs modulate E2F1 expression, Nature, 2005, pp. 839-843.
Okada, H. et al., "MicroRNAs in Immune Regulation—Opportunities for Cancer Immunotherapy," The International Journal of Biochemistry & Cell Biology, 2010, pp. 1256-1261, vol. 42.
Okuda, et al., Natural History of Hepatocellular Carcinoma and Prognosis in Relation to Treatment, Cancer, 1985, vol. 56, 4, pp. 918-928.
Pallante, et al., MicroRNA deregulation in human thyroid papillary carcinomas, Endocr. Relat. Cancer, 2006, vol. 13, 2, pp. 497-508.
Pan, M. R. et al. Non-Steroidal Anti-Inflammatory Drugs Suppress The ERK, Cellular Signaling, 20, 2008, pp. 1134-1141.
Panarelli, et al., MicroRNA Expression Aids the Preoperative Diagnosis of Pancreatic Ductal Adenocarcinoma, Pancreas, 2012, vol. 41, pp. 685-690.
Papageorgiou, et al., Interferon-α Induces TRAIL Expression and Cell Death Via an IRF-1-Dependent Mechanism in Human Bladder Cancer Cells, Cancer Biol Ther, 2007, vol. 6, No. 6, pp. 872-879.
Park, et al., Antisense inhibition of microRNA-21 or-221 arrests cell cycle, induces apoptosis, and sensitizes the effects of gemcitabine in pancreatic adenocarcinoma, Pancreas, 2009, Abstract.
Park, J.-K. et al., "miR-221 Silencing Blocks Hepatocellular Carcinoma and Promotes Survival," Cancer Research, Dec. 2011, pp. 7608-7616, vol. 71, No. 24.
Parkin, et al., Global Cancer Statistics, 2002, CA, Cancer, J. Clin., 2005, vol. 55, 2, pp. 74-108.
Partha, D. et al., "Early Detection of Ovarian Cancer," NIH Public Access Author Manuscript, Jun. 2008, pp. 1-17, Retrieved from the Internet.
Pasquinelli, et al., MicroRNAs: a developing story, Current Opinion in Genetics and Development, vol. 15, 2005, pp. 200-205.
Pathi, S. S., et al., GT-094, a No-NSAID, Inhibits Colon, Molecular Cancer Research, 2011, vol. 9, pp. 195-202.
Petrocca, F. et al., "MicroRNAs Deregulation in Gastric Cancer," PNAS, Apr. 2006, p. 1338, vol. 47, Abstract # 5690.
Pichiorri et al., "Downregulation of p53-Inducible MicroRNAs 192, 194 and 215 Impairs the p53/MDM2 Autoregulatory Loop in Multiple Myeloma Development," Cancer Cell, 2010, pp. 367-381, vol. 18.
Pichiorri, F. et al., "MicroRNA Signatures in Multiple Myeloma," 99th AACR Annual Meeting, Apr. 12-16, 2008, pp. 1203, vol. 49, Abstract.
Poliseno, et al., MicroRNAs modulate the angiogenic properties of HUVECs, Blood, 2006.
Pouponnot, C. et al., "Cell Context Reveals A Dual Role for Maf in Oncogenesis," Oncogene, 2006, pp. 1299-1310, vol. 25.
Poy, et al., A pancreatic islet-specific microRNA regulates insulin secretion, Nature, 2004, vol. 432, pp. 226-230.
Pu, et al., Circulating miR-221 directly amplified from plasma is a potential diagnostic and prognostic marker of colorectal cancer and is correlated with p53 expression, J. Gastroenterol Hepatol, 2010, vol. 25, pp. 1674-1680.
Ren, et al., Co-delivery of as-miR-21 and 5-FU by Poly (amidoamine) Dendrimer Attenuates Human Glioma Cell Growth in Vitro, Journal of Biomedical Science, 2010, vol. 21, pp. 303-314.
Resnick, et al., The detection of differentially expressed microRNAs from the serum of ovarian cancer patients using a novel real-time PCR platform, Science Direct, 2009, vol. 112, pp. 55-59.
Ribas, J. et al., "The Transcriptional Regulation of miR-21, Its Multiple Transcripts, and Their Implication in Prostate Cancer," Cell Cycle, 2010, pp. 923-929, vol. 9.
Rosa, et al., The miR-430/427/302 Family Controls Mesendodermal Fate Specification via Species-Specific Target Selection, Development Cell, 16, 2009, pp. 517-527.
Rossi, S. et al., "MicroRNA Fingerprinting of CLL Patients with Chromosome 17p Deletion Identify a miR-21 Score that Stratifies Early Survival," Blood, Aug. 2010, pp. 945-952, vol. 116, No. 6.
Ryu, J.K. et al., "Aberrant MicroRNA-155 Expression is an Early Event in the Multistep Progression of Pancreatic Adenocarcinoma," Pancreatology, 2010, pp. 66-73, vol. 10.
Sah., et al, Translation Inhibitors Sensitize Prostate Cancer Cells to Apoptosis Induced by Tumor Necrosis Factor-related Apoptosis-inducing Ligand (TRAIL) by Activating c-Jun N-terminal Kinase, J. Biol Chem 2003, vol. 278, pp. 20593-20602.
Schetter, et al., MicroRNA Expression Profiles Associated With Prognosis and Therapeutic Outcome in Colon Adenocarcinoma, Journal of America Medical Association, 2008, vol. 299, pp. 426-436.
Schrump, et al.,Targeting the Epigenome for the Treatment and Prevention of Lung Cancer Semin Oncol, 32, 2005, pp. 488-502.
Science Daily, Web address: http://www.sciencedaily.com/release/2009/05/090522171001.html Nov. 2013.

(56) References Cited

OTHER PUBLICATIONS

Selvendiran, K. et al. NCX-4016 a Nitro-derivative of Aspirin, Cell Cycle, 2008, 7:1, pp. 81-88.

Shih, K.K. et al., "Exosomal MicroRNAs Step into the Biomarker Arena," Gynecologic Oncology, Jul. 2008, pp. 1-2, vol. 110, No. 1.

Slaby, et al., AlteredExpressionofmiR21-miR31, Oncology, 2007, vol. 72, pp. 1-6.

Sonoki, T. et al., "Insertion of MicroRNA-125b-1, A Human Homologue of lin-4, into a Rearranged Immunoglobulin Heavy Chain Gene Locus in a Patient with Precursor B-Cell Acute Lymphoblastic Leukemia," Leukemia, 2005, pp. 1-2, vol. 19.

Stamatopoulos, B. et al., "MicroRNA-29c and MicroRNA-233 Down-Regulation has In Vivo Significance in Chronic Lymphocytic Leukemia and Improves Disease Risk Stratification," Blood, May 2009, pp. 5237-5245, vol. 113, No. 21.

Stenvang, et al., The utility of LNA in microRNA-based cancer diagnostics and therapeutics, Cancer Biology, 2008, pp. 89-102.

Sugito, et al., RNASEN regulates Cell Proliferation and Affects Survival in Esophageal Cancer Patients, Clin Canc Res, 2006[1], vol. 12, pp. 7322-7328.

Suh, et al., Human embryonic stem cells express a unique set of microRNAs, Dev. Biol., 270, 2004, pp. 488-498.

Sun Kai, Analysis of microRNA expression patterns Chinese Journal of Experimental Surgery, 2006, vol. 23, No. 8, pp. 945-947.

Sun, et al., MicroRNA-221 inhibits CDKN1C/p57 expression in human colorectal carcinoma, Acta Pharmacologica Sinica, 2011, vol. 32, pp. 375-384.

Suzuki, et al., RNA Interference-Mediated Knockdown of DNA Methyltransferase 1 Leads to Promoter Demethylation and Gene Re-Expression in Human Lung and Breast Cancer CellsCancer, Research, 64, 2004, pp. 3137-3143.

Szymanski M., et al., A new frontier for molecular medicine: Noncoding RNAs, BBA, vol. 1756, No. 1, Sep. 25, 2005, pp. 65-75.

TAM, The Emergent Role of MicroRNA's in Molecular Diagnostics of Cancer, Journal of Molecular Diagnostics, 2008, vol. 10, pp. 411-414.

Tanner et al., BAALC, the human member of a novel mammalian neuroectoderm gene lineage, is implicated in hematopoiesis and acute leukemia, PNAS, Nov. 20, 2001, vol. 98, No. 24, pp. 13901-13906.

Tanzer, Molecular Evolution of a MicroRNA Cluster, J. Mol. Biol, 2004, vol. 339, 2, pp. 327-335.

Tatsuya, et al., Oncogenic All1 fusion proteins target Drosha-mediated microRNA processing, PNAS, 2007, vol. 104, pp. 10980-10985.

Teachey, et al., Mammalian target of rapamycin inhibitors and their potential role in therapy in leukemia and other haematogical malignancies, BJH, 2009[1], vol. 145, pp. 569-580.

Thomson, et al., Extensive post-transcriptional regulation of microRNAs and its implications for cancer Genes, Dev. 20, 2006, pp. 2202-2207.

Thomson, M., Supplementary data for "A Custon Microarray Platform for Analysis of MicroRNA Gene Expression," Nature Methods, Oct. 2004, pp. 47-53, vol. 1, No. 1.

Thorgeirsson, et al., Molecular pathogenesis of human hepatocellular carcinoma, Nat, Genet. 2002, vol. 31, 4, pp. 339-346.

Tibshirani, et al., Diagnosis of multiple cancer types by shrunken centroids of gene expression, Proc. Natl. Acad. Sci., 2002, vol. 99, 10, pp. 6567-6572.

Tkachuk, et al., Involvement of a Homolog of *Drosophila trithorax* by 11 q23 Chromosomal Translocations in Acute Leukemias Cell, vol. 71, 1992, pp. 691-700.

Tokarz, et al., The Role of microRNA in metastatic colorectal cancer and its significance in cancer prognosis and treatment, ACTA, 2012, vol. 59, pp. 467-474.

Tsunoda, et al., Oncogenic KRAS regulates miR-200c and miR-221, 222 in a 3D-specific manner in colorectal cancer cells, Anticancer Research, 2011, Abstract.

Tusher, et al., Significance analysis of microarrays applied to the ionizing radiation response, Proc. Natl. Acad. Sci., 2001, vol. 98, 9, pp. 5116-5121.

Ulivi, et al., p16INK4A and CDH13 Hypermethylation in Tumor and Serum of Non-Small Cell Lung Cancer Patients Journal of Cell, Physiol, 206, 2006, pp. 611-615.

Valeri, et al., MicroRNA-21 induces resistance to 5-fluorouracil by down-regulating human DNA MutS homolog 2 hMSH2 ,PNAS, 2010, vol. 107, pp. 21098-21103.

Vandeneynde, et al., Is Tailored Adjuvant Treatment for Colon Cancer Possible, Clinical Colorectal Cancer, 2010, vol. 9, pp. 15-21.

Varotti, et al., Comparison between the fifth and sixth editions of the AJCC/UICC TNM staging systems for hepatocellular carcinoma: multicentric study on 393 cirrhotic resected patients, Eur. J. Surg. Oncol, 2005, vol. 31, 7, pp. 760-767.

Vassilev et al., "In Vivo Activation of the p53 Pathway by Small-Molecule Antagonists of MDM2," Science, 2004, pp. 844-848, vol. 303.

Vatolin, et al., A Novel Method to Detect Functional MicroRNA Targets, J. Mol. Biol., 358, 2006, pp. 983-996.

Volinia, et al., Breast cancer signatures for invasiveness and prognosis defined by deep sequencing of microRNA, PNAS, Feb. 21, 2012, vol. 109, No. pp. 3024-3029.

Volinia, Prognostic microRNA/mRNA signature from the integrated analysis of patients with invasive breast cancer, PNAS, pp. 1-5.

Watson, D.I. et al., "MicroRNA Expression Profiles in Barrett's Oesophagus," RACS Annual Scientific Congress, 2007, pp. A45, vol. 77.

Wiemer et al., "The Role of MicroRNAs in Cancer: No Small Matter," European Journal of Cancer, Jun. 12, 2007, vol. 43, No. 10, pp. 1529-1544.

Wildi, et al., Critical evaluation of the different staging systems for hepatocellular carcinoma, Br. J. Surg., 2004, vol. 91, 4, pp. 400-408.

Williams, C.S., "OncomiRs: The Discovery and Progress of MicroRNAs in Cancers," Molecular Cancer, Sep. 2007, pp. 259-269, vol. 6, No. 4.

Wu, D. et al., "Micro-RNA: A New Kind of Gene Regulators," Agricultural Sciences in China, Jan. 2006, pp. 77-80, vol. 5, No. 1.

Xi, Y. et al., "Prognostic Values of MicroRNAs in Colorectal Cancer," Biomarker Insights, Jan. 2006, pp. 113-121, vol. 1.

Ye, et al., Predicting hepatitis B virus-positive metastatic hepatocellular carcinomas using gene expression profiling and supervised machine learning, Nat. Med., 2003, vol. 9, 4, pp. 416-423.

Yekta, et al., MicroRNA-Directed Cleavage of HOXB8 MRNA, Science, 2004, vol. 304, pp. 594-596.

Yi, et al., Exportin-5 mediates the nuclear export of pre-microRNAs and short hairpin RNAs, Genes Dev, 2003, vol. 17, 24, pp. 3011-3016.

Yoo, et al., Epigenetic therapy of cancer: past, present and future, Nature Reviews Drug Discov 5, 2006, pp. 37-50.

Yu, et al., Human microRNA clusters: Genomic organization and expression profile in leukemia cell lines, Biomed Biophys Res Comm, 2006, pp. 59-68.

Yuki, et al., Growth and Spread of Hepatocellular Carcinoma, Cancer, 1990, vol. 66, 10, pp. 2174-2179.

Zaman, et al., Current status and implications of microRNAs in ovarian cancer diagnosis and therapy, J Ovarian Res, 2012[1].

Zhao et al., "p53 Mediates the Negative Regulation of MDM2 by Orphan Receptor TR3," The EMBO Journal, 2006, pp. 5703-5715, vol. 25.

Zhou, et al., Binding of NF-kappaB p65 subunit to the promoter elements is involved in LPS-induced transactivation of miRNA genes in human biliary epithelial cells, Nucleic Acids Research, 2010, vol. 38, No. 10, pp. 3222-3232 [1].

* cited by examiner

MICRORNA FINGERPRINTS DURING HUMAN MEGAKARYOCYTOPOIESIS

CROSS-REFERENCE TO RELATED APPLICATIONS

This application is a divisional application of U.S. patent application Ser. No. 13/595,204, having a filing date of Aug. 27, 2012, now allowed, which is a divisional application of U.S. patent application Ser. No. 13/169,184, having a 371 filing date of Jun. 27, 2011, now U.S. Pat. No. 8,354,224 issued Jan. 15, 2013, which claims priority to parent U.S. patent application Ser. No. 12/293,471, having a 371 filing date of Oct. 9, 2008, now U.S. Pat. No. 7,985,584 issued Jul. 26, 2011, which is a national stage application of international application PCT/US2007/006824 filed Mar. 19, 2007, which claims priority to U.S. Provisional Application Ser. No. 60/743,585 filed Mar. 20, 2006, the entire disclosures of which are expressly incorporated herein by reference for all purposes.

STATEMENT REGARDING FEDERALLY SPONSORED RESEARCH

The invention was supported, in whole or in part, by National Institutes of Health Program Project Grants $PO_1CA76259$, $PO_1CA16058$, $PO_1CA81534$ and P01CA16672. The Government has certain rights in the invention.

BACKGROUND OF THE INVENTION

MicroRNAs (miRNAs) are a small non-coding family of 19-25 nucleotide RNAs that regulate gene expression by targeting messenger RNAs (mRNA) in a sequence specific manner, inducing translational repression or mRNA degradation depending on the degree of complementarity between miRNAs and their targets (Bartel, D. P. (2004) *Cell* 116, 281-297; Ambros, V. (2004) *Nature* 431, 350-355). Many miRNAs are conserved in sequence between distantly related organisms, suggesting that these molecules participate in essential processes. Indeed, miRNAs are involved in the regulation of gene expression during development (Xu, P., et al. (2003) *Curr. Biol.* 13, 790-795), cell proliferation (Xu, P., et al. (2003) *Curr. Biol.* 13, 790-795), apoptosis (Cheng, A. M., et al. (2005) *Nucl. Acids Res.* 33, 1290-1297), glucose metabolism (Poy, M. N., et al. (2004) *Nature* 432, 226-230), stress resistance (Dresios, J., et al. (2005) *Proc. Natl. Acad. Sci. USA* 102, 1865-1870) and cancer (Calin, G. A, et al. (2002) *Proc. Natl. Acad. Sci. USA* 99, 1554-15529; Calin, G. A., et al. (2004) *Proc. Natl. Acad. Sci. USA* 101, 11755-11760; He, L., et al. (2005) *Nature* 435, 828-833; and Lu, J., et al. (2005) *Nature* 435:834-838).

There is also strong evidence that miRNAs play a role in mammalian hematopoiesis. In mice, miR-181, miR-223 and miR-142 are differentially expressed in hematopoietic tissues, and their expression is regulated during hematopoiesis and lineage commitment (Chen, C. Z., et al. (2004) *Science* 303, 83-86). The ectopic expression of miR-181 in murine hematopoietic progenitor cells led to proliferation in the B-cell compartment (Chen, C. Z., et al. (2004) *Science* 303, 83-86). Systematic miRNA gene profiling in cells of the murine hematopoietic system revealed different miRNA expression patterns in the hematopoietic system compared with neuronal tissues, and identified individual miRNA expression changes that occur during cell differentiation (Monticelli, S., et al. (2005) *Genome Biology* 6, R71). A recent study has identified down-modulation of miR-221 and miR-222 in human erythropoietic cultures of $CD34^+$ cord blood progenitor cells (Felli, N., et al. (2005) *Proc. Natl. Acad. Sci. USA.* 102, 18081-18086). These miRNAs were found to target the oncogene c-Kit. Further functional studies indicated that the decline of these two miRNAs in erythropoietic cultures unblocks Kit protein production at the translational level leading to expansion of early erythroid cells (Felli, N., et al. (2005) *Proc. Natl. Acad. Sci. USA.* 102, 18081-18086). In line with the hypothesis of miRNAs regulating cell differentiation, miR-223 was found to be a key member of a regulatory circuit involving C/EBPa and NH-A, which controls granulocytic differentiation in all-trans retinoic acid-treated acute promyelocytic leukemic cell lines (Fazi, F., et al. (2005) *Cell* 123, 819-831).

miRNAs have also been found deregulated in hematopoietic malignancies. Indeed, the first report linking miRNAs and cancer involved the deletion and down regulation of the miR-15a and miR-16-1 cluster, located at chromosome 13q14.3, a commonly-deleted region in chronic lymphocytic leukemia (Calin, G. A, et al. (2002) *Proc. Natl. Acad. Sci. USA* 99, 1554-15529). High expression of miR-155 and host gene BIC was also reported in B-cell lymphomas (Metzler M., et al. (2004) *Genes Chromosomes and Cancer* 39; 167-169). More recently it was shown that the miR-17-92 cluster, which is located in a genomic region of amplification in lymphomas, is overexpressed in human B-cell lymphomas and the enforced expression of this cluster acted in concert with c-MYC expression to accelerate tumor development in a mouse B cell lymphoma model (He, L., et al. (2005) *Nature* 435, 828-833). These observations indicate that miRNAs are important regulators of hematopoiesis and can be involved in malignant transformation.

Platelets play an essential role in hemostasis and thrombosis. They are produced from in large numbers from their parent cells, bone marrow megakaryocytes, and arise from fragmentation of the cytoplasm. Only recently has the molecular basis of what may turn out to be a large family of related disorders affecting platelet production started to be defined. If the level of circulating platelets drops below a certain number (thrombocytopenia), the patient runs the risk of catastrophic hemorrhage. Patients with cancer who have received chemotherapy or bone marrow transplants usually have thrombocytopenia, and the slow recovery of platelet count in these patients has been a concern. The demand for platelet units for transfusion has been steadily increasing primarily because of the need to maintain a certain platelet level in such patients with cancer or those undergoing major cardiac surgery.

Identification of microRNAs that are differentially-expressed in cancer cells (e.g., leukemia cells) may help pinpoint specific miRNAs that are involved in cancer and other disorders (e.g., platelet disorders). Furthermore, the identification of putative targets of these miRNAs may help to unravel their pathogenic role. In particular, discovering the patterns and sequence of miRNA expression during hematopoietic differentiation may provide insights about the functional roles of these tiny non-coding genes in normal and malignant hematopoiesis.

There is a need for novel methods and compositions for the diagnosis, prognosis and treatment of cancer, myeloproliferative disorders and platelet disorders (e.g., inherited platelet disorders).

SUMMARY OF THE INVENTION

The present invention is based, in part, on the identification of specific miRNAs that are involved in megakaryocytic differentiation and/or have altered expression levels in cancerous cells (e.g., in acute megakaryoblastic leukemia (AMKL cell lines)). In the present study, the miRNA gene expression in human megakaryocyte cultures from bone marrow $CD34^+$ progenitors and acute megakaryoblastic leukemia cell lines was investigated. The results of this analysis indicate that several miRNAs are downregulated during normal megakaryocytic differentiation. The results further demonstrate that these miRNAs target genes involved in megakaryocytopoiesis, while others are over expressed in cancer cells.

Accordingly, the invention encompasses methods of diagnosing or prognosticating cancer and/or a myeloproliferative disorder in a subject (e.g., a human). According to the methods of the invention, the level of at least one miR gene product in a test sample from the subject is compared to the level of a corresponding miR gene product in a control sample. An alteration (e.g., an increase, a decrease) in the level of the miR gene product in the test sample, relative to the level of a corresponding miR gene product in the control sample, is indicative of the subject either having, or being at risk for developing, cancer and/or a myeloproliferative disorder. In one embodiment, the level of the miR gene product in the test sample from the subject is greater than that of the control. In another embodiment, the at least one miR gene product is selected from the group consisting of miR-101, miR-126, miR-99a, miR-99-prec, miR-106, miR-339, miR-99b, miR-149, miR-33, miR-135 and miR-20. In still another embodiment, the at least one miR gene product is selected from the group consisting of miR-101, miR-126, miR-106, miR-20 and miR-135. In yet another embodiment, the at least one miR gene product is selected from the group consisting of miR-106, miR-20 and miR-135. In particular embodiments, the cancer that is diagnosed or prognosticated is a leukemia (e.g., acute myeloid leukemia (e.g., acute megakaryoblastic leukemia)) or multiple myeloma. In other embodiments, the myeloproliferative disorder is selected from the group consisting of essential thrombocytemia (ET), polycythemia vera (PV), myelodisplasia, myelofibrosis (e.g., agnogenic myeloid metaplasia (AMM) (also referred to as idiopathic myelofibrosis)) and chronic myelogenous leukemia (CML).

In another embodiment, the invention is a method of treating a cancer and/or a myeloproliferative disorder in a subject (e.g., a human). In the method, an effective amount of a compound for inhibiting expression of at least one miR gene product selected from the group consisting of miR-101, miR-126, miR-99a, miR-99-prec, miR-106, miR-339, miR-99b, miR-149, miR-33, miR-135 and miR-20 is administered to the subject. In one embodiment, the compound for inhibiting expression of at least one miR gene product inhibits expression of a miR gene product selected from the group consisting of miR-101, miR-126, miR-106, miR-20 and miR-135. In another embodiment, the compound for inhibiting expression of at least one miR gene product inhibits expression of a miR gene product selected from the group consisting of miR-106, miR-20 and miR-135. In particular embodiments, the cancer that is treated is a leukemia (e.g., acute myeloid leukemia (e.g., acute megakaryoblastic leukemia)) or multiple myeloma. In other embodiments, the myeloproliferative disorder is selected from the group consisting of essential thrombocytemia (ET), polycythemia vera (PV), myelodisplasia, myelofibrosis (e.g., agnogenic myeloid metaplasia (AMM)) and chronic myelogenous leukemia (CML).

In another embodiment, the invention is a method of treating a cancer and/or a myeloproliferative disorder associated with overexpression of a MAFB gene product in a subject (e.g., a human). In the method, an effective amount of at least one miR gene product or a variant or biologically-active fragment thereof, which binds to, and decreases expression of, the MAFB gene product, is administered to the subject. In one embodiment, the at least one miR gene product, variant or biologically-active fragment thereof comprises a nucleotide sequence that is complementary to a nucleotide sequence in the MAFB gene product. In another embodiment, the at least one miR gene product is miR-130a or a variant or biologically-active fragment thereof. Cancers and myeloproliferative disorders suitable for treatment using this method include, for example, those described herein.

In another embodiment, the invention is a method of treating a cancer and/or a myeloproliferative disorder associated with overexpression of a HOXA1 gene product in a subject (e.g., a human). In the method, an effective amount of at least one miR gene product or a variant or biologically-active fragment thereof, which binds to, and decreases expression of, the HOXA1 gene product, is administered to the subject. In one embodiment, the at least one miR gene product, variant or biologically-active fragment thereof comprises a nucleotide sequence that is complementary to a nucleotide sequence in the HOXA1 gene product. In another embodiment, the at least one miR gene product is miR-10a or a variant or biologically-active fragment thereof. Cancers and myeloproliferative disorders suitable for treatment using this method include, for example, those described herein.

In one embodiment, the invention is a method of determining and/or predicting megakaryocytic differentiation. In this method, the level of at least one miR gene product in a sample (e.g., a sample from a subject (e.g., a human)) comprising megakaryocyte progeny and/or megakaryocytes is determined. That level is compared to the level of the corresponding miR gene product in a control. An alteration in the level of the at least one miR gene product in the sample, relative to that of the control, is indicative of megakaryocytic differentiation. In one embodiment, the alteration is a decrease in the level of the at least one miR gene product in the sample. In another embodiment, the at least one miR gene product is selected from the group consisting of miR-10a, miR-126, miR-106, miR-010b, miR-130a, miR-130a-prec, miR-124a, miR-032-prec, miR-101, miR-30c, miR-213, miR-132-prec, miR-150, miR-020, miR-339, let-7a, let-7d, miR-181c, miR-181b and miR-017. In still another embodiment, the at least one miR gene product is selected from the group consisting of miR-10a, miR-10b, miR-30c, miR-106, miR-126, miR-130a, miR-132, and miR-143.

The invention further provides pharmaceutical compositions for treating cancer and/or a myeloproliferative disorder. In one embodiment, the pharmaceutical compositions of the invention comprise at least one miR expression-inhibition compound and a pharmaceutically-acceptable carrier. In a particular embodiment, the at least one miR expression-inhibition compound is specific for a miR gene product whose expression is greater in cancer cells (e.g., acute megakaryoblastic leukemia (AMKL) cells) than control cells (i.e., it is upregulated). In one embodiment, the miR expression-inhibition compound is specific for one or more miR gene products selected from the group consisting of miR-101, miR-126, miR-99a, miR-99-prec, miR-106, miR-339, miR-99b, miR-149, miR-33, miR-135 and miR-20. In another embodiment, the miR expression-inhibition compound is specific for one or more miR gene products selected from the group consisting of miR-101, miR-126, miR-106, miR-20, and miR-135. In still another embodiment, the miR expression-inhibition compound is specific for one or more miR gene products selected from the group consisting of miR-106, miR-20 and miR-135. In yet another embodiment, the pharmaceutical composition further comprises at least one anti-cancer agent.

In one embodiment, the invention is a pharmaceutical composition for treating a cancer associated with overexpression of a MAFB gene product and/or a myeloproliferative disorder associated with overexpression of a MAFB gene product. Such pharmaceutical compositions comprise an effective amount of at least one miR gene product and a pharmaceutically-acceptable carrier, wherein the at least one miR gene product binds to, and decreases expression of, the MAFB gene product. In another embodiment, the at least one miR gene product comprises a nucleotide sequence that is complementary to a nucleotide sequence in the MAFB gene product. In still another embodiment, the at least one miR gene product is miR-130a or a variant or biologically-active fragment thereof. In yet another embodiment, the pharmaceutical composition further comprises at least one anti-cancer agent.

In one embodiment, the invention is a pharmaceutical composition for treating a cancer associated with overexpression of a HOXA1 gene product and/or a myeloproliferative disorder associated with overexpression of a HOXA1 gene product. Such pharmaceutical compositions comprise an effective amount of at least one miR gene product and a pharmaceutically-acceptable carrier, wherein the at least one miR gene product binds to, and decreases expression of, the HOXA1 gene product. In another embodiment, the at least one miR gene product comprises a nucleotide sequence that is complementary to a nucleotide sequence in the HOXA1 gene product. In still another embodiment, the at least one miR gene product is miR-10a or a variant or biologically-active fragment thereof. In yet another embodiment, the pharmaceutical composition further comprises at least one anti-cancer agent.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts Northern Blots for miR-130a, miR-10a and miR-223. A loading RNA control was performed with U6.

FIG. 1B is a graph depicting RT-miRNA-PCR for miR-10a, miR-106, miR-126 and miR-130a. miRNA expression is presented as fold difference with respect to $CD34^+$ cells before culture.

FIG. 1C is a graph depicting temporal expression of miR-223 by microarray.

FIG. 1D is a graph depicting temporal expression of miR-15-1 and miR-16-1 by RT-miRNA PCR.

FIGS. 2A-2C demonstrate that MAFB is a target of miR-130a.

FIG. 2A depicts MAFB mRNA and protein expression data in $CD34^+$ progenitors induced to megakaryocytic differentiation. β-Actin was used for RT-PCR and Western blot loading controls.

FIG. 2B is a graph depicting relative repression of luciferase activity in MEGO1 cells co-transfected with miR-10a and PGL3 3'UTR MAFB, miR-10a with PGL3 3'UTR, miR-10a seed match mutated and scramble with mutated, and wild type 3'UTR MAFB.

FIG. 2C depicts Western blots of MAFB total protein lysates in K562 cells transfected with miR-130a and scramble.

FIG. 3A is a graph depicting RT-PCR results for HOXA1 gene expression in differentiated megakaryocytes (Relative amount of transcript with respect to $CD34^+$ progenitors at baseline).

FIG. 3B is a Western blot showing hoxal protein expression in differentiated megakaryocytes.

FIG. 3C is a graph depicting relative repression of luciferase activity of HOXA1 3' UTR cloned PGL3 reporter plasmid when co-transfected with miR-10a and control scramble.

FIG. 3D is a schematic showing complementarity between miR-10a (SEQ ID NO: 322) and the HOXA1 3'UTR (SEQ ID NO: 507) as predicted by PICTAR.

FIG. 3E depicts RT-PCR results for miR-10a gene expression in scramble and miR-10a precursor transfected K562 cells.

FIG. 3F depicts RT-PCR results for HOXA1 gene expression in scramble and miR-10a precursor transfected K562 cells.

FIG. 3G is a Western blot showing HOXA1 expression in K562 cells transfected with control scramble and precursor miR-10a.

FIG. 4A depicts May-Giemsa stains that were performed on cytospin preparations from $CD34^+$ progenitors in culture at different days of culture (day 6, day 10, day 12 and day 14). At day 4, most of the cells were immature, as evidenced by the high nucleous:cytoplasmic ratio. Larger and multinuclear cells were observed by day 10. At day 14, predominantly larger, polyploid cells with long cytoplasmic processes and numerous membrane blebs with invaginations and vacuoles (original magnification 400×) were observed.

FIG. 4B depicts FACS analysis of CD34 in vitro-differentiated megakaryocytes. The membrane phenotype of $CD34^+$ progenitor cells that are grown in culture is shown. Cells were harvested at days 10 (D+10), 14 (D+14) and 16 (D+16) and were analyzed by single fluorescent labeling using an anti-CD41 antibody, an anti-CD61a antibody, an anti-CD42a antibody and their respective isotype monoclonal antibodies (D+10 isotype; D+14 isotype; D+16 isotype). Double labeling was performed with anti-CD41a and CD61b monoclonal Abs at day 14 only.

DETAILED DESCRIPTION OF THE PREFERRED EMBODIMENT

Figure 1A:
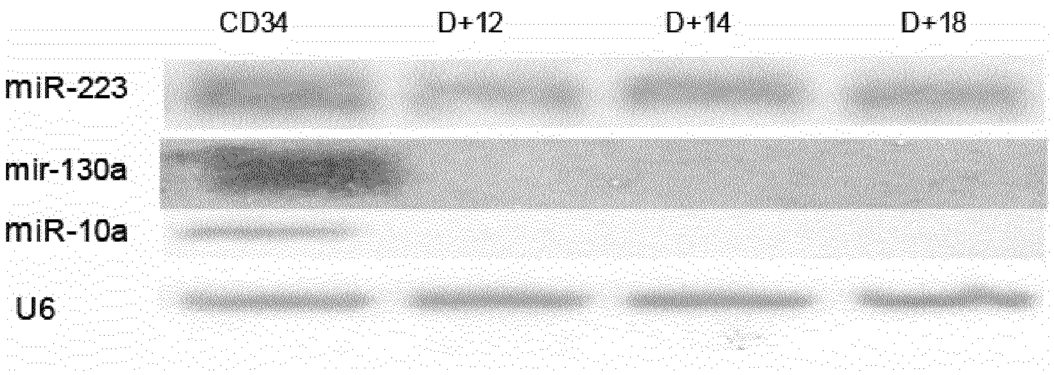
FIGS. 1A-1D depict Northern Blots and Real Time miRNA-PCR results, which validate microRNA chip data in CD34 progenitor differentiation experiments.
Figure 1B:
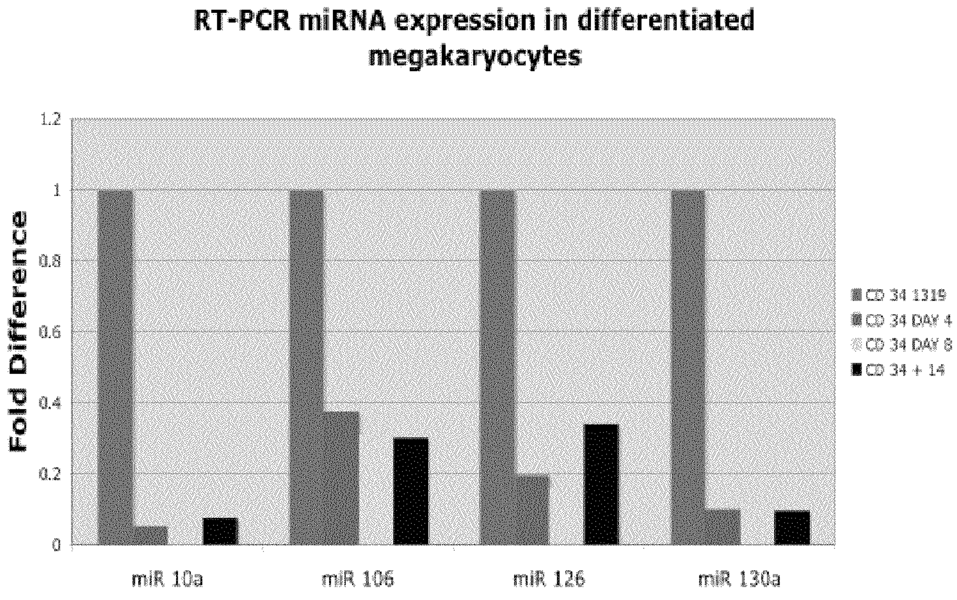

The present invention is based, in part, on the identification of specific microRNAs (miRNAs) that are involved in megakaryocytic differentiation and/or have altered expression levels in cancerous cells (e.g., in acute megakaryoblastic leukemia (AMKL cell lines)). The invention is further based, in part, on association of these miRNAs with particular diagnostic, prognostic and therapeutic features. As described and exemplified herein:

i) particular miRNA are downregulated during megakaryocytic differentiation;

ii) the transcription factor MAFB is a target for miR-130a;

iii) miR-10a expression parallels that of HOXB gene expression;

iv) miR-10a downregulates HOXA1 expression; and v) particular miRNA are upregulated in cancerous cells (e.g., acute megakaryoblastic leukemia (AMKL) cells).

As used herein interchangeably, a "miR gene product," "microRNA," "miR," "miR" or "miRNA" refers to the unprocessed or processed RNA transcript from a miR gene. As the miR gene products are not translated into protein, the term "miR gene products" does not include proteins. The unprocessed miR gene transcript is also called a "miR precursor," and typically comprises an RNA transcript of about 70-100 nucleotides in length. The miR precursor can be processed by digestion with an RNAse (for example, Dicer, Argonaut, RNAse III (e.g., *E. coli* RNAse III)) into an active 19-25 nucleotide RNA molecule. This active 19-25 nucleotide RNA molecule is also called the "processed" miR gene transcript or "mature" miRNA.

The active 19-25 nucleotide RNA molecule can be obtained from the miR precursor through natural processing routes (e.g., using intact cells or cell lysates) or by synthetic processing routes (e.g., using isolated processing enzymes, such as isolated Dicer, Argonaut, or RNAse III). It is understood that the active 19-25 nucleotide RNA molecule can also be produced directly by biological or chemical synthesis, without having to be processed from the miR precursor. When a microRNA is referred to herein by name, the name corresponds to both the precursor and mature forms, unless otherwise indicated.

Tables 1a and 1b depict the nucleotide sequences of particular precursor and mature human microRNAs.

TABLE 1a

Human microRNA Precursor Sequences.

| Precursor Name | Sequence (5' To 3')* | SEQ ID NO. |
|---|---|---|
| let-7a-1 | CACUGUGGGAUGAGGUAGUAGGUUGUAUAGUUUUAGGG UCACACCCACCACUGGGAGAUAACUAUACAAUCUACUGU CUUUCCUAACGUG | 1 |
| let-7a-2 | AGGUUGAGGUAGUAGGUUGUAUAGUUUAGAAUUACAUC AAGGGAGAUAACUGUACAGCCUCCUAGCUUUCCU | 2 |
| let-7a-3 | GGGUGAGGUAGUAGGUUGUAUAGUUUGGGGCUCUGCCC UGCUAUGGGAUAACUAUACAAUCUACUGUCUUUCCU | 3 |
| let-7a-4 | GUGACUGCAUGCUCCCAGGUUGAGGUAGUAGGUUGUAU AGUUUAGAAUUACACAAGGGAGAUAACUGUACAGCCUC CUAGCUUUCCUUGGGUCUUGCACUAAACAAC | 4 |
| let-7b | GGCGGGGUGAGGUAGUAGGUUGUGUGGUUUCAGGGCAG UGAUGUUGCCCCUCGGAAGAUAACUAUACAACCUACUGC CUUCCCUG | 5 |
| let-7c | GCAUCCGGGUUGAGGUAGUAGGUUGUAUGGUUUAGAGU UACACCCUGGGAGUUAACUGUACAACCUUCUAGCUUUCC UUGGAGC | 6 |
| let-7d | CCUAGGAAGAGGUAGUAGGUUGCAUAGUUUUAGGGCAG GGAUUUUGCCCACAAGGAGGUAACUAUACGACCUGCUGC CUUUCUUAGG | 7 |
| let-7d-v1 | CUAGGAAGAGGUAGUAGUUUGCAUAGUUUUAGGGCAAA GAUUUUGCCCACAAGUAGUUAGCUAUACGACCUGCAGCC UUUUGUAG | 8 |

TABLE 1a -continued

Human microRNA Precursor Sequences.

| Precursor Name | Sequence (5' To 3')* | SEQ ID NO. |
|---|---|---|
| let-7d-v2 | CUGGCUGAGGUAGUAGUUUGUGCUGUUGGUCGGGUUGUGACAUUGCCCGCUGUGGAGAUAACUGCGCAAGCUACUGCCUUGCUAG | 9 |
| let-7e | CCCGGGCUGAGGUAGGAGGUUGUAUAGUUGAGGAGGACACCCAAGGAGAUCACUAUACGGCCUCCUAGCUUUCCCCAGG | 10 |
| let-7f-1 | UCAGAGUGAGGUAGUAGAUUGUAUAGUUGUGGGGUAGUGAUUUUACCCUGUUCAGGAGAUAACUAUACAAUCUAUUGCCUUCCCUGA | 11 |
| let-7f-2-1 | CUGUGGGAUGAGGUAGUAGAUUGUAUAGUUGUGGGGUAGUGAUUUUACCCUGUUCAGGAGAUAACUAUACAAUCUAUUGCCUUCCCUGA | 12 |
| let-7f-2-2 | CUGUGGGAUGAGGUAGUAGAUUGUAUAGUUUUAGGGUCAUACCCCAUCUUGGAGAUAACUAUACAGUCUACUGUCUUUCCCACGG | 13 |
| let-7g | UUGCCUGAUUCCAGGCUGAGGUAGUAGUUUGUACAGUUUGAGGGUCUAUGAUACCACCCGGUACAGGAGAUAACUGUACAGGCCACUGCCUUGCCAGGAACAGCGCGC | 14 |
| let-7i | CUGGCUGAGGUAGUAGUUUGUGCUGUUGGUCGGGUUGUGACAUUGCCCGCUGUGGAGAUAACUGCGCAAGCUACUGCCUUGCUAG | 15 |
| miR-1b-1-1 | ACCUACUCAGAGUACAUACUUCUUUAUGUACCCAUAUGAACAUACAAUGCUAUGGAAUGUAAAGAAGUAUGUAUUUUUGGUAGGC | 16 |
| miR-1b-1-2 | CAGCUAACAACUUAGUAAUACCUACUCAGAGUACAUACUUCUUUAUGUACCCAUAUGAACAUACAAUGCUAUGGAAUGUAAAGAAGUAUGUAUUUUUGGUAGGCAAUA | 17 |
| miR-1b-2 | GCCUGCUUGGGAAACAUACUUCUUUAUAUGCCCAUAUGGACCUGCUAAGCUAUGGAAUGUAAAGAAGUAUGUAUCUCAGGCCGGG | 18 |
| miR-1b | UGGGAAACAUACUUCUUUAUAUGCCCAUAUGGACCUGCUAAGCUAUGGAAUGUAAAGAAGUAUGUAUCUCA | 19 |
| miR-1d | ACCUACUCAGAGUACAUACUUCUUUAUGUACCCAUAUGAACAUACAAUGCUAUGGAAUGUAAAGAAGUAUGUAUUUUUGGUAGGC | 20 |
| miR-7-1a | UGGAUGUUGGCCUAGUUCUGUGUGGAAGACUAGUGAUUUUGUUGUUUUUAGAUAACUAAAUCGACAACAAAUCACAGUCUGCCAUAUGGCACAGGCCAUGCCUCUACA | 21 |
| miR-7-1b | UUGGAUGUUGGCCUAGUUCUGUGUGGAAGACUAGUGAUUUUGUUGUUUUUAGAUAACUAAAUCGACAACAAAUCACAGUCUGCCAUAUGGCACAGGCCAUGCCUCUACAG | 22 |
| miR-7-2 | CUGGAUACAGAGUGGACCGGCUGGCCCCAUCUGGAAGACUAGUGAUUUUGUUGUUGUCUUACUGCGCUCAACAACAAAUCCCAGUCUACCUAAUGGUGCCAGCCAUCGCA | 23 |
| miR-7-3 | AGAUUAGAGUGGCUGUGGUCUAGUGCUGUGUGGAAGACUAGUGAUUUUGUUGUUCUGAUGUACUACGACAACAAGUCACAGCCGGCCUCAUAGCGCAGACUCCCUUCGAC | 24 |
| miR-9-1 | CGGGGUUGGUUGUUAUCUUUGGUUAUCUAGCUGUAUGAGUGGUGUGGAGUCUUCAUAAAGCUAGAUAACCGAAAGUAAAAAUAACCCCA | 25 |
| miR-9-2 | GGAAGCGAGUUGUUAUCUUUGGUUAUCUAGCUGUAUGAGUGUAUUGGUCUUCAUAAAGCUAGAUAACCGAAAGUAAAAACUCCUUCA | 26 |
| miR-9-3 | GGAGGCCCGUUUCUCUCUUUGGUUAUCUAGCUGUAUGAGUGCCACAGAGCCGUCAUAAAGCUAGAUAACCGAAAGUAGAAAUGAUUCUCA | 27 |

TABLE 1a -continued

Human microRNA Precursor Sequences.

| Precursor Name | Sequence (5' To 3')* | SEQ ID NO. |
|---|---|---|
| miR-10a | GAUCUGUCUGUCUUCUGUAUAUACCCUGUAGAUCCGAA<br>UUUGUGUAAGGAAUUUUGUGGUCACAAAUUCGUAUCUA<br>GGGGAAUAUGUAGUUGACAUAAACACUCCGCUCU | 28 |
| miR-10b | CCAGAGGUUGUAACGUUGUCUAUAUAUACCCUGUAGAA<br>CCGAAUUUGUGUGGUAUCCGUAUAGUCACAGAUUCGAU<br>UCUAGGGGAAUAUAUGGUCGAUGCAAAAACUUCA | 29 |
| miR-15a-2 | GCGCGAAUGUGUGUUUAAAAAAAAUAAAACCUUGGAGU<br>AAAGUAGCAGCACAUAAUGGUUUGUGGAUUUUGAAAAG<br>GUGCAGGCCAUAUUGUGCUGCCUCAAAAAUAC | 30 |
| miR-15a | CCUUGGAGUAAAGUAGCAGCACAUAAUGGUUUGUGGAU<br>UUUGAAAAGGUGCAGGCCAUAUUGUGCUGCCUCAAAAA<br>UACAAGG | 31 |
| miR-15b-1 | CUGUAGCAGCACAUCAUGGUUUACAUGCUACAGUCAAG<br>AUGCGAAUCAUUAUUUGCUGCUCUAG | 32 |
| miR-15b-2 | UUGAGGCCUUAAAGUACUGUAGCAGCACAUCAUGGUUU<br>ACAUGCUACAGUCAAGAUGCGAAUCAUUAUUUGCUGCU<br>CUAGAAAUUUAAGGAAAUUCAU | 33 |
| miR-16-1 | GUCAGCAGUGCCUUAGCAGCACGUAAAUAUUGGCGUUA<br>AGAUUCUAAAAUUAUCUCCAGUAUUAACUGUGCUGCUG<br>AAGUAAGGUUGAC | 34 |
| miR-16-2 | GUUCCACUCUAGCAGCACGUAAAUAUUGGCGUAGUGAA<br>AUAUAUAUUAAACACCAAUAUUACUGUGCUGCUUUAGU<br>GUGAC | 35 |
| miR-16-13 | GCAGUGCCUUAGCAGCACGUAAAUAUUGGCGUUAAGAU<br>UCUAAAAUUAUCUCCAGUAUUAACUGUGCUGCUGAAGU<br>AAGGU | 36 |
| miR-17 | GUCAGAAUAAUGUCAAAGUGCUUACAGUGCAGGUAGUG<br>AUAUGUGCAUCUACUGCAGUGAAGGCACUUGUAGCAUU<br>AUGGUGAC | 37 |
| miR-18 | UGUUCUAAGGUGCAUCUAGUGCAGAUAGUGAAGUAGAU<br>UAGCAUCUACUGCCCUAAGUGCUCCUUCUGGCA | 38 |
| miR-18-13 | UUUUUGUUCUAAGGUGCAUCUAGUGCAGAUAGUGAAGU<br>AGAUUAGCAUCUACUGCCCUAAGUGCUCCUUCUGGCAUA<br>AGAA | 39 |
| miR-19a | GCAGUCCUCUGUUAGUUUUGCAUAGUUGCACUACAAGA<br>AGAAUGUAGUUGUGCAAAUCUAUGCAAAACUGAUGGUG<br>GCCUGC | 40 |
| miR-19a-13 | CAGUCCUCUGUUAGUUUUGCAUAGUUGCACUACAAGAA<br>GAAUGUAGUUGUGCAAAUCUAUGCAAAACUGAUGGUGG<br>CCUG | 41 |
| miR-19b-1 | CACUGUUCUAUGGUUAGUUUUGCAGGUUUGCAUCCAGC<br>UGUGUGAUAUUCUGCUGUGCAAAUCCAUGCAAAACUGA<br>CUGUGGUAGUG | 42 |
| miR-19b-2 | ACAUUGCUACUUACAAUUAGUUUUGCAGGUUUGCAUUU<br>CAGCGUAUAUAUGUAUAUGUGGCUGUGCAAAUCCAUGC<br>AAAACUGAUUGUGAUAAUGU | 43 |
| miR-19b-13 | UUCUAUGGUUAGUUUUGCAGGUUUGCAUCCAGCUGUGU<br>GAUAUUCUGCUGUGCAAAUCCAUGCAAAACUGACUGUG<br>GUAG | 44 |
| miR-19b-X | UUACAAUUAGUUUUGCAGGUUUGCAUUUCAGCGUAUAU<br>AUGUAUAUGUGGCUGUGCAAAUCCAUGCAAAACUGAUU<br>GUGAU | 45 |
| miR-20 (miR-20a) | GUAGCACUAAAGUGCUUAUAGUGCAGGUAGUGUUUAGU<br>UAUCUACUGCAUUAUGAGCACUUAAAGUACUGC | 46 |
| miR-21 | UGUCGGGUAGCUUAUCAGACUGAUGUUGACUGUUGAAU<br>CUCAUGGCAACACCAGUCGAUGGGCUGUCUGACA | 47 |

TABLE 1a -continued

Human microRNA Precursor Sequences.

| Precursor Name | Sequence (5' To 3')* | SEQ ID NO. |
|---|---|---|
| miR-21-17 | ACCUUGUCGGGUAGCUUAUCAGACUGAUGUUGACUGUUGAAUCUCAUGGCAACACCAGUCGAUGGGCUGUCUGACAUUUUG | 48 |
| miR-22 | GGCUGAGCCGCAGUAGUUCUUCAGUGGCAAGCUUUAUGUCCUGACCCAGCUAAAGCUGCCAGUUGAAGAACUGUUGCCCUCUGCC | 49 |
| miR-23a | GGCCGGCUGGGGUUCCUGGGGAUGGGAUUUGCUUCCUGUCACAAAUCACAUUGCCAGGGAUUUCCAACCGACC | 50 |
| miR-23b | CUCAGGUGCUCUGGCUGCUUGGGUUCCUGGCAUGCUGAUUUGUGACUUAAGAUUAAAAUCACAUUGCCAGGGAUUACCACGCAACCACGACCUUGGC | 51 |
| miR-23-19 | CCACGGCCGGCUGGGGUUCCUGGGGAUGGGAUUUGCUUCCUGUCACAAAUCACAUUGCCAGGGAUUUCCAACCGACCCUGA | 52 |
| miR-24-1 | CUCCGGUGCCUACUGAGCUGAUAUCAGUUCUCAUUUUACACACUGGCUCAGUUCAGCAGGAACAGGAG | 53 |
| miR-24-2 | CUCUGCCUCCCGUGCCUACUGAGCUGAAACACAGUUGGUUUGUGUACACUGGCUCAGUUCAGCAGGAACAGGG | 54 |
| miR-24-19 | CCCUGGGCUCUGCCUCCCGUGCCUACUGAGCUGAAACACAGUUGGUUUGUGUACACUGGCUCAGUUCAGCAGGAACAGGGG | 55 |
| miR-24-9 | CCCUCCGGUGCCUACUGAGCUGAUAUCAGUUCUCAUUUUACACACUGGCUCAGUUCAGCAGGAACAGCAUC | 56 |
| miR-25 | GGCCAGUGUUGAGAGGCGGAGACUUGGGCAAUUGCUGGACGCUGCCCUGGGCAUUGCACUUGUCUCGGUCUGACAGUGCCGGCC | 57 |
| miR-26a | AGGCCGUGGCCUCGUUCAAGUAAUCCAGGAUAGGCUGUGCAGGUCCCAAUGGCCUAUCUUGGUUACUUGCACGGGGACGCGGGCCU | 58 |
| miR-26a-1 | GUGGCCUCGUUCAAGUAAUCCAGGAUAGGCUGUGCAGGUCCCAAUGGGCCUAUUCUUGGUUACUUGCACGGGGACGC | 59 |
| miR-26a-2 | GGCUGUGGCUGGAUUCAAGUAAUCCAGGAUAGGCUGUUUCCAUCUGUGAGGCCUAUUCUUGAUUACUUGUUUCUGGAGGCAGCU | 60 |
| miR-26b | CCGGGACCCAGUUCAAGUAAUUCAGGAUAGGUUGUGUGCUGUCCAGCCUGUUCUCCAUUACUUGGCUCGGGGACCGG | 61 |
| miR-27a | CUGAGGAGCAGGGCUUAGCUGCUUGUGAGCAGGGUCCACACCAAGUCGUGUUCACAGUGGCUAAGUUCCGCCCCCCAG | 62 |
| miR-27b-1 | AGGUGCAGAGCUUAGCUGAUUGGUGAACAGUGAUUGGUUUCCGCUUUGUUCACAGUGGCUAAGUUCUGCACCU | 63 |
| miR-27b-2 | ACCUCUCUAACAAGGUGCAGAGCUUAGCUGAUUGGUGAACAGUGAUUGGUUUCCGCUUUGUUCACAGUGGCUAAGUUCUGCACCUGAAGAGAAGGUG | 64 |
| miR-27-19 | CCUGAGGAGCAGGGCUUAGCUGCUUGUGAGCAGGGUCCACACCAAGUCGUGUUCACAGUGGCUAAGUUCCGCCCCCCAGG | 65 |
| miR-28 | GGUCCUUGCCCUCAAGGAGCUCACAGUCUAUUGAGUUACCUUUCUGACUUUCCCACUAGAUUGUGAGCUCCUGGAGGGCAGGCACU | 66 |
| miR-29a-2 | CCUUCUGUGACCCCUUAGAGGAUGACUGAUUUCUUUUGGUGUUCAGAGUCAAUAUAAUUUUCUAGCACCAUCUGAAAUCGGUUAUAAUGAUUGGGGAAGAGCACCAUG | 67 |
| miR-29a | AUGACUGAUUUCUUUUGGUGUUCAGAGUCAAUAUAAUUUUCUAGCACCAUCUGAAAUCGGUUAU | 68 |

TABLE 1a -continued

Human microRNA Precursor Sequences.

| Precursor Name | Sequence (5' To 3')* | SEQ ID NO. |
|---|---|---|
| miR-29b-1 | CUUCAGGAAGCUGGUUUCAUAUGGUGGUUUAGAUUUAAAUAGUGAUUGUCUAGCACCAUUUGAAAUCAGUGUUCUUGGGGG | 69 |
| miR-29b-2 | CUUCUGGAAGCUGGUUUCACAUGGUGGCUUAGAUUUUUCCAUCUUUGUAUCUAGCACCAUUUGAAAUCAGUGUUUUAGGAG | 70 |
| miR-29c | ACCACUGGCCCAUCUCUUACACAGGCUGACCGAUUUCUCCUGGUGUUCAGAGUCUGUUUUUGUCUAGCACCAUUUGAAAUCGGUUAUGAUGUAGGGGGAAAAGCAGCAGC | 71 |
| miR-30a | GCGACUGUAAACAUCCUCGACUGGAAGCUGUGAAGCCACAGAUGGGCUUUCAGUCGGAUGUUUGCAGCUGC | 72 |
| miR-30b-1 | AUGUAAACAUCCUACACUCAGCUGUAAUACAUGGAUUGGCUGGGAGGUGGAUGUUUACGU | 73 |
| miR-30b-2 | ACCAAGUUUCAGUUCAUGUAAACAUCCUACACUCAGCUGUAAUACAUGGAUUGGCUGGGAGGUGGAUGUUUACUUCAGCUGACUUGGA | 74 |
| miR-30c | AGAUACUGUAAACAUCCUACACUCUCAGCUGUGGAAAGUAAGAAAGCUGGGAGAAGGCUGUUUACUCUUUCU | 75 |
| miR-30d | GUUGUUGUAAACAUCCCCGACUGGAAGCUGUAAGACACAGCUAAGCUUUCAGUCAGAUGUUUGCUGCUAC | 76 |
| miR-30e | CUGUAAACAUCCUUGACUGGAAGCUGUAAGGUGUUCAGAGGAGCUUUCAGUCGGAUGUUUACAG | 77 |
| miR-31 | GGAGAGGAGGCAAGAUGCUGGCAUAGCUGUUGAACUGGGAACCUGCUAUGCCAACAUAUUGCCAUCUUUCC | 78 |
| miR-32 | GGAGAUAUUGCACAUUACUAAGUUGCAUGUUGUCACGGCCUCAAUGCAAUUUAGUGUGUGUGAUAUUUUC | 79 |
| miR-33b | GGGGGCCGAGAGAGGCGGGCGGCCCCGCGGUGCAUUGCUGUUGCAUUGCACGUGUGUGAGGCGGGUGCAGUGCCUCGGCAGUGCAGCCCGGAGCCGGCCCCUGGCACCAC | 80 |
| miR-33b-2 | ACCAAGUUUCAGUUCAUGUAAACAUCCUACACUCAGCUGUAAUACAUGGAUUGGCUGGGAGGUGGAUGUUUACUUCAGCUGACUUGGA | 81 |
| miR-33 | CUGUGGUGCAUUGUAGUUGCAUUGCAUGUUCUGGUGGUACCCAUGCAAUGUUUCCACAGUGCAUCACAG | 82 |
| miR-34-a | GGCCAGCUGUGAGUGUUUCUUUGGCAGUGUCUUAGCUGGUUGUUGUGAGCAAUAGUAAGGAAGCAAUCAGCAAGUAUACUGCCCUAGAAGUGCUGCACGUUGUGGGGCCC | 83 |
| miR-34-b | GUGCUCGGUUUGUAGGCAGUGUCAUUAGCUGAUUGUACUGUGGUGGUUACAAUCACUAACUCCACUGCCAUCAAAACAAGGCAC | 84 |
| miR-34-c | AGUCUAGUUACUAGGCAGUGUAGUUAGCUGAUUGCUAAUAGUACCAAUCACUAACCACACGGCCAGGUAAAAAGAUU | 85 |
| miR-91-13 | UCAGAAUAAUGUCAAAGUGCUUACAGUGCAGGUAGUGAUAUGUGCAUCUACUGCAGUGAAGGCACUUGUAGCAUUAUGGUGA | 86 |
| miR-92-1 | CUUUCUACACAGGUUGGGAUCGGUUGCAAUGCUGUGUUUCUGUAUGGUAUUGCACUUGUCCCGGCCUGUUGAGUUUGG | 87 |
| miR-92-2 | UCAUCCCUGGGUGGGGAUUUGUUGCAUUACUUGUGUUCUAUAUAAAGUAUUGCACUUGUCCCGGCCUGUGGAAGA | 88 |
| miR-93-1 (miR-93-2) | CUGGGGGCUCCAAAGUGCUGUUCGUGCAGGUAGUGUGAUUACCCAACCUACUGCUGAGCUAGCACUUCCCGAGCCCCCGG | 89 |

TABLE 1a -continued

Human microRNA Precursor Sequences.

| Precursor Name | Sequence (5' To 3')* | SEQ ID NO. |
|---|---|---|
| miR-95-4 | AACACAGUGGGCACUCAAUAAAUGUCUGUUGAAUUGAAAUGCGUUACAUUCAACGGGUAUUUAUUGAGCACCCACUCUGUG | 90 |
| miR-96-7 | UGGCCGAUUUUGGCACUAGCACAUUUUUGCUUGUGUCUCUCCGCUCUGAGCAAUCAUGUGCAGUGCCAAUAUGGGAAA | 91 |
| miR-97-6 (miR-30*) | GUGAGCGACUGUAAACAUCCUCGACUGGAAGCUGUGAAGCCACAGAUGGGCUUUCAGUCGGAUGUUUGCAGCUGCCUACU | 92 |
| miR-98 | GUGAGGUAGUAAGUUGUAUUGUUGUGGGGUAGGGAUAUUAGGCCCCAAUUAGAAGAUAACUAUACAACUUACUACUUUCC | 93 |
| miR-99b | GGCACCCACCCGUAGAACCGACCUUGCGGGGCCUUCGCCGCACACAAGCUCGUGUCUGUGGGUCCGUGUC | 94 |
| miR-99a | CCCAUUGGCAUAAACCCGUAGAUCCGAUCUUGUGGUGAAGUGGACCGCACAAGCUCGCUUCUAUGGGUCUGUGUCAGUGUG | 95 |
| miR-100-1/2 | AAGAGAGAAGAUAUUGAGGCCUGUUGCCACAAACCCGUAGAUCCGAACUUGUGGUAUUAGUCCGCACAAGCUUGUAUCUAUAGGUAUGUGUCUGUUAGGCAAUCUCAC | 96 |
| miR-100-11 | CCUGUUGCCACAAACCCGUAGAUCCGAACUUGUGGUAUUAGUCCGCACAAGCUUGUAUCUAUAGGUAUGUGUCUGUUAGG | 97 |
| miR-101-1/2 | AGGCUGCCCUGGCUCAGUUAUCACAGUGCUGAUGCUGUCUAUUCUAAAGGUACAGUACUGUGAUAACUGAAGGAUGGCAGCCAUCUUACCUUCCAUCAGAGGAGCCUCAC | 98 |
| miR-101 | UCAGUUAUCACAGUGCUGAUGCUGUCCAUUCUAAAGGUACAGUACUGUGAUAACUGA | 99 |
| miR-101-1 | UGCCCUGGCUCAGUUAUCACAGUGCUGAUGCUGUCUAUUCUAAAGGUACAGUACUGUGAUAACUGAAGGAUGGCA | 100 |
| miR-101-2 | ACUGUCCUUUUUCGGUUAUCAUGGUACCGAUGCUGUAUAUCUGAAAGGUACAGUACUGUGAUAACUGAAGAAUGGUGGU | 101 |
| miR-101-9 | UGUCCUUUUUCGGUUAUCAUGGUACCGAUGCUGUAUAUCUGAAAGGUACAGUACUGUGAUAACUGAAGAAUGGUG | 102 |
| miR-102-1 | CUUCUGGAAGCUGGUUUCACAUGGUGGCUUAGAUUUUUCCAUCUUUGUAUCUAGCACCAUUUGAAAUCAGUGUUUUAGGAG | 103 |
| miR-102-7.1 (miR-102-7.2) | CUUCAGGAAGCUGGUUUCAUAUGGUGGUUUAGAUUUAAAUAGUGAUUGUCUAGCACCAUUUGAAAUCAGUGUUCUUGGGGG | 104 |
| miR-103-2 | UUGUGCUUUCAGCUUCUUUACAGUGCUGCCUUGUAGCAUUCAGGUCAAGCAACAUUGUACAGGGCUAUGAAAGAACCA | 105 |
| miR-103-1 | UACUGCCCUCGGCUUCUUUACAGUGCUGCCUUGUUGCAUAUGGAUCAAGCAGCAUUGUACAGGGCUAUGAAGGCAUUG | 106 |
| miR-104-17 | AAAUGUCAGACAGCCCAUCGACUGGUGUUGCCAUGAGAUUCAACAGUCAACAUCAGUCUGAUAAGCUACCCGACAAGG | 107 |
| miR-105-1 | UGUGCAUCGUGGUCAAAUGCUCAGACUCCUGUGGUGGCUGCUCAUGCACCACGGAUGUUUGAGCAUGUGCUACGGUGUCUA | 108 |
| miR-105-2 | UGUGCAUCGUGGUCAAAUGCUCAGACUCCUGUGGUGGCUGCUUAUGCACCACGGAUGUUUGAGCAUGUGCUAUGGUGUCUA | 109 |

TABLE 1a -continued

Human microRNA Precursor Sequences.

| Precursor Name | Sequence (5' To 3')* | SEQ ID NO. |
|---|---|---|
| miR-106-a | CCUUGGCCAUGUAAAAGUGCUUACAGUGCAGGUAGCUU UUUGAGAUCUACUGCAAUGUAAGCACUUCUUACAUUAC CAUGG | 110 |
| miR-106-b | CCUGCCGGGGCUAAAGUGCUGACAGUGCAGAUAGUGGU CCUCUCCGUGCUACCGCACUGUGGGUACUUGCUGCUCCA GCAGG | 111 |
| miR-107 | CUCUCUGCUUUCAGCUUCUUUACAGUGUUGCCUUGUGGC AUGGAGUUCAAGCAGCAUUGUACAGGGCUAUCAAAGCA CAGA | 112 |
| MIR-108-1-SMALL | ACACUGCAAGAACAAUAAGGAUUUUUAGGGGCAUUAUG ACUGAGUCAGAAAACACAGCUGCCCCUGAAAGUCCCUCA UUUUUCUUGCUGU | 113 |
| MIR-108-2-SMALL | ACUGCAAGAGCAAUAAGGAUUUUUAGGGGCAUUAUGAU AGUGGAAUGGAAACACAUCUGCCCCCAAAAGUCCCUCAU UUU | 114 |
| miR-122a-1 | CCUUAGCAGAGCUGUGGAGUGUGACAAUGGUGUUUGUG UCUAAACUAUCAAACGCCAUUAUCACACUAAAUAGCUAC UGCUAGGC | 115 |
| miR-122a-2 | AGCUGUGGAGUGUGACAAUGGUGUUUGUGUCCAAACUA UCAAACGCCAUUAUCACACUAAAUAGCU | 116 |
| miR-123 | ACAUUAUUACUUUUGGUACGCGCUGUGACACUUCAAAC UCGUACCGUGAGUAAUAAUGCGC | 117 |
| miR-124a-1 | AGGCCUCUCUCUCCGUGUUCACAGCGGACCUUGAUUUAA AUGUCCAUACAAUUAAGGCACGCGGUGAAUGCCAAGAA UGGGGCUG | 118 |
| miR-124a-2 | AUCAAGAUUAGAGGCUCUGCUCUCCGUGUUCACAGCGGA CCUUGAUUUAAUGUCAUACAAUUAAGGCACGCGGUGAA UGCCAAGAGCGGAGCCUACGGCUGCACUUGAAG | 119 |
| miR-124a-3 | UGAGGGCCCCUCUGCGUGUUCACAGCGGACCUUGAUUUA AUGUCUAUACAAUUAAGGCACGCGGUGAAUGCCAAGAG AGGCGCCUCC | 120 |
| miR-124a | CUCUGCGUGUUCACAGCGGACCUUGAUUUAAUGUCUAU ACAAUUAAGGCACGCGGUGAAUGCCAAGAG | 121 |
| miR-124b | CUCUCCGUGUUCACAGCGGACCUUGAUUUAAUGUCAUAC AAUUAAGGCACGCGGUGAAUGCCAAGAG | 122 |
| miR-125a-1 | UGCCAGUCUCUAGGUCCCUGAGACCCUUUAACCUGUGAG GACAUCCAGGGUCACAGGUGAGGUUCUUGGGAGCCUGG CGUCUGGCC | 123 |
| miR-125a-2 | GGUCCCUGAGACCCUUUAACCUGUGAGGACAUCCAGGGU CACAGGUGAGGUUCUUGGGAGCCUGG | 124 |
| miR-125b-1 | UGCGCUCCUCUCAGUCCCUGAGACCCUAACUUGUGAUGU UUACCGUUUAAAUCCACGGGUUAGGCUCUUGGGAGCUG CGAGUCGUGCU | 125 |
| miR-125b-2 | ACCAGACUUUUCCUAGUCCCUGAGACCCUAACUUGUGAG GUAUUUUAGUAACAUCACAAGUCAGGCUCUUGGGACCU AGGCGGAGGGGA | 126 |
| miR-126-1 | CGCUGGCGACGGGACAUUAUUACUUUUGGUACGCGCUG UGACACUUCAAACUCGUACCGUGAGUAAUAAUGCGCCGU CCACGGCA | 127 |
| miR-126-2 | ACAUUAUUACUUUUGGUACGCGCUGUGACACUUCAAAC UCGUACCGUGAGUAAUAAUGCGC | 128 |
| miR-127-1 | UGUGAUCACUGUCUCCAGCCUGCUGAAGCUCAGAGGGCU CUGAUUCAGAAAGAUCAUCGGAUCCGUCUGAGCUUGGC UGGUCGGAAGUCUCAUCAUC | 129 |

TABLE 1a -continued

Human microRNA Precursor Sequences.

| Precursor Name | Sequence (5' To 3')* | SEQ ID NO. |
| --- | --- | --- |
| miR-127-2 | CCAGCCUGCUGAAGCUCAGAGGGCUCUGAUUCAGAAAGA UCAUCGGAUCCGUCUGAGCUUGGCUGGUCGG | 130 |
| miR-128a | UGAGCUGUUGGAUUCGGGGCCGUAGCACUGUCUGAGAG GUUUACAUUUCUCACAGUGAACCGGUCUCUUUUUCAGCU GCUUC | 131 |
| miR-128b | GCCCGGCAGCCACUGUGCAGUGGGAAGGGGGGCCGAUAC ACUGUACGAGAGUGAGUAGCAGGUCUCACAGUGAACCG GUCUCUUUCCCUACUGUGUCACACUCCUAAUGG | 132 |
| miR-128 | GUUGGAUUCGGGGCCGUAGCACUGUCUGAGAGGUUUAC AUUUCUCACAGUGAACCGGUCUCUUUUUCAGC | 133 |
| miR-129-1 | UGGAUCUUUUUGCGGUCUGGGCUUGCUGUUCCUCUCAAC AGUAGUCAGGAAGCCCUUACCCCAAAAAGUAUCUA | 134 |
| MIR-129-2 | UGCCCUUCGCGAAUCUUUUUGCGGUCUGGGCUUGCUGUA CAUAACUCAAUAGCCGGAAGCCCUUACCCCAAAAAGCAU UUGCGGAGGGCG | 135 |
| miR-130a | UGCUGCUGGCCAGAGCUCUUUUCACAUUGUGCUACUGUC UGCACCUGUCACUAGCAGUGCAAUGUUAAAAGGGCAUU GGCCGUGUAGUG | 136 |
| miR-131-1 | GCCAGGAGGCGGGGUUGGUUGUUAUCUUUGGUUAUCUA GCUGUAUGAGUGGUGUGGAGUCUUCAUAAAGCUAGAUA ACCGAAAGUAAAAAUAACCCCAUACACUGCGCAG | 137 |
| miR-131-3 | CACGGCGCGGCAGCGGCACUGGCUAAGGGAGGCCCGUUU CUCUCUUUGGUUAUCUAGCUGUAUGAGUGCCACAGAGCC GUCAUAAAGCUAGAUAACCGAAAGUAGAAAUG | 138 |
| miR-131 | GUUGUUAUCUUUGGUUAUCUAGCUGUAUGAGUGUAUUG GUCUUCAUAAAGCUAGAUAACCGAAAGUAAAAAC | 139 |
| miR-132-1 | CCGCCCCCGCGUCUCCAGGGCAACCGUGGCUUUCGAUUG UUACUGUGGGAACUGGAGGUAACAGUCUACAGCCAUGG UCGCCCCGCAGCACGCCCACGCGC | 140 |
| miR-132-2 | GGGCAACCGUGGCUUUCGAUUGUUACUGUGGGAACUGG AGGUAACAGUCUACAGCCAUGGUCGCCC | 141 |
| miR-133a-1 | ACAAUGCUUUGCUAGAGCUGGUAAAAUGGAACCAAAUC GCCUCUUCAAUGGAUUUGGUCCCCUUCAACCAGCUGUAG CUAUGCAUUGA | 142 |
| miR-133a-2 | GGGAGCCAAAUGCUUUGCUAGAGCUGGUAAAAUGGAAC CAAAUCGACUGUCCAAUGGAUUUGGUCCCCUUCAACCAG CUGUAGCUGUGCAUUGAUGGCGCCG | 143 |
| miR-133 | GCUAGAGCUGGUAAAAUGGAACCAAAUCGCCUCUUCAA UGGAUUUGGUCCCCUUCAACCAGCUGUAGC | 144 |
| miR-133b | CCUCAGAAGAAAGAUGCCCCCUGCUCUGGCUGGUCAAAC GGAACCAAGUCCGUCUUCCUGAGAGGUUUGGUCCCCUUC AACCAGCUACAGCAGGGCUGGCAAUGCCCAGUCCUUGGA GA | 145 |
| MIR-133B-SMALL | GCCCCCUGCUCUGGCUGGUCAAACGGAACCAAGUCCGUC UUCCUGAGAGGUUUGGUCCCCUUCAACCAGCUACAGCAG GG | 146 |
| miR-134-1 | CAGGGUGUGUGACUGGUUGACCAGAGGGGCAUGCACUG UGUUCACCCUGUGGGCCACCUAGUCACCAACCCUC | 147 |
| miR-134-2 | AGGGUGUGUGACUGGUUGACCAGAGGGGCAUGCACUGU GUUCACCCUGUGGGCCACCUAGUCACCAACCCU | 148 |
| miR-135a-1 | AGGCCUCGCUGUUCUCUAUGGCUUUUUAUUCCUAUGUG AUUCUACUGCUCACUCAUAUAGGGAUUGGAGCCGUGGC GCACGGCGGGGACA | 149 |

TABLE 1a -continued

Human microRNA Precursor Sequences.

| Precursor Name | Sequence (5' To 3')* | SEQ ID NO. |
|---|---|---|
| miR-135a-2 (miR-135-2) | AGAUAAAUUCACUCUAGUGCUUUAUGGCUUUUUAUUCCUAUGUGAUAGUAAUAAAGUCUCAUGUAGGGAUGGAAGCCAUGAAAUACAUUGUGAAAAAUCA | 150 |
| miR-135 | CUAUGGCUUUUUAUUCCUAUGUGAUUCUACUGCUCACUCAUAUAGGGAUUGGAGCCGUGG | 151 |
| miR-135b | CACUCUGCUGUGGCCUAUGGCUUUUCAUUCCUAUGUGAUUGCUGUCCCAAACUCAUGUAGGGCUAAAAGCCAUGGGCUACAGUGAGGGGCGAGCUCC | 152 |
| miR-136-1 | UGAGCCCUCGGAGGACUCCAUUUGUUUUGAUGAUGGAUUCUUAUGCUCCAUCAUCGUCUCAAAUGAGUCUUCAGAGGGUUCU | 153 |
| miR-136-2 | GAGGACUCCAUUUGUUUUGAUGAUGGAUUCUUAUGCUCCAUCAUCGUCUCAAAUGAGUCUUC | 154 |
| miR-137 | CUUCGGUGACGGGUAUUCUUGGGUGGAUAAUACGGAUUACGUUGUUAUUGCUUAAGAAUACGCGUAGUCGAGG | 155 |
| miR-138-1 | CCCUGGCAUGGUGUGGUGGGGCAGCUGGUGUUGUGAAUCAGGCCGUUGCCAAUCAGAGAACGGCUACUUCACAACACCAGGGCCACACCACACUACAGG | 156 |
| miR-138-2 | CGUUGCUGCAGCUGGUGUUGUGAAUCAGGCCGACGAGCAGCGCAUCCUCUUACCCGGCUAUUUCACGACACCAGGGUUGCAUCA | 157 |
| miR-138 | CAGCUGGUGUUGUGAAUCAGGCCGACGAGCAGCGCAUCCUCUUACCCGGCUAUUUCACGACACCAGGGUUG | 158 |
| miR-139 | GUGUAUUCUACAGUGCACGUGUCUCCAGUGUGGCUCGGAGGCUGGAGACGCGGCCCUGUUGGAGUAAC | 159 |
| miR-140 | UGUGUCUCUCUCUGUGUCCUGCCAGUGGUUUUACCCUAUGGUAGGUUACGUCAUGCUGUUCUACCACAGGGUAGAACCACGGACAGGAUACCGGGGCACC | 160 |
| miR-140as | UCCUGCCAGUGGUUUUACCCUAUGGUAGGUUACGUCAUGCUGUUCUACCACAGGGUAGAACCACGGACAGGA | 161 |
| miR-140s | CCUGCCAGUGGUUUUACCCUAUGGUAGGUUACGUCAUGCUGUUCUACCACAGGGUAGAACCACGGACAGG | 162 |
| miR-141-1 | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC | 163 |
| miR-141-2 | GGGUCCAUCUUCCAGUACAGUGUUGGAUGGUCUAAUUGUGAAGCUCCUAACACUGUCUGGUAAAGAUGGCCC | 164 |
| miR-142 | ACCCAUAAAGUAGAAAGCACUACUAACAGCACUGGAGGGUGUAGUGUUUCCUACUUUAUGGAUG | 165 |
| miR-143-1 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | 166 |
| miR-143-2 | CCUGAGGUGCAGUGCUGCAUCUCUGGUCAGUUGGGAGUCUGAGAUGAAGCACUGUAGCUCAGG | 167 |
| miR-144-1 | UGGGGCCCUGGCUGGGAUAUCAUCAUAUACUGUAAGUUUGCGAUGAGACACUACAGUAUAGAUGAUGUACUAGUCCGGGCACCCCC | 168 |
| miR-144-2 | GGCUGGGAUAUCAUCAUAUACUGUAAGUUUGCGAUGAGACACUACAGUAUAGAUGAUGUACUAGUC | 169 |
| miR-145-1 | CACCUUGUCCUCACGGUCCAGUUUUCCCAGGAAUCCCUUAGAUGCUAAGAUGGGGAUUCCUGGAAAUACUGUUCUUGAGGUCAUGGUU | 170 |
| miR-145-2 | CUCACGGUCCAGUUUUCCCAGGAAUCCCUUAGAUGCUAAGAUGGGGAUUCCUGGAAAUACUGUUCUUGAG | 171 |

TABLE 1a -continued

Human microRNA Precursor Sequences.

| Precursor Name | Sequence (5' To 3')* | SEQ ID NO. |
|---|---|---|
| miR-146-1 | CCGAUGUGUAUCCUCAGCUUUGAGAACUGAAUUCCAUG<br>GGUUGUGUCAGUGUCAGACCUCUGAAAUUCAGUUCUUC<br>AGCUGGGAUAUCUCUGUCAUCGU | 172 |
| miR-146-2 | AGCUUUGAGAACUGAAUUCCAUGGGUUGUGUCAGUGUC<br>AGACCUGUGAAAUUCAGUUCUUCAGCU | 173 |
| miR-147 | AAUCUAAAGACAACAUUUCUGCACACACACCAGACUAUG<br>GAAGCCAGUGUGUGGAAAUGCUUCUGCUAGAUU | 174 |
| miR-148a (miR-148) | GAGGCAAAGUUCUGAGACACUCCGACUCUGAGUAUGAU<br>AGAAGUCAGUGCACUACAGAACUUUGUCUC | 175 |
| miR-148b | CAAGCACGAUUAGCAUUUGAGGUGAAGUUCUGUUAUAC<br>ACUCAGGCUGUGGCUCUCUGAAAGUCAGUGCAUCACAGA<br>ACUUUGUCUCGAAAGCUUUCUA | 176 |
| MIR-148B-SMALL | AAGCACGAUUAGCAUUUGAGGUGAAGUUCUGUUAUACA<br>CUCAGGCUGUGGCUCUCUGAAAGUCAGUGCAU | 177 |
| miR-149-1 | GCCGGCGCCCGAGCUCUGGCUCCGUGUCUUCACUCCCGU<br>GCUUGUCCGAGGAGGGAGGGAGGGACGGGGGCUGUGCU<br>GGGGCAGCUGGA | 178 |
| miR-149-2 | GCUCUGGCUCCGUGUCUUCACUCCCGUGCUUGUCCGAGG<br>AGGGAGGGAGGGAC | 179 |
| miR-150-1 | CUCCCCAUGGCCCUGUCUCCCAACCCUUGUACCAGUGCU<br>GGGCUCAGACCCUGGUACAGGCCUGGGGGACAGGGACCU<br>GGGGAC | 180 |
| miR-150-2 | CCCUGUCUCCCAACCCUUGUACCAGUGCUGGGCUCAGAC<br>CCUGGUACAGGCCUGGGGGACAGGG | 181 |
| miR-151 | UUUCCUGCCCUCGAGGAGCUCACAGUCUAGUAUGUCUCA<br>UCCCCUACUAGACUGAAGCUCCUUGAGGACAGG | 182 |
| MIR-151-2 | CCUGUCCUCAAGGAGCUUCAGUCUAGUAGGGGAUGAGA<br>CAUACUAGACUGUGAGCUCCUCGAGGGCAGG | 183 |
| miR-152-1 | UGUCCCCCCCGGCCCAGGUUCUGUGAUACACUCCGACUC<br>GGGCUCUGGAGCAGUCAGUGCAUGACAGAACUUGGGCCC<br>GGAAGGACC | 184 |
| miR-152-2 | GGCCCAGGUUCUGUGAUACACUCCGACUCGGGCUCUGGA<br>GCAGUCAGUGCAUGACAGAACUUGGGCCCCGG | 185 |
| miR-153-1-1 | CUCACAGCUGCCAGUGUCAUUUUUGUGAUCUGCAGCUAG<br>UAUUCUCACUCCAGUUGCAUAGUCACAAAAGUGAUCAU<br>UGGCAGGUGUGGC | 186 |
| miR-153-1-2 | UCUCUCUCUCCCUCACAGCUGCCAGUGUCAUUGUCACAA<br>AAGUGAUCAUUGGCAGGUGUGGCUGCUGCAUG | 187 |
| miR-153-2-1 | AGCGGUGGCCAGUGUCAUUUUUGUGAUGUUGCAGCUAG<br>UAAUAUGAGCCCAGUUGCAUAGUCACAAAAGUGAUCAU<br>UGGAAACUGUG | 188 |
| miR-153-2-2 | CAGUGUCAUUUUUGUGAUGUUGCAGCUAGUAAUAUGAG<br>CCCAGUUGCAUAGUCACAAAAGUGAUCAUUG | 189 |
| miR-154-1 | GUGGUACUUGAAGAUAGGUUAUCCGUGUUGCCUUCGCU<br>UUAUUUGUGACGAAUCAUACACGGUUGACCUAUUUUUC<br>AGUACCAA | 190 |
| miR-154-2 | GAAGAUAGGUUAUCCGUGUUGCCUUCGCUUUAUUUGUG<br>ACGAAUCAUACACGGUUGACCUAUUUUU | 191 |
| miR-155 | CUGUUAAUGCUAAUCGUGAUAGGGGUUUUUGCCUCCAA<br>CUGACUCCUACAUAUUAGCAUUAACAG | 192 |
| MIR-156 = MIR-157 = OVERLAP MIR-141 | CCUAACACUGUCUGGUAAAGAUGGCUCCCGGGUGGGUUC<br>UCUCGGCAGUAACCUUCAGGGAGCCCUGAAGACCAUGGA<br>GGAC | 193 |

TABLE 1a -continued

| Human microRNA Precursor Sequences. | | |
|---|---|---|
| Precursor Name | Sequence (5' To 3')* | SEQ ID NO. |
| MIR-158-SMALL = MIR-192 | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC | 194 |
| MIR-159-1-SMALL | UCCCGCCCCCUGUAACAGCAACUCCAUGUGGAAGUGCCCACUGGUUCCAGUGGGGCUGCUGUUAUCUGGGGCGAGGGCCA | 195 |
| MIR-161-SMALL | AAAGCUGGGUUGAGAGGGCGAAAAAGGAUGAGGUGACUGGUCUGGGCUACGCUAUGCUGCGGCGCUCGGG | 196 |
| MIR-163-1B-SMALL | CAUUGGCCUCCUAAGCCAGGGAUUGUGGGUUCGAGUCCCACCCGGGGUAAAGAAAGGCCGAAUU | 197 |
| MIR-163-3-SMALL | CCUAAGCCAGGGAUUGUGGGUUCGAGUCCCACCUGGGGUAGAGGUGAAAGUUCCUUUUACGGAAUUUUUU | 198 |
| miR-162 | CAAUGUCAGCAGUGCCUUAGCAGCACGUAAAUAUUGGCGUUAAGAUUCUAAAAUUAUCUCCAGUAUUAACUGUGCUGCUGAAGUAAGGUUGACCAUACUCUACAGUUG | 199 |
| MIR-175-SMALL = MIR-224 | GGGCUUUCAAGUCACUAGUGGUUCCGUUUAGUAGAUGAUUGUGCAUUGUUUCAAAAUGGUGCCCUAGUGACUACAAAGCCC | 200 |
| MIR-177-SMALL | ACGCAAGUGUCCUAAGGUGAGCUCAGGGAGCACAGAAACCUCCAGUGGAACAGAAGGGCAAAAGCUCAUU | 201 |
| MIR-180-SMALL | CAUGUGUCACUUUCAGGUGGAGUUUCAAGAGUCCCUUCCUGGUUCACCGUCUCCUUUGCUCUUCCACAAC | 202 |
| miR-181a | AGAAGGGCUAUCAGGCCAGCCUUCAGAGGACUCCAAGGAACAUUCAACGCUGUCGGUGAGUUUGGGAUUUGAAAAAACCACUGACCGUUGACUGUACCUUGGGGUCCUUA | 203 |
| miR-181b-1 | CCUGUGCAGAGAUUAUUUUUUAAAAGGUCACAAUCAACAUUCAUUGCUGUCGGUGGGUUGAACUGUGUGGACAAGCUCACUGAACAAUGAAUGCAACUGUGGCCCCGCUU | 204 |
| miR-181b-2 | CUGAUGGCUGCACUCAACAUUCAUUGCUGUCGGUGGGUUUGAGUCUGAAUCAACUCACUGAUCAAUGAAUGCAAACUGCGGACCAAACA | 205 |
| miR-181c | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | 206 |
| miR-182-as | GAGCUGCUUGCCUCCCCCCGUUUUUGGCAAUGGUAGAACUCACACUGGUGAGGUAACAGGAUCCGGUGGUUCUAGACUUGCCAACUAUGGGGCGAGGACUCAGCCGGCAC | 207 |
| miR-182 | UUUUUGGCAAUGGUAGAACUCACACUGGUGAGGUAACAGGAUCCGGUGGUUCUAGACUUGCCAACUAUGG | 208 |
| miR-183 | CCGCAGAGUGUGACUCCUGUUCUGUGUAUGGCACUGGUAGAAUUCACUGUGAACAGUCUCAGUCAGUGAAUUACCGAAGGGCCAUAAACAGAGCAGAGACAGAUCCACGA | 209 |
| miR-184-1 | CCAGUCACGUCCCCUUAUCACUUUUCCAGCCCAGCUUUGUGACUGUAAGUGUUGGACGGAGAACUGAUAAGGGUAGGUGAUUGA | 210 |
| miR-184-2 | CCUUAUCACUUUUCCAGCCCAGCUUUGUGACUGUAAGUGUUGGACGGAGAACUGAUAAGGGUAGG | 211 |
| miR-185-1 | AGGGGGCGAGGGAUUGGAGAGAAAGGCAGUUCCUGAUGGUCCCCUCCCCAGGGGCUGGCUUUCCUCUGGUCCUUCCCUCCCA | 212 |
| miR-185-2 | AGGGAUUGGAGAGAAAGGCAGUUCCUGAUGGUCCCCUCCCCAGGGGCUGGCUUUCCUCUGGUCCUU | 213 |
| miR-186-1 | UGCUUGUAACUUUCCAAAGAAUUCUCCUUUUGGGCUUUCUGGUUUUAUUUUAAGCCCAAAGGUGAAUUUUUUGGGAAGUUUGAGCU | 214 |

TABLE 1a -continued

Human microRNA Precursor Sequences.

| Precursor Name | Sequence (5' To 3')* | SEQ ID NO. |
|---|---|---|
| miR-186-2 | ACUUUCCAAAGAAUUCUCCUUUUGGGCUUUCUGGUUUU AUUUUAAGCCCAAAGGUGAAUUUUUUGGGAAGU | 215 |
| miR-187 | GGUCGGGCUCACCAUGACACAGUGUGAGACUCGGGCUAC AACACAGGACCCGGGGCGCUGCUCUGACCCCUCGUGUCU UGUGUUGCAGCCGGAGGGACGCAGGUCCGCA | 216 |
| miR-188-1 | UGCUCCCUCUCUCACAUCCCUUGCAUGGUGGAGGGUGAG CUUUCUGAAAACCCCUCCCACAUGCAGGGUUUGCAGGAU GGCGAGCC | 217 |
| miR-188-2 | UCUCACAUCCCUUGCAUGGUGGAGGGUGAGCUUUCUGA AAACCCCUCCCACAUGCAGGGUUUGCAGGA | 218 |
| miR-189-1 | CUGUCGAUUGGACCCGCCCUCCGGUGCCUACUGAGCUGA UAUCAGUUCUCAUUUUACACACUGGCUCAGUUCAGCAGG AACAGGAGUCGAGCCCUUGAGCAA | 219 |
| miR-189-2 | CUCCGGUGCCUACUGAGCUGAUAUCAGUUCUCAUUUUAC ACACUGGCUCAGUUCAGCAGGAACAGGAG | 220 |
| miR-190-1 | UGCAGGCCUCUGUGUGAUAUGUUUGAUAUAUUAGGUUG UUAUUUAAUCCAACUAUAUAUCAAACAUAUUCCUACAG UGUCUUGCC | 221 |
| miR-190-2 | CUGUGUGAUAUGUUUGAUAUAUUAGGUUGUUAUUUAAU CCAACUAUAUAUCAAACAUAUUCCUACAG | 222 |
| miR-191-1 | CGGCUGGACAGCGGGCAACGGAAUCCCAAAAGCAGCUGU UGUCUCCAGAGCAUUCCAGCUGCGCUUGGAUUUCGUCCC CUGCUCUCCUGCCU | 223 |
| miR-191-2 | AGCGGGCAACGGAAUCCCAAAAGCAGCUGUUGUCUCCAG AGCAUUCCAGCUGCGCUUGGAUUUCGUCCCCUGCU | 224 |
| miR-192-2/3 | CCGAGACCGAGUGCACAGGGCUCUGACCUAUGAAUUGAC AGCCAGUGCUCUCGUCUCCCCUCUGGCUGCCAAUUCCAU AGGUCACAGGUAUGUUCGCCUCAAUGCCAG | 225 |
| miR-192 | GCCGAGACCGAGUGCACAGGGCUCUGACCUAUGAAUUGA CAGCCAGUGCUCUCGUCUCCCCUCUGGCUGCCAAUUCCA UAGGUCACAGGUAUGUUCGCCUCAAUGCCAGC | 226 |
| miR-193-1 | CGAGGAUGGGAGCUGAGGGCUGGGUCUUUGCGGGCGAG AUGAGGGUGUCGGAUCAACUGGCCUACAAAGUCCCAGU UCUCGGCCCCCG | 227 |
| miR-193-2 | GCUGGGUCUUUGCGGGCGAGAUGAGGGUGUCGGAUCAA CUGGCCUACAAAGUCCCAGU | 228 |
| miR-194-1 | AUGGUGUUAUCAAGUGUAACAGCAACUCCAUGUGGACU GUGUACCAAUUUCCAGUGGAGAUGCUGUUACUUUUGAU GGUUACCAA | 229 |
| miR-194-2 | GUGUAACAGCAACUCCAUGUGGACUGUGUACCAAUUUCC AGUGGAGAUGCUGUUACUUUUGAU | 230 |
| miR-195-1 | AGCUUCCCUGGCUCUAGCAGCACAGAAAUAUUGGCACAG GGAAGCGAGUCUGCCAAUAUUGGCUGUGCUGCUCCAGGC AGGGUGGUG | 231 |
| miR-195-2 | UAGCAGCACAGAAAUAUUGGCACAGGGAAGCGAGUCUG CCAAUAUUGGCUGUGCUGCU | 232 |
| miR-196-1 | CUAGAGCUUGAAUUGGAACUGCUGAGUGAAUUAGGUAG UUUCAUGUUGUUGGGCCUGGGUUUCUGAACACAACAAC AUUAAACCACCCGAUUCACGGCAGUUACUGCUCC | 233 |
| miR-196a-1 | GUGAAUUAGGUAGUUUCAUGUUGUUGGGCCUGGGUUUC UGAACACAACAACAUUAAACCACCCGAUUCAC | 234 |
| miR-196a-2 (miR-196-2) | UGCUCGCUCAGCUGAUCUGUGGCUUAGGUAGUUUCAUG UUGUUGGGAUUGAGUUUUGAACUCGGCAACAGAAACU GCCUGAGUUACAUCAGUCGGUUUUCGUCGAGGGC | 235 |

TABLE 1a -continued

Human microRNA Precursor Sequences.

| Precursor Name | Sequence (5' To 3')* | SEQ ID NO. |
|---|---|---|
| miR-196 | GUGAAUUAGGUAGUUUCAUGUUGUUGGGCCUGGGUUUC UGAACACAACAACAUUAAACCACCCGAUUCAC | 236 |
| miR-196b | ACUGGUCGGUGAUUUAGGUAGUUUCCUGUUGUUGGGAU CCACCUUUCUCUCGACAGCACGACACUGCCUUCAUUACU UCAGUUG | 237 |
| miR-197 | GGCUGUGCCGGGUAGAGAGGGCAGUGGGAGGUAAGAGC UCUUCACCCUUCACCACCUUCUCCACCCAGCAUGGCC | 238 |
| MIR-197-2 | GUGCAUGUGUAUGUAUGUGUGCAUGUGCAUGUGUAUGU GUAUGAGUGCAUGCGUGUGUGC | 239 |
| miR-198 | UCAUUGGUCCAGAGGGGAGAUAGGUUCCUGUGAUUUUU CCUUCUUCUCUAUAGAAUAAAUGA | 240 |
| miR-199a-1 | GCCAACCCAGUGUUCAGACUACCUGUUCAGGAGGCUCUC AAUGUGUACAGUAGUCUGCACAUUGGUUAGGC | 241 |
| miR-199a-2 | AGGAAGCUUCUGGAGAUCCUGCUCCGUCGCCCCAGUGUU CAGACUACCUGUUCAGGACAAUGCCGUUGUACAGUAGUC UGCACAUUGGUUAGACUGGGCAAGGGAGAGCA | 242 |
| miR-199b | CCAGAGGACACCUCCACUCCGUCUACCCAGUGUUUAGAC UAUCUGUUCAGGACUCCCAAAUUGUACAGUAGUCUGCAC AUUGGUUAGGCUGGGCUGGGUUAGACCCUCGG | 243 |
| miR-199s | GCCAACCCAGUGUUCAGACUACCUGUUCAGGAGGCUCUC AAUGUGUACAGUAGUCUGCACAUUGGUUAGGC | 244 |
| miR-200a | GCCGUGGCCAUCUUACUGGGCAGCAUUGGAUGGAGUCA GGUCUCUAAUACUGCCUGGUAAUGAUGACGGC | 245 |
| miR-200b | CCAGCUCGGGCAGCCGUGGCCAUCUUACUGGGCAGCAUU GGAUGGAGUCAGGUCUCUAAUACUGCCUGGUAAUGAUG ACGGCGGAGCCCUGCACG | 246 |
| miR-200c | CCCUCGUCUUACCCAGCAGUGUUUGGGUGCGGUUGGGAG UCUCUAAUACUGCCGGGUAAUGAUGGAGG | 247 |
| miR-202 | GUUCCUUUUUCCUAUGCAUAUACUUCUUUGAGGAUCUG GCCUAAAGAGGUAUAGGGCAUGGGAAGAUGGAGC | 248 |
| miR-203 | GUGUUGGGGACUCGCGCGCUGGGUCCAGUGGUUCUUAA CAGUUCAACAGUUCUGUAGCGCAAUUGUGAAAUGUUUA GGACCACUAGACCCGGCGGGCGCGGCGACAGCGA | 249 |
| miR-204 | GGCUACAGUCUUUCUUCAUGUGACUCGUGGACUUCCCUU UGUCAUCCUAUGCCUGAGAAUAUAUGAAGGAGGCUGGG AAGGCAAAGGGACGUUCAAUUGUCAUCACUGGC | 250 |
| miR-205 | AAAGAUCCUCAGACAAUCCAUGUGCUUCUCUUGUCCUUC AUUCCACCGGAGUCUGUCUCAUACCCAACCAGAUUUCAG UGGAGUGAAGUUCAGGAGGCAUGGAGCUGACA | 251 |
| miR-206-1 | UGCUUCCCGAGGCCACAUGCUUCUUUAUAUCCCCAUAUG GAUUACUUUGCUAUGGAAUGUAAGGAAGUGUGUGGUUU CGGCAAGUG | 252 |
| miR-206-2 | AGGCCACAUGCUUCUUUAUAUCCCCAUAUGGAUUACUUU GCUAUGGAAUGUAAGGAAGUGUGUGGUUUU | 253 |
| miR-208 | UGACGGGCGAGCUUUUGGCCCGGGUUAUACCUGAUGCUC ACGUAUAAGACGAGCAAAAAGCUUGUUGGUCA | 254 |
| miR-210 | ACCCGGCAGUGCCUCCAGGCGCAGGGCAGCCCCUGCCCA CCGCACACUGCGCUGCCCCAGACCCACUGUGCGUGUGAC AGCGGCUGAUCUGUGCCUGGGCAGCGCGACCC | 255 |
| miR-211 | UCACCUGGCCAUGUGACUUGUGGGCUUCCCUUUGUCAUC CUUCGCCUAGGGCUCUGAGCAGGGCAGGGACAGCAAAGG GGUGCUCAGUUGUCACUUCCCACAGCACGGAG | 256 |

TABLE 1a -continued

Human microRNA Precursor Sequences.

| Precursor Name | Sequence (5' To 3')* | SEQ ID NO. |
|---|---|---|
| miR-212 | CGGGGCACCCCGCCCGGACAGCGCGCCGGCACCUUGGCU CUAGACUGCUUACUGCCCGGGCCGCCCUCAGUAACAGUC UCCAGUCACGGCCACCGACGCCUGGCCCCGCC | 257 |
| miR-213-2 | CCUGUGCAGAGAUUAUUUUUUAAAAGGUCACAAUCAAC AUUCAUUGCUGUCGGUGGGUUGAACUGUGUGGACAAGC UCACUGAACAAUGAAUGCAACUGUGGCCCCGCUU | 258 |
| miR-213 | GAGUUUUGAGGUUGCUUCAGUGAACAUUCAACGCUGUC GGUGAGUUUGGAAUUAAAAUCAAAACCAUCGACCGUUG AUUGUACCCUAUGGCUAACCAUCAUCUACUCC | 259 |
| miR-214 | GGCCUGGCUGGACAGAGUUGUCAUGUGUCUGCCUGUCU ACACUUGCUGUGCAGAACAUCCGCUCACCUGUACAGCAG GCACAGACAGGCAGUCACAUGACAACCCAGCCU | 260 |
| miR-215 | AUCAUUCAGAAAUGGUAUACAGGAAAAUGACCUAUGAA UUGACAGACAAUAUAGCUGAGUUUGUCUGUCAUUUCUU UAGGCCAAUAUUCUGUAUGACUGUGCUACUUCAA | 261 |
| miR-216 | GAUGGCUGUGAGUUGGCUUAAUCUCAGCUGGCAACUGU GAGAUGUUCAUACAAUCCCUCACAGUGGUCUCUGGGAU UAUGCUAAACAGAGCAAUUUCCUAGCCCUCACGA | 262 |
| miR-217 | AGUAUAAUUAUUACAUAGUUUUUGAUGUCGCAGAUACU GCAUCAGGAACUGAUUGGAUAAGAAUCAGUCACCAUCA GUUCCUAAUGCAUUGCCUUCAGCAUCUAAACAAG | 263 |
| miR-218-1 | GUGAUAAUGUAGCGAGAUUUUCUGUUGUGCUUGAUCUA ACCAUGUGGUUGCGAGGUAUGAGUAAAACAUGGUUCCG UCAAGCACCAUGGAACGUCACGCAGCUUUCUACA | 264 |
| miR-218-2 | GACCAGUCGCUGCGGGGCUUUCCUUUGUGCUUGAUCUAA CCAUGUGGUGGAACGAUGGAAACGGAACAUGGUUCUGU CAAGCACCGCGGAAAGCACCGUGCUCUCCUGCA | 265 |
| miR-219 | CCGCCCCGGGCCGCGGCUCCUGAUUGUCCAAACGCAAUU CUCGAGUCUAUGGCUCCGGCCGAGAGUUGAGUCUGGACG UCCCGAGCCGCCGCCCCCAAACCUCGAGCGGG | 266 |
| miR-219-1 | CCGCCCCGGGCCGCGGCUCCUGAUUGUCCAAACGCAAUU CUCGAGUCUAUGGCUCCGGCCGAGAGUUGAGUCUGGACG UCCCGAGCCGCCGCCCCCAAACCUCGAGCGGG | 267 |
| miR-219-2 | ACUCAGGGGCUUCGCCACUGAUUGUCCAAACGCAAUUCU UGUACGAGUCUGCGGCCAACCGAGAAUUGUGGCUGGAC AUCUGUGGCUGAGCUCCGGG | 268 |
| miR-220 | GACAGUGUGGCAUUGUAGGGCUCCACACCGUAUCUGACA CUUUGGGCGAGGGCACCAUGCUGAAGGUGUUCAUGAUG CGGUCUGGGAACUCCUCACGGAUCUUACUGAUG | 269 |
| miR-221 | UGAACAUCCAGGUCUGGGGCAUGAACCUGGCAUACAAU GUAGAUUUCUGUGUUCGUUAGGCAACAGCUACAUUGUC UGCUGGGUUUCAGGCUACCUGGAAACAUGUUCUC | 270 |
| miR-222 | GCUGCUGGAAGGUGUAGGUACCCUCAAUGGCUCAGUAG CCAGUGUAGAUCCUGUCUUUCGUAAUCAGCAGCUACAUC UGGCUACUGGGUCUCUGAUGGCAUCUUCUAGCU | 271 |
| miR-223 | CCUGGCCUCCUGCAGUGCCACGCUCCGUGUAUUUGACAA GCUGAGUUGGACACUCCAUGUGGUAGAGUGUCAGUUUG UCAAAUACCCCAAGUGCGGCACAUGCUUACCAG | 272 |
| miR-224 | GGGCUUUCAAGUCACUAGUGGUUCCGUUUAGUAGAUGA UUGUGCAUUGUUUCAAAAUGGUGCCCUAGUGACUACAA AGCCC | 273 |
| MIR-294-1 (CHR16) | CAAUCUUCCUUUAUCAUGGUAUUGAUUUUUCAGUGCUU CCCUUUUGUGUGAGAGAAGAUA | 274 |
| miR-296 | AGGACCCUUCCAGAGGGCCCCCCCUCAAUCCUGUUGUGC CUAAUUCAGAGGGUUGGGUGGAGGCUCUCCUGAAGGGC UCU | 275 |

TABLE 1a -continued

| Precursor Name | Sequence (5' To 3')* | SEQ ID NO. |
|---|---|---|
| | Human microRNA Precursor Sequences. | |
| miR-299 | AAGAAAUGGUUUACCGUCCCACAUACAUUUUGAAUAUG UAUGUGGGAUGGUAAACCGCUUCUU | 276 |
| miR-301 | ACUGCUAACGAAUGCUCUGACUUUAUUGCACUACUGUAC UUUACAGCUAGCAGUGCAAUAGUAUUGUCAAAGCAUCU GAAAGCAGG | 277 |
| miR-302a | CCACCACUUAAACGUGGAUGUACUUGCUUUGAAACUAA AGAAGUAAGUGCUUCCAUGUUUUGGUGAUGG | 278 |
| miR-302b | GCUCCCUUCAACUUUAACAUGGAAGUGCUUUCUGUGACU UUAAAAGUAAGUGCUUCCAUGUUUUAGUAGGAGU | 279 |
| miR-302c | CCUUUGCUUUAACAUGGGGGUACCUGCUGUGUGAAACA AAAGUAAGUGCUUCCAUGUUUCAGUGGAGG | 280 |
| miR-302d | CCUCUACUUUAACAUGGAGGCACUUGCUGUGACAUGACA AAAAUAAGUGCUUCCAUGUUUGAGUGUGG | 281 |
| miR-320 | GCUUCGCUCCCCUCCGCCUUCUCUUCCCGGUUCUUCCCG GAGUCGGGAAAAGCUGGGUUGAGAGGGCGAAAAAGGAU GAGGU | 282 |
| miR-321 | UUGGCCUCCUAAGCCAGGGAUUGUGGGUUCGAGUCCCAC CCGGGGUAAAGAAAGGCCGA | 283 |
| miR-323 | UUGGUACUUGGAGAGAGGUGGUCCGUGGCGCGUUCGCU UUAUUUAUGGCGCACAUUACACGGUCGACCUCUUUGCAG UAUCUAAUC | 284 |
| miR-324 | CUGACUAUGCCUCCCCGCAUCCCCUAGGGCAUUGGUGUA AAGCUGGAGACCCACUGCCCCAGGUGCUGCUGGGGGUUG UAGUC | 285 |
| miR-325 | AUACAGUGCUUGGUUCCUAGUAGGUGUCCAGUAAGUGU UUGUGACAUAAUUUGUUUAUUGAGGACCUCCUAUCAAU CAAGCACUGUGCUAGGCUCUGG | 286 |
| miR-326 | CUCAUCUGUCUGUUGGGCUGGAGGCAGGGCCUUUGUGA AGGCGGGUGGUGCUCAGAUCGCCUCUGGGCCCUUCCUCC AGCCCCGAGGCGGAUUCA | 287 |
| miR-328 | UGGAGUGGGGGGGCAGGAGGGGCUCAGGGAGAAAGUGC AUACAGCCCCUGGCCCUCUCUGCCCUUCCGUCCCCUG | 288 |
| miR-330 | CUUUGGCGAUCACUGCCUCUCUGGGCCUGUGUCUUAGGC UCUGCAAGAUCAACCGAGCAAAGCACACGGCCUGCAGAG AGGCAGCGCUCUGCCC | 289 |
| miR-331 | GAGUUUGGUUUUGUUUGGGUUUGUUCUAGGUAUGGUCC CAGGGAUCCCAGAUCAAACCAGGCCCCUGGGCCUAUCCU AGAACCAACCUAAGCUC | 290 |
| miR-335 | UGUUUUGAGCGGGGGUCAAGAGCAAUAACGAAAAAUGU UUGUCAUAAACCGUUUUUCAUUAUUGCUCCUGACCUCCU CUCAUUUGCUAUAUUCA | 291 |
| miR-337 | GUAGUCAGUAGUUGGGGGGUGGGAACGGCUUCAUACAG GAGUUGAUGCACAGUUAUCCAGCUCCUAUAUGAUGCCU UUCUUCAUCCCCUUCAA | 292 |
| miR-338 | UCUCCAACAAUAUCCUGGUGCUGAGUGAUGACUCAGGCG ACUCCAGCAUCAGUGAUUUUGUUGAAGA | 293 |
| miR-339 | CGGGGCGGCCGCUCUCCCUGUCCUCCAGGAGCUCACGUG UGCCUGCCUGUGAGCGCCUCGACGACAGAGCCGGCGCCU GCCCCAGUGUCUGCGC | 294 |
| miR-340 | UUGUACCUGGUGUGAUUAUAAAGCAAUGAGACUGAUUG UCAUAUGUCGUUUGUGGGAUCCGUCUCAGUUACUUUAU AGCCAUACCUGGUAUCUUA | 295 |
| miR-342 | GAAACUGGGCUCAAGGUGAGGGGUGCUAUCUGUGAUUG AGGGACAUGGUUAAUGGAAUUGUCUCACACAGAAAUCG CACCCGUCACCUUGGCCUACUUA | 296 |

TABLE 1a -continued

| Human microRNA Precursor Sequences. | | |
|---|---|---|
| Precursor Name | Sequence (5' To 3')* | SEQ ID NO. |
| miR-345 | ACCCAAACCCUAGGUCUGCUGACUCCUAGUCCAGGGCUC GUGAUGGCUGGUGGGCCCUGAACGAGGGGUCUGGAGGC CUGGGUUUGAAUAUCGACAGC | 297 |
| miR-346 | GUCUGUCUGCCCGCAUGCCUGCCUCUCUGUUGCUCUGAA GGAGGCAGGGGCUGGGCCUGCAGCUGCCUGGGCAGAGCG GCUCCUGC | 298 |
| miR-367 | CCAUUACUGUUGCUAAUAUGCAACUCUGUUGAAUAUAA AUUGGAAUUGCACUUUAGCAAUGGUGAUGG | 299 |
| miR-368 | AAAAGGUGGAUAUUCCUUCUAUGUUUAUGUUAUUUAUG GUUAAACAUAGAGGAAAUUCCACGUUUU | 300 |
| miR-369 | UUGAAGGGAGAUCGACCGUGUUAUAUUCGCUUUAUUGA CUUCGAAUAAUACAUGGUUGAUCUUUUCUCAG | 301 |
| miR-370 | AGACAGAGAAGCCAGGUCACGUCUCUGCAGUUACACAGC UCACGAGUGCCUGCUGGGGUGGAACCUGGUCUGUCU | 302 |
| miR-371 | GUGGCACUCAAACUGUGGGGGCACUUUCUGCUCUCUGGU GAAAGUGCCGCCAUCUUUUGAGUGUUAC | 303 |
| miR-372 | GUGGGCCUCAAAUGUGGAGCACUAUUCUGAUGUCCAAG UGGAAAGUGCUGCGACAUUUGAGCGUCAC | 304 |
| miR-373 | GGGAUACUCAAAAUGGGGGCGCUUUCCUUUUUGUCUGU ACUGGGAAGUGCUUCGAUUUUGGGGUGUCCC | 305 |
| miR-374 | UACAUCGGCCAUUAUAAUACAACCUGAUAAGUGUUAUA GCACUUAUCAGAUUGUAUUGUAAUUGUCUGUGUA | 306 |
| mir-hes1 | AUGGAGCUGCUCACCCUGUGGGCCUCAAAUGUGGAGGA ACUAUUCUGAUGUCCAAGUGGAAAGUGCUGCGACAUUU GAGCGUCACCGGUGACGCCCAUAUCA | 307 |
| mir-hes2 | GCAUCCCCUCAGCCUGUGGCACUCAAACUGUGGGGGCAC UUUCUGCUCUCUGGUGAAAGUGCCGCCAUCUUUUGAGU GUUACCGCUUGAGAAGACUCAACC | 308 |
| mir-hes3 | CGAGGAGCUCAUACUGGGAUACUCAAAAUGGGGGCGCU UUCCUUUUUGUCUGUUACUGGGAAGUGCUUCGAUUUUG GGGUGUCCCUGUUUGAGUAGGGCAUC | 309 |

*An underlined sequence within a precursor sequence corresponds to a mature processed miR transcript (see Table 1b). Some precursor sequences have two underlined sequences denoting two different mature miRs that are derived from the same precursor. All sequences are human.

TABLE 1b

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| let-7a | UGAGGUAGUAGGUUGUA UAGUU | 310 | let-7a-1; let-7a-2; let-7a-3; let-7a-4 |
| let-7b | UGAGGUAGUAGGUUGUG UGGUU | 311 | let-7b |
| let-7c | UGAGGUAGUAGGUUGUA UGGUU | 312 | let-7c |
| let-7d | AGAGGUAGUAGGUUGCA UAGU | 313 | let-7d; let-7d-v1 |
| let-7e | UGAGGUAGGAGGUUGUA UAGU | 314 | let-7e |
| let-7f | UGAGGUAGUAGAUUGUA UAGUU | 315 | let-7f-1; let-7f-2-1; let-7f-2-2 |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| let-7g | UGAGGUAGUAGUUUGUA CAGU | 316 | let-7g |
| let-7i | UGAGGUAGUAGUUUGUG CU | 317 | let-7i |
| miR-1 | UGGAAUGUAAAGAAGUA UGUA | 318 | miR-1b; miR-1b-1; miR-1b-2 |
| miR-7 | UGGAAGACUAGUGAUUU UGUU | 319 | miR-7-1; miR-7-1a; miR-7-2; miR-7-3 |
| miR-9 | UCUUUGGUUAUCUAGCU GUAUGA | 320 | miR-9-1; miR-9-2; miR-9-3 |
| miR-9* | UAAAGCUAGAUAACCGA AAGU | 321 | miR-9-1; miR-9-2; miR-9-3 |
| miR-10a | UACCCUGUAGAUCCGAA UUUGUG | 322 | miR-10a |
| miR-10b | UACCCUGUAGAACCGAA UUUGU | 323 | miR-10b |
| miR-15a | UAGCAGCACAUAAUGGU UUGUG | 324 | miR-15a; miR-15a-2 |
| miR-15b | UAGCAGCACAUCAUGGU UUACA | 325 | miR-15b |
| miR-16 | UAGCAGCACGUAAAUAU UGGCG | 326 | miR-16-1; miR-16-2; miR-16-13 |
| miR-17-5p | CAAAGUGCUUACAGUGC AGGUAGU | 327 | miR-17 |
| miR-17-3p | ACUGCAGUGAAGGCACU UGU | 328 | miR-17 |
| miR-18 | UAAGGUGCAUCUAGUGC AGAUA | 329 | miR-18; miR-18-13 |
| miR-19a | UGUGCAAAUCUAUGCAA AACUGA | 330 | miR-19a; miR-19a-13 |
| miR-19b | UGUGCAAAUCCAUGCAA AACUGA | 331 | miR-19b-1; miR-19b-2 |
| miR-20 | UAAAGUGCUUAUAGUGC AGGUA | 332 | miR-20 (miR-20a) |
| miR-21 | UAGCUUAUCAGACUGAU GUUGA | 333 | miR-21; miR-21-17 |
| miR-22 | AAGCUGCCAGUUGAAGA ACUGU | 334 | miR-22 |
| miR-23a | AUCACAUUGCCAGGGAU UUCC | 335 | miR-23a |
| miR-23b | AUCACAUUGCCAGGGAU UACCAC | 336 | miR-23b |
| miR-24 | UGGCUCAGUUCAGCAGG AACAG | 337 | miR-24-1; miR-24-2; miR-24-19; miR-24-9 |
| miR-25 | CAUUGCACUUGUCUCGG UCUGA | 338 | miR-25 |
| miR-26a | UUCAAGUAAUCCAGGAU AGGCU | 339 | miR-26a; miR-26a-1; miR-26a-2 |
| miR-26b | UUCAAGUAAUUCAGGAU AGGU | 340 | miR-26b |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| miR-27a | UUCACAGUGGCUAAGUU CCGCC | 341 | miR-27a |
| miR-27b | UUCACAGUGGCUAAGUU CUG | 342 | miR-27b-1; miR-27b-2 |
| miR-28 | AAGGAGCUCACAGUCUA UUGAG | 343 | miR-28 |
| miR-29a | CUAGCACCAUCUGAAAU CGGUU | 344 | miR-29a-2; miR-29a |
| miR-29b | UAGCACCAUUUGAAAUC AGU | 345 | miR-29b-1; miR-29b-2 |
| miR-29c | UAGCACCAUUUGAAAUC GGUUA | 346 | miR-29c |
| miR-30a-5p | UGUAAACAUCCUCGACU GGAAGC | 347 | miR-30a |
| miR-30a-3p | CUUUCAGUCGGAUGUUU GCAGC | 348 | miR-30a |
| miR-30b | UGUAAACAUCCUACACU CAGC | 349 | miR-30b-1; miR-30b-2 |
| miR-30c | UGUAAACAUCCUACACU CUCAGC | 350 | miR-30c |
| miR-30d | UGUAAACAUCCCCGACU GGAAG | 351 | miR-30d |
| miR-30e | UGUAAACAUCCUUGACU GGA | 352 | miR-30e |
| miR-31 | GGCAAGAUGCUGGCAUA GCUG | 353 | miR-31 |
| miR-32 | UAUUGCACAUUACUAAG UUGC | 354 | miR-32 |
| miR-33 | GUGCAUUGUAGUUGCAU UG | 355 | miR-33; miR-33b |
| miR-34a | UGGCAGUGUCUUAGCUG GUUGU | 356 | miR-34a |
| miR-34b | AGGCAGUGUCAUUAGCU GAUUG | 357 | miR-34b |
| miR-34c | AGGCAGUGUAGUUAGCU GAUUG | 358 | miR-34c |
| miR-92 | UAUUGCACUUGUCCCGG CCUGU | 359 | miR-92-2; miR-92-1 |
| miR-93 | AAAGUGCUGUUCGUGCA GGUAG | 360 | miR-93-1; miR-93-2 |
| miR-95 | UUCAACGGGUAUUUAUU GAGCA | 361 | miR-95 |
| miR-96 | UUUGGCACUAGCACAUU UUUGC | 362 | miR-96 |
| miR-98 | UGAGGUAGUAAGUUGUA UUGUU | 363 | miR-98 |
| miR-99a | AACCCGUAGAUCCGAUC UUGUG | 364 | miR-99a |
| miR-99b | CACCCGUAGAACCGACC UUGCG | 365 | miR-99b |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| miR-100 | UACAGUACUGUGAUAAC UGAAG | 366 | miR-100 |
| miR-101 | UACAGUACUGUGAUAAC UGAAG | 367 | miR-101-1; miR-101-2 |
| miR-103 | AGCAGCAUUGUACAGGG CUAUGA | 368 | miR-103-1 |
| miR-105 | UCAAAUGCUCAGACUCC UGU | 369 | miR-105 |
| miR-106-a | AAAAGUGCUUACAGUGC AGGUAGC | 370 | miR-106-a |
| miR-106-b | UAAAGUGCUGACAGUGC AGAU | 371 | miR-106-b |
| miR-107 | AGCAGCAUUGUACAGGG CUAUCA | 372 | miR-107 |
| miR-122a | UGGAGUGUGACAAUGGU GUUUGU | 373 | miR-122a-1; miR-122a-2 |
| miR-124a | UUAAGGCACGCGGUGAA UGCCA | 374 | miR-124a-1; miR-124a-2; miR-124a-3 |
| miR-125a | UCCCUGAGACCCUUUAA CCUGUG | 375 | miR-125a-1; miR-125a-2 |
| miR-125b | UCCCUGAGACCCUAACU UGUGA | 376 | miR-125b-1; miR-125b-2 |
| miR-126* | CAUUAUUACUUUUGGUA CGCG | 377 | miR-126-1; miR-126-2 |
| miR-126 | UCGUACCGUGAGUAAUA AUGC | 378 | miR-126-1; miR-126-2 |
| miR-127 | UCGGAUCCGUCUGAGCU UGGCU | 379 | miR-127-1; miR-127-2 |
| miR-128a | UCACAGUGAACCGGUCU CUUUU | 380 | miR-128; miR-128a |
| miR-128b | UCACAGUGAACCGGUCU CUUUC | 381 | miR-128b |
| miR-129 | CUUUUUGCGGUCUGGGC UUGC | 382 | miR-129-1; miR-129-2 |
| miR-130a | CAGUGCAAUGUUAAAAG GGC | 383 | miR-130a |
| miR-130b | CAGUGCAAUGAUGAAAG GGCAU | 384 | miR-130b |
| miR-132 | UAACAGUCUACAGCCAU GGUCG | 385 | miR-132-1 |
| miR-133a | UUGGUCCCCUUCAACCA GCUGU | 386 | miR-133a-1; miR-133a-2 |
| miR-133b | UUGGUCCCCUUCAACCA GCUA | 387 | miR-133b |
| miR-134 | UGUGACUGGUUGACCAG AGGG | 388 | miR-134-1; miR-134-2 |
| miR-135a | UAUGGCUUUUUAUUCCU AUGUGA | 389 | miR-135a; miR-135a-2 (miR-135-2) |
| miR-135b | UAUGGCUUUUCAUUCCU AUGUG | 390 | miR-135b |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| miR-136 | ACUCCAUUUGUUUUGAU GAUGGA | 391 | miR-136-1; miR-136-2 |
| miR-137 | UAUUGCUUAAGAAUACG CGUAG | 392 | miR-137 |
| miR-138 | AGCUGGUGUUGUGAAUC | 393 | miR-138-1; miR-138-2 |
| miR-139 | UCUACAGUGCACGUGUC U | 394 | miR-139 |
| miR-140 | AGUGGUUUUACCCUAUG GUAG | 395 | miR-140; miR-140as; miR-140s |
| miR-141 | AACACUGUCUGGUAAAG AUGG | 396 | miR-141-1; miR-141-2 |
| miR-142-3p | UGUAGUGUUUCCUACUU UAUGGA | 397 | miR-142 |
| miR-142-5p | CAUAAAGUAGAAAGCAC UAC | 398 | miR-142 |
| miR-143 | UGAGAUGAAGCACUGUA GCUCA | 399 | miR-143-1 |
| miR-144 | UACAGUAUAGAUGAUGU ACUAG | 400 | miR-144-1; miR-144-2 |
| miR-145 | GUCCAGUUUUCCCAGGA AUCCCUU | 401 | miR-145-1; miR-145-2 |
| miR-146 | UGAGAACUGAAUUCCAU GGGUU | 402 | miR-146-1; miR-146-2 |
| miR-147 | GUGUGUGGAAAUGCUUC UGC | 403 | miR-147 |
| miR-148a | UCAGUGCACUACAGAAC UUUGU | 404 | miR-148a (miR-148) |
| miR-148b | UCAGUGCAUCACAGAAC UUUGU | 405 | miR-148b |
| miR-149 | UCUGGCUCCGUGUCUUC ACUCC | 406 | miR-149 |
| miR-150 | UCUCCCAACCCUUGUACC AGUG | 407 | miR-150-1; miR-150-2 |
| miR-151 | ACUAGACUGAAGCUCCU UGAGG | 408 | miR-151 |
| miR-152 | UCAGUGCAUGACAGAAC UUGG | 409 | miR-152-1; miR-152-2 |
| miR-153 | UUGCAUAGUCACAAAAG UGA | 410 | miR-153-1-1; miR-153-1-2; miR-153-2-1; miR-153-2-2 |
| miR-154 | UAGGUUAUCCGUGUUGC CUUCG | 411 | miR-154-1; miR-154-2 |
| miR-154* | AAUCAUACACGGUUGAC CUAUU | 412 | miR-154-1; miR-154-2 |
| miR-155 | UUAAUGCUAAUCGUGAU AGGGG | 413 | miR-155 |
| miR-181a | AACAUUCAACGCUGUCG GUGAGU | 414 | miR-181a |
| miR-181b | AACAUUCAUUGCUGUCG GUGGGUU | 415 | miR-181b-1; miR-181b-2 |

TABLE 1b -continued

Human Mature microRNA Sequences.

| Mature miRNA Name | Mature miRNA Sequence (5' to 3') | SEQ ID NO. | Corresponding precursor microRNA(s); see Table 1a |
|---|---|---|---|
| miR-181c | AACAUUCAACCUGUCGG UGAGU | 416 | miR-181c |
| miR-182 | UUUGGCAAUGGUAGAAC UCACA | 417 | miR-182; miR-182as |
| miR-182* | UGGUUCUAGACUUGCCA ACUA | 418 | miR-182; miR-182as |
| miR-183 | UAUGGCACUGGUAGAAU UCACUG | 419 | miR-183 |
| miR-184 | UGGACGGAGAACUGAUA AGGGU | 420 | miR-184-1; miR-184-2 |
| miR-185 | UGGAGAGAAAGGCAGUU C | 421 | miR-185-1; miR-185-2 |
| miR-186 | CAAAGAAUUCUCCUUUU GGGCUU | 422 | miR-186-1; miR-186-2 |
| miR-187 | UCGUGUCUUGUGUUGCA GCCG | 423 | miR-187 |
| miR-188 | CAUCCCUUGCAUGGUGG AGGGU | 424 | miR-188 |
| miR-189 | GUGCCUACUGAGCUGAU AUCAGU | 425 | miR-189-1; miR-189-2 |
| miR-190 | UGAUAUGUUUGAUAUAU UAGGU | 426 | miR-190-1; miR-190-2 |
| miR-191 | CAACGGAAUCCCAAAAG CAGCU | 427 | miR-191-1; miR-191-2 |
| miR-192 | CUGACCUAUGAAUUGAC AGCC | 428 | miR-192 |
| miR-193 | AACUGGCCUACAAAGUC CCAG | 429 | miR-193-1; miR-193-2 |
| miR-194 | UGUAACAGCAACUCCAU GUGGA | 430 | miR-194-1; miR-194-2 |
| miR-195 | UAGCAGCACAGAAAUAU UGGC | 431 | miR-195-1; miR-195-2 |
| miR-196a | UAGGUAGUUUCAUGUUG UUGG | 432 | miR-196a; miR-196a-2 (miR196-2) |
| miR-196b | UAGGUAGUUUCCUGUUG UUGG | 433 | miR-196b |
| miR-197 | UUCACCACCUUCUCCACC CAGC | 434 | miR-197 |
| miR-198 | GGUCCAGAGGGGAGAUA GG | 435 | miR-198 |
| miR-199a | CCCAGUGUUCAGACUAC CUGUUC | 436 | miR-199a-1; miR-199a-2 |
| miR-199a* | UACAGUAGUCUGCACAU UGGUU | 437 | miR-199a-1; miR-199a-2; miR-199s; miR-199b |
| miR-199b | CCCAGUGUUUAGACUAU CUGUUC | 438 | miR-199b |
| miR-200a | UAACACUGUCUGGUAAC GAUGU | 439 | miR-200a |
| miR-200b | CUCUAAUACUGCCUGGU AAUGAUG | 440 | miR-200b |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| miR-200c | AAUACUGCCGGGUAAUG AUGGA | 441 | miR-200c |
| miR-202 | AGAGGUAUAGGGCAUGG GAAGA | 442 | miR-202 |
| miR-203 | GUGAAAUGUUUAGGACC ACUAG | 443 | miR-203 |
| miR-204 | UUCCCUUUGUCAUCCUA UGCCU | 444 | miR-204 |
| miR-205 | UCCUUCAUUCCACCGGA GUCUG | 445 | miR-205 |
| miR-206 | UGGAAUGUAAGGAAGUG UGUGG | 446 | miR-206-1; miR-206-2 |
| miR-208 | AUAAGACGAGCAAAAAG CUUGU | 447 | miR-208 |
| miR-210 | CUGUGCGUGUGACAGCG GCUG | 448 | miR-210 |
| miR-211 | UUCCCUUUGUCAUCCUU CGCCU | 449 | miR-211 |
| miR-212 | UAACAGUCUCCAGUCAC GGCC | 450 | miR-212 |
| miR-213 | ACCAUCGACCGUUGAUU GUACC | 451 | miR-213 |
| miR-214 | ACAGCAGGCACAGACAG GCAG | 452 | miR-214 |
| miR-215 | AUGACCUAUGAAUUGAC AGAC | 453 | miR-215 |
| miR-216 | UAAUCUC AGCUGGCAAC UGUG | 454 | miR-216 |
| miR-217 | UACUGCAUCAGGAACUG AUUGGAU | 455 | miR-217 |
| miR-218 | UUGUGCUUGAUCUAACC AUGU | 456 | miR-218-1; miR-218-2 |
| miR-219 | UGAUUGUCCAAACGCAA UUCU | 457 | miR-219; miR-219-1; miR-219-2 |
| miR-220 | CCACACCGUAUCUGACA CUUU | 458 | miR-220 |
| miR-221 | AGCUACAUUGUCUGCUG GGUUUC | 459 | miR-221 |
| miR-222 | AGCUACAUCUGGCUACU GGGUCUC | 460 | miR-222 |
| miR-223 | UGUCAGUUUGUCAAAUA CCCC | 461 | miR-223 |
| miR-224 | CAAGUCACUAGUGGUUC CGUUUA | 462 | miR-224 |
| miR-296 | AGGGCCCCCCCUCAAUCC UGU | 463 | miR-296 |
| miR-299 | UGGUUUACCGUCCCACA UACAU | 464 | miR-299 |
| miR-301 | CAGUGCAAUAGUAUUGU CAAAGC | 465 | miR-301 |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| miR-302a | UAAGUGCUUCCAUGUUU UGGUGA | 466 | miR-302a |
| miR-302b* | ACUUUAACAUGGAAGUG CUUUCU | 467 | miR-302b |
| miR-302b | UAAGUGCUUCCAUGUUU UAGUAG | 468 | miR-302b |
| miR-302c* | UUUAACAUGGGGGUACC UGCUG | 469 | miR-302c |
| miR-302c | UAAGUGCUUCCAUGUUU CAGUGG | 470 | miR-302c |
| miR-302d | UAAGUGCUUCCAUGUUU GAGUGU | 471 | miR-302d |
| miR-320 | AAAAGCUGGGUUGAGAG GGCGAA | 472 | miR-320 |
| miR-321 | UAAGCCAGGGAUUGUGG GUUC | 473 | miR-321 |
| miR-323 | GCACAUUACACGGUCGA CCUCU | 474 | miR-323 |
| miR-324-5p | CGCAUCCCCUAGGGCAU UGGUGU | 475 | miR-324 |
| miR-324-3p | CCACUGCCCCAGGUGCU GCUGG | 476 | miR-324 |
| miR-325 | CCUAGUAGGUGUCCAGU AAGU | 477 | miR-325 |
| miR-326 | CCUCUGGGCCCUUCCUCC AG | 478 | miR-326 |
| miR-328 | CUGGCCCUCUCUGCCCUU CCGU | 479 | miR-328 |
| miR-330 | GCAAAGCACACGGCCUG CAGAGA | 480 | miR-330 |
| miR-331 | GCCCCUGGGCCUAUCCU AGAA | 481 | miR-331 |
| miR-335 | UCAAGAGCAAUAACGAA AAAUGU | 482 | miR-335 |
| miR-337 | UCCAGCUCCUAUAUGAU GCCUUU | 483 | miR-337 |
| miR-338 | UCCAGCAUCAGUGAUUU UGUUGA | 484 | miR-338 |
| miR-339 | UCCCUGUCCUCCAGGAG CUCA | 485 | miR-339 |
| miR-340 | UCCGUCUCAGUUACUUU AUAGCC | 486 | miR-340 |
| miR-342 | UCUCACACAGAAAUCGC ACCCGUC | 487 | miR-342 |
| miR-345 | UGCUGACUCCUAGUCCA GGGC | 488 | miR-345 |
| miR-346 | UGUCUGCCCGCAUGCCU GCCUCU | 489 | miR-346 |
| miR-367 | AAUUGCACUUUAGCAAU GGUGA | 490 | miR-367 |

TABLE 1b -continued

| Human Mature microRNA Sequences. | | | |
|---|---|---|---|
| Mature miRNA Name | Mature miRNA Sequence (5' to 3') | SEQ ID NO. | Corresponding precursor microRNA(s); see Table 1a |
| miR-368 | ACAUAGAGGAAAUUCCACGUUU | 491 | miR-368 |
| miR-369 | AAUAAUACAUGGUUGAUCUUU | 492 | miR-369 |
| miR-370 | GCCUGCUGGGGUGGAACCUGG | 493 | miR-370 |
| miR-371 | GUGCCGCCAUCUUUUGAGUGU | 494 | miR-371 |
| miR-372 | AAAGUGCUGCGACAUUUGAGCGU | 495 | miR-372 |
| miR-373* | ACUCAAAAUGGGGGCGCUUUCC | 496 | miR-373 |
| miR-373 | GAAGUGCUUCGAUUUUGGGGUGU | 497 | miR-373 |
| miR-374 | UUAUAAUACAACCUGAUAAGUG | 498 | miR-374 |

The present invention encompasses methods of diagnosing or prognosticating whether a subject has, or is at risk for developing, a cancer and/or myeloproliferative disorder. The methods comprise determining the level of at least one miR gene product in a sample from the subject and comparing the level of the miR gene product in the sample to a control. As used herein, a "subject" can be any mammal that has, or is suspected of having, a cancer and/or myeloproliferative disorder. In a preferred embodiment, the subject is a human who has, or is suspected of having, a cancer, myeloproliferative disorder and/or a platelet disorder.

The level of at least one miR gene product can be measured in cells of a biological sample obtained from the subject. For example, a tissue sample can be removed from a subject suspected of having cancer and/or a myeloproliferative disorder by conventional biopsy techniques. In another embodiment, a blood sample can be removed from the subject, and white blood cells can be isolated for DNA extraction by standard techniques. In one embodiment, the blood or tissue sample is obtained from the subject prior to initiation of radiotherapy, chemotherapy or other therapeutic treatment. A corresponding control tissue or blood sample, or a control reference sample (e.g., obtained from a population of control samples), can be obtained from unaffected tissues of the subject, from a normal human individual or population of normal individuals, or from cultured cells corresponding to the majority of cells in the subject's sample. The control tissue or blood sample can then processed along with the sample from the subject, so that the levels of miR gene product produced from a given miR gene in cells from the subject's sample can be compared to the corresponding miR gene product levels from cells of the control sample. Alternatively, a reference sample can be obtained and processed separately (e.g., at a different time) from the test sample and the level of a miR gene product produced from a given miR gene in cells from the test sample can be compared to the corresponding miR gene product level from the reference sample.

In one embodiment, the level of the at least one miR gene product in the test sample is greater than the level of the corresponding miR gene product in the control sample (i.e., expression of the miR gene product is "upregulated"). As used herein, expression of a miR gene product is "upregulated" when the amount of miR gene product in a cell or tissue sample from a subject is greater than the amount of the same gene product in a control (e.g., a reference standard, a control cell sample, a control tissue sample). In another embodiment, the level of the at least one miR gene product in the test sample is less than the level of the corresponding miR gene product in the control sample (i.e., expression of the miR gene product is "downregulated"). As used herein, expression of a miR gene is "downregulated" when the amount of miR gene product produced from that gene in a cell or tissue sample from a subject is less than the amount produced from the same gene in a control cell or tissue sample. The relative miR gene expression in the control and normal samples can be determined with respect to one or more RNA expression standards. The standards can comprise, for example, a zero miR gene expression level, the miR gene expression level in a standard cell line, the miR gene expression level in unaffected tissues of the subject, or the average level of miR gene expression previously obtained for a population of normal human controls (e.g., a control reference standard).

An alteration (i.e., an increase or decrease) in the level of a miR gene product in the sample obtained from the subject, relative to the level of a corresponding miR gene product in a control sample, is indicative of the presence of cancer and/or a myeloproliferative disorder in the subject. In one embodiment, the level of the at least one miR gene product in the test sample is greater than the level of the corresponding miR gene product in the control sample. miR gene products having higher expression levels in cancer cell lines (e.g., AMKL cell lines) than control cells (e.g., in vitro $CD34^+$-differentiated megakaryocytes) are described and exemplified herein (see, e.g., Example 5). In one embodiment, the at least one miR gene product is selected from the group consisting of miR-101, miR-126, miR-99a, miR-99-prec, miR-106, miR-339, miR-99b, miR-149, miR-33, miR-135, miR-20 and combinations thereof. In another embodiment, the at least one miR gene product is selected from the group consisting of miR-101, miR-126, miR-106, miR-20 and miR-135 and combinations thereof. In yet another embodiment, the at least one miR gene product is selected from the group consisting of miR-106, miR-20 and miR-135 and combinations thereof. As described and exemplified herein, the increased expression of such miR gene products discriminates cancerous cells from corresponding non-cancerous cells.

As described herein, the diagnostic and prognostic methods of the invention can be used to diagnose or prognosticate cancers and/or myeloproliferative disorders. In particular embodiments, the diagnostic and prognostic methods are used to diagnose or prognosticate a cancer in a subject, tissue sample, cell sample or fluid sample. The diagnostic and prognostic methods can be used to diagnose or prognosticate any type of cancer. In particular embodiments, the diagnostic and prognostic methods can be used to diagnose or prognosticate a leukemia. In one embodiment, the leukemia that is diagnosed or prognosticated is acute myeloid leukemia (e.g., acute megakaryoblastic leukemia). In other embodiments, the diagnostic and prognostic methods can be used to diagnose or prognosticate multiple myeloma.

The diagnostic and prognostic methods of the invention can also be used to diagnose or prognosticate hematologic malignancies (e.g., myeloproliferative disorders). In one embodiment, the myeloproliferative disorder that is diagnosed or prognosticated is selected from the group consisting of essential thrombocytemia (ET), polycythemia vera (PV), myelodisplasia, myelofibrosis (e.g., agnogenic myeloid metaplasia (AMM) (also referred to as idiopathic myelofibrosis)) and chronic myelogenous leukemia (CML).

In particular embodiments, the diagnostic, prognostic and therapeutic methods of the invention can also be used to diagnose, prognosticate and/or treat platelet disorders (e.g., inherited platelet disorders). For example, the diagnostic, prognostic and therapeutic methods can be used to diagnose, prognosticate and/or treat defects in platelet-vessel wall interactions (i.e., disorders of adhesion). Such adhesion disorders include, e.g., von Willebrand disease (deficiency or defect in plasma vWF) and Bernard-Soulier syndrome (deficiency or defect in GPIb). In other embodiments, the diagnostic, prognostic and therapeutic methods can be used to diagnose, prognosticate and/or treat defects in platelet-platelet interaction (i.e., disorders of aggregation). Such aggregation disorders include, e.g., congenital afibrinogenemia (deficiency of plasma fibrinogen) and glanzmann thrombasthenia (deficiency or defect in GPIIb-IIIa). In other embodiments, the diagnostic, prognostic and therapeutic methods can be used to diagnose, prognosticate and/or treat disorders of platelet secretion and abnormalities of granules. Such disorders of platelet secretion and abnormalities of granules include, e.g., storage pool deficiency and Quebec platelet disorder. In yet other embodiments, the diagnostic, prognostic and therapeutic methods can be used to diagnose, prognosticate and/or treat disorders of platelet secretion and signal transduction (primary secretion defects). Such primary secretion defects include, e.g., defects in platelet-agonist interaction (receptor defects) (e.g., thromboxane $A_2$, collagen, ADP, epinephrine), defects in G-protein activation (e.g., Gaq deficiency, Gas abnormalities, Gai deficiency), defects in phosphatidylinositol metabolism (e.g., phospholipase C-2 deficiency), defects in calcium mobilization, defects in protein phosphorylation (pleckstrin) PKC-y deficiency, and abnormalities in arachidonic acid pathways and thromboxane synthesis (e.g., cyclooxygenase deficiency, thromboxane synthase deficiency). In other embodiments, the diagnostic, prognostic and therapeutic methods can be used to diagnose, prognosticate and/or treat defects in cytoskeletal regulation (e.g., Wiskott-Aldrich syndrome). In still other embodiments, the diagnostic, prognostic and therapeutic methods can be used to diagnose, prognosticate and/or treat disorders of platelet coagulant-protein interaction (membrane phospholipid defects) (e.g., Scott syndrome). Other platelet disorders (e.g., inherited platelet disorders) can also be diagnosed, prognosticated and/or treated using the methods of the invention.

The invention also provides methods of determining the prognosis of a subject with cancer and/or a myeloproliferative disorder. In this method, the level of at least one miR gene product, which is associated with a particular prognosis in cancer and/or a myeloproliferative disorder (e.g., a good or positive prognosis, a poor or adverse prognosis), is measured in a test sample from the subject. An alteration (e.g., an increase, a decrease) in the level of the miR gene product in the test sample, relative to the level of a corresponding miR gene product in a control sample, is indicative of the subject having a cancer and/or myeloproliferative disorder with a particular prognosis. In one embodiment, the miR gene product is associated with an adverse (i.e., poor) prognosis. Examples of an adverse prognosis include, but are not limited to, low survival rate and rapid disease progression. In one embodiment, the level of the at least one miR gene product in the test sample is greater than the level of the corresponding miR gene product in a control sample (i.e., it is upregulated). In a particular embodiment, the at least one miR gene product that is upregulated is selected from the group consisting of miR-101, miR-126, miR-99a, miR-99-prec, miR-106, miR-339, miR-99b, miR-149, miR-33, miR-135, miR-20 and combinations thereof. In another embodiment, the at least one miR gene product that is upregulated is selected from the group consisting of miR-101, miR-126, miR-106, miR-20 and miR-135 and combinations thereof. In yet another embodiment, the at least one miR gene product that is upregulated is selected from the group consisting of miR-106, miR-20 and miR-135 and combinations thereof. The increased expression of such miR gene products can correlate with an adverse prognosis and the severity of a subject's cancer and/or myeloproliferative disorder.

In certain embodiments of the diagnostic and prognostic methods described herein, the level of the at least one miR gene product is measured by reverse transcribing RNA from a test sample obtained from the subject to provide a set of target oligodeoxynucleotides, hybridizing the target oligodeoxynucleotides to a microarray that comprises miRNA-specific probe oligonucleotides to provide a hybridization profile for the test sample, and comparing the test sample hybridization profile to a hybridization profile generated from a control sample.

Identification of targets of particular miR gene products (e.g., those miR gene products exhibiting upregulated or downregulated expression relative to a control sample) can aid in elucidating mechanisms of action of microRNAs. As described and exemplified herein, particular targets and putative targets of select microRNAs were identified (see, e.g., Tables 2, 3 and 5 and Exemplification). For example, the transcription factor MAFB was identified as a target of mi-130a (Example 2). Similarly, HOXA1 was identified as a target of miR-10a (Example 5). For both miRs, direct interaction of the miR with the 3' UTR of its respective target was demonstrated (Examples 2 and 5). Moreover, an inverse relation in the expression of the miR and its respective target were demonstrated. Thus, expression of pre-miR-130a resulted in decreased expression of MAFB (see, e.g., FIG. 2C) while expression of pre-miR-10a resulted in decreased expression of HOXA1 (see, e.g., FIGS. 3C, 3F and 3G). Thus, in one embodiment, expression of target genes of particular microRNAs (e.g., those listed in Tables 2, 3 and 5) can be used to diagnose cancer and/or a myeloproliferative disorder. Such target genes display inverse expression to the respective miR that targets it. One of skill in the art can measure the expression levels of any of these target genes using known methods and/or methods described herein for measuring the expression levels of microRNAs (e.g., quantitative or semi-quantitative RT-PCR, Northern blot analysis, solution hybridization detection, microarray analysis), without undue experimentation. In particular embodiments, the target gene that is measured is MAFB or HOXA1.

The level of the at least one miR gene product can be measured using a variety of techniques that are well known to those of skill in the art (e.g., quantitative or semi-quantitative RT-PCR, Northern blot analysis, solution hybridization detection). In a particular embodiment, the level of at least one miR gene product is measured by reverse transcribing RNA from a test sample obtained from the subject to provide a set of target oligodeoxynucleotides, hybridizing the target oligodeoxynucleotides to one or more miRNA-specific probe oligonucleotides (e.g., a microarray that comprises miRNA-specific probe oligonucleotides) to provide a hybridization profile for the test sample, and comparing the test sample hybridization profile to a hybridization profile generated from a control sample. An alteration in the signal of at least one miRNA in the test sample relative to the control sample is indicative of the subject either having, or being at risk for developing cancer and/or a myeloproliferative disorder. In one embodiment, the signal of at least one miRNA is upregulated, relative to the signal generated from the control sample. In another embodiment, the signal of at least one miRNA is downregulated, relative to the signal generated from the control sample. In a particular embodiment, the microarray comprises miRNA-specific probe oligonucleotides for a substantial portion of all known human miRNAs (e.g., the miRNAs listed in Tables 1a and 1b plus other known or discovered miRNAs). In a further embodiment, the microarray comprises miRNA-specific probe oligonucleotides for one or more miRNAs selected from the group consisting of miR-101, miR-126, miR-99a, miR-99-prec, miR-106, miR-339, miR-99b, miR-149, miR-33, miR-135, miR-20 and a combination thereof. In one embodiment, the microarray comprises miRNA-specific probe oligonucleotides for one or more miRNAs selected from the group consisting of miR-101, miR-126, miR-106, miR-20, miR-135 and a combination thereof.

The microarray can be prepared from gene-specific oligonucleotide probes generated from known miRNA sequences. The array may contain two different oligonucleotide probes for each miRNA, one containing the active, mature sequence and the other being specific for the precursor of the miRNA. The array may also contain controls, such as one or more mouse sequences differing from human orthologs by only a few bases, which can serve as controls for hybridization stringency conditions. tRNAs and other RNAs (e.g., rRNAs, mRNAs) from both species may also be printed on the microchip, providing an internal, relatively stable, positive control for specific hybridization. One or more appropriate controls for non-specific hybridization may also be included on the microchip. For this purpose, sequences are selected based upon the absence of any homology with any known miRNAs.

The microarray may be fabricated using techniques known in the art. For example, probe oligonucleotides of an appropriate length, e.g., 40 nucleotides, are 5'-amine modified at position C6 and printed using commercially available microarray systems, e.g., the GeneMachine OmniGrid™ 100 Microarrayer and Amersham CodeLink™ activated slides. Labeled cDNA oligomer corresponding to the target RNAs is prepared by reverse transcribing the target RNA with labeled primer. Following first strand synthesis, the RNA/DNA hybrids are denatured to degrade the RNA templates. The labeled target cDNAs thus prepared are then hybridized to the microarray chip under hybridizing conditions, e.g., 6×SSPE/30% formamide at 25° C. for 18 hours, followed by washing in 0.75×TNT at 37° C. for 40 minutes. At positions on the array where the immobilized probe DNA recognizes a complementary target cDNA in the sample, hybridization occurs. The labeled target cDNA marks the exact position on the array where binding occurs, allowing automatic detection and quantification. The output consists of a list of hybridization events, indicating the relative abundance of specific cDNA sequences, and therefore the relative abundance of the corresponding complementary miRs, in the patient sample. According to one embodiment, the labeled cDNA oligomer is a biotin-labeled cDNA, prepared from a biotin-labeled primer. The microarray is then processed by direct detection of the biotin-containing transcripts using, e.g., Streptavidin-Alexa647 conjugate, and scanned utilizing conventional scanning methods. Image intensities of each spot on the array are proportional to the abundance of the corresponding miR in the patient sample.

The use of the array has several advantages for miRNA expression detection. First, the global expression of several hundred genes can be identified in the same sample at one time point. Second, through careful design of the oligonucleotide probes, expression of both mature and precursor molecules can be identified. Third, in comparison with Northern blot analysis, the chip requires a small amount of RNA, and provides reproducible results using 2.5 μg of total RNA. The relatively limited number of miRNAs (a few hundred per species) allows the construction of a common microarray for several species, with distinct oligonucleotide probes for each. Such a tool would allow for analysis of trans-species expression for each known miR under various conditions.

In addition to use for quantitative expression level assays of specific miRs, a microchip containing miRNA-specific probe oligonucleotides corresponding to a substantial portion of the miRNome, preferably the entire miRNome, may be employed to carry out miR gene expression profiling, for analysis of miR expression patterns. Distinct miR signatures can be associated with established disease markers, or directly with a disease state.

According to the expression profiling methods described herein, total RNA from a sample from a subject suspected of having a cancer and/or a myeloproliferative disorder is quantitatively reverse transcribed to provide a set of labeled target oligodeoxynucleotides complementary to the RNA in the sample. The target oligodeoxynucleotides are then hybridized to a microarray comprising miRNA-specific probe oligonucleotides to provide a hybridization profile for the sample. The result is a hybridization profile for the sample representing the expression pattern of miRNA in the sample. The hybridization profile comprises the signal from the binding of the target oligodeoxynucleotides from the sample to the miRNA-specific probe oligonucleotides in the microarray. The profile may be recorded as the presence or absence of binding (signal vs. zero signal). More preferably, the profile recorded includes the intensity of the signal from each hybridization. The profile is compared to the hybridization profile generated from a normal (e.g., noncancerous, non-myeloproliferative disorder) control sample or reference sample. An alteration in the signal is indicative of the presence of, or propensity to develop, cancer in the subject.

Other techniques for measuring miR gene expression are also within the skill in the art, and include various techniques for measuring rates of RNA transcription and degradation.

The invention also provides methods of diagnosing whether a subject has, or is at risk for developing, a cancer and/or myeloproliferative disorder with an adverse prognosis. In this method, the level of at least one miR gene product, which is associated with an adverse prognosis in a cancer and/or myeloproliferative disorder, is measured by reverse transcribing RNA from a test sample obtained from the subject to provide a set of target oligodeoxynucleotides. The target oligodeoxynucleotides are then hybridized to one or more miRNA-specific probe oligonucleotides (e.g., a microarray that comprises miRNA-specific probe oligonucleotides) to provide a hybridization profile for the test sample, and the test sample hybridization profile is compared to a hybridization profile generated from a control sample. An alteration in the signal of at least one miRNA in the test sample relative to the control sample is indicative of the subject either having, or being at risk for developing, a cancer and/or myeloproliferative disorder with an adverse prognosis. miRs suitable for use in this method include, e.g., those that are upregulated in cancerous cells (e.g., AMKL cells).

In particular embodiments of the diagnostic, prognostic and therapeutic methods of the invention, as well as the pharmaceutical compositions of the invention, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

As described herein, the level of a miR gene product in a sample can be measured using any technique that is suitable for detecting RNA expression levels in a biological sample. Suitable techniques (e.g., Northern blot analysis, RT-PCR, in situ hybridization) for determining RNA expression levels in a biological sample (e.g., cells, tissues) are well known to those of skill in the art. In a particular embodiment, the level of at least one miR gene product is detected using Northern blot analysis. For example, total cellular RNA can be purified from cells by homogenization in the presence of nucleic acid extraction buffer, followed by centrifugation. Nucleic acids are precipitated, and DNA is removed by treatment with DNase and precipitation. The RNA molecules are then separated by gel electrophoresis on agarose gels according to standard techniques, and transferred to nitrocellulose filters. The RNA is then immobilized on the filters by heating. Detection and quantification of specific RNA is accomplished using appropriately labeled DNA or RNA probes complementary to the RNA in question. See, for example, Molecular Cloning: A Laboratory Manual, J. Sambrook et al., eds., 2nd edition, Cold Spring Harbor Laboratory Press, 1989, Chapter 7, the entire disclosure of which is incorporated by reference.

Suitable probes (e.g., DNA probes, RNA probes) for Northern blot hybridization of a given miR gene product can be produced from the nucleic acid sequences provided in Table 1a and Table 1b and include, but are not limited to, probes having at least about 70%, 75%, 80%, 85%, 90%, 95%, 98% or 99% complementarity to a miR gene product of interest, as well as probes that have complete complementarity to a miR gene product of interest. Methods for preparation of labeled DNA and RNA probes, and the conditions for hybridization thereof to target nucleotide sequences, are described in Molecular Cloning: A Laboratory Manual, J. Sambrook et al., eds., 2nd edition, Cold Spring Harbor Laboratory Press, 1989, Chapters 10 and 11, the disclosures of which are incorporated herein by reference.

For example, the nucleic acid probe can be labeled with, e.g., a radionuclide, such as $^{3}H$, $^{32}P$, $^{33}P$, $^{14}C$, or $^{35}S$; a heavy metal; a ligand capable of functioning as a specific binding pair member for a labeled ligand (e.g., biotin, avidin or an antibody); a fluorescent molecule; a chemiluminescent molecule; an enzyme or the like.

Probes can be labeled to high specific activity by either the nick translation method of Rigby et al. (1977), *J. Mol. Biol.* 113:237-251 or by the random priming method of Fienberg et al. (1983), *Anal. Biochem.* 132:6-13, the entire disclosures of which are incorporated herein by reference. The latter is the method of choice for synthesizing $^{32}P$-labeled probes of high specific activity from single-stranded DNA or from RNA templates. For example, by replacing preexisting nucleotides with highly radioactive nucleotides according to the nick translation method, it is possible to prepare $^{32}P$-labeled nucleic acid probes with a specific activity well in excess of $10^8$ cpm/microgram. Autoradiographic detection of hybridization can then be performed by exposing hybridized filters to photographic film. Densitometric scanning of the photographic films exposed by the hybridized filters provides an accurate measurement of miR gene transcript levels. Using another approach, miR gene transcript levels can be quantified by computerized imaging systems, such as the Molecular Dynamics 400-B 2D Phosphorimager available from Amersham Biosciences, Piscataway, N.J.

Where radionuclide labeling of DNA or RNA probes is not practical, the random-primer method can be used to incorporate an analogue, for example, the dTTP analogue 5-(N—(N-biotinyl-epsilon-aminocaproyl)-3-aminoallyl)deoxyuridine triphosphate, into the probe molecule. The biotinylated probe oligonucleotide can be detected by reaction with biotin-binding proteins, such as avidin, streptavidin and antibodies (e.g., anti-biotin antibodies) coupled to fluorescent dyes or enzymes that produce color reactions.

In addition to Northern and other RNA hybridization techniques, determining the levels of RNA transcripts can be accomplished using the technique of in situ hybridization. This technique requires fewer cells than the Northern blotting technique and involves depositing whole cells onto a microscope cover slip and probing the nucleic acid content of the cell with a solution containing radioactive or otherwise labeled nucleic acid (e.g., cDNA or RNA) probes. This technique is particularly well-suited for analyzing tissue biopsy samples from subjects. The practice of the in situ hybridization technique is described in more detail in U.S. Pat. No. 5,427,916, the entire disclosure of which is incorporated herein by reference. Suitable probes for in situ hybridization of a given miR gene product can be produced from the nucleic acid sequences provided in Table 1a and Table 1b, and include, but are not limited to, probes having at least about 70%, 75%, 80%, 85%, 90%, 95%, 98% or 99% complementarity to a miR gene product of interest, as well as probes that have complete complementarity to a miR gene product of interest, as described above.

The relative number of miR gene transcripts in cells can also be determined by reverse transcription of miR gene transcripts, followed by amplification of the reverse-transcribed transcripts by polymerase chain reaction (RT-PCR), for example, as exemplified herein. The levels of miR gene transcripts can be quantified in comparison with an internal standard, for example, the level of mRNA from a "housekeeping" gene present in the same sample. A suitable "housekeeping" gene for use as an internal standard includes, e.g., U6 small nuclear RNA, myosin or glyceraldehyde-3-phosphate dehydrogenase (G3PDH). Methods for performing quantitative and semi-quantitative RT-PCR, and variations thereof, are well known to those of skill in the art.

In some instances, it may be desirable to simultaneously determine the expression level of a plurality of different miR gene products in a sample. In other instances, it may be desirable to determine the expression level of the transcripts of all known miR genes correlated with a cancer and/or myeloproliferative disorder. Assessing cancer-specific expression levels for hundreds of miR genes or gene products is time consuming and requires a large amount of total RNA (e.g., at least 20 μg for each Northern blot) and autoradiographic techniques that require radioactive isotopes.

To overcome these limitations, an oligolibrary, in microchip format (i.e., a microarray), may be constructed containing a set of oligonucleotide (e.g., oligodeoxynucleotide) probes that are specific for a set of miR genes. Using such a microarray, the expression level of multiple microRNAs in a biological sample can be determined by reverse transcribing the RNAs to generate a set of target oligodeoxynucleotides, and hybridizing them to probe the oligonucleotides on the microarray to generate a hybridization, or expression, profile. The hybridization profile of the test sample can then be compared to that of a control sample to determine which microRNAs have an altered expression level in cancer cells and/or cells exhibiting a myeloproliferative disorder. As used herein, "probe oligonucleotide" or "probe oligodeoxynucleotide" refers to an oligonucleotide that is capable of hybridizing to a target oligonucleotide. "Target oligonucleotide" or "target oligodeoxynucleotide" refers to a molecule to be detected (e.g., via hybridization). By "miR-specific probe oligonucleotide" or "probe oligonucleotide specific for a miR" is meant a probe oligonucleotide that has a sequence selected to hybridize to a specific miR gene product, or to a reverse transcript of the specific miR gene product.

An "expression profile" or "hybridization profile" of a particular sample is essentially a fingerprint of the state of the sample; while two states may have any particular gene similarly expressed, the evaluation of a number of genes simultaneously allows the generation of a gene expression profile that is unique to the state of the cell. That is, normal tissue, cell or fluid samples may be distinguished from corresponding cancerous and/or myeloproliferative disorder-exhibiting tissue, cell or fluid samples. Within cancerous and/or myeloproliferative disorder-exhibiting tissue, cell or fluid samples, different prognosis states (for example, good or poor long term survival prospects) may be determined. By comparing expression profiles of cancerous and/or myeloproliferative disorder-exhibiting tissue, cell or fluid samples in different states, information regarding which genes are important (including both upregulation and downregulation of genes) in each of these states is obtained. The identification of sequences that are differentially expressed in cancerous and/or myeloproliferative disorder-exhibiting tissue, cell or fluid samples, as well as differential expression resulting in different prognostic outcomes, allows the use of this information in a number of ways. For example, a particular treatment regime may be evaluated (e.g., to determine whether a chemotherapeutic drug acts to improve the long-term prognosis in a particular subject). Similarly, diagnosis may be done or confirmed by comparing samples from a subject with known expression profiles. Furthermore, these gene expression profiles (or individual genes) allow screening of drug candidates that suppress the cancer and/or myeloproliferative disorder expression profile or convert a poor prognosis profile to a better prognosis profile.

Without wishing to be bound by any one theory, it is believed that alterations in the level of one or more miR gene products in cells can result in the deregulation of one or more intended targets for these miRs, which can lead to aberrant megakaryocytic differentiation and/or the formation of cancer, a myeloproliferative disorder and/or a platelet disorder. Therefore, altering the level of the miR gene product (e.g., by decreasing the level of a miR that is upregulated in cancerous and/or myeloproliferative disorder-exhibiting cells, by increasing the level of a miR that is downregulated in cancerous and/or myeloproliferative disorder-exhibiting cells) may successfully treat the cancer, myeloproliferative disorder and/or platelet disorder.

Accordingly, the present invention encompasses methods of treating a cancer and/or myeloproliferative disorder in a subject, wherein at least one miR gene product is deregulated (e.g., downregulated, upregulated) in the cells (e.g., cancerous cells and/or myeloproliferative disorder-exhibiting cells) of the subject. In one embodiment, the level of at least one miR gene product in a test sample (e.g., a sample comprising cancerous and/or myeloproliferative disorder-exhibiting tissues, cells or fluid) is greater than the level of the corresponding miR gene product in a control or reference sample. In another embodiment, the level of at least one miR gene product in a test sample (e.g., a sample comprising cancerous and/or myeloproliferative disorder-exhibiting tissues, cells or fluid) is less than the level of the corresponding miR gene product in a control sample. When the at least one isolated miR gene product is downregulated in the test sample (e.g., a sample comprising cancerous and/or myeloproliferative disorder-exhibiting tissues, cells or fluid), the method comprises administering an effective amount of the at least one isolated miR gene product, or an isolated variant or biologically-active fragment thereof, such that proliferation of the cancerous and/or myeloproliferative disorder-exhibiting cells in the subject is inhibited. For example, when a miR gene product is downregulated in a cancer cell in a subject, administering an effective amount of an isolated miR gene product to the subject can inhibit proliferation of the cancer cell. The isolated miR gene product that is administered to the subject can be identical to an endogenous wild-type miR gene product (e.g., a miR gene product shown in Table 1a or Table 1b) that is downregulated in the cancer cell or it can be a variant or biologically-active fragment thereof. As defined herein, a "variant" of a miR gene product refers to a miRNA that has less than 100% identity to a corresponding wild-type miR gene product and possesses one or more biological activities of the corresponding wild-type miR gene product. Examples of such biological activities include, but are not limited to, inhibition of expression of a target RNA molecule (e.g., inhibiting translation of a target RNA molecule, modulating the stability of a target RNA molecule, inhibiting processing of a target RNA molecule) and inhibition of a cellular process associated with cancer and/or a myeloproliferative disorder (e.g., cell differentiation, cell growth, cell death). These variants include species variants and variants that are the consequence of one or more mutations (e.g., a substitution, a deletion, an insertion) in a miR gene. In certain embodiments, the variant is at least about 70%, 75%, 80%, 85%, 90%, 95%, 98%, or 99% identical to a corresponding wild-type miR gene product.

As defined herein, a "biologically-active fragment" of a miR gene product refers to an RNA fragment of a miR gene product that possesses one or more biological activities of a corresponding wild-type miR gene product. As described above, examples of such biological activities include, but are not limited to, inhibition of expression of a target RNA molecule and inhibition of a cellular process associated with cancer and/or a myeloproliferative disorder. In certain embodiments, the biologically-active fragment is at least about 5, 7, 10, 12, 15, or 17 nucleotides in length. In a particular embodiment, an isolated miR gene product can be administered to a subject in combination with one or more additional anti-cancer treatments. Suitable anti-cancer treatments include, but are not limited to, chemotherapy, radiation therapy and combinations thereof (e.g., chemoradiation).

When the at least one isolated miR gene product is upregulated in the cancer cells, the method comprises administering to the subject an effective amount of a compound that inhibits expression of the at least one miR gene product, such that proliferation of the cancer and/or myeloproliferative disorder-exhibiting cells is inhibited. Such compounds are referred to herein as miR gene expression-inhibition compounds. Examples of suitable miR gene expression-inhibition compounds include, but are not limited to, those described herein (e.g., double-stranded RNA, antisense nucleic acids and enzymatic RNA molecules). In a particular embodiment, a miR gene expression-inhibiting compound can be administered to a subject in combination with one or more additional anti-cancer treatments. Suitable anti-cancer treatments include, but are not limited to, chemotherapy, radiation therapy and combinations thereof (e.g., chemoradiation).

As described, when the at least one isolated miR gene product is upregulated in cancer cells (e.g., AMKL cells), the method comprises administering to the subject an effective amount of at least one compound for inhibiting expression of the at least one miR gene product, such that proliferation of cancer cells is inhibited. In one embodiment, the compound for inhibiting expression of the at least one miR gene product inhibits a miR gene product selected from the group consisting of miR-101, miR-126, miR-99a, miR-99-prec, miR-106, miR-339, miR-99b, miR-149, miR-33, miR-135, miR-20 and a combination thereof. In another embodiment, the compound for inhibiting expression of the at least one miR gene product inhibits a miR gene product selected from the group consisting of miR-101, miR-126, miR-106, miR-20, miR-135 and a combination thereof. In yet another embodiment, the compound for inhibiting expression of the at least one miR gene product inhibits a miR gene product selected from the group consisting of miR-106, miR-20, miR-135 and a combination thereof.

As described and exemplified herein, the transcription factor MAFB, which is upregulated in megakaryocytic differentiation, is a target of miR-130a. Moreover, an inverse relation in the expression of miR-130a and its respective target were demonstrated. Thus, expression of pre-miR-130a resulted in decreased expression of MAFB (see, e.g., FIG. 2C). MAFB is known to be deregulated in cancer (e.g., multiple myeloma and acute myeloid leukemia). For example, ectopic expression of MAFB has been observed in human myeloma cells carrying (14; 20)(q32; q11) chromosomal translocations (Hanamura, I., et al. (2001) *Jpn. J. Cancer Res.* 92(6):638-644 (2001)). Accordingly, in one embodiment, the invention is a method of treating a cancer and/or myeloproliferative disorder in a subject comprising administering an effective amount of at least one miR gene product or an isolated variant or biologically-active fragment thereof to the subject, wherein:

the cancer and/or myeloproliferative disorder is associated with overexpression of a MAFB gene product; and the at least one miR gene product binds to, and decreases expression of, the MAFB gene product.

In one embodiment, the at least one miR gene product or isolated variant or biologically-active fragment thereof comprises a nucleotide sequence that is complementary to a nucleotide sequence in the MAFB gene product (e.g., complementary to the 3' UTR of MAFB). In a particular embodiment, the at least one miR gene product is miR-130a or an isolated variant or biologically-active fragment thereof.

Also as described and exemplified herein, mRNA of HOXA1, one of the members of the HOX family of proteins, is upregulated 7-fold in megakaryocytic differentiation (see, e.g., Example 4). Moreover, HOXA1 is a target of miR-10a and its expression is inversely related to the expression of miR-10a. Thus, expression of pre-miR-10a resulted in decreased expression of HOXA1 (see, e.g., FIGS. 3C, 3F and 3G). HOXA1. Expression of HOXA1 has been demonstrated to be sufficient to result in the oncogenic transformation of immortalized human mammary epithelial cells with aggressive in vivo tumor formation (Zhang, X., et al., (2002) *J. Biol. Chem.* 278(9):7580-7590). Further, forced expression of HOXA1 in mammary carcinoma cells, in a Bcl-2-dependent manner, resulted in a dramatic enhancement of anchorage-independent proliferation and colony formation in soft agar. Id. Accordingly, in one embodiment, the invention is a method of treating a cancer and/or myeloproliferative disorder in a subject comprising administering an effective amount of at least one miR gene product or an isolated variant or biologically-active fragment thereof to the subject, wherein:

the cancer and/or myeloproliferative disorder is associated with overexpression of a HOXA1 gene product; and the at least one miR gene product binds to, and decreases expression of, the HOXA1 gene product.

In one embodiment, the at least one miR gene product or isolated variant or biologically-active fragment thereof comprises a nucleotide sequence that is complementary to a nucleotide sequence in the HOXA1 gene product (e.g., complementary to the 3' UTR of HOXA1). In a particular embodiment, the at least one miR gene product is miR-10a or an isolated variant or biologically-active fragment thereof.

In a related embodiment, the methods of treating cancer and/or a myeloproliferative disorder in a subject additionally comprise the step of first determining the amount of at least one miR gene product in a sample from the subject, and comparing that level of the miR gene product to the level of a corresponding miR gene product in a control. If expression of the miR gene product is deregulated (e.g., downregulated, upregulated) in the sample from the subject, the methods further comprise altering the amount of the at least one miR gene product expressed in the sample from the subject. In one embodiment, the amount of the miR gene product expressed in the sample from the subject is less than the amount of the miR gene product expressed in the control, and an effective amount of the miR gene product, or an isolated variant or biologically-active fragment thereof, is administered to the subject. In another embodiment, the amount of the miR gene product expressed in the sample from the subject is greater than the amount of the miR gene product expressed in the control, and an effective amount of at least one compound for inhibiting expression of the at least one miR gene is administered to the subject. Suitable miRs and compounds that inhibit expression of miR genes include, for example, those described herein.

The terms "treat", "treating" and "treatment", as used herein, refer to ameliorating symptoms associated with a disease or condition, for example, cancer and/or a myeloproliferative disorder, including preventing or delaying the onset of the disease symptoms, and/or lessening the severity or frequency of symptoms of the disease or condition. The terms "subject", "patient" and "individual" are defined herein to include animals, such as mammals, including, but not limited to, primates, cows, sheep, goats, horses, dogs, cats, rabbits, guinea pigs, rats, mice or other bovine, ovine, equine, canine, feline, rodent, or murine species. In a preferred embodiment, the animal is a human.

As used herein, an "effective amount" of an isolated miR gene product is an amount sufficient to inhibit proliferation of cells (e.g., cancerous cells, cells exhibiting a myeloproliferative disorder) in a subject suffering from cancer and/or a myeloproliferative disorder. One skilled in the art can readily determine an effective amount of a miR gene product to be administered to a given subject, by taking into account factors, such as the size and weight of the subject; the extent of disease penetration; the age, health and sex of the subject; the route of administration; and whether the administration is regional or systemic.

For example, an effective amount of an isolated miR gene product can be based on the approximate weight of a tumor mass to be treated. The approximate weight of a tumor mass can be determined by calculating the approximate volume of the mass, wherein one cubic centimeter of volume is roughly equivalent to one gram. An effective amount of the isolated miR gene product based on the weight of a tumor mass can be in the range of about 10-500 micrograms/gram of tumor mass. In certain embodiments, the tumor mass can be at least about 10 micrograms/gram of tumor mass, at least about 60 micrograms/gram of tumor mass or at least about 100 micrograms/gram of tumor mass.

An effective amount of an isolated miR gene product can also be based on the approximate or estimated body weight of a subject to be treated. Preferably, such effective amounts are administered parenterally or enterally, as described herein. For example, an effective amount of the isolated miR gene product that is administered to a subject can range from about 5-3000 micrograms/kg of body weight, from about 700-1000 micrograms/kg of body weight, or greater than about 1000 micrograms/kg of body weight.

One skilled in the art can also readily determine an appropriate dosage regimen for the administration of an isolated miR gene product to a given subject. For example, a miR gene product can be administered to the subject once (e.g., as a single injection or deposition). Alternatively, a miR gene product can be administered once or twice daily to a subject for a period of from about three to about twenty-eight days, more particularly from about seven to about ten days. In a particular dosage regimen, a miR gene product is administered once a day for seven days. Where a dosage regimen comprises multiple administrations, it is understood that the effective amount of the miR gene product administered to the subject can comprise the total amount of gene product administered over the entire dosage regimen.

As used herein, an "isolated" miR gene product is one that is synthesized, or altered or removed from the natural state through human intervention. For example, a synthetic miR gene product, or a miR gene product partially or completely separated from the coexisting materials of its natural state, is considered to be "isolated." An isolated miR gene product can exist in a substantially-purified form, or can exist in a cell into which the miR gene product has been delivered. Thus, a miR gene product that is deliberately delivered to, or expressed in, a cell is considered an "isolated" miR gene product. A miR gene product produced inside a cell from a miR precursor molecule is also considered to be an "isolated" molecule. According to the invention, the isolated miR gene products described herein can be used for the manufacture of a medicament for treating cancer and/or a myeloproliferative disorder in a subject (e.g., a human).

Isolated miR gene products can be obtained using a number of standard techniques. For example, the miR gene products can be chemically synthesized or recombinantly produced using methods known in the art. In one embodiment, miR gene products are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., U.S.A.), Pierce Chemical (part of Perbio Science, Rockford, Ill., U.S.A.), Glen Research (Sterling, Va., U.S.A.), ChemGenes (Ashland, Mass., U.S.A.) and Cruachem (Glasgow, UK).

Alternatively, the miR gene products can be expressed from recombinant circular or linear DNA plasmids using any suitable promoter. Suitable promoters for expressing RNA from a plasmid include, e.g., the U6 or H1 RNA pol III promoter sequences, or the cytomegalovirus promoters. Selection of other suitable promoters is within the skill in the art. The recombinant plasmids of the invention can also comprise inducible or regulatable promoters for expression of the miR gene products in cells (e.g., cancerous cells, cells exhibiting a myeloproliferative disorder).

The miR gene products that are expressed from recombinant plasmids can be isolated from cultured cell expression systems by standard techniques. The miR gene products that are expressed from recombinant plasmids can also be delivered to, and expressed directly in, cells (e.g., cancerous cells, cells exhibiting a myeloproliferative disorder). The use of recombinant plasmids to deliver the miR gene products to cells (e.g., cancerous cells, cells exhibiting a myeloproliferative disorder) is discussed in more detail below.

The miR gene products can be expressed from a separate recombinant plasmid, or they can be expressed from the same recombinant plasmid. In one embodiment, the miR gene products are expressed as RNA precursor molecules from a single plasmid, and the precursor molecules are processed into the functional miR gene product by a suitable processing system, including, but not limited to, processing systems extant within a cancer cell. Other suitable processing systems include, e.g., the in vitro *Drosophila* cell lysate system (e.g., as described in U.S. Published Patent Application No. 2002/0086356 to Tuschl et al., the entire disclosure of which is incorporated herein by reference) and the *E. coli* RNAse III system (e.g., as described in U.S. Published Patent Application No. 2004/0014113 to Yang et al., the entire disclosure of which is incorporated herein by reference).

Selection of plasmids suitable for expressing the miR gene products, methods for inserting nucleic acid sequences into the plasmid to express the gene products, and methods of delivering the recombinant plasmid to the cells of interest are within the skill in the art. See, for example, Zeng et al. (2002), *Molecular Cell* 9:1327-1333; Tuschl (2002), *Nat. Biotechnol,* 20:446-448; Brummelkamp et al. (2002), *Science* 296:550-553; Miyagishi et al. (2002), *Nat. Biotechnol.* 20:497-500; Paddison et al. (2002), *Genes Dev.* 16:948-958; Lee et al. (2002), *Nat. Biotechnol.* 20:500-505; and Paul et al. (2002), *Nat. Biotechnol.* 20:505-508, the entire disclosures of which are incorporated herein by reference.

In one embodiment, a plasmid expressing the miR gene products comprises a sequence encoding a miR precursor RNA under the control of the CMV intermediate-early promoter. As used herein, "under the control" of a promoter means that the nucleic acid sequences encoding the miR gene product are located 3' of the promoter, so that the promoter can initiate transcription of the miR gene product coding sequences.

The miR gene products can also be expressed from recombinant viral vectors. It is contemplated that the miR gene products can be expressed from two separate recombinant viral vectors, or from the same viral vector. The RNA expressed from the recombinant viral vectors can either be isolated from cultured cell expression systems by standard techniques, or can be expressed directly in cells (e.g., cancerous cells, cells exhibiting a myeloproliferative disorder). The use of recombinant viral vectors to deliver the miR gene products to cells (e.g., cancerous cells, cells exhibiting a myeloproliferative disorder) is discussed in more detail below.

The recombinant viral vectors of the invention comprise sequences encoding the miR gene products and any suitable promoter for expressing the RNA sequences. Suitable promoters include, but are not limited to, the U6 or H1 RNA pol III promoter sequences, or the cytomegalovirus promoters. Selection of other suitable promoters is within the skill in the art. The recombinant viral vectors of the invention can also comprise inducible or regulatable promoters for expression of the miR gene products in a cancer cell.

Any viral vector capable of accepting the coding sequences for the miR gene products can be used; for example, vectors derived from adenovirus (AV); adeno-associated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate.

For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV 2/5 vector. Techniques for constructing AAV vectors that express different capsid protein serotypes are within the skill in the art; see, e.g., Rabinowitz, J. E., et al. (2002), *J. Virol.* 76:791-801, the entire disclosure of which is incorporated herein by reference.

Selection of recombinant viral vectors suitable for use in the invention, methods for inserting nucleic acid sequences for expressing RNA into the vector, methods of delivering the viral vector to the cells of interest, and recovery of the expressed RNA products are within the skill in the art. See, for example, Dornburg (1995), *Gene Therapy* 2:301-310; Eglitis (1988), *Biotechniques* 6:608-614; Miller (1990), *Hum. Gene Therapy* 1:5-14; and Anderson (1998), *Nature* 392:25-30, the entire disclosures of which are incorporated herein by reference.

Particularly suitable viral vectors are those derived from AV and AAV. A suitable AV vector for expressing the miR gene products, a method for constructing the recombinant AV vector, and a method for delivering the vector into target cells, are described in Xia et al. (2002), *Nat. Biotech.* 20:1006-1010, the entire disclosure of which is incorporated herein by reference. Suitable AAV vectors for expressing the miR gene products, methods for constructing the recombinant AAV vector, and methods for delivering the vectors into target cells are described in Samulski et al. (1987), *J. Virol.* 61:3096-3101; Fisher et al. (1996), *J. Virol.,* 70:520-532; Samulski et al. (1989), *J. Virol.* 63:3822-3826; U.S. Pat. No. 5,252,479; U.S. Pat. No. 5,139,941; International Patent Application No. WO 94/13788; and International Patent Application No. WO 93/24641, the entire disclosures of which are incorporated herein by reference. In one embodiment, the miR gene products are expressed from a single recombinant AAV vector comprising the CMV intermediate early promoter.

In a certain embodiment, a recombinant AAV viral vector of the invention comprises a nucleic acid sequence encoding a miR precursor RNA in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR sequences from the vector, the polyT termination signals act to terminate transcription.

In other embodiments of the treatment methods of the invention, an effective amount of at least one compound that inhibits miR expression can be administered to the subject. As used herein, "inhibiting miR expression" means that the production of the precursor and/or active, mature form of miR gene product after treatment is less than the amount produced prior to treatment. One skilled in the art can readily determine whether miR expression has been inhibited in cells (e.g., cancerous cells, cells exhibiting a myeloproliferative disorder), using, for example, the techniques for determining miR transcript level discussed herein. Inhibition can occur at the level of gene expression (i.e., by inhibiting transcription of a miR gene encoding the miR gene product) or at the level of processing (e.g., by inhibiting processing of a miR precursor into a mature, active miR).

As used herein, an "effective amount" of a compound that inhibits miR expression is an amount sufficient to inhibit proliferation of cells (e.g., cancerous cells, cells exhibiting a myeloproliferative disorder) in a subject suffering from cancer and/or a myeloproliferative disorder. One skilled in the art can readily determine an effective amount of a miR expression-inhibiting compound to be administered to a given subject, by taking into account factors, such as the size and weight of the subject; the extent of disease penetration; the age, health and sex of the subject; the route of administration; and whether the administration is regional or systemic.

For example, an effective amount of the expression-inhibiting compound can be based on the approximate weight of a tumor mass to be treated, as described herein. An effective amount of a compound that inhibits miR expression can also be based on the approximate or estimated body weight of a subject to be treated, as described herein.

One skilled in the art can also readily determine an appropriate dosage regimen for administering a compound that inhibits miR expression to a given subject, as described herein. Suitable compounds for inhibiting miR gene expression include double-stranded RNA (such as short- or small-interfering RNA or "siRNA"), antisense nucleic acids, and enzymatic RNA molecules, such as ribozymes. Each of these compounds can be targeted to a given miR gene product and interfere with the expression (e.g., by inhibiting translation, by inducing cleavage and/or degradation) of the target miR gene product.

For example, expression of a given miR gene can be inhibited by inducing RNA interference of the miR gene with an isolated double-stranded RNA ("dsRNA") molecule which has at least 90%, for example, at least 95%, at least 98%, at least 99%, or 100%, sequence homology with at least a portion of the miR gene product. In a particular embodiment, the dsRNA molecule is a "short or small interfering RNA" or "siRNA."

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence that is substantially identical to a nucleic acid sequence contained within the target miR gene product.

As used herein, a nucleic acid sequence in an siRNA that is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area.

The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in certain embodiments, the siRNA comprises at least one 3' overhang of from 1 to about 6 nucleotides (which includes ribonucleotides or deoxyribonucleotides) in length, from 1 to about 5 nucleotides in length, from 1 to about 4 nucleotides in length, or from about 2 to about 4 nucleotides in length. In a particular embodiment, the 3' overhang is present on both strands of the siRNA, and is 2 nucleotides in length. For example, each strand of the siRNA can comprise 3' overhangs of dithymidylic acid ("TT") or diuridylic acid ("uu").

The siRNA can be produced chemically or biologically, or can be expressed from a recombinant plasmid or viral vector, as described above for the isolated miR gene products. Exemplary methods for producing and testing dsRNA or siRNA molecules are described in U.S. Published Patent Application No. 2002/0173478 to Gewirtz and in U.S. Published Patent Application No. 2004/0018176 to Reich et al., the entire disclosures of both of which are incorporated herein by reference.

Expression of a given miR gene can also be inhibited by an antisense nucleic acid. As used herein, an "antisense nucleic acid" refers to a nucleic acid molecule that binds to target RNA by means of RNA-RNA, RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, peptide nucleic acids (PNA)) that generally comprise a nucleic acid sequence complementary to a contiguous nucleic acid sequence in a miR gene product. The antisense nucleic acid can comprise a nucleic acid sequence that is 50-100% complementary, 75-100% complementary, or 95-100% complementary to a contiguous nucleic acid sequence in a miR gene product. Nucleic acid sequences of particular human miR gene products are provided in Table 1a and Table 1b. Without wishing to be bound by any theory, it is believed that the antisense nucleic acids activate RNase H or another cellular nuclease that digests the miR gene product/antisense nucleic acid duplex.

Antisense nucleic acids can also contain modifications to the nucleic acid backbone or to the sugar and base moieties (or their equivalent) to enhance target specificity, nuclease resistance, delivery or other properties related to efficacy of the molecule. Such modifications include cholesterol moieties, duplex intercalators, such as acridine, or one or more nuclease-resistant groups.

Antisense nucleic acids can be produced chemically or biologically, or can be expressed from a recombinant plasmid or viral vector, as described above for the isolated miR gene products. Exemplary methods for producing and testing are within the skill in the art; see, e.g., Stein and Cheng (1993), *Science* 261:1004 and U.S. Pat. No. 5,849,902 to Woolf et al., the entire disclosures of which are incorporated herein by reference.

Expression of a given miR gene can also be inhibited by an enzymatic nucleic acid. As used herein, an "enzymatic nucleic acid" refers to a nucleic acid comprising a substrate binding region that has complementarity to a contiguous nucleic acid sequence of a miR gene product, and which is able to specifically cleave the miR gene product. The enzymatic nucleic acid substrate binding region can be, for example, 50-100% complementary, 75-100% complementary, or 95-100% complementary to a contiguous nucleic acid sequence in a miR gene product. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described above for the isolated miR gene products. Exemplary methods for producing and testing dsRNA or siRNA molecules are described in Werner and Uhlenbeck (1995), *Nucleic Acids Res.* 23:2092-96; Hammann et al. (1999), *Antisense and Nucleic Acid Drug Dev.* 9:25-31; and U.S. Pat. No. 4,987,071 to Cech et al, the entire disclosures of which are incorporated herein by reference.

Administration of at least one miR gene product, or at least one compound for inhibiting miR expression, will inhibit the proliferation of cells (e.g., cancerous cells, cells exhibiting a myeloproliferative disorder) in a subject who has a cancer and/or a myeloproliferative disorder. As used herein, to "inhibit the proliferation of cancerous cells or cells exhibiting a myeloproliferative disorder" means to kill the cells, or permanently or temporarily arrest or slow the growth of the cells Inhibition of cell proliferation can be inferred if the number of such cells in the subject remains constant or decreases after administration of the miR gene products or miR gene expression-inhibiting compounds. An inhibition of proliferation of cancerous cells or cells exhibiting a myeloproliferative disorder can also be inferred if the absolute number of such cells increases, but the rate of tumor growth decreases.

The number of cancer cells in the body of a subject can be determined by direct measurement, or by estimation from the size of primary or metastatic tumor masses. For example, the number of cancer cells in a subject can be measured by immunohistological methods, flow cytometry, or other techniques designed to detect characteristic surface markers of cancer cells.

The size of a tumor mass can be ascertained by direct visual observation, or by diagnostic imaging methods, such as X-ray, magnetic resonance imaging, ultrasound, and scintigraphy. Diagnostic imaging methods used to ascertain size of the tumor mass can be employed with or without contrast agents, as is known in the art. The size of a tumor mass can also be ascertained by physical means, such as palpation of the tissue mass or measurement of the tissue mass with a measuring instrument, such as a caliper.

The miR gene products or miR gene expression-inhibiting compounds can be administered to a subject by any means suitable for delivering these compounds to cells (e.g., cancer cells, cells exhibiting a myeloproliferative disorder) of the subject. For example, the miR gene products or miR expression-inhibiting compounds can be administered by methods suitable to transfect cells of the subject with these compounds, or with nucleic acids comprising sequences encoding these compounds. In one embodiment, the cells are transfected with a plasmid or viral vector comprising sequences encoding at least one miR gene product or miR gene expression-inhibiting compound.

Transfection methods for eukaryotic cells are well known in the art, and include, e.g., direct injection of the nucleic acid into the nucleus or pronucleus of a cell; electroporation; liposome transfer or transfer mediated by lipophilic materials; receptor-mediated nucleic acid delivery, bioballistic or particle acceleration; calcium phosphate precipitation, and transfection mediated by viral vectors.

For example, cells can be transfected with a liposomal transfer compound, e.g., DOTAP (N-[1-(2,3-dioleoyloxy) propyl]-N,N,N-trimethyl-ammonium methylsulfate, Boehringer-Mannheim) or an equivalent, such as LIPOFECTIN. The amount of nucleic acid used is not critical to the practice of the invention; acceptable results may be achieved with 0.1-100 micrograms of nucleic acid/$10^5$ cells. For example, a ratio of about 0.5 micrograms of plasmid vector in 3 micrograms of DOTAP per $10^5$ cells can be used.

A miR gene product or miR gene expression-inhibiting compound can also be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., peri-tumoral and intra-tumoral injection, intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. Particularly suitable administration routes are injection, infusion and direct injection into the tumor.

In the present methods, a miR gene product or miR gene product expression-inhibiting compound can be administered to the subject either as naked RNA, in combination with a delivery reagent, or as a nucleic acid (e.g., a recombinant plasmid or viral vector) comprising sequences that express the miR gene product or miR gene expression-inhibiting compound. Suitable delivery reagents include, e.g., the Minis Transit TKO lipophilic reagent; LIPOFECTIN; lipofectamine; cellfectin; polycations (e.g., polylysine) and liposomes.

Recombinant plasmids and viral vectors comprising sequences that express the miR gene products or miR gene expression-inhibiting compounds, and techniques for delivering such plasmids and vectors to cancer cells, are discussed herein and/or are well known in the art.

In a particular embodiment, liposomes are used to deliver a miR gene product or miR gene expression-inhibiting compound (or nucleic acids comprising sequences encoding them) to a subject. Liposomes can also increase the blood half-life of the gene products or nucleic acids. Suitable liposomes for use in the invention can be formed from standard vesicle-forming lipids, which generally include neutral or negatively charged phospholipids and a sterol, such as cholesterol. The selection of lipids is generally guided by consideration of factors, such as the desired liposome size and half-life of the liposomes in the blood stream. A variety of methods are known for preparing liposomes, for example, as described in Szoka et al. (1980), *Ann. Rev. Biophys. Bioeng.* 9:467; and U.S. Pat. Nos. 4,235,871, 4,501,728, 4,837,028, and 5,019,369, the entire disclosures of which are incorporated herein by reference.

The liposomes for use in the present methods can comprise a ligand molecule that targets the liposome to cancer cells. Ligands that bind to receptors prevalent in cancer cells, such as monoclonal antibodies that bind to tumor cell antigens, are preferred.

The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the liposome structure. In a particularly preferred embodiment, a liposome of the invention can comprise both an opsonization-inhibition moiety and a ligand.

Opsonization-inhibiting moieties for use in preparing the liposomes of the invention are typically large hydrophilic polymers that are bound to the liposome membrane. As used herein, an opsonization-inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is incorporated herein by reference.

Opsonization-inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) or derivatives thereof; e.g., methoxy PEG or PPG, and PEG or PPG stearate; synthetic polymers, such as polyacrylamide or poly N-vinyl pyrrolidone; linear, branched, or dendrimeric polyamidoamines; polyacrylic acids; polyalcohols, e.g., polyvinylalcohol and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization-inhibiting polymer can be a block copolymer of PEG and either a polyamino acid, polysaccharide, polyamidoamine, polyethyleneamine, or polynucleotide. The opsonization-inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; aminated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or a derivative thereof. Liposomes modified with PEG or PEG-derivatives are sometimes called "PEGylated liposomes."

The opsonization-inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive amination using $Na(CN)BH_3$ and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects, for example, solid tumors, will efficiently accumulate these liposomes; see Gabizon, et al. (1988), Proc. Natl. Acad. Sci., U.S.A., 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR gene products or miR gene expression-inhibition compounds (or nucleic acids comprising sequences encoding them) to tumor cells.

The miR gene products or miR gene expression-inhibition compounds can be formulated as pharmaceutical compositions, sometimes called "medicaments," prior to administering them to a subject, according to techniques known in the art. Accordingly, the invention encompasses pharmaceutical compositions for treating cancer and/or a myeloproliferative disorder.

In one embodiment, the pharmaceutical composition of the invention comprises at least one miR expression-inhibition compound and a pharmaceutically-acceptable carrier. In a particular embodiment, the at least one miR expression-inhibition compound is specific for a miR gene product whose expression is greater in cancer cells than control cells (i.e., it is upregulated). In another embodiment, the miR expression-inhibition compound is specific for one or more miR gene products selected from the group consisting of miR-101, miR-126, miR-99a, miR-99-prec, miR-106, miR-339, miR-99b, miR-149, miR-33, miR-135 and miR-20. In another embodiment, the miR expression-inhibition compound is specific for one or more miR gene products selected from the group consisting of miR-101, miR-126, miR-106, miR-20, and miR-135. In yet another embodiment, the miR expression-inhibition compound is specific for one or more miR gene products selected from the group consisting of miR-106, miR-20 and miR-135.

In other embodiments, the pharmaceutical compositions comprise an effective amount of at least one miR gene product, or an isolated variant or biologically-active fragment thereof, and a pharmaceutically-acceptable carrier. In one embodiment, the invention is a pharmaceutical composition for treating a cancer and/or a myeloproliferative disorder, wherein the cancer and/or myeloproliferative disorder is associated with overexpression of a MAFB gene product. In this embodiment, the pharmaceutical composition comprises at least one miR gene product that binds to, and decreases expression of, the MAFB gene product. In a particular embodiment, the at least one miR gene product comprises a nucleotide sequence that is complementary to a nucleotide sequence in the MAFB gene product. In another embodiment, the at least one miR gene product is miR-130a or an isolated variant or biologically-active fragment thereof.

In one embodiment, the invention is a pharmaceutical composition for treating a cancer and/or a myeloproliferative disorder, wherein the cancer and/or myeloproliferative disorder is associated with overexpression of a HOXA1 gene product. In this embodiment, the pharmaceutical composition comprises at least one miR gene product that binds to, and decreases expression of, the HOXA1 gene product. In a particular embodiment, the at least one miR gene product comprises a nucleotide sequence that is complementary to a nucleotide sequence in the HOXA1 gene product. In another embodiment, the at least one miR gene product is miR-10a or an isolated variant or biologically-active fragment thereof.

Pharmaceutical compositions of the present invention are characterized as being at least sterile and pyrogen-free. As used herein, "pharmaceutical compositions" include formulations for human and veterinary use. Methods for preparing pharmaceutical compositions of the invention are within the skill in the art, for example, as described in Remington's Pharmaceutical Science, 17th ed., Mack Publishing Company, Easton, Pa. (1985), the entire disclosure of which is incorporated herein by reference.

The present pharmaceutical compositions comprise at least one miR gene product or miR gene expression-inhibition compound (or at least one nucleic acid comprising a sequence encoding the miR gene product or miR gene expression-inhibition compound) (e.g., 0.1 to 90% by weight), or a physiologically-acceptable salt thereof, mixed with a pharmaceutically-acceptable carrier. In certain embodiments, the pharmaceutical composition of the invention additionally comprises one or more anti-cancer agents (e.g., chemotherapeutic agents). The pharmaceutical formulations of the invention can also comprise at least one miR gene product or miR gene expression-inhibition compound (or at least one nucleic acid comprising a sequence encoding the miR gene product or miR gene expression-inhibition compound), which are encapsulated by liposomes and a pharmaceutically-acceptable carrier. In one embodiment, the pharmaceutical composition comprises a miR gene or gene product that is not miR-15, miR-16, miR-143 and/or miR-145.

Especially suitable pharmaceutically-acceptable carriers are water, buffered water, normal saline, 0.4% saline, 0.3% glycine, hyaluronic acid and the like.

In a particular embodiment, the pharmaceutical compositions of the invention comprise at least one miR gene product or miR gene expression-inhibition compound (or at least one nucleic acid comprising a sequence encoding the miR gene product or miR gene expression-inhibition compound) that is resistant to degradation by nucleases. One skilled in the art can readily synthesize nucleic acids that are nuclease resistant, for example by incorporating one or more ribonucleotides that is modified at the 2'-position into the miR gene product. Suitable 2'-modified ribonucleotides include those modified at the 2'-position with fluoro, amino, alkyl, alkoxy and O-allyl.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized For solid pharmaceutical compositions of the invention, conventional nontoxic solid pharmaceutically-acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the at least one miR gene product or miR gene expression-inhibition compound (or at least one nucleic acid comprising sequences encoding them). A pharmaceutical composition for aerosol (inhalational) administration can comprise 0.01-20% by weight, preferably 1%-10% by weight, of the at least one miR gene product or miR gene expression-inhibition compound (or at least one nucleic acid comprising a sequence encoding the miR gene product or miR gene expression-inhibition compound) encapsulated in a liposome as described above, and a propellant. A carrier can also be included as desired; e.g., lecithin for intranasal delivery.

The pharmaceutical compositions of the invention can further comprise one or more anti-cancer agents. In a particular embodiment, the compositions comprise at least one miR gene product or miR gene expression-inhibition compound (or at least one nucleic acid comprising a sequence encoding the miR gene product or miR gene expression-inhibition compound) and at least one chemotherapeutic agent. Chemotherapeutic agents that are suitable for the methods of the invention include, but are not limited to, DNA-alkylating agents, anti-tumor antibiotic agents, anti-metabolic agents, tubulin stabilizing agents, tubulin destabilizing agents, hormone antagonist agents, topoisomerase inhibitors, protein kinase inhibitors, HMG-CoA inhibitors, CDK inhibitors, cyclin inhibitors, caspase inhibitors, metalloproteinase inhibitors, antisense nucleic acids, triple-helix DNAs, nucleic acids aptamers, and molecularly-modified viral, bacterial and exotoxic agents. Examples of suitable agents for the compositions of the present invention include, but are not limited to, cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel and FOLFOX4.

The invention also encompasses methods of identifying an anti-cancer agent, comprising providing a test agent to a cell and measuring the level of at least one miR gene product in the cell. In one embodiment, the method comprises providing a test agent to a cell and measuring the level of at least one miR gene product associated with increased expression levels in cancer cells (e.g., in AMKL cells). A decrease in the level of the miR gene product that is associated with increased expression levels in cancer, relative to a suitable control (e.g., the level of the miR gene product in control cells), is indicative of the test agent being an anti-cancer agent. In a particular embodiment, the at least one miR gene product associated with increased expression levels in cancer cells is selected from the group consisting of miR-101, miR-126, miR-99a, miR-99-prec, miR-106, miR-339, miR-99b, miR-149, miR-33, miR-135 and miR-20. In another embodiment, the at least one miR gene product associated with increased expression levels in cancer cells is selected from the group consisting of miR-101, miR-126, miR-106, miR-20 and miR-135. In yet another embodiment, the at least one miR gene product associated with increased expression levels in cancer cells is selected from the group consisting of miR-106, miR-20 and miR-135. In one embodiment, the miR gene product is not one or more of let7a-2, let-7c, let-7g, let-7i, miR-7-2, miR-7-3, miR-9, miR-9-1, miR-10a, miR-15a, miR-15b, miR-16-1, miR-16-2, miR-17-5p, miR-20a, miR-21, miR-24-1, miR-24-2, miR-25, miR-29b-2, miR-30, miR-30a-5p, miR-30c, miR-30d, miR-31, miR-32, miR-34, miR-34a, miR-34a prec, miR-34a-1, miR-34a-2, miR-92-2, miR-96, miR-99a, miR-99b prec, miR-100, miR-103, miR-106a, miR-107, miR-123, miR-124a-1, miR-125b-1, miR-125b-2, miR-126*, miR-127, miR-128b, miR-129, miR-129-1/2 prec, miR-132, miR-135-1, miR-136, miR-137, miR-141, miR-142-as, miR-143, miR-146, miR-148, miR-149, miR-153, miR-155, miR 159-1, miR-181, miR-181b-1, miR-182, miR-186, miR-191, miR-192, miR-195, miR-196-1, miR-196-1 prec, miR-196-2, miR-199a-1, miR-199a-2, miR-199b, miR-200b, miR-202, miR-203, miR-204, miR-205, miR-210, miR-211, miR-212, miR-214, miR-215, miR-217, miR-221 and/or miR-223.

In one embodiment, the method comprises providing a test agent to a cell and measuring the level of at least one miR gene product associated with decreased expression levels in cancerous cells. An increase in the level of the miR gene product in the cell, relative to a suitable control (e.g., the level of the miR gene product in a control cell), is indicative of the test agent being an anti-cancer agent.

Suitable agents include, but are not limited to drugs (e.g., small molecules, peptides), and biological macromolecules (e.g., proteins, nucleic acids). The agent can be produced recombinantly, synthetically, or it may be isolated (i.e., purified) from a natural source. Various methods for providing such agents to a cell (e.g., transfection) are well known in the art, and several of such methods are described hereinabove. Methods for detecting the expression of at least one miR gene product (e.g., Northern blotting, in situ hybridization, RT-PCR, expression profiling) are also well known in the art. Several of these methods are also described herein.

The invention will now be illustrated by the following non-limiting examples.

EXEMPLIFICATION

Unless otherwise noted, the following materials and methods were used in the Examples.

Materials and Methods

Cell Lines and Human $CD34^+$ Cells.

The human chronic myeloid leukemia (CML) blast crisis cell lines K-562 and MEG-01 were obtained from American Type Tissue Culture (ATCC, Manassas, Va.) and maintained in RPMI 1640 (GIBCO, Carlsbad, Calif.) containing 10% FBS with penicillin-gentamycin at 37° C. with 5% CO2. The human megakaryoblastic leukemia cells UT-7, and CMK, and the chronic myeloid leukemia (CML) in blast crisis LAMA were obtained from DSMZ (Braunsweig, Germany). All cells were maintained in RPMI medium 1640 with 20% FBS and antibiotics, except UT-7 which is factor-dependent and was cultured in MEM—with 20% FBS and 5 ng/ml GM-CSF. Fresh and frozen human bone marrow $CD34^+$ cells were obtained from Stemcell Technologies (Vancouver, B. C., Canada). FACS analysis for CD34 antigen revealed a purity >98%.

Human Progenitor $CD34^+$ Cell Cultures.

Human bone marrow $CD34^+$ cells were grown in STEM-media (Stemcell Technologies), which includes Isocove modified Dulbecco's medium supplemented with human transferrin, insulin, bovine serine albumin, human low density lipoprotein and glutamine, in the presence of 100 ng/ml human recombinant thrombopoietin (TPO) for the first 4 days, followed by a combination of 100 ng/ml TPO, IL3, and SCF (cytokine mixture CC-200, Stemcell Technologies). The initial cell density was 100,000 cells/ml; three times a week, the cell density was adjusted to 100,000 to 200,000 cells/ml. To increase the purity of the cells for microarray analysis, cell sorting was performed at day 10 of culture. Cells were incubated on ice for 45 minutes with anti-human $CD34^+$, anti-human $CD41^+$, anti-human $CD61^+$, and their respective isotypes. After washing twice with PBS 3% FBS, cells were sorted using a FACS Aria sorting machine in bulk in two separate populations; $CD34^-CD61^+$ and $CD34^+CD61^+$ cells for culture and RNA extraction. The purity of the sorted populations was greater than 95%.

Megakaryocytes Characterization.

Cytospin preparations of $CD34^+$ progenitors in culture were performed and stained with May—Grunwald Giemsa at different time points during the megakaryocytic differentiation induction. For FACS analysis, the primary antibodies that were used were as follows: CD41A, CD61A, CD42B, and CD34 with their respective isotypes (BD Pharmingen, San Diego, Calif.). Cytometric studies were performed as previously described (Tajima, S., et al. (1996) *J. Exp. Med.* 184, 1357-1364) using a FACScalibur (BD Biosciences) and the CELLQUEST software (BD Biosciences).

RNA Extraction, Northern Blotting and miRNA Microarray Experiments.

Procedures were performed as described in detail elsewhere (Liu, C. G., et al. (2002) *Proc. Natl. Acad. Sci. USA* 101, 9740-9744). Raw data were normalized and analyzed in GENESPRING 7.2 software (zcomSilicon Genetics, Redwood City, Calif.). Expression data were median-centered by using both GENESPRING normalization option and global median normalization of the BIOCONDUCTOR package with similar results. Statistical comparisons were done by using the GENESPRING ANOVA tool, predictive analysis of microarray (PAM) and the significance analysis of microarray (SAM) software.

Reverse Transcriptase PCR (RT-PCR) and Real Time PCR.

Total RNA isolated with Trizol reagent (Invitrogen, Carlsbad, Calif.) was processed after DNAase treatment (Ambion, Austin, Tex.) directly to cDNA by reverse transcription using Superscript II (Invitrogen). Comparative real-time PCR was performed in triplicate. Primers and probes were obtained from Applied Biosystems (Foster City, Calif.) for the following genes: HOXA1, HOXA3, HOXB4, HOXB5, and HOXD10. Gene expression levels were quantified by using the ABI Prism 7900 Sequence detection system (Applied Biosystems). Normalization was performed by using the 18S RNA primer kit. Relative expression was calculated by using the computed tomography (CT) method. RT-PCR also was performed by using the following oligonucleotide primers:

```
MAFB FW;
                                    (SEQ ID NO: 499)
5'-AACTTTGTCTTGGGGGACAC-3';

MAFB RW;
                                    (SEQ ID NO: 500)
5'-GAGGGGAGGATCTGTTTTCC-3';
```

-continued

```
HOXA1 FW;
                                    (SEQ ID NO: 501)
5'-CCAGGAGCTCAGGAAGAAGA GAT-3';
and

HOXA1 RW;
                                    (SEQ ID NO: 502)
5'-CCCTCTGAGGCATCTGATTGGGTTT-3'.
```

Real-Time Quantification of miRNAs by Stem-Loop RT-PCR.

Real time-PCR for pri-miRNAs 10a, miR15a, miR16-1, miR-130a, miR-20, miR-106, miR-17-5, miR-181b, miR-99a, and miR-126 were performed as described (Chen, C., et al. (2005) *Nucl. Acids Res.* 33, e179. 18S was used for normalization. All reagents and primers were obtained from Applied Biosystems.

Bioinformatics.

miRNA target prediction of the differentially expressed miRNAs was performed by using TARGETSCAN, MIRANDA, and PICTAR software.

Cell Transfection with miRNA Precursors.

miRNA precursors miR-10a and miR-130a were purchased from Ambion. Five million K562 cells were nucleoporated by using Amaxa (Gaithesburg, Md.) with 5 μg of precursor oligonucleotides in a total volume of 10 ml. The expression of the oligonucleotides was assessed by Northern blots and RT-PCR as described.

Luciferase Reporter Experiments.

The 3' UTR segments containing the target sites for miR-10a and miR-130a from HOXA1 and MAFB genes, respectively, were amplified by PCR from genomic DNA and inserted into the pGL3 control vector (Promega, Madison, Wis.), by using the XbaI site immediately downstream from the stop codon of luciferase. The following oligonucleotide primer sets were used to generate specific fragments:

```
MAFB FW
                                    (SEQ ID NO: 503)
5'-GCATCTAGAGCACCCCAGAGGAGTGT-3';

MAFB RW
                                    (SEQ ID NO: 504)
5'-GCATCTAGACAAGCACCATGCGGTTC-3';

HOXA1 FW
                                    (SEQ ID NO: 505)
5'-TACTCTAGACCAGGAGCTCAGGAAGA-3';
and

HOXA1 RW
                                    (SEQ ID NO: 506)
5'-MCATTCTAGATGAGGCATCTGATTGGG-3'.
```

We also generated two inserts with deletions of 5 by and 9 bp, respectively, from the site of perfect complementarity by using the QuikChange XL-site directed Mutagenesis Kit (Stratagene, La Jolla, Calif.). Wild type (WT) and mutant insert were confirmed by sequencing.

Human chronic myeloid leukemia (CML) in megakaryoblastic crisis cell line (MEG-01) was cotransfected in six-well plates by using Lipofectamine 2000 (Invitrogen) according to the manufacturer's protocol with 0.4 μg of the firefly luciferase report vector and 0.08 μg of the control vector containing *Renilla luciferase*, pRL-TK (Promega). For each well, 10 nM of the premiR-130a and premiR-10a precursors (Ambion) were used. Firefly and *Renilla* luciferase activities were measured consecutively by using the dual luciferase assays (Promega) 24 hours after transfection.

Western Blots.

Total and nuclear protein extracts from K562 cells transfected with miR-10a and miR-130a, as well as $CD34^+$ cells at different stages of megakaryocytic differentiation were extracted by using RIPA buffer or Nuclear extraction Kit (Pierce, Rockford, Ill.). Protein expression was analyzed by Western blotting with the following primary antibodies: MAFB (Santa Cruz Biotechnology, Santa Cruz, Calif.), HOXA1 (R&D Systems, Minneapolis, Minn.), β-Actin and Nucleolin (Santa Cruz Biotechnology). Appropriate secondary antibodies were used (Santa Cruz Biotechnology).

Example 1 miRNA Expression During In Vitro Megakaryocytic Differentiation of $CD34^+$ Progenitors Using a combination of a specific megakaryocytic growth factor (thrombopoietin) and nonspecific cytokines (SCF and IL-3), we were able to generate in vitro pure, abundant megakaryocyte progeny from $CD34^+$ bone marrow progenitors suitable for microarray studies (FIG. 4). Total RNA was obtained for miRNA chip analysis from three different CD34 progenitors at baseline and at days 10, 12, 14 and 16 of culture with cytokines. We initially compared the expression of miRNA between the $CD34^+$ progenitors and the pooled $CD34^+$ differentiated megakaryocytes at all points during the differentiation process. 17 miRNAs (Table 1) that are sharply down regulated during megakaryocytic differentiation were identified. There were no statistically significant miRNAs upregulated during megakaryocytic differentiation. Using predictive analysis of microarray (PAM), we identified 8 microRNAs that predicted megakaryocytic differentiation with no misclassification error: miR-10a, miR-10b, miR-30c, miR-106, miR-126, miR-130a, miR-132, and miR-143. All of these miRNAs, except miR-143, are included in the 17 miRNAs identified by significance analysis of microarray (SAM). Northern blots and real-time PCR for several miRNAs confirmed the results obtained by miRNA chip analysis (FIG. 1).

Because we found mainly downregulation of miRNAs during megakaryocytopoiesis, we hypothesized that these miRNAs may unblock target genes involved in differentiation. In line with this hypothesis, miRNAs that are sharply downregulated in our system are predicted to target genes with important roles in megakaryocytic differentiation. Among the transcription factors with well-known function in megakaryocytopoiesis, RUNX-1 (Elagib, K. E., et al. (2003) *Blood,* 101:4333-4341), Fli-1 (Athanasoiu, M., et al. (1996) *Cell Growth Differ.* 7, 1525-1534), FLT1 (Casella, I., et al. (2003) *Blood* 101, 1316-1323), ETV6 (Hock, H., et al. (2004) *Genes Dev.* 18:2336-2341), TAL1 (Begley, C. G., and Green, A. R. (1999) *Blood,* 93:2760-2770), ETS1 (Jackers, P., et al. (2004) *J. Biol. Chem.* 279:52183-52190) and CRK (Lannutti, B. J., et al. (2003) *Exp. Hematol.* 12:1268-1274) are putative targets for several miRNAs downregulated in differentiated megakaryocytes. Moreover, each of these transcription factors has more than one miRNA predicted to be its regulator. For example, RUNX1 (AML1) is predicted to be the target of miR-106, miR-181b, miR-101, let7d and the miR-17-92 cluster. The multiplicity of miRNAs predicted to target AML1 suggests a combinatorial model of regulation.

Figure 1C:
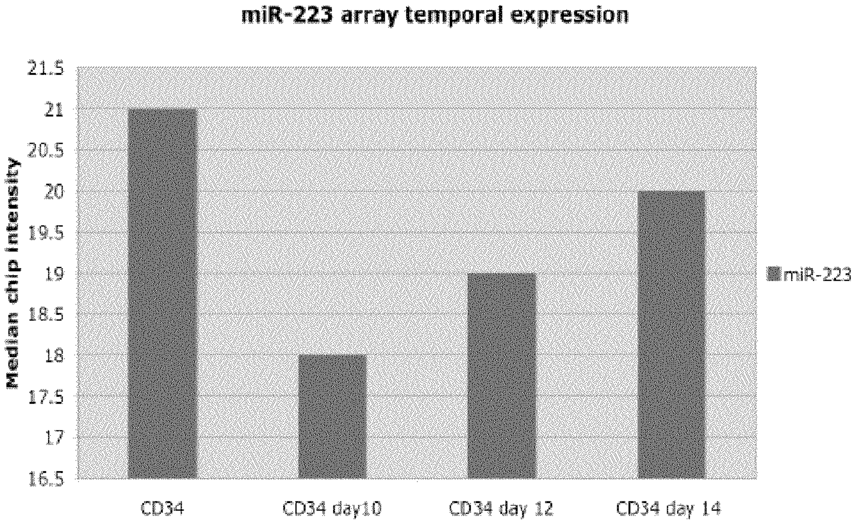
Figure 1D:
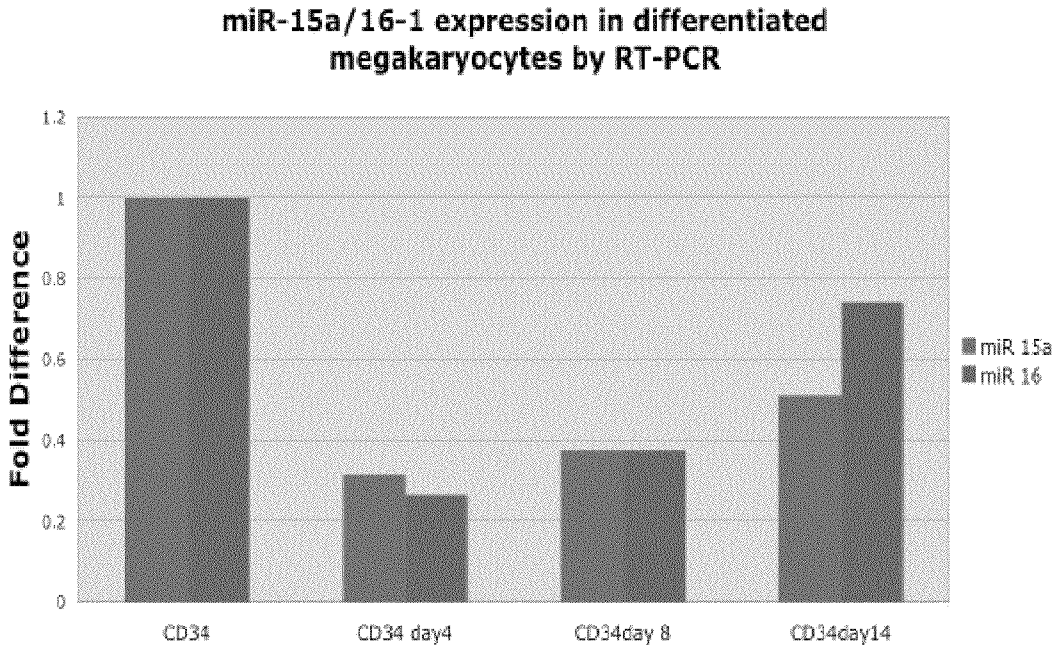
Figure 5:
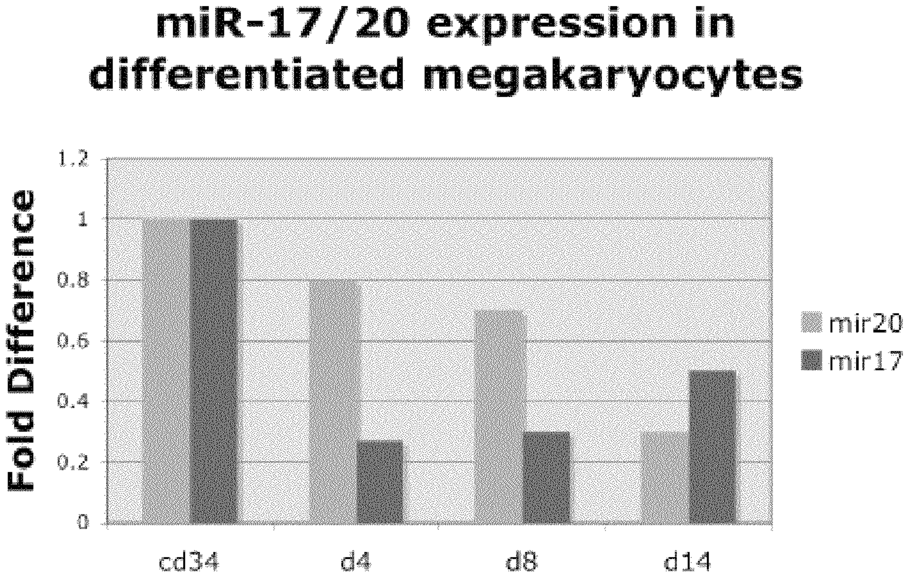
FIG. 5 is a graph depicting RT-PCR expression results for miR-20 and miR-17 in differentiated megakaryocytes. The results are presented as fold difference with respect to $CD34^+$ cells at baseline after normalization with 18S and delta Ct calculations.
Figure 6A:
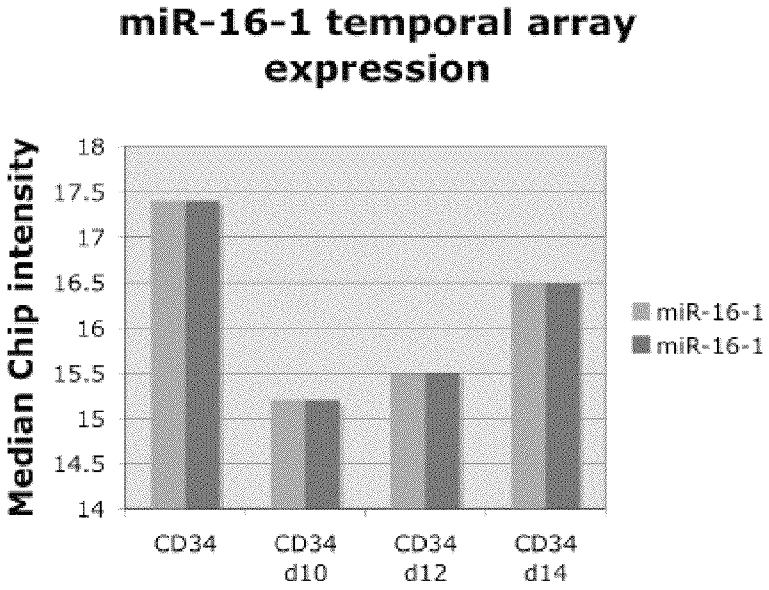
FIG. 6A is a graph depicting temporal expression of miR-16-1 during megakaryocytic differentiation. The absolute expression value of miR-16-1 was determined by a per-chip median normalization.
Figure 6B:
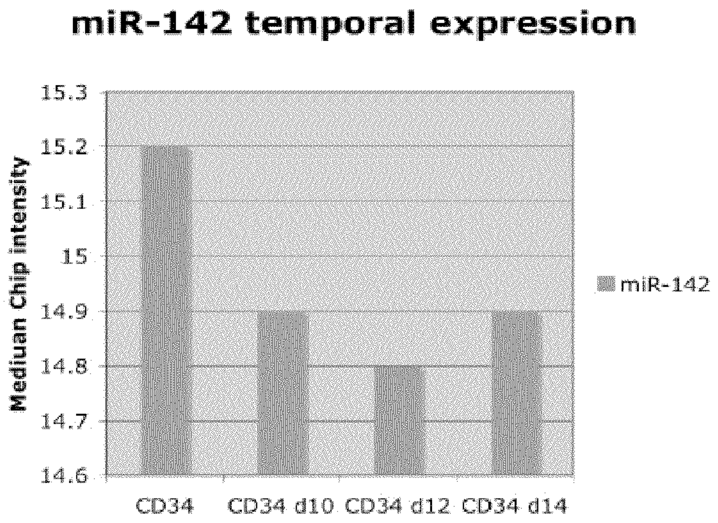
FIG. 6B is a graph depicting temporal expression of miR-142 during megakaryocytic differentiation. The absolute expression value of miR-142 was determined by a per-chip median normalization.
Figure 6C:
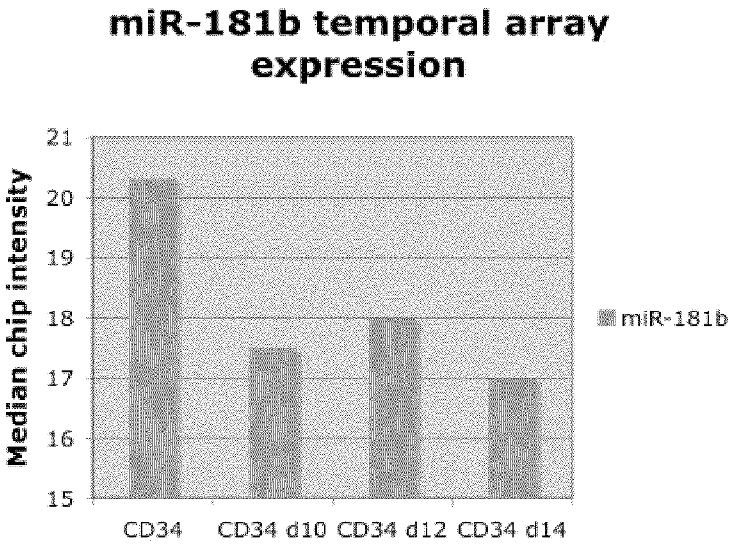
FIG. 6C is a graph depicting temporal expression of miR-181b during megakaryocytic differentiation. The absolute expression value of miR-181b was determined by a per-chip median normalization.

We then looked at the temporal expression of miRNAs during the megakaryocytic differentiation process from $CD34^+$ progenitors. We focused on miRNAs that have been described in hematopoietic tissues, such as miR-223, miR-181, miR-155, miR-142, miR-15a, miR-16, miR-106 and the cluster of miR-17-92 (FIG. 5). We found sequential changes in the expression of miR-223. Initially, miR-223 is downregulated during megakaryocytic differentiation, but after 14 days in culture, its expression returns to levels comparable with that of CD34 progenitors (FIG. 1C). The miR-15a and miR-16-1 cluster also follows the same pattern of expression as miR-223 (FIG. 1D), whereas miR-181b, miR-155, miR-106a, miR-17, and miR-20 were downregulated during differentiation (FIG. 6). The temporal variation of the expression of miR-223 and miR-15a/mir-16-1 suggests a stage-specific function.

TABLE 2 miRNAs downregulated during in vitro $CD34^+$ megakaryocytic differentiation. All differentially expressed miRNAs have q value <0.01 (false-positive rate).

| miRNA | Chromosomal Location | T-test (†) | Fold Change | Putative targets |
|---|---|---|---|---|
| hsa-mir-010a* | 17 q21 | −9.10 | 50.00 | HOXA1, HOXA3, HOXD10, CRK, FLT1 |
| hsa-mir-126* | 9q34 | −2.73 | 8.33 | CRK , EVI2, HOXA9, MAFB, CMAF |
| hsa-mir-106* | xq26.2 | −2.63 | 2.86 | TAL1, FLT1, SKI, RUNX1, FOG2, FLI, PDGFRA, CRK |
| hsa-mir-010b* | 2q31 | −2.17 | 11.11 | HOXA1, HOXA3, HOXD10, ETS-1, CRK, FLT1 |
| hsa-mir-130a* | 11q12 | −2.08 | 4.76 | MAFB, MYB, FOG2, CBFB, PDGFRA, SDFR1, CXCL12 |
| hsa-mir-130a-prec* | 11q12 | −2.07 | 7.69 | NA± |
| hsa-mir-124a | 8q23 | −1.81 | 2.78 | TAL1, SKI, FLT1, FOG2, ETS-1, CBFB, RAF1, MYB |
| hsa-mir-032-prec | 9q31 | −1.76 | 3.57 | NA± |
| hsa-mir-101 | 1p31.3 | −1.75 | 3.33 | TAL1, CXCL12, MEIS1, MEIS2, ETS-1 RUNX1, MYB |
| hsa-mir-30c | 6q13 | −1.71 | 2.56 | CBFB, MAFG, HOXA1, SBF1, NCOR2, ERG |
| hsa-mir-213* | 1q31.3 | −1.69 | 2.38 | MAX-SATB2 |
| hsa-mir-132-prec | 17p13 | −1.67 | 4.17 | NA± |

TABLE 2-continued miRNAs downregulated during in vitro CD34+ megakaryocytic differentiation. All differentially expressed miRNAs have q value <0.01 (false-positive rate).

| miRNA | Chromosomal Location | T-test (†) | Fold Change | Putative targets |
|---|---|---|---|---|
| hsa-mir-150* | 19q13.3 | −1.63 | 5.26 | MYB, SDFR1 |
| hsa-mir-020 | 13q31 | −1.62 | 2.17 | TAL1, SKI, RUNX-1, FLT1, CRK, FOG2, RARB |
| hsa-mir-339 | 7p22 | −1.60 | 3.03 | SKI, ETV6, GATA2, FLT1, RAP1B, JUNB, MEIS2 |
| hsa-let-7a | 9q22 | −1.58 | 2.94 | HOXA1, HOXA9, MEIS2, ITGB3, PLDN |
| hsa-let-7d | 9q22 | −1.56 | 2.17 | HOXA1, HOXD1, ITGB3, RUNX1, PDGFRA |
| hsa-mir-181c | 19p13 | −1.55 | 2.50 | RUNX-1, KIT, HOXA1, MEIS2, ETS-1 ETV6, PDGFRA |
| hsa-mir-181b | 1q31.3 | −1.53 | 2.13 | RUNX-1, KIT, ITGA3, HOXA1, MEIS2, ETS-1, SDFR1, |
| hsa-mir-017 | 13q31 | −1.38 | 1.82 | TAL1, SKI, FLT1, RUNX1, CRK, FOG1, ETS-1, MEIS1 |

† t test $p < 0.05$.

*These miRNAs were identified by PAM as predictors of a megakaryocytic class with the lowest misclassification error. All, except miR-143 are downregulated during megakaryocytic differentiation.

NA±: miRNA precursor sequence that does not contain the mature miRNA, therefore no putative target is shown.

Example 2

MAFB Transcription Factor is a Target of miR-130a

Figure 2A:
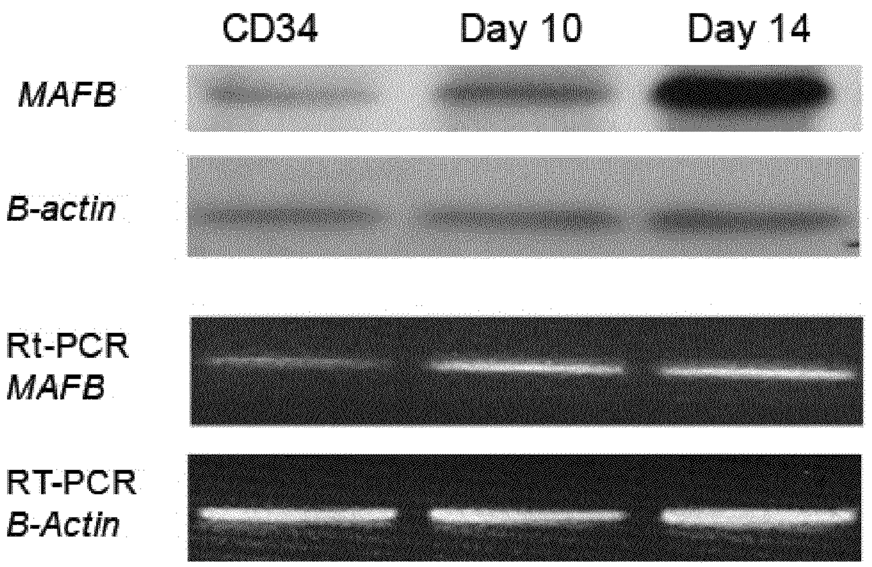

By using three target prediction algorithms (TARGETSCAN, MIRANDA, and PICTAR), we identified that miR-130a is predicted to target MAFB, a transcription factor that is upregulated during megakaryocytic differentiation and induces the GPIIb gene, in synergy with GATA1, SP1 and ETS-1 (Sevinsky, J. R., et al. (2004) *Mol. Cell. Biol.* 24, 4534-4545). To investigate this putative interaction, first, we examined MAFB protein and mRNA levels in CD34+ progenitors at baseline and after cytokine stimulation (FIG. 2A). We found that the MAFB protein is upregulated during in vitro megakaryocytic differentiation. Although the mRNA levels for MAFB by PCR increase with differentiation, this increase does not correlate well with the intensity of its protein expression. The inverse pattern of expression of MAFB and miR-130a suggested in vivo interaction that was further investigated.

Figure 2B:
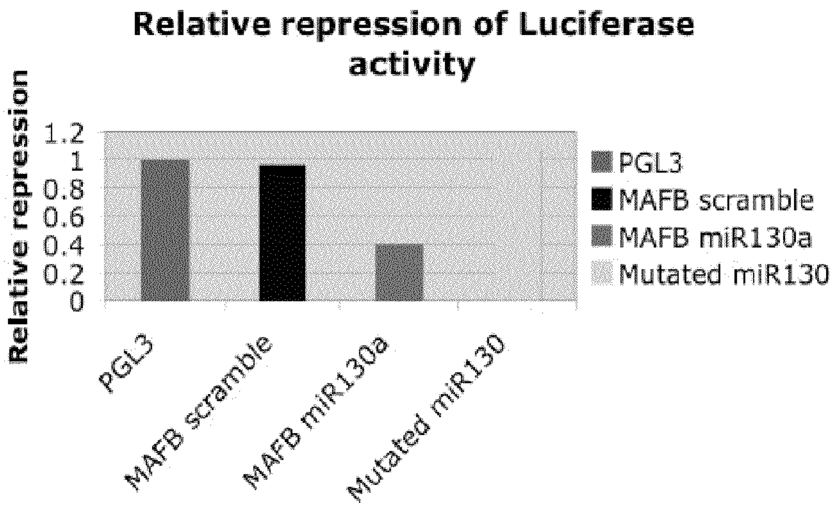

To demonstrate a direct interaction between the 3' UTRs of MAFB with miR-130a, we inserted the 3' UTR regions predicted to interact with this miRNA into a luciferase vector. This experiment revealed a repression of about ~60% of luciferase activity compared with control vector (FIG. 2B). As an additional control experiment, we used a mutated target mRNA sequence for MAFB lacking five of the complementary bases. As expected, the mutations completely abolished the interaction between miR-130a and its target 3'UTRs (FIG. 2B).

Figure 2C:
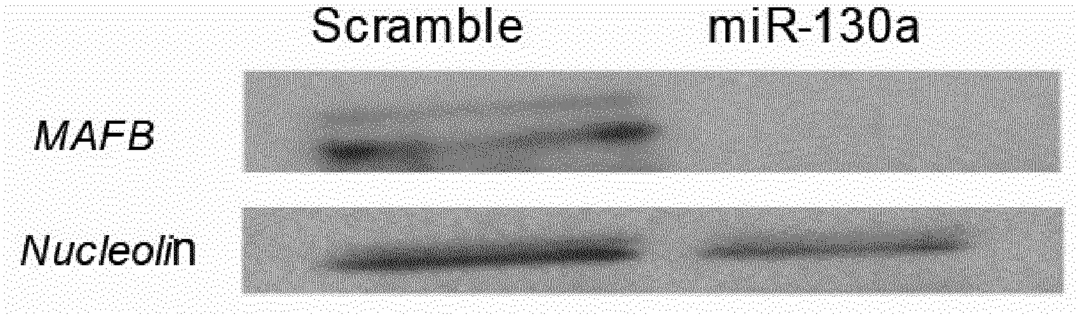
Figure 7:
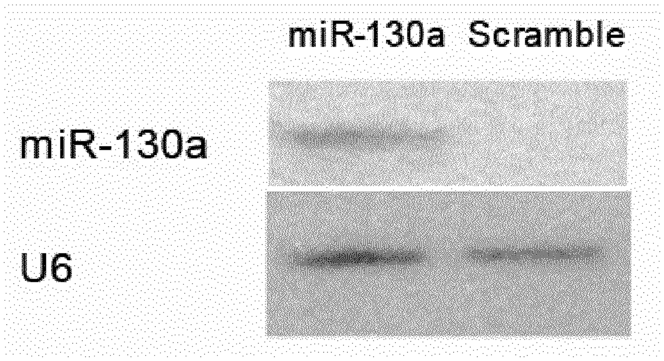
FIG. 7 is a Northern Blot of total RNA obtained from K562 cells transfected with miR-130a precursor and scramble sequences hybridized with the probe for miR-130a. An RNA loading control was performed using U6 hybridization.

We also determined the in vivo consequences of overexpressing miR-130a on MAFB expression. The pre-miR-130a and a negative control were transfected by electroporation into K562 cells, which naturally express MAFB and lack miR-130a. Transfection of the pre-miR-130a, but not the control, resulted in a decrease in the protein levels at 48 hours (FIG. 2C). Northern blotting confirmed successful ectopic expression of miR-130a in K562 cells (FIG. 7).

Example 3

MiR-10a Correlates with HOXB Gene Expression

Figure 8:
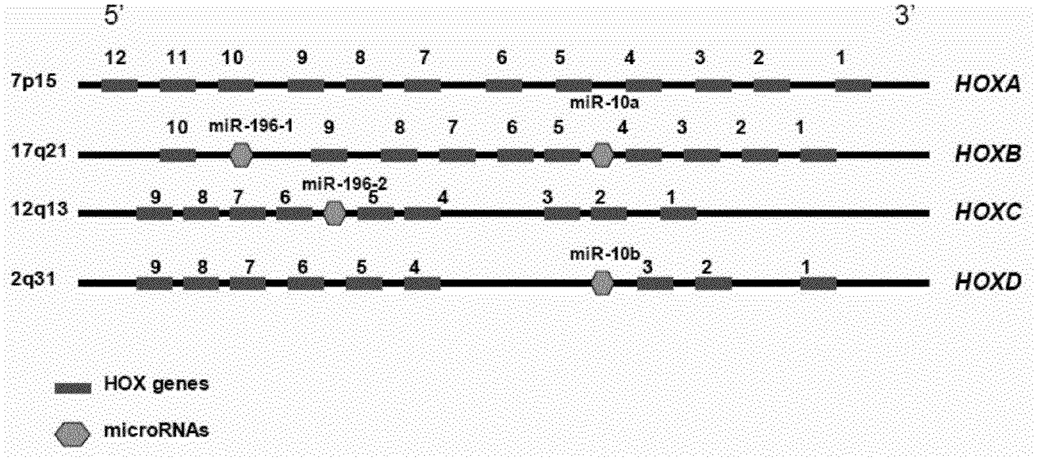
FIG. 8 is a schematic depicting microRNAs that are located in the HOXA, HOXB, HOXC and HOXD gene clusters.

It has been reported that in mouse embryos, miR-10a, miR-10b, and miR-196 are expressed in HOX-like patterns (Mansfield, J. H., et al. (2004) *Nature* 36, 1079-1083) and closely follow their "host" HOX cluster during evolution (Tanzer, A., et al. (2005) *J. Exp. Zool. B Mol. Dev. Evol.* 304B, 75-85). These data suggest common regulatory elements across paralog clusters. MiR-10a is located at chromosome 17q21 within the cluster of the HOXB genes (FIG. 8) and miR-10b is located at chromosome 2q31 within the HOXD gene cluster. To determine whether the miR-10a expression pattern correlates with the expression of HOXB genes, we performed RT-PCR for HOXB4 and HOXB5, which are the genes located 5' and 3', respectively, to miR-10a in the HOXB cluster. As shown in FIG. 8, HOXB4 and HOXB5 expression paralleled that of miR-10a, suggesting a common regulatory mechanism.

Example 4

MiR-10a Downregulates HOXA1

Figure 3A:
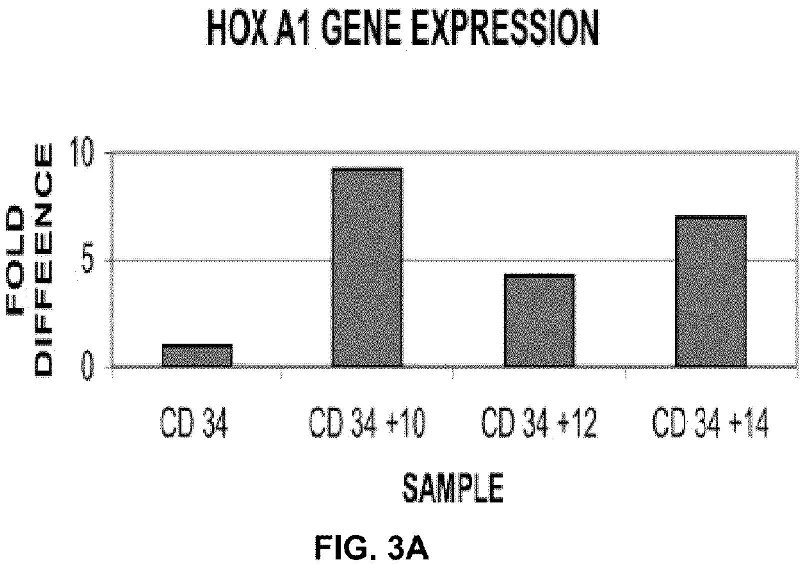
FIGS. 3A-3G demonstrate that MiR-10a downregulates HOXA1 by mediating RNA cleavage.
Figure 3B:
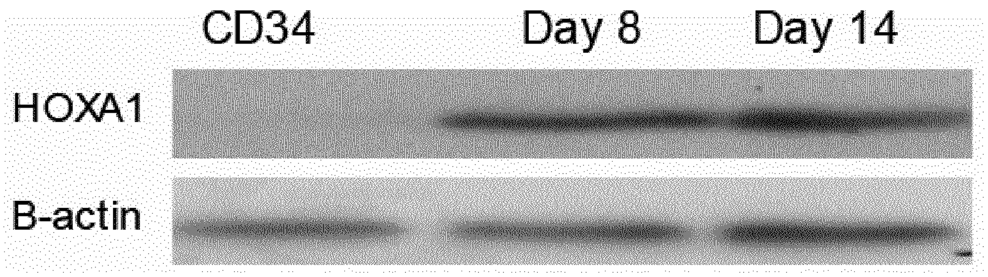
Figure 3C:
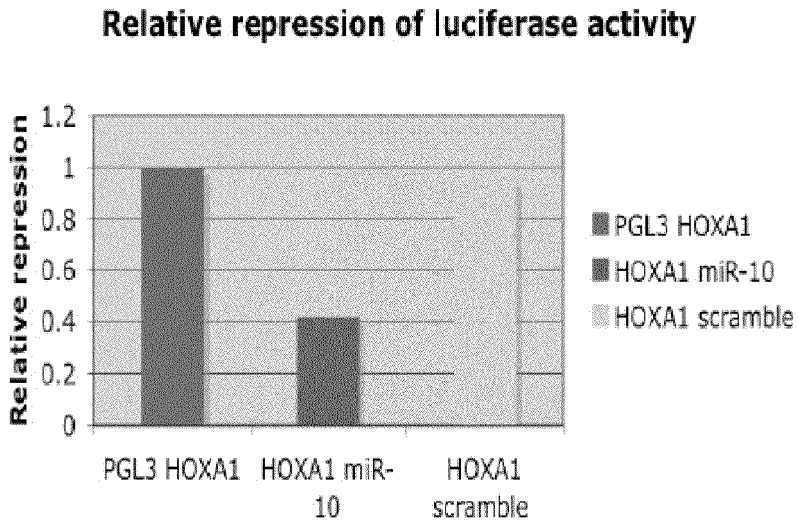
Figure 3D:
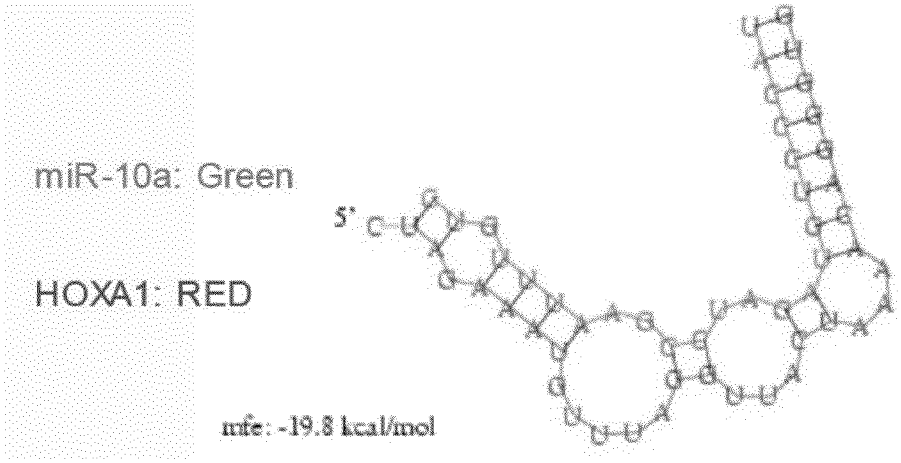
Figure 9A:
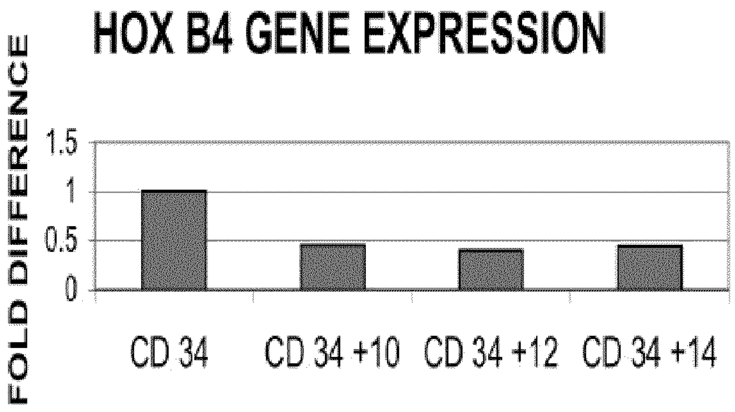
FIG. 9A is a graph depicting HOXB4 gene expression in differentiated megakaryocytes. RT-PCR results for HOXB4 are shown as fold difference in the expression level with respect to $CD34^+$ progenitors at baseline (before culture).
Figure 9B:
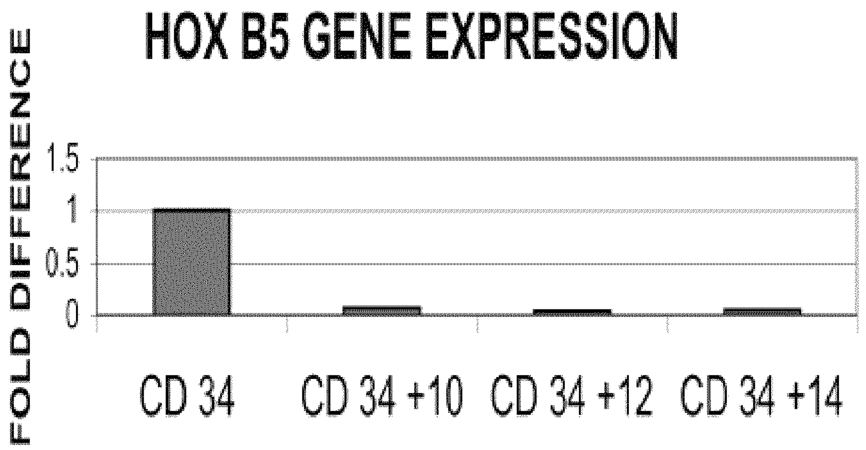
FIG. 9B is a graph depicting HOXB5 gene expression in differentiated megakaryocytes. RT-PCR results for HOXB5 are shown as fold difference in the expression levels with respect to $CD34^+$ progenitors at baseline (before culture).

We determined by miRNA array and Northern blot that miR-10a is sharply downregulated during megakaryocytic differentiation. Interestingly, we found several HOX genes as putative targets for miR-10a (Table 2). We thus investigated whether miR-10a could target a HOX gene. We performed real-time PCR for the predicted HOX targets of miR-10: HOXA1, HOXA3, and HOXD10. After normalization with 18S RNA, we found that HOXA1 mRNA is upregulated 7-fold during megakaryocytic differentiation compared with CD34 progenitors (FIG. 3A; see also FIG. 9). HOXA1 protein levels were also upregulated during megakaryocytic differentiation (FIG. 3B). These results are in sharp contrast with the downregulation of miR-10a in megakaryocytic differentiation, suggesting that miR-10a could be an inhibitor of HOXA1 expression. To demonstrate a direct interaction of miR-10a and the 3' UTR sequences of the HOXA1 gene, we carried out a luciferase reporter assay as described in Material and Methods. When the miRNA precursor miR-10a was introduced in the MEG01 cells along with the reporter plasmid containing the 3' UTR sequence of HOXA1, a 50% reduction in luciferase activity was observed (FIG. 3C). The degree of complementarity between miR-10a and the HOXA1 3' UTR is shown in FIG. 3D, as predicted by PICTAR.

Figure 3E:
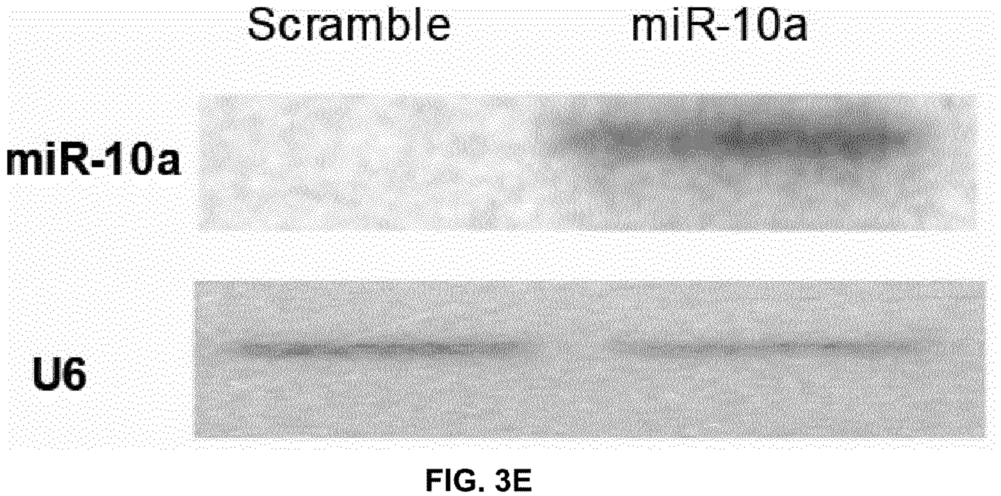
Figure 3F:
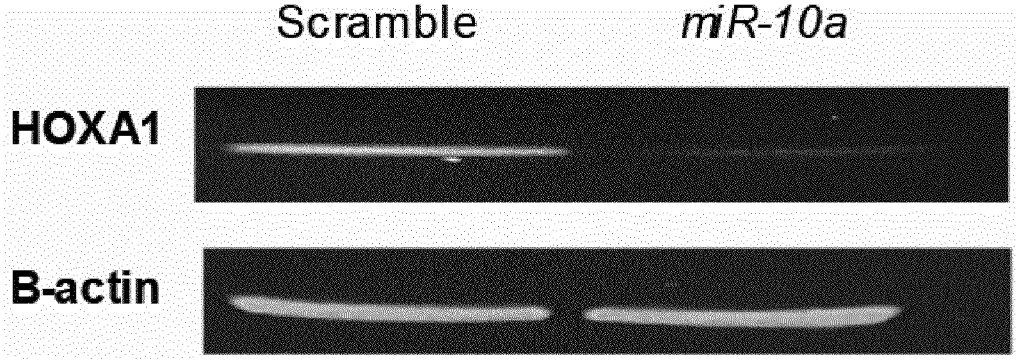
Figure 3G:
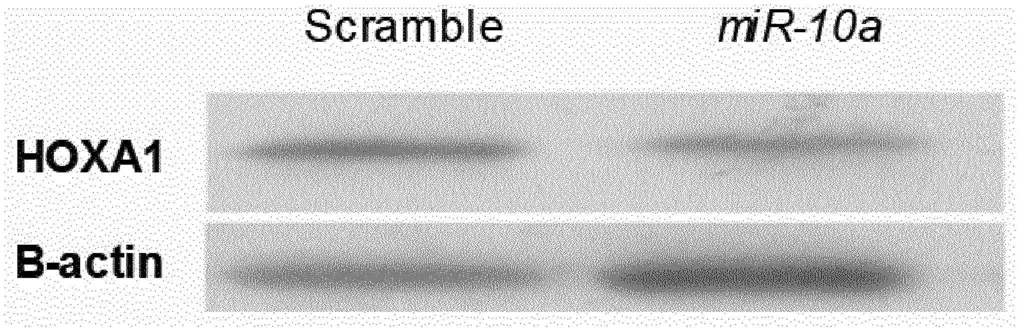
Figure 4A:
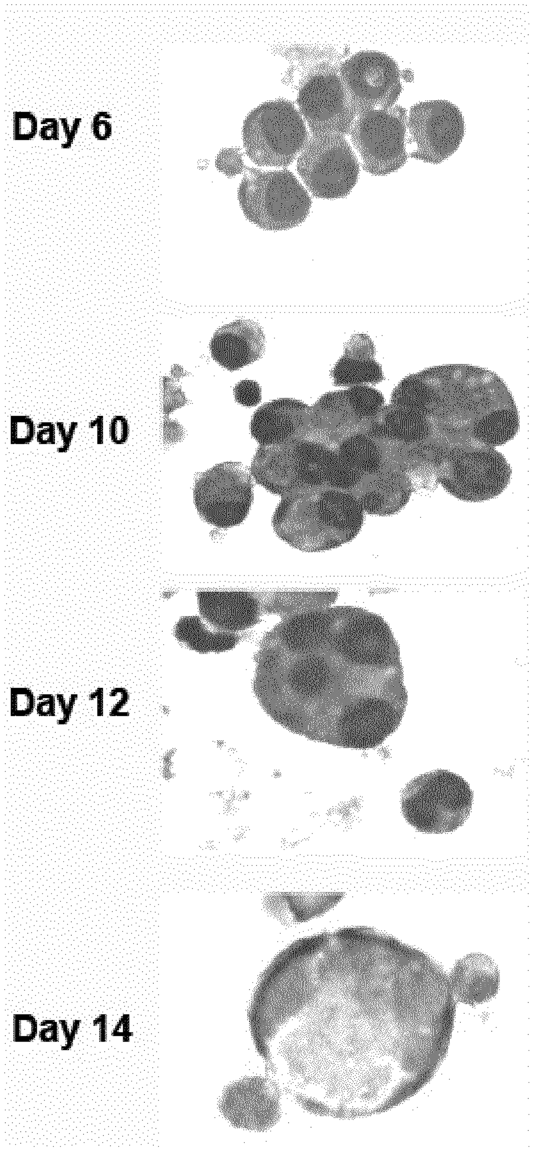
FIGS. 4A and 4B show phenotypic characterization results of in vitro-differentiated $CD34^+$ progenitors.
Figure 4B:
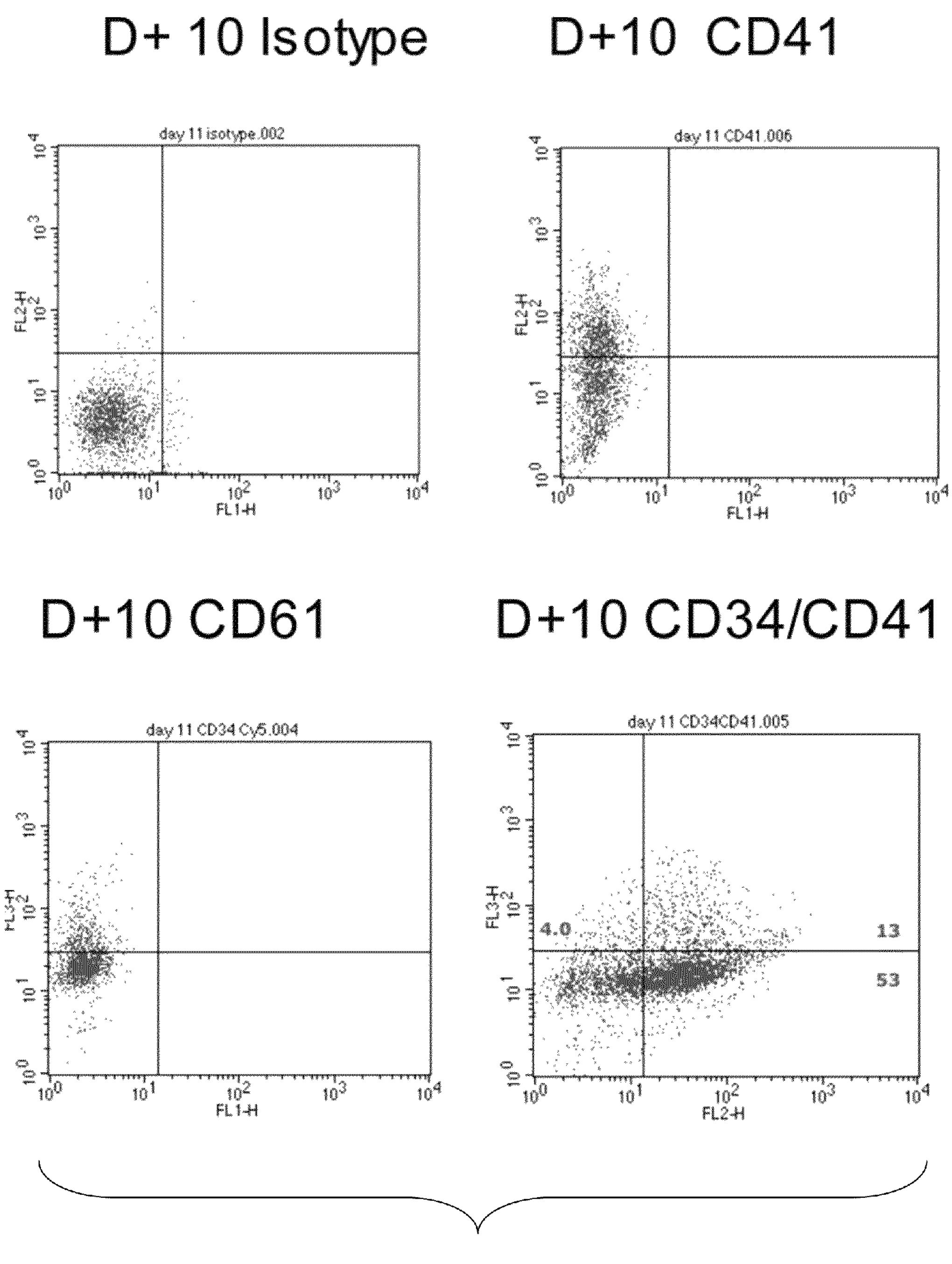
Figure 4B:
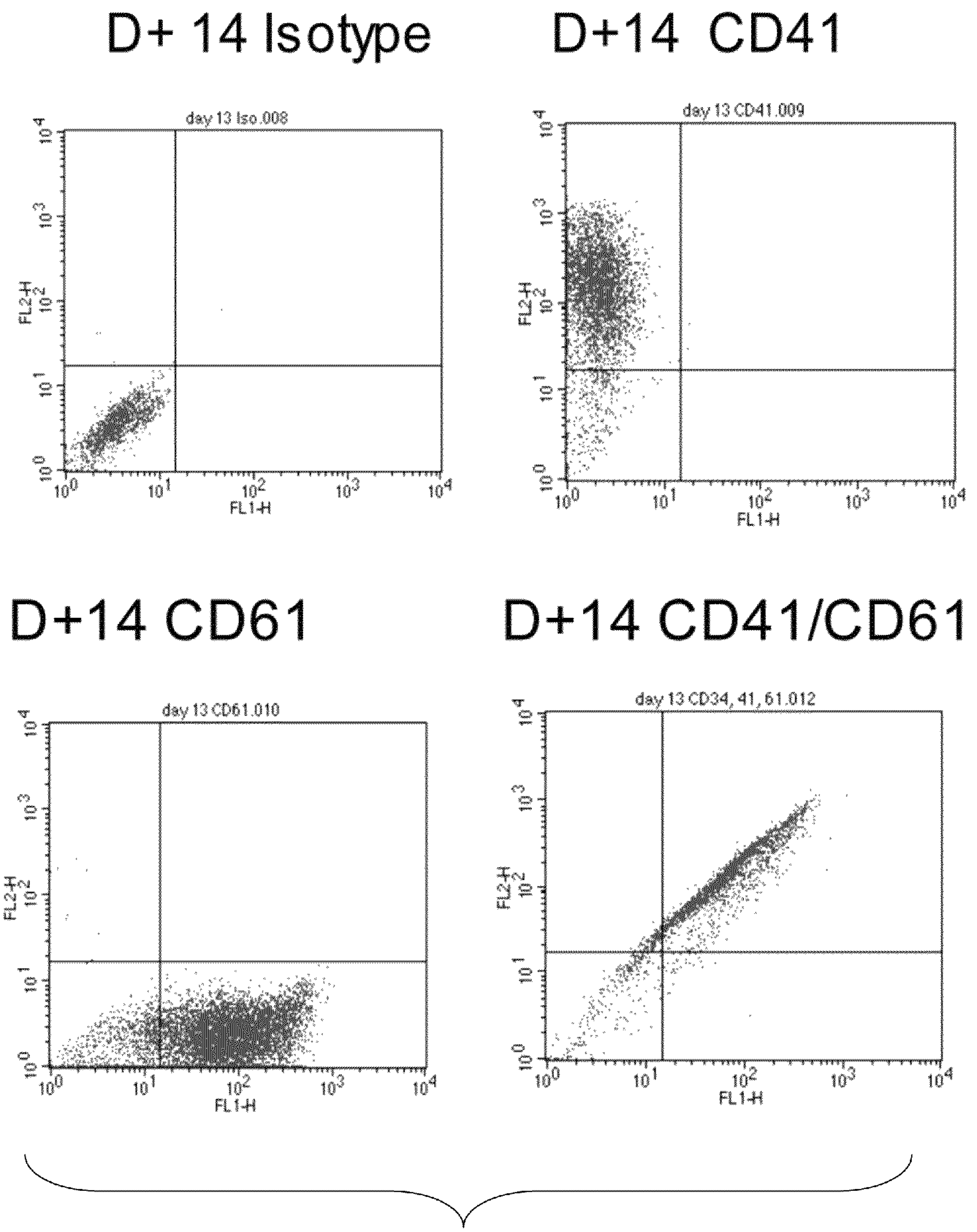
Figure 4B:
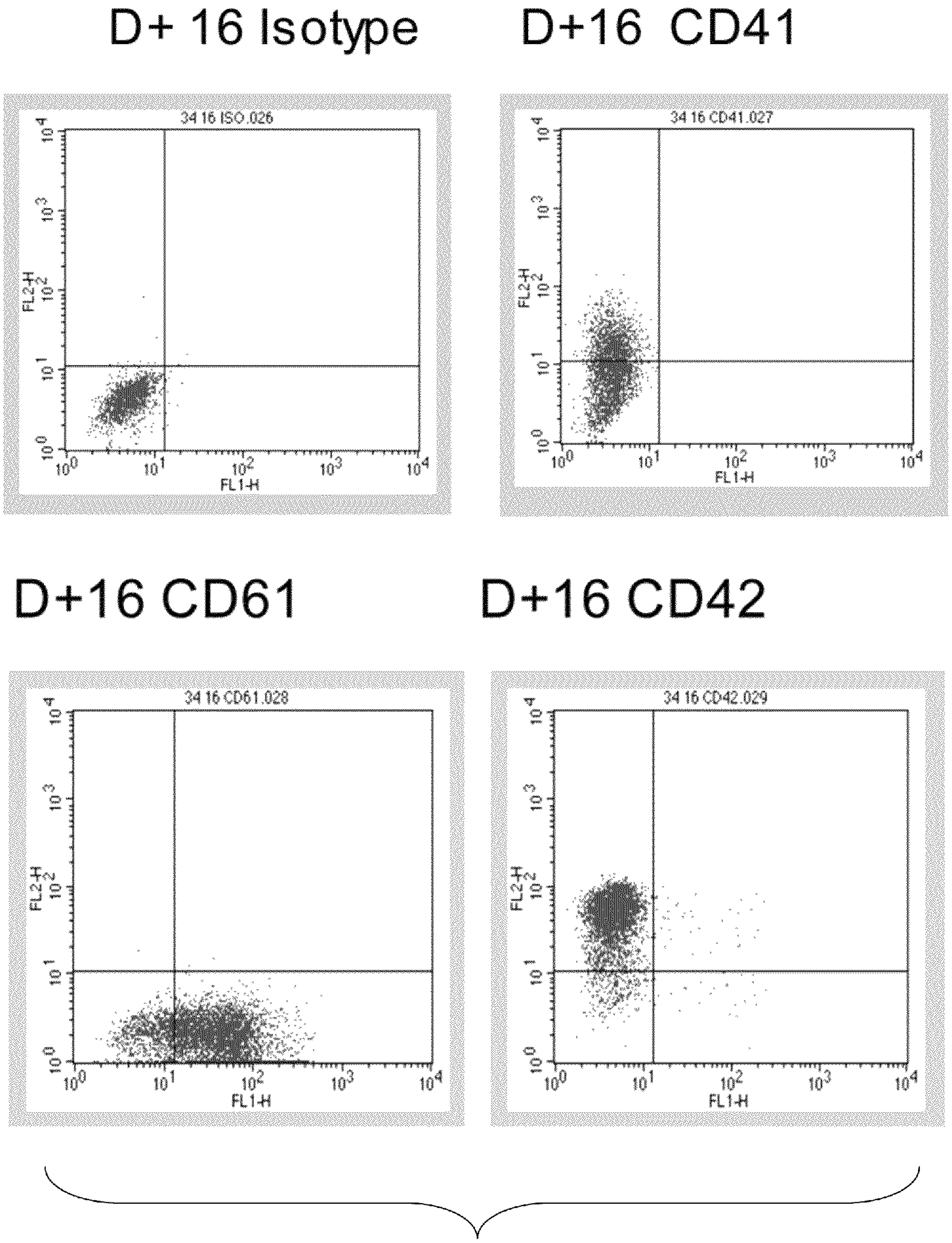

To confirm in vivo these findings, we transfected K562 cells with the pre-miR-10a precursor using nucleoporation and measured HOXA1 mRNA expression by RT-PCR and HOXA1 protein levels by Western blotting. Successful ectopic expression of miR-10a was documented by Northern Blot (FIG. 3E). A significant reduction at the mRNA and protein levels for HOXA1 was found for K562 cells transfected with the miR-10a precursor but not with the negative control (FIGS. 3F and 3G). These data indicate that miR-10a targets HOXA1 in vitro and in vivo.

It has been reported that miR-196 induces cleavage of HOXB8 mRNA, pointing to a posttranscriptional restriction mechanism of HOX gene expression (Yekta, S., et al. (2004) Science, 304:594-596). Contrary to the miR-196-HOXB8 interaction, where an almost perfect complementarity exists, the degree of pairing between miR-10a and the human HOXA1 3' UTR is suboptimal (FIG. 4). Although our results indicated target mRNA degradation, further studies are needed to determine whether cleavage or translational repression is the primary mechanism of downregulation of the HOXA1 gene in this system. A previous study using microarray analysis showed that a large number of target mRNA genes are downregulated by miRNA at the level of transcription (Lim, L. P., et al. (2005) *Nature:* 433, 769-771). These data raise the question whether target degradation is a consequence of translational repression and subsequent relocalization of the miR-target complexes to cytoplasmic processing bodies or is a primary event (Pillai, R. (2005) *RNA* 11, 1753-1761).

Example 5 miRNA Profiling in Acute Megakaryoblastic Leukemia (AMKL) Cell Lines

Figure 10:
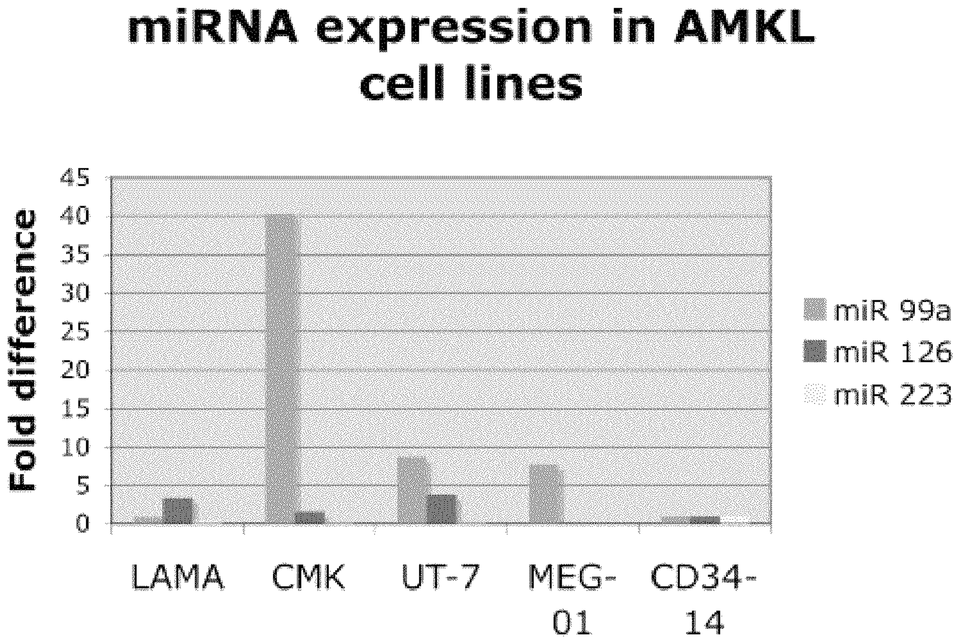
FIG. 10 is a graph depicting microRNA expression in acute megakaryoblastic cell lines by RT-PCR. Results are expressed as fold difference with respect to CD34-differentiated megakaryocytes after normalization with 18S and delta Ct calculations.

After the identification of the microRNA expression profile of $CD34^+$ cells during megakaryocytic differentiation, we then investigated miRNA expression in AMKL cell lines with the goal to identify differentially expressed miRNAs that could have a pathogenic role in megakaryoblastic leukemia. We initially compared miRNA expression in four AMKL cell lines with that of in vitro $CD34^+$-differentiated megakaryocytes. Using significance analysis of microarray (SAM), we identified 10 miRNAs upregulated in AMKL cell lines compared with that of CD34 in vitro-differentiated megakaryocytes (Table 3; see also Table 4). These miRNAs are as follows (in order of the fold increase with respect to differentiated megakaryocytes): miR-101, miR-126, miR-99a, miR-99-prec, miR-106, miR-339, miR-99b, miR-149, miR-33 and miR-135. Results were validated by RT-PCR as shown in FIG. 10. Using PAM, we compared miRNA expression in $CD34^+$ cells with in vitro-differentiated megakaryocytes and AMKL cell lines (FIG. 10). Interestingly, we found five miRNAs involved in the megakaryocytic differentiation signature (miR-101, miR-126, miR-106, miR-20, and miR-135) that were upregulated in the leukemic cell lines (Tables 3, 5 and 6). Whether this profile represents merely a differentiation state of the cells or has a truly pathogenic role remains to be elucidated. Supporting the second hypothesis, miR-106, miR-135, and miR-20 are predicted to target RUNX1, which is one of the genes most commonly associated with leukemia (Nakao, M., et al. (2004) *Oncogene* 125, 709-719). Moreover, mutations of RUNX1 have been described in familial thrombocytopenias with a propensity to develop acute myeloid leukemia (Song, W. J., et al. (1999) *Nat. Genet.* 23, 166-175).

TABLE 3 microRNAs upregulated in acute megakaryoblastic cell lines compared with in vitro-differentiated megakaryocytes.

| microRNA | Chromosomal Location | t test Score | Fold Change | Putative Targets |
|---|---|---|---|---|
| hsa-mir-101 | 1p31.3 | 6.14 | 11.85 | MEIS2, RUNX1, ETS-1, C-MYB, FOS, RARB, NFE2L2 |
| hsa-mir-126 | 9q34 | 4.91 | 11.97 | V-CRK |
| hsa-mir-099a | 21q21 | 3.30 | 6.83 | HOXA1, EIF2C, FOXA1 |
| hsa-mir-099b-prec | 21q21 | 2.85 | 7.59 | NA |
| hsa-mir-106 | xq26.2 | 2.79 | 3.33 | FLT1, SKI, E2F1, NCOA3, PDGFRA, CRK |
| hsa-mir-339 | 7p22 | 2.58 | 3.36 | HOXA1, FLT1, PTP4A1, RAP1B |
| hsa-mir-099b | 19q13 | 2.46 | 4.19 | HOXA1, MYCBP2 |
| hsa-mir-149 | 2q37 | 2.29 | 3.53 | RAP1A, MAFF, PDGFRA, SP1, NFIB |
| hsa-mir-033 | 2q13 | 2.27 | 3.23 | PDGFRA, HIF1A, MEIS2 |
| hsa-mir-135 | 3p21 | 2.12 | 3.97 | SP1, HIF1A, SP3, HNRPA1, HOXA10, RUNX1 |

All the miRNAs have a q value < 0.01 (false discovery rate).

The same miRNAs, except miR-339 and miR-149, were found by using PAM to predict a megakaryoblastic leukemia class with no misclassification error.

The results described herein demonstrate that there is a downregulation of miRNAs during megakaryocytopoiesis. Hypothetically, the downregulation of miRNAs unblocks target genes involved in differentiation. In line with this hypothesis, miRNAs that are sharply downregulated in our system are predicted to target genes with important roles in megakaryocytic differentiation. Thus, we have shown that miR-130a targets MAFB and miR-10a modulates HOXA1. The fact that we found several differentially expressed miRNAs during differentiation and leukemia that are predicted to target HOXA1 suggests a function for HOXA1 in megakaryocytopoiesis. Loss and gain studies will ultimately be needed to define the role of HOXA1 in this differentiation process. Our findings delineate the expression of miRNAs in megakaryocytic differentiation and suggest a role for miRNA modulation of this lineage by targeting megakaryocytic transcription factors. Furthermore, in megakaryoblastic leukemia cell lines, we have found inverse expression of miRNAs involved in normal megakaryocytic differentiation. These data provide a starting point for future studies of miRNAs in megakaryocytopoiesis and leukemia.

TABLE 4

Signature of megakaryocytic differentiation.

| microRNA | CD34 Expression | Megakaryocytic Expression |
|---|---|---|
| hsa-mir-010a | up | Down |
| hsa-mir-126 | up | Down |
| hsa-mir-130a-prec | up | Down |
| hsa-mir-010b | up | Down |
| hsa-mir-106 | up | Down |
| hsa-mir-130a | up | Down |
| hsa-mir-132 | up | Down |
| hsa-mir-30c | up | Down |
| hsa-mir-143-prec | Down | up |

PAM selected microRNAs with a very low misclassification error.

TABLE 5

| Signature of megakaryoblastic leukemia cell lines | | | | |
|---|---|---|---|---|
| microRNA | t test Score | Fold Change | Level of Expression in AML M7 | Putative Targets |
| hsa-mir-101- | 6.14 | 11.85 | up | MEIS2, RUNX1, C-MYB, FOS, RARb, NFE2L2 |
| hsa-mir-126 | 4.91 | 11.97 | up | V-CRK |
| hsa-mir-099a | 3.30 | 6.83 | up | HOXA1, EIF2C, FOXA1 |
| hsa-mir-095 | | | up | SHOX2 |
| hsa-mir-033 | 2.27 | 3.23 | up | PDGFRA, HIF1A, MEIS2 |
| hsa-mir-135 | 2.12 | 3.97 | up | SP1, HIF1A, SP3, HNRPA1, HOXA10, RUNX1 |
| hsa-mir-099b | 2.85 | 7.59 | up | HOXA1, MYCBP2 |
| hsa-mir-339 | 2.58 | 3.36 | up | HOXA1, FLT1, PTP4A1, RAP1B |
| hsa-mir-106 | 2.79 | 3.33 | up | HOXA1, EIF2C, FOXA1 |
| hsa-mir-124a | 2.07 | 2.78 | up | SDFR1, RXRa |
| hsa-mir-155 | | | down | ETS-1 |
| hsa-mir-020 | 2.00 | 3.09 | up | TAL1, SKI, RUNX-1, FLT1, CRK, FOG2, RARB |
| hsa-mir-025 | 1.98 | 4.24 | up | GATA2, |
| hsa-mir-140 | | | down | GATA1 |

PAM selected microRNAs. The fold change of miRNA expression is shown alongside t test score (SAM) and putative targets.

MicroRNAs are a highly conserved class of non-coding RNAs with important regulatory functions in proliferation, apoptosis, development and differentiation. As described herein, to discover novel regulatory pathways during megakaryocytic differentiation, we performed microRNA expression profiling of in vitro-differentiated megakaryocytes derived from $CD34^+$ hematopoietic progenitors. One major finding was downregulation of miR-10a, miR-126, miR-106, miR-10b, miR-17 and miR-20. Without wishing to be bound to any theory, it is believed that the downregulation of microRNAs unblocks target genes involved in differentiation. It was confirmed in vitro and in vivo that miR-130a targets the transcription factor MAFB, which is involved in the activation of the GPIIB promoter, a key protein for platelet physiology. In addition, it was shown that miR-10a expression in differentiated megakaryocytes is inverse to that of HOXA1, and HOXA1 is a direct target of miR-10a. Finally, the microRNA expression of megakaryoblastic leukemic cell lines was compared to that of in vitro-differentiated megakaryocytes and $CD34^+$ progenitors. This analysis revealed upregulation of miR-101, miR-126, miR-99a, miR-135, and miR-20 in the cancerous cell line. The data and results described herein delineate the expression of microRNAs during megakaryocytopoiesis and demonstrate a regulatory role of microRNAs in this process by targeting megakaryocytic transcription factors.

TABLE 6

| Three class analysis showing the different regulated microRNAs among the three cell types: $CD34^+$ progenitors, acute megakaryoblastic leukemia cell lines(AMKL) and in vitro-differentiated megakaryocytes. | | | | |
|---|---|---|---|---|
| microRNA | Chromosomal Location | $CD34^+$ Score | AML M7 cell lines score | In Vitro-differentiated Megakaryocytes Score |
| hsa-mir-010a | 17q21 | 1.0198 | 0 | −0.3562 |
| hsa-mir-101 | 1p31.3 | 0 | 0.814 | −0.432 |
| hsa-mir-126 | 9q34 | 0.0621 | 0.4882 | −0.4514 |
| hsa-mir-099a | 21q21 | 0 | 0.4685 | −0.2875 |
| hsa-mir-033 | 22q13 | 0 | 0.4258 | −0.2294 |
| hsa-mir-095 | 4p16 | 0 | 0.4142 | −0.3567 |
| hsa-mir-010b | 2q31 | 0.3308 | 0 | 0 |
| hsa-mir-155 | 21q21 | 0 | −0.3217 | 0 |
| hsa-mir-130a | 11q12 | 0.2755 | 0 | 0 |
| hsa-let-7d | 9q22 | 0.263 | −0.274 | 0 |
| hsa-mir-099b-prec | 21q21 | 0 | 0.266 | −0.1078 |
| hsa-mir-135-2-prec | 12q23 | 0 | 0.2279 | −0.2566 |
| hsa-mir-339 | 7p22 | 0 | 0.2456 | −0.1176 |
| hsa-mir-099b | 19q13 | 0 | 0.2275 | −0.1025 |
| hsa-mir-106 | xq26 | 0 | 0.0575 | −0.1891 |
| hsa-let-7c | 21q21 | 0.0289 | −0.1753 | 0 |
| hsa-mir-148 | 7p15 | 0 | −0.1748 | 0 |
| hsa-mir-132-prec | 17p13 | 0.1721 | 0 | 0 |
| hsa-mir-020 | 13q31 | 0 | 0.0374 | −0.1509 |

There are three patterns of miRNA expression among the three different cell types. The first pattern is defined by miRNA highly expressed in $CD34^+$ cells and downregulated in AMKL and differentiated megakaryocytes. miR-10a and miR-130a follow this pattern of expression; however, miR-10a is upregulated in AMKL relative to differentiated megakaryocytes. The second pattern is miRNA that is upregulated in AMKL, downregulated in $CD34^+$ cells and differentiated megakaryocytes and includes the following miRNAs: miR-126, miR-99, miR-101, let 7A, and miR-100. The last two miRNAs are equally expressed in $CD34^+$ and differentiated megakaryocytes, rather than showing a gradual decline in expression, as evidenced by miR-126, miR-99 and miR-101. The last pattern includes miRNA-106 and miRNA-135-2, which are upregulated in $CD34^+$ cells and AMKL, but low in differentiated megakaryocytes.

The relevant teachings of all publications cited herein that have not explicitly been incorporated by reference, are incorporated herein by reference in their entirety. While this invention has been particularly shown and described with references to preferred embodiments thereof, it will be understood by those skilled in the art that various changes in form and details may be made therein without departing from the scope of the invention encompassed by the appended claims.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof. Therefore, it is intended that the invention not be limited to the particular embodiment disclosed herein contemplated for carrying out this invention, but that the invention will include all embodiments falling within the scope of the claims.

What is claimed is:

1. A pharmaceutical composition for treating a subject exhibiting a cancer and/or a myeloproliferative disorder associated with overexpression of a transcription factor gene product from the homeobox gene family (HOXA1), wherein the cancer and/or myeloproliferative disorder is selected from the group consisting of: acute myeloid leukemia (AML), acute megakaryoblastic leukemia (AMKL), multiple myeloma (MM), and chronic myelogenous leukemia (CML), the composition comprising an effective amount of at least one miR-10a gene product and a pharmaceutically-acceptable carrier, wherein the at least one miR-10a gene product binds to, and decreases expression of, the HOXA1 gene product in the subject, wherein the at least one miR-10a gene product comprises one or more chemical modifications selected from the group consisting of: sugar modifications, backbone modifications, and combinations thereof; and wherein the subject has been diagnosed with acute myeloid leukemia (AML).

2. The pharmaceutical composition of claim 1, wherein the at least one miR-10a gene product comprises a nucleotide sequence that is complementary to a nucleotide sequence in the HOXA1 gene product.

3. The pharmaceutical composition of claim 1, wherein the pharmaceutical composition further comprises at least one anti-cancer agent.

4. The pharmaceutical composition of claim 3, wherein the at least one anti-cancer agent is selected from the group consisting of: cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel, and FOLFOX4.

5. The pharmaceutical composition of claim 1, wherein the at least one miR-10a gene product consists of a sequence having at least 90% identity to SEQ ID: 28 and/or SEQ ID: 322.

6. The pharmaceutical composition of claim 1, wherein the at least one miR-10a gene product comprises a sequence having at least 95% identity to SEQ ID: 28 and/or SEQ ID: 322.

7. The pharmaceutical composition of claim 1, wherein the at least one miR-10a gene product is synthetic pre-miR-10a.

8. A pharmaceutical composition for treating a subject exhibiting a cancer and/or a myeloproliferative disorder associated with overexpression of a transcription factor gene product from the homeobox gene family (HOXA1), wherein the cancer and/or myeloproliferative disorder is selected from the group consisting of: acute myeloid leukemia (AML), acute megakaryoblastic leukemia (AMKL), multiple myeloma (MM), and chronic myelogenous leukemia (CML), the composition comprising an effective amount of at least one miR-10a gene product and a pharmaceutically-acceptable carrier, wherein the at least one miR-10a gene product binds to, and decreases expression of, the HOXA1 gene product in the subject, wherein the at least one miR-10a gene product is produced recombinantly, and wherein the subject has been diagnosed with acute myeloid leukemia (AML).

9. The pharmaceutical composition of claim 8, wherein the at least one miR-10a gene product comprises a nucleotide sequence that is complementary to a nucleotide sequence in the HOXA1 gene product.

10. The pharmaceutical composition of claim 8, wherein the pharmaceutical composition further comprises at least one anti-cancer agent.

11. The pharmaceutical composition of claim 10, wherein the at least one anti-cancer agent is selected from the group consisting of: cytidine arabinoside, methotrexate, vincristine, etoposide (VP-16), doxorubicin (adriamycin), cisplatin (CDDP), dexamethasone, arglabin, cyclophosphamide, sarcolysin, methylnitrosourea, fluorouracil, 5-fluorouracil (5FU), vinblastine, camptothecin, actinomycin-D, mitomycin C, hydrogen peroxide, oxaliplatin, irinotecan, topotecan, leucovorin, carmustine, streptozocin, CPT-11, taxol, tamoxifen, dacarbazine, rituximab, daunorubicin, 1-β-D-arabinofuranosylcytosine, imatinib, fludarabine, docetaxel, and FOLFOX4.

12. The pharmaceutical composition of claim 8, wherein the at least one miR-10a gene product consists of a sequence having at least 90% identity to SEQ ID: 28 and/or SEQ ID: 322.

13. The pharmaceutical composition of claim 8, wherein the at least one miR-10a gene product comprises a sequence having at least 95% identity to SEQ ID: 28 and/or SEQ ID: 322.

14. The pharmaceutical composition of claim 8, wherein the at least one miR-10a gene product is synthetic pre-miR-10a.

* * * * *

UNITED STATES PATENT AND TRADEMARK OFFICE

CERTIFICATE OF CORRECTION

PATENT NO. : 8,865,885 B2
APPLICATION NO. : 13/925954
DATED : October 21, 2014
INVENTOR(S) : Carlo M. Croce, Ramiro Garzon and George A. Calin It is certified that error appears in the above-identified patent and that said Letters Patent is hereby corrected as shown below:

In the Specification

Column 1, Lines 25-29 replace the Government Support Clause with:
--This invention was made with government support under grant numbers P01 CA076259, P01 CA081534, P01 CA016058, and P01 CA016672 awarded by the National Institutes of Health. The government has certain rights in the invention.--

Signed and Sealed this
Fourth Day of August, 2020

Andrei Iancu
*Director of the United States Patent and Trademark Office*

SEQUENCE LISTING

<160> NUMBER OF SEQ ID NOS: 507

<210> SEQ ID NO 1
<211> LENGTH: 90
<212> TYPE: RNA
<213> ORGANISM: Homo sapiens

<400> SEQUENCE: 1
cacuguggga ugagguagua gguuguauag uuuuaggguc acacccacca cugggagaua 60
acuauacaau cuacugucuu uccuaacgug 90

<210> SEQ ID NO 2
<211> LENGTH: 72
<212> TYPE: RNA
<213> ORGANISM: Homo sapiens

<400> SEQUENCE: 2
agguugaggu aguagguugu auaguuuaga auuacaucaa gggagauaac uguacagccu 60
ccuagcuuuc cu 72

<210> SEQ ID NO 3
<211> LENGTH: 74
<212> TYPE: RNA
<213> ORGANISM: Homo sapiens

<400> SEQUENCE: 3
gggugaggua guagguugua uaguuugggg cucugcccug cuaugggaua acuauacaau 60
cuacugucuu uccu 74

<210> SEQ ID NO 4
<211> LENGTH: 107
<212> TYPE: RNA
<213> ORGANISM: Homo sapiens

<400> SEQUENCE: 4
gugacugcau gcucccaggu ugagguagua gguuguauag uuuagaauua cacaagggag 60
auaacuguac agccuccuag cuuuccuugg gucuugcacu aaacaac 107

<210> SEQ ID NO 5
<211> LENGTH: 85
<212> TYPE: RNA
<213> ORGANISM: Homo sapiens

<400> SEQUENCE: 5
ggcgggguga gguaguaggu ugugugguuu cagggcagug auguugcccc ucggaagaua 60
acuauacaac cuacugccuu cccug 85

<210> SEQ ID NO 6
<211> LENGTH: 84
<212> TYPE: RNA
<213> ORGANISM: Homo sapiens

<400> SEQUENCE: 6
gcauccgggu ugagguagua gguuguaugg uuuagaguua cacccuggga guuaacugua 60
caaccuucua gcuuuccuug gagc 84

-continued

<210> SEQ ID NO 7
<211> LENGTH: 87
<212> TYPE: RNA
<213> ORGANISM: Homo sapiens

<400> SEQUENCE: 7
ccuaggaaga gguaguaggu ugcauaguuu uagggcaggg auuuugccca caaggaggua 60
acuauacgac cugcugccuu ucuuagg 87

<210> SEQ ID NO 8
<211> LENGTH: 85
<212> TYPE: RNA
<213> ORGANISM: Homo sapiens

<400> SEQUENCE: 8
cuaggaagag guaguaguuu gcauaguuuu agggcaaaga uuuugcccac aaguaguuag 60
cuauacgacc ugcagccuuu uguag 85

<210> SEQ ID NO 9
<211> LENGTH: 85
<212> TYPE: RNA
<213> ORGANISM: Homo sapiens

<400> SEQUENCE: 9
cuggcugagg uaguaguuug ugcuguuggu cggguuguga cauugcccgc uguggagaua 60
acugcgcaag cuacugccuu gcuag 85

<210> SEQ ID NO 10
<211> LENGTH: 79
<212> TYPE: RNA
<213> ORGANISM: Homo sapiens

<400> SEQUENCE: 10
cccgggcuga gguaggaggu uguauaguug aggaggacac ccaaggagau cacuauacgg 60
ccuccuagcu uuccccagg 79

<210> SEQ ID NO 11
<211> LENGTH: 87
<212> TYPE: RNA
<213> ORGANISM: Homo sapiens

<400> SEQUENCE: 11
ucagagugag guaguagauu guauaguugu gggguaguga uuuuacccug uucaggagau 60
aacuauacaa ucuauugccu ucccuga 87

<210> SEQ ID NO 12
<211> LENGTH: 89
<212> TYPE: RNA
<213> ORGANISM: Homo sapiens

<400> SEQUENCE: 12
cugugggaug agguaguaga uuguauaguu gugggguagu gauuuuaccc uguucaggag 60
auaacuauac aaucuauugc cuucccuga 89

<210> SEQ ID NO 13
<211> LENGTH: 85
<212> TYPE: RNA
<213> ORGANISM: Homo sapiens

<400> SEQUENCE: 13
cugugggaug agguaguaga uuguauaguu uuagggucau accccaucuu ggagauaacu 60
auacagucua cugucuuucc cacgg 85

<210> SEQ ID NO 14
<211> LENGTH: 108
<212> TYPE: RNA
<213> ORGANISM: Homo sapiens

<400> SEQUENCE: 14
uugccugauu ccaggcugag guaguaguuu guacaguuug agggucuaug auaccacccg 60
guacaggaga uaacuguaca ggccacugcc uugccaggaa cagcgcgc 108

<210> SEQ ID NO 15
<211> LENGTH: 85
<212> TYPE: RNA
<213> ORGANISM: Homo sapiens

<400> SEQUENCE: 15
cuggcugagg uaguaguuug ugcuguuggu cggguuguga cauugcccgc uguggagaua 60
acugcgcaag cuacugccuu gcuag 85

<210> SEQ ID NO 16
<211> LENGTH: 85
<212> TYPE: RNA
<213> ORGANISM: Homo sapiens

<400> SEQUENCE: 16
accuacucag aguacauacu ucuuuaugua cccauaugaa cauacaaugc uauggaaugu 60
aaagaaguau guauuuuugg uaggc 85

<210> SEQ ID NO 17
<211> LENGTH: 108
<212> TYPE: RNA
<213> ORGANISM: Homo sapiens

<400> SEQUENCE: 17
cagcuaacaa cuuaguaaua ccuacucaga guacauacuu cuuuauguac ccauaugaac 60
auacaaugcu auggaaugua aagaaguaug uauuuuuggu aggcaaua 108

<210> SEQ ID NO 18
<211> LENGTH: 85
<212> TYPE: RNA
<213> ORGANISM: Homo sapiens

<400> SEQUENCE: 18
gccugcuugg gaaacauacu ucuuuauaug cccauaugga ccugcuaagc uauggaaugu 60
aaagaaguau guaucucagg ccggg 85

<210> SEQ ID NO 19
<211> LENGTH: 71
<212> TYPE: RNA
<213> ORGANISM: Homo sapiens

<400> SEQUENCE: 19
ugggaaacau acuucuuuau augcccauau ggaccugcua agcuauggaa uguaaagaag 60
uauguaucuc a 71

<210> SEQ ID NO 20
<211> LENGTH: 85
<212> TYPE: RNA
<213> ORGANISM: Homo sapiens

<400> SEQUENCE: 20
accuacucag aguacauacu ucuuuaugua cccauaugaa cauacaaugc uauggaaugu 60
aaagaaguau guauuuuugg uaggc 85

<210> SEQ ID NO 21
<211> LENGTH: 108
<212> TYPE: RNA
<213> ORGANISM: Homo sapiens

<400> SEQUENCE: 21
uggauguugg ccuaguucug uguggaagac uagugauuuu guuguuuuua gauaacuaaa 60
ucgacaacaa aucacagucu gccauauggc acaggccaug ccucuaca 108

<210> SEQ ID NO 22
<211> LENGTH: 110
<212> TYPE: RNA
<213> ORGANISM: Homo sapiens

<400> SEQUENCE: 22
uuggauguug gccuaguucu guguggaaga cuagugauuu uguuguuuuu agauaacuaa 60
aucgacaaca aaucacaguc ugccauaugg cacaggccau gccucuacag 110

<210> SEQ ID NO 23
<211> LENGTH: 110
<212> TYPE: RNA
<213> ORGANISM: Homo sapiens

<400> SEQUENCE: 23
cuggauacag aguggaccgg cuggccccau cuggaagacu agugauuuug uuguugucuu 60
acugcgcuca acaacaaauc ccagucuacc uaauggugcc agccaucgca 110

<210> SEQ ID NO 24
<211> LENGTH: 110
<212> TYPE: RNA
<213> ORGANISM: Homo sapiens

<400> SEQUENCE: 24
agauuagagu ggcugugguc uagugcugug uggaagacua gugauuuugu uguucugaug 60
uacuacgaca acaagucaca gccggccuca uagcgcagac ucccuucgac 110

<210> SEQ ID NO 25
<211> LENGTH: 89
<212> TYPE: RNA
<213> ORGANISM: Homo sapiens

<400> SEQUENCE: 25 cggguuggu uguuaucuuu gguuaucuag cuguaugagu ggugugggagu cuucauaaag 60 cuagauaacc gaaaguaaaa auaacccca 89

<210> SEQ ID NO 26
<211> LENGTH: 87
<212> TYPE: RNA
<213> ORGANISM: Homo sapiens

<400> SEQUENCE: 26

-continued ggaagcgagu uguuaucuuu gguuaucuag cuguaugagu guauuggucu ucauaaagcu 60
agauaaccga aaguaaaaac uccuuca 87

<210> SEQ ID NO 27
<211> LENGTH: 90
<212> TYPE: RNA
<213> ORGANISM: Homo sapiens

<400> SEQUENCE: 27
ggaggcccgu uucucucuuu gguuaucuag cuguaugagu gccacagagc cgucauaaag 60
cuagauaacc gaaaguagaa augauucuca 90

<210> SEQ ID NO 28
<211> LENGTH: 110
<212> TYPE: RNA
<213> ORGANISM: Homo sapiens

<400> SEQUENCE: 28
gaucugucug ucuucuguau auacccugua gauccgaauu uguguaagga auuuuguggu 60
cacaaauucg uaucuagggg aauauguagu ugacauaaac acuccgcucu 110

<210> SEQ ID NO 29
<211> LENGTH: 110
<212> TYPE: RNA
<213> ORGANISM: Homo sapiens

<400> SEQUENCE: 29
ccagagguug uaacguuguc uauauauacc cuguagaacc gaauuugugu gguauccgua 60
uagucacaga uucgauucua ggggaauaua uggucgaugc aaaaacuuca 110

<210> SEQ ID NO 30
<211> LENGTH: 108
<212> TYPE: RNA
<213> ORGANISM: Homo sapiens

<400> SEQUENCE: 30
gcgcgaaugu guguuuaaaa aaaauaaaac cuuggaguaa aguagcagca cauaaugguu 60
uguggauuuu gaaaaggugc aggccauauu gugcugccuc aaaaauac 108

<210> SEQ ID NO 31
<211> LENGTH: 83
<212> TYPE: RNA
<213> ORGANISM: Homo sapiens

<400> SEQUENCE: 31
ccuuggagua aaguagcagc acauaauggu uuguggauuu ugaaaaggug caggccauau 60
ugugcugccu caaaaauaca agg 83

<210> SEQ ID NO 32
<211> LENGTH: 64
<212> TYPE: RNA
<213> ORGANISM: Homo sapiens

<400> SEQUENCE: 32
cuguagcagc acaucauggu uuacaugcua cagucaagau gcgaaucauu auuugcugcu 60
cuag 64

<210> SEQ ID NO 33
<211> LENGTH: 98

<212> TYPE: RNA
<213> ORGANISM: Homo sapiens

<400> SEQUENCE: 33
uugaggccuu aaaguacugu agcagcacau caugguuuac augcuacagu caagaugcga 60
aucauuauuu gcugcucuag aaauuuaagg aaauucau 98

<210> SEQ ID NO 34
<211> LENGTH: 89
<212> TYPE: RNA
<213> ORGANISM: Homo sapiens

<400> SEQUENCE: 34
gucagcagug ccuuagcagc acguaaauau uggcguuaag auucuaaaau uaucuccagu 60
auuaacugug cugcugaagu aagguugac 89

<210> SEQ ID NO 35
<211> LENGTH: 81
<212> TYPE: RNA
<213> ORGANISM: Homo sapiens

<400> SEQUENCE: 35
guuccacucu agcagcacgu aaauauuggc guagugaaau auauauuaaa caccaauauu 60
acugugcugc uuuaguguga c 81

<210> SEQ ID NO 36
<211> LENGTH: 81
<212> TYPE: RNA
<213> ORGANISM: Homo sapiens

<400> SEQUENCE: 36
gcagugccuu agcagcacgu aaauauuggc guuaagauuc uaaaauuauc uccaguauua 60
acugugcugc ugaaguaagg u 81

<210> SEQ ID NO 37
<211> LENGTH: 84
<212> TYPE: RNA
<213> ORGANISM: Homo sapiens

<400> SEQUENCE: 37
gucagaauaa ugucaaagug cuuacagugc agguagugau augugcaucu acugcaguga 60
aggcacuugu agcauuaugg ugac 84

<210> SEQ ID NO 38
<211> LENGTH: 71
<212> TYPE: RNA
<213> ORGANISM: Homo sapiens

<400> SEQUENCE: 38
uguucuaagg ugcaucuagu gcagauagug aaguagauua gcaucuacug cccuaagugc 60
uccuucuggc a 71

<210> SEQ ID NO 39
<211> LENGTH: 81
<212> TYPE: RNA
<213> ORGANISM: Homo sapiens

<400> SEQUENCE: 39
uuuuuguucu aaggugcauc uagugcagau agugaaguag auuagcaucu acugcccuaa 60
gugcuccuuc uggcauaaga a 81

<210> SEQ ID NO 40
<211> LENGTH: 82
<212> TYPE: RNA
<213> ORGANISM: Homo sapiens

<400> SEQUENCE: 40
gcaguccucu guuaguuuug cauaguugca cuacaagaag aauguaguug ugcaaaucua 60
ugcaaaacug augguggccu gc 82

<210> SEQ ID NO 41
<211> LENGTH: 80
<212> TYPE: RNA
<213> ORGANISM: Homo sapiens

<400> SEQUENCE: 41
caguccucug uuaguuuugc auaguugcac uacaagaaga auguaguugu gcaaaucuau 60
gcaaaacuga ugguggccug 80

<210> SEQ ID NO 42
<211> LENGTH: 87
<212> TYPE: RNA
<213> ORGANISM: Homo sapiens

<400> SEQUENCE: 42
cacuguucua ugguuaguuu ugcagguuug cauccagcug ugugauauuc ugcugugcaa 60
auccaugcaa aacugacugu gguagug 87

<210> SEQ ID NO 43
<211> LENGTH: 96
<212> TYPE: RNA
<213> ORGANISM: Homo sapiens

<400> SEQUENCE: 43
acauugcuac uuacaauuag uuuugcaggu uugcauuuca gcguauauau guauaugugg 60
cugugcaaau ccaugcaaaa cugauuguga uaaugu 96

<210> SEQ ID NO 44
<211> LENGTH: 80
<212> TYPE: RNA
<213> ORGANISM: Homo sapiens

<400> SEQUENCE: 44
uucuaugguu aguuuugcag guuugcaucc agcuguguga uauucugcug ugcaaaucca 60
ugcaaaacug acugugguag 80

<210> SEQ ID NO 45
<211> LENGTH: 81
<212> TYPE: RNA
<213> ORGANISM: Homo sapiens

<400> SEQUENCE: 45
uuacaauuag uuuugcaggu uugcauuuca gcguauauau guauaugugg cugugcaaau 60
ccaugcaaaa cugauuguga u 81

<210> SEQ ID NO 46
<211> LENGTH: 71
<212> TYPE: RNA
<213> ORGANISM: Homo sapiens

<400> SEQUENCE: 46
guagcacuaa agugcuuaua gugcagguag uguuuaguua ucuacugcau uaugagcacu 60
uaaaguacug c 71

<210> SEQ ID NO 47
<211> LENGTH: 72
<212> TYPE: RNA
<213> ORGANISM: Homo sapiens

<400> SEQUENCE: 47
ugucggguag cuuaucagac ugauguugac uguugaaucu cauggcaaca ccagucgaug 60
ggcugucuga ca 72

<210> SEQ ID NO 48
<211> LENGTH: 81
<212> TYPE: RNA
<213> ORGANISM: Homo sapiens

<400> SEQUENCE: 48
accuugucgg guagcuuauc agacugaugu ugacuguuga aucucauggc aacaccaguc 60
gaugggcugu cugacauuuu g 81

<210> SEQ ID NO 49
<211> LENGTH: 85
<212> TYPE: RNA
<213> ORGANISM: Homo sapiens

<400> SEQUENCE: 49
ggcugagccg caguaguucu ucaguggcaa gcuuuauguc cugacccagc uaaagcugcc 60
aguugaagaa cuguugcccu cugcc 85

<210> SEQ ID NO 50
<211> LENGTH: 73
<212> TYPE: RNA
<213> ORGANISM: Homo sapiens

<400> SEQUENCE: 50
ggccggcugg gguuccuggg gaugggauuu gcuuccuguc acaaaucaca uugccaggga 60
uuuccaaccg acc 73

<210> SEQ ID NO 51
<211> LENGTH: 97
<212> TYPE: RNA
<213> ORGANISM: Homo sapiens

<400> SEQUENCE: 51
cucaggugcu cuggcugcuu ggguuccugg caugcugauu ugugacuuaa gauuaaaauc 60
acauugccag ggauuaccac gcaaccacga ccuuggc 97

<210> SEQ ID NO 52
<211> LENGTH: 81
<212> TYPE: RNA
<213> ORGANISM: Homo sapiens

<400> SEQUENCE: 52
ccacggccgg cuggggguucc uggggauggg auuugcuucc ugucacaaau cacauugcca 60
gggauuucca accgacccug a 81

<210> SEQ ID NO 53
<211> LENGTH: 68
<212> TYPE: RNA
<213> ORGANISM: Homo sapiens

<400> SEQUENCE: 53
cuccggugcc uacugagcug auaucaguuc ucauuuuaca cacuggcuca guucagcagg 60
aacaggag 68

<210> SEQ ID NO 54
<211> LENGTH: 73
<212> TYPE: RNA
<213> ORGANISM: Homo sapiens

<400> SEQUENCE: 54
cucugccucc cgugccuacu gagcugaaac acaguugguu uguguacacu ggcucaguuc 60
agcaggaaca ggg 73

<210> SEQ ID NO 55
<211> LENGTH: 81
<212> TYPE: RNA
<213> ORGANISM: Homo sapiens

<400> SEQUENCE: 55
cccugggcuc ugccucccgu gccuacugag cugaaacaca guugguuugu guacacuggc 60
ucaguucagc aggaacaggg g 81

<210> SEQ ID NO 56
<211> LENGTH: 71
<212> TYPE: RNA
<213> ORGANISM: Homo sapiens

<400> SEQUENCE: 56
cccuccggug ccuacugagc ugauaucagu ucucauuuua cacacuggcu caguucagca 60
ggaacagcau c 71

<210> SEQ ID NO 57
<211> LENGTH: 84
<212> TYPE: RNA
<213> ORGANISM: Homo sapiens

<400> SEQUENCE: 57
ggccaguguu gagaggcgga gacuugggca auugcuggac gcugcccugg gcauugcacu 60
ugucucgguc ugacagugcc ggcc 84

<210> SEQ ID NO 58
<211> LENGTH: 86
<212> TYPE: RNA
<213> ORGANISM: Homo sapiens

<400> SEQUENCE: 58
aggccguggc cucguucaag uaauccagga uaggcugugc aggucccaau ggccuaucuu 60
gguuacuugc acggggacgc gggccu 86

<210> SEQ ID NO 59
<211> LENGTH: 77
<212> TYPE: RNA
<213> ORGANISM: Homo sapiens

<400> SEQUENCE: 59
guggccucgu ucaaguaauc caggauaggc ugugcagguc ccaaugggcc uauucuuggu 60
uacuugcacg gggacgc 77

<210> SEQ ID NO 60
<211> LENGTH: 84
<212> TYPE: RNA
<213> ORGANISM: Homo sapiens

<400> SEQUENCE: 60
ggcuguggcu ggauucaagu aauccaggau aggcuguuuc caucugugag gccuauucuu 60
gauuacuugu uucuggaggc agcu 84

<210> SEQ ID NO 61
<211> LENGTH: 77
<212> TYPE: RNA
<213> ORGANISM: Homo sapiens

<400> SEQUENCE: 61
ccgggaccca guucaaguaa uucaggauag guugugugcu guccagccug uucuccauua 60
cuuggcucgg ggaccgg 77

<210> SEQ ID NO 62
<211> LENGTH: 78
<212> TYPE: RNA
<213> ORGANISM: Homo sapiens

<400> SEQUENCE: 62
cugaggagca gggcuuagcu gcuugugagc aggguccaca ccaagucgug uucacagugg 60
cuaaguuccg ccccccag 78

<210> SEQ ID NO 63
<211> LENGTH: 73
<212> TYPE: RNA
<213> ORGANISM: Homo sapiens

<400> SEQUENCE: 63
aggugcagag cuuagcugau uggugaacag ugauugguuu ccgcuuuguu cacaguggcu 60
aaguucugca ccu 73

<210> SEQ ID NO 64
<211> LENGTH: 97
<212> TYPE: RNA
<213> ORGANISM: Homo sapiens

<400> SEQUENCE: 64
accucucuaa caaggugcag agcuuagcug auuggugaac agugauuggu uuccgcuuug 60
uucacagugg cuaaguucug caccugaaga gaaggug 97

<210> SEQ ID NO 65
<211> LENGTH: 80
<212> TYPE: RNA
<213> ORGANISM: Homo sapiens

<400> SEQUENCE: 65
ccugaggagc agggcuuagc ugcuugugag cagggguccac accaagucgu guucacagug 60
gcuaaguucc gccccccagg 80

<210> SEQ ID NO 66

<211> LENGTH: 86
<212> TYPE: RNA
<213> ORGANISM: Homo sapiens

<400> SEQUENCE: 66 ggucccuugcc cucaaggagc ucacagucua uugaguuacc uuucugacuu ucccacuaga 60
uugugagcuc cuggagggca ggcacu 86

<210> SEQ ID NO 67
<211> LENGTH: 108
<212> TYPE: RNA
<213> ORGANISM: Homo sapiens

<400> SEQUENCE: 67
ccuucuguga ccccuuagag gaugacugau uucuuuuggu guucagaguc aauauaauuu 60
ucuagcacca ucugaaaucg guuauaauga uuggggaaga gcaccaug 108

<210> SEQ ID NO 68
<211> LENGTH: 64
<212> TYPE: RNA
<213> ORGANISM: Homo sapiens

<400> SEQUENCE: 68
augacugauu ucuuuuggug uucagaguca auauaauuuu cuagcaccau cugaaaucgg 60
uuau 64

<210> SEQ ID NO 69
<211> LENGTH: 81
<212> TYPE: RNA
<213> ORGANISM: Homo sapiens

<400> SEQUENCE: 69
cuucaggaag cugguuucau augguguuu agauuuaaau agugauuguc uagcaccauu 60
ugaaaucagu guucuugggg g 81

<210> SEQ ID NO 70
<211> LENGTH: 81
<212> TYPE: RNA
<213> ORGANISM: Homo sapiens

<400> SEQUENCE: 70
cuucuggaag cugguuucac augguggcuu agauuuuucc aucuuuguau cuagcaccau 60
uugaaaucag uguuuuagga g 81

<210> SEQ ID NO 71
<211> LENGTH: 110
<212> TYPE: RNA
<213> ORGANISM: Homo sapiens

<400> SEQUENCE: 71
accacuggcc caucucuuac acaggcugac cgauuucucc ugguguucag agucuguuuu 60
ugucuagcac cauuugaaau cgguuaugau guagggggaa aagcagcagc 110

<210> SEQ ID NO 72
<211> LENGTH: 71
<212> TYPE: RNA
<213> ORGANISM: Homo sapiens

<400> SEQUENCE: 72
gcgacuguaa acauccucga cuggaagcug ugaagccaca gaugggcuuu cagucggaug 60
uuugcagcug c 71

<210> SEQ ID NO 73
<211> LENGTH: 60
<212> TYPE: RNA
<213> ORGANISM: Homo sapiens

<400> SEQUENCE: 73
auguaaacau ccuacacuca gcuguaauac auggauuggc ugggaggugg auguuuacgu 60

<210> SEQ ID NO 74
<211> LENGTH: 88
<212> TYPE: RNA
<213> ORGANISM: Homo sapiens

<400> SEQUENCE: 74
accaaguuuc aguucaugua aacauccuac acucagcugu aauacaugga uuggcuggga 60
gguggauguu uacuucagcu gacuugga 88

<210> SEQ ID NO 75
<211> LENGTH: 72
<212> TYPE: RNA
<213> ORGANISM: Homo sapiens

<400> SEQUENCE: 75
agauacugua aacauccuac acucucagcu guggaaagua agaaagcugg gagaaggcug 60
uuuacucuuu cu 72

<210> SEQ ID NO 76
<211> LENGTH: 70
<212> TYPE: RNA
<213> ORGANISM: Homo sapiens

<400> SEQUENCE: 76
guuguuguaa acauccccga cuggaagcug uaagacacag cuaagcuuuc agucagaugu 60
uugcugcuac 70

<210> SEQ ID NO 77
<211> LENGTH: 64
<212> TYPE: RNA
<213> ORGANISM: Homo sapiens

<400> SEQUENCE: 77
cuguaaacau ccuugacugg aagcuguaag guguucagag gagcuuucag ucggauguuu 60
acag 64

<210> SEQ ID NO 78
<211> LENGTH: 71
<212> TYPE: RNA
<213> ORGANISM: Homo sapiens

<400> SEQUENCE: 78
ggagaggagg caagaugcug gcauagcugu ugaacuggga accugcuaug ccaacauauu 60
gccaucuuuc c 71

<210> SEQ ID NO 79
<211> LENGTH: 70
<212> TYPE: RNA
<213> ORGANISM: Homo sapiens

<400> SEQUENCE: 79
ggagauauug cacauuacua aguugcaugu ugucacggcc ucaaugcaau uuagugugug 60
ugauauuuuc 70

<210> SEQ ID NO 80
<211> LENGTH: 110
<212> TYPE: RNA
<213> ORGANISM: Homo sapiens

<400> SEQUENCE: 80
gggggccgag agaggcgggc ggccccgcgg ugcauugcug uugcauugca cgugugugag 60
gcgggugcag ugccucggca gugcagcccg gagccggccc cuggcaccac 110

<210> SEQ ID NO 81
<211> LENGTH: 88
<212> TYPE: RNA
<213> ORGANISM: Homo sapiens

<400> SEQUENCE: 81
accaaguuuc aguucaugua aacauccuac acucagcugu aauacaugga uuggcuggga 60
gguggauguu uacuucagcu gacuugga 88

<210> SEQ ID NO 82
<211> LENGTH: 69
<212> TYPE: RNA
<213> ORGANISM: Homo sapiens

<400> SEQUENCE: 82
cuguggugca uuguaguugc auugcauguu cuggugguac ccaugcaaug uuuccacagu 60
gcaucacag 69

<210> SEQ ID NO 83
<211> LENGTH: 110
<212> TYPE: RNA
<213> ORGANISM: Homo sapiens

<400> SEQUENCE: 83
ggccagcugu gaguguuucu uuggcagugu cuuagcuggu uguugugagc aauaguaagg 60
aagcaaucag caaguauacu gcccuagaag ugcugcacgu uguggggccc 110

<210> SEQ ID NO 84
<211> LENGTH: 84
<212> TYPE: RNA
<213> ORGANISM: Homo sapiens

<400> SEQUENCE: 84
gugcucgguu uguaggcagu gucauuagcu gauuguacug uggugguuac aaucacuaac 60
uccacugcca ucaaaacaag gcac 84

<210> SEQ ID NO 85
<211> LENGTH: 77
<212> TYPE: RNA
<213> ORGANISM: Homo sapiens

<400> SEQUENCE: 85
agucuaguua cuaggcagug uaguuagcug auugcuaaua guaccaauca cuaaccacac 60
ggccagguaa aaagauu 77

<210> SEQ ID NO 86
<211> LENGTH: 82
<212> TYPE: RNA
<213> ORGANISM: Homo sapiens

<400> SEQUENCE: 86
ucagaauaau gucaaagugc uuacagugca gguagugaua ugugcaucua cugcagugaa 60
ggcacuugua gcauuauggu ga 82

<210> SEQ ID NO 87
<211> LENGTH: 78
<212> TYPE: RNA
<213> ORGANISM: Homo sapiens

<400> SEQUENCE: 87
cuuucuacac agguugggau cgguugcaau gcuguguuuc uguaugguau ugcacuuguc 60
ccggccuguu gaguuugg 78

<210> SEQ ID NO 88
<211> LENGTH: 75
<212> TYPE: RNA
<213> ORGANISM: Homo sapiens

<400> SEQUENCE: 88
ucaucccugg guggggauuu guugcauuac uuguguucua uauaaaguau ugcacuuguc 60
ccggccugug gaaga 75

<210> SEQ ID NO 89
<211> LENGTH: 80
<212> TYPE: RNA
<213> ORGANISM: Homo sapiens

<400> SEQUENCE: 89
cugggggcuc caaagugcug uucgugcagg uagugugauu acccaaccua cugcugagcu 60
agcacuuccc gagcccccgg 80

<210> SEQ ID NO 90
<211> LENGTH: 81
<212> TYPE: RNA
<213> ORGANISM: Homo sapiens

<400> SEQUENCE: 90
aacacagugg gcacucaaua aaugucuguu gaauugaaau gcguuacauu caacggguau 60
uuauugagca cccacucugu g 81

<210> SEQ ID NO 91
<211> LENGTH: 78
<212> TYPE: RNA
<213> ORGANISM: Homo sapiens

<400> SEQUENCE: 91
uggccgauuu uggcacuagc acauuuuugc uugugucucu ccgcucugag caaucaugug 60
cagugccaau augggaaa 78

<210> SEQ ID NO 92
<211> LENGTH: 80
<212> TYPE: RNA
<213> ORGANISM: Homo sapiens

<400> SEQUENCE: 92
gugagcgacu guaaacaucc ucgacuggaa gcugugaagc cacagauggg cuuucagucg 60
gauguuugca gcugccuacu 80

<210> SEQ ID NO 93
<211> LENGTH: 80
<212> TYPE: RNA
<213> ORGANISM: Homo sapiens

<400> SEQUENCE: 93
gugagguagu aaguuguauu guuguggggu agggauauua ggccccaauu agaagauaac 60
uauacaacuu acuacuuucc 80

<210> SEQ ID NO 94
<211> LENGTH: 70
<212> TYPE: RNA
<213> ORGANISM: Homo sapiens

<400> SEQUENCE: 94
ggcacccacc cguagaaccg accuugcggg gccuucgccg cacacaagcu cgugucugug 60
gguccguguc 70

<210> SEQ ID NO 95
<211> LENGTH: 81
<212> TYPE: RNA
<213> ORGANISM: Homo sapiens

<400> SEQUENCE: 95
cccauuggca uaaacccgua gauccgaucu uguggugaag uggaccgcac aagcucgcuu 60
cuaugggucu gugucagugu g 81

<210> SEQ ID NO 96
<211> LENGTH: 108
<212> TYPE: RNA
<213> ORGANISM: Homo sapiens

<400> SEQUENCE: 96
aagagagaag auauugaggc cuguugccac aaacccguag auccgaacuu gugguauuag 60
uccgcacaag cuuguaucua uagguaugug ucuguuaggc aaucucac 108

<210> SEQ ID NO 97
<211> LENGTH: 80
<212> TYPE: RNA
<213> ORGANISM: Homo sapiens

<400> SEQUENCE: 97
ccuguugcca caaacccgua gauccgaacu ugugguauua guccgcacaa gcuuguaucu 60
auagguaugu gucuguuagg 80

<210> SEQ ID NO 98
<211> LENGTH: 110
<212> TYPE: RNA
<213> ORGANISM: Homo sapiens

<400> SEQUENCE: 98
aggcugcccu ggcucaguua ucacagugcu gaugcugucu auucuaaagg uacaguacug 60
ugauaacuga aggauggcag ccaucuuacc uuccaucaga ggagccucac 110

<210> SEQ ID NO 99
<211> LENGTH: 57

<212> TYPE: RNA
<213> ORGANISM: Homo sapiens

<400> SEQUENCE: 99
ucaguuauca cagugcugau gcuguccauu cuaaagguac aguacuguga uaacuga 57

<210> SEQ ID NO 100
<211> LENGTH: 75
<212> TYPE: RNA
<213> ORGANISM: Homo sapiens

<400> SEQUENCE: 100
ugcccuggcu caguuaucac agugcugaug cugucuauuc uaaagguaca guacugugau 60
aacugaagga uggca 75

<210> SEQ ID NO 101
<211> LENGTH: 79
<212> TYPE: RNA
<213> ORGANISM: Homo sapiens

<400> SEQUENCE: 101
acuguccuuu uucgguuauc augguaccga ugcuguauau cugaaaggua caguacugug 60
auaacugaag aauggugu 79

<210> SEQ ID NO 102
<211> LENGTH: 75
<212> TYPE: RNA
<213> ORGANISM: Homo sapiens

<400> SEQUENCE: 102
uguccuuuuu cgguuaucau gguaccgaug cuguauaucu gaaagguaca guacugugau 60
aacugaagaa uggug 75

<210> SEQ ID NO 103
<211> LENGTH: 81
<212> TYPE: RNA
<213> ORGANISM: Homo sapiens

<400> SEQUENCE: 103
cuucuggaag cugguuucac augguggcuu agauuuuucc aucuuuguau cuagcaccau 60
uugaaaucag uguuuuagga g 81

<210> SEQ ID NO 104
<211> LENGTH: 81
<212> TYPE: RNA
<213> ORGANISM: Homo sapiens

<400> SEQUENCE: 104
cuucaggaag cugguuucau augguggguuu agauuuaaau agugauuguc uagcaccauu 60
ugaaaucagu guucuugggg g 81

<210> SEQ ID NO 105
<211> LENGTH: 78
<212> TYPE: RNA
<213> ORGANISM: Homo sapiens

<400> SEQUENCE: 105
uugugcuuuc agcuucuuua cagugcugcc uuguagcauu caggucaagc aacauuguac 60
agggcuauga aagaacca 78

<210> SEQ ID NO 106
<211> LENGTH: 78
<212> TYPE: RNA
<213> ORGANISM: Homo sapiens

<400> SEQUENCE: 106
uacugcccuc ggcuucuuua cagugcugcc uuguugcaua uggaucaagc agcauuguac 60
agggcuauga aggcauug 78

<210> SEQ ID NO 107
<211> LENGTH: 78
<212> TYPE: RNA
<213> ORGANISM: Homo sapiens

<400> SEQUENCE: 107
aaaugucaga cagcccaucg acugguguug ccaugagauu caacagucaa caucagucug 60
auaagcuacc cgacaagg 78

<210> SEQ ID NO 108
<211> LENGTH: 81
<212> TYPE: RNA
<213> ORGANISM: Homo sapiens

<400> SEQUENCE: 108
ugugcaucgu ggucaaaugc ucagacuccu gugguggcug cucaugcacc acggauguuu 60
gagcaugugc uacggugucu a 81

<210> SEQ ID NO 109
<211> LENGTH: 81
<212> TYPE: RNA
<213> ORGANISM: Homo sapiens

<400> SEQUENCE: 109
ugugcaucgu ggucaaaugc ucagacuccu gugguggcug cuuaugcacc acggauguuu 60
gagcaugugc uauggugucu a 81

<210> SEQ ID NO 110
<211> LENGTH: 81
<212> TYPE: RNA
<213> ORGANISM: Homo sapiens

<400> SEQUENCE: 110
ccuuggccau guaaaagugc uuacagugca gguagcuuuu ugagaucuac ugcaauguaa 60
gcacuucuua cauuaccaug g 81

<210> SEQ ID NO 111
<211> LENGTH: 82
<212> TYPE: RNA
<213> ORGANISM: Homo sapiens

<400> SEQUENCE: 111
ccugccgggg cuaaagugcu gacagugcag auaguggucc ucuccgugcu accgcacugu 60
ggguacuugc ugcuccagca gg 82

<210> SEQ ID NO 112
<211> LENGTH: 81
<212> TYPE: RNA
<213> ORGANISM: Homo sapiens

<400> SEQUENCE: 112

-continued cucucugcuu ucagcuucuu uacaguguug ccuuguggca uggaguucaa gcagcauugu 60
acagggcuau caaagcacag a 81

<210> SEQ ID NO 113
<211> LENGTH: 90
<212> TYPE: RNA
<213> ORGANISM: Homo sapiens

<400> SEQUENCE: 113
acacugcaag aacaauaagg auuuuuaggg gcauuaugac ugagucagaa aacacagcug 60
ccccugaaag ucccucauuu uucuugcugu 90

<210> SEQ ID NO 114
<211> LENGTH: 80
<212> TYPE: RNA
<213> ORGANISM: Homo sapiens

<400> SEQUENCE: 114
acugcaagag caauaaggau uuuuaggggc auuaugauag uggaauggaa acacaucugc 60
ccccaaaagu cccucauuuu 80

<210> SEQ ID NO 115
<211> LENGTH: 85
<212> TYPE: RNA
<213> ORGANISM: Homo sapiens

<400> SEQUENCE: 115
ccuuagcaga gcuguggagu gugacaaugg uguuuguguc uaaacuauca aacgccauua 60
ucacacuaaa uagcuacugc uaggc 85

<210> SEQ ID NO 116
<211> LENGTH: 66
<212> TYPE: RNA
<213> ORGANISM: Homo sapiens

<400> SEQUENCE: 116
agcuguggag ugugacaaug guguuugugu ccaaacuauc aaacgccauu aucacacuaa 60
auagcu 66

<210> SEQ ID NO 117
<211> LENGTH: 61
<212> TYPE: RNA
<213> ORGANISM: Homo sapiens

<400> SEQUENCE: 117
acauuauuac uuuugguacg cgcugugaca cuucaaacuc guaccgugag uaauaaugcg 60
c 61

<210> SEQ ID NO 118
<211> LENGTH: 85
<212> TYPE: RNA
<213> ORGANISM: Homo sapiens

<400> SEQUENCE: 118
aggccucucu cuccguguuc acagcggacc uugauuuaaa uguccauaca auuaaggcac 60
gcggugaaug ccaagaaugg ggcug 85

<210> SEQ ID NO 119

<211> LENGTH: 110
<212> TYPE: RNA
<213> ORGANISM: Homo sapiens

<400> SEQUENCE: 119
aucaagauua gaggcucugc ucuccguguu cacagcggac cuugauuuaa ugucauacaa 60
uuaaggcacg cggugaaugc caagagcgga gccuacggcu gcacuugaag 110

<210> SEQ ID NO 120
<211> LENGTH: 87
<212> TYPE: RNA
<213> ORGANISM: Homo sapiens

<400> SEQUENCE: 120
ugagggcccc ucugcguguu cacagcggac cuugauuuaa ugucuauaca auuaaggcac 60
gcggugaaug ccaagagagg cgccucc 87

<210> SEQ ID NO 121
<211> LENGTH: 68
<212> TYPE: RNA
<213> ORGANISM: Homo sapiens

<400> SEQUENCE: 121
cucugcgugu ucacagcgga ccuugauuua augucuauac aauuaaggca cgcggugaau 60
gccaagag 68

<210> SEQ ID NO 122
<211> LENGTH: 67
<212> TYPE: RNA
<213> ORGANISM: Homo sapiens

<400> SEQUENCE: 122
cucuccgugu ucacagcgga ccuugauuua augucauaca auuaaggcac gcggugaaug 60
ccaagag 67

<210> SEQ ID NO 123
<211> LENGTH: 86
<212> TYPE: RNA
<213> ORGANISM: Homo sapiens

<400> SEQUENCE: 123
ugccagucuc uaggucccug agacccuuua accugugagg acauccaggg ucacagguga 60
gguucuuggg agccuggcgu cuggcc 86

<210> SEQ ID NO 124
<211> LENGTH: 65
<212> TYPE: RNA
<213> ORGANISM: Homo sapiens

<400> SEQUENCE: 124
ggucccugag acccuuuaac cugugaggac auccaggguc acaggugagg uucuugggag 60
ccugg 65

<210> SEQ ID NO 125
<211> LENGTH: 88
<212> TYPE: RNA
<213> ORGANISM: Homo sapiens

<400> SEQUENCE: 125
ugcgcuccuc ucagucccug agacccuaac uugugauguu uaccguuuaa auccacgggu 60

```
uaggcucuug ggagcugcga gucgugcu                                              88

<210> SEQ ID NO 126
<211> LENGTH: 89
<212> TYPE: RNA
<213> ORGANISM: Homo sapiens

<400> SEQUENCE: 126

accagacuuu uccuaguccc ugagacccua acuugugagg uauuuuagua acaucacaag           60

ucaggcucuu gggaccuagg cggagggga                                             89

<210> SEQ ID NO 127
<211> LENGTH: 85
<212> TYPE: RNA
<213> ORGANISM: Homo sapiens

<400> SEQUENCE: 127

cgcuggcgac gggacauuau uacuuuuggu acgcgcugug acacuucaaa cucguaccgu           60

gaguaauaau gcgccgucca cggca                                                 85

<210> SEQ ID NO 128
<211> LENGTH: 61
<212> TYPE: RNA
<213> ORGANISM: Homo sapiens

<400> SEQUENCE: 128

acauuauuac uuuugguacg cgcugugaca cuucaaacuc guaccgugag uaauaaugcg           60

c                                                                           61

<210> SEQ ID NO 129
<211> LENGTH: 97
<212> TYPE: RNA
<213> ORGANISM: Homo sapiens

<400> SEQUENCE: 129

ugugaucacu gucuccagcc ugcugaagcu cagagggcuc ugauucagaa agaucaucgg           60

auccgucuga gcuuggcugg ucggaagucu caucauc                                    97

<210> SEQ ID NO 130
<211> LENGTH: 70
<212> TYPE: RNA
<213> ORGANISM: Homo sapiens

<400> SEQUENCE: 130

ccagccugcu gaagcucaga gggcucugau ucagaaagau caucggaucc gucugagcuu           60

ggcuggucgg                                                                  70

<210> SEQ ID NO 131
<211> LENGTH: 82
<212> TYPE: RNA
<213> ORGANISM: Homo sapiens

<400> SEQUENCE: 131

ugagcuguug gauucggggc cguagcacug ucugagaggu uuacauuucu cacagugaac           60

cggucucuuu uucagcugcu uc                                                    82

<210> SEQ ID NO 132
<211> LENGTH: 110
<212> TYPE: RNA
```

<213> ORGANISM: Homo sapiens

<400> SEQUENCE: 132
gcccggcagc cacugugcag ugggaagggg ggccgauaca cuguacgaga gugaguagca    60
ggucucacag ugaaccgguc ucuuucccua cugugucaca cuccuaaugg              110

<210> SEQ ID NO 133
<211> LENGTH: 70
<212> TYPE: RNA
<213> ORGANISM: Homo sapiens

<400> SEQUENCE: 133
guuggauucg gggccguagc acugucugag agguuuacau uucucacagu gaaccggucu    60
cuuuuucagc                                                          70

<210> SEQ ID NO 134
<211> LENGTH: 74
<212> TYPE: RNA
<213> ORGANISM: Homo sapiens

<400> SEQUENCE: 134
uggaucuuuu ugcggucugg gcuugcuguu ccucucaaca guagucagga agcccuuacc    60
ccaaaaagua ucua                                                     74

<210> SEQ ID NO 135
<211> LENGTH: 90
<212> TYPE: RNA
<213> ORGANISM: Homo sapiens

<400> SEQUENCE: 135
ugcccuucgc gaaucuuuuu gcggucuggg cuugcuguac auaacucaau agccggaagc    60
ccuuacccca aaaagcauuu gcggagggcg                                    90

<210> SEQ ID NO 136
<211> LENGTH: 89
<212> TYPE: RNA
<213> ORGANISM: Homo sapiens

<400> SEQUENCE: 136
ugcugcuggc cagagcucuu uucacauugu gcuacugucu gcaccuguca cuagcagugc    60
aauguuaaaa gggcauuggc cguguagug                                     89

<210> SEQ ID NO 137
<211> LENGTH: 110
<212> TYPE: RNA
<213> ORGANISM: Homo sapiens

<400> SEQUENCE: 137
gccaggaggc ggguugguu guuaucuuug guuaucuagc uguaugagug guguggaguc    60
uucauaaagc uagauaaccg aaaguaaaaa uaaccccaua cacugcgcag              110

<210> SEQ ID NO 138
<211> LENGTH: 110
<212> TYPE: RNA
<213> ORGANISM: Homo sapiens

<400> SEQUENCE: 138
cacggcgcgg cagcggcacu ggcuaaggga ggcccguuuc ucucuuuggu uaucuagcug    60
uaugagugcc acagagccgu cauaaagcua gauaaccgaa aguagaaaug              110

<210> SEQ ID NO 139
<211> LENGTH: 72
<212> TYPE: RNA
<213> ORGANISM: Homo sapiens

<400> SEQUENCE: 139
guuguuaucu uugguuaucu agcuguauga guguauuggu cuucauaaag cuagauaacc 60
gaaaguaaaa ac 72

<210> SEQ ID NO 140
<211> LENGTH: 101
<212> TYPE: RNA
<213> ORGANISM: Homo sapiens

<400> SEQUENCE: 140
ccgcccccgc gucuccaggg caaccguggc uuucgauugu uacuguggga acuggaggua 60
acagucuaca gccauggucg ccccgcagca cgcccacgcg c 101

<210> SEQ ID NO 141
<211> LENGTH: 66
<212> TYPE: RNA
<213> ORGANISM: Homo sapiens

<400> SEQUENCE: 141
gggcaaccgu ggcuuucgau uguuacugug ggaacuggag guaacagucu acagccaugg 60
ucgccc 66

<210> SEQ ID NO 142
<211> LENGTH: 88
<212> TYPE: RNA
<213> ORGANISM: Homo sapiens

<400> SEQUENCE: 142
acaaugcuuu gcuagagcug guaaaaugga accaaaucgc cucuucaaug gauuuggucc 60
ccuucaacca gcuguagcua ugcauuga 88

<210> SEQ ID NO 143
<211> LENGTH: 102
<212> TYPE: RNA
<213> ORGANISM: Homo sapiens

<400> SEQUENCE: 143
gggagccaaa ugcuuugcua gagcugguaa aauggaacca aaucgacugu ccaauggauu 60
ugguccccuu caaccagcug uagcugugca uugauggcgc cg 102

<210> SEQ ID NO 144
<211> LENGTH: 68
<212> TYPE: RNA
<213> ORGANISM: Homo sapiens

<400> SEQUENCE: 144
gcuagagcug guaaaaugga accaaaucgc cucuucaaug gauuuggucc ccuucaacca 60
gcuguagc 68

<210> SEQ ID NO 145
<211> LENGTH: 119
<212> TYPE: RNA
<213> ORGANISM: Homo sapiens

<400> SEQUENCE: 145
ccucagaaga aagaugcccc cugcucuggc uggucaaacg gaaccaaguc cgucuuccug 60
agagguuugg uccccuucaa ccagcuacag cagggcuggc aaugcccagu ccuuggaga 119

<210> SEQ ID NO 146
<211> LENGTH: 80
<212> TYPE: RNA
<213> ORGANISM: Homo sapiens

<400> SEQUENCE: 146
gcccccugcu cuggcugguc aaacggaacc aaguccgucu uccugagagg uuuggucccc 60
uucaaccagc uacagcaggg 80

<210> SEQ ID NO 147
<211> LENGTH: 73
<212> TYPE: RNA
<213> ORGANISM: Homo sapiens

<400> SEQUENCE: 147
cagggugugu gacugguuga ccagaggggc augcacugug uucacccugu gggccaccua 60
gucaccaacc cuc 73

<210> SEQ ID NO 148
<211> LENGTH: 71
<212> TYPE: RNA
<213> ORGANISM: Homo sapiens

<400> SEQUENCE: 148
agggugugug acugguugac cagaggggca ugcacugugu ucacccugug ggccaccuag 60
ucaccaaccc u 71

<210> SEQ ID NO 149
<211> LENGTH: 90
<212> TYPE: RNA
<213> ORGANISM: Homo sapiens

<400> SEQUENCE: 149
aggccucgcu guucucuaug gcuuuuuauu ccuaugugau ucuacugcuc acucauauag 60
ggauuggagc cguggcgcac ggcggggaca 90

<210> SEQ ID NO 150
<211> LENGTH: 100
<212> TYPE: RNA
<213> ORGANISM: Homo sapiens

<400> SEQUENCE: 150
agauaaauuc acucuagugc uuuauggcuu uuuauuccua ugugauagua auaaagucuc 60
auguagggau ggaagccaug aaauacauug ugaaaaauca 100

<210> SEQ ID NO 151
<211> LENGTH: 60
<212> TYPE: RNA
<213> ORGANISM: Homo sapiens

<400> SEQUENCE: 151
cuauggcuuu uuauuccuau gugauucuac ugcucacuca uauagggauu ggagccgugg 60

<210> SEQ ID NO 152
<211> LENGTH: 97

-continued

<212> TYPE: RNA
<213> ORGANISM: Homo sapiens

<400> SEQUENCE: 152
cacucugcug uggccuaugg cuuuucauuc cuaugugauu gcugucccaa acucauguag 60
ggcuaaaagc caugggcuac agugaggggc gagcucc 97

<210> SEQ ID NO 153
<211> LENGTH: 82
<212> TYPE: RNA
<213> ORGANISM: Homo sapiens

<400> SEQUENCE: 153
ugagcccucg gaggacucca uuuguuuuga ugauggauuc uuaugcucca ucaucgucuc 60
aaaugagucu ucagaggguu cu 82

<210> SEQ ID NO 154
<211> LENGTH: 62
<212> TYPE: RNA
<213> ORGANISM: Homo sapiens

<400> SEQUENCE: 154
gaggacucca uuuguuuuga ugauggauuc uuaugcucca ucaucgucuc aaaugagucu 60
uc 62

<210> SEQ ID NO 155
<211> LENGTH: 73
<212> TYPE: RNA
<213> ORGANISM: Homo sapiens

<400> SEQUENCE: 155
cuucggugac ggguauucuu ggguggauaa uacggauuac guuguuauug cuuaagaaua 60
cgcguagucg agg 73

<210> SEQ ID NO 156
<211> LENGTH: 99
<212> TYPE: RNA
<213> ORGANISM: Homo sapiens

<400> SEQUENCE: 156
cccuggcaug guguggguggg gcagcuggug uugugaauca ggccguugcc aaucagagaa 60
cggcuacuuc acaacaccag ggccacacca cacuacagg 99

<210> SEQ ID NO 157
<211> LENGTH: 84
<212> TYPE: RNA
<213> ORGANISM: Homo sapiens

<400> SEQUENCE: 157
cguugcugca gcugguguug ugaaucaggc cgacgagcag cgcauccucu uacccggcua 60
uuucacgaca ccaggguugc auca 84

<210> SEQ ID NO 158
<211> LENGTH: 71
<212> TYPE: RNA
<213> ORGANISM: Homo sapiens

<400> SEQUENCE: 158
cagcuggugu ugugaaucag gccgacgagc agcgcauccu cuuacccggc uauuucacga 60
caccagggUU g 71

<210> SEQ ID NO 159
<211> LENGTH: 68
<212> TYPE: RNA
<213> ORGANISM: Homo sapiens

<400> SEQUENCE: 159
guguauucua cagugcacgu gucuccagug uggcucggag gcuggagacg cggcccuguu 60
ggaguaac 68

<210> SEQ ID NO 160
<211> LENGTH: 100
<212> TYPE: RNA
<213> ORGANISM: Homo sapiens

<400> SEQUENCE: 160
ugugucucuc ucuguguccu gccagugguu uuacccuaug guagguuacg ucaugcuguu 60
cuaccacagg guagaaccac ggacaggaua ccggggcacc 100

<210> SEQ ID NO 161
<211> LENGTH: 72
<212> TYPE: RNA
<213> ORGANISM: Homo sapiens

<400> SEQUENCE: 161
uccugccagu gguuuuaccc uaugguaggu uacgucaugc uguucuacca caggguagaa 60
ccacggacag ga 72

<210> SEQ ID NO 162
<211> LENGTH: 70
<212> TYPE: RNA
<213> ORGANISM: Homo sapiens

<400> SEQUENCE: 162
ccugccagug guuuuacccu augguagguu acgucaugcu guucuaccac aggguagaac 60
cacggacagg 70

<210> SEQ ID NO 163
<211> LENGTH: 95
<212> TYPE: RNA
<213> ORGANISM: Homo sapiens

<400> SEQUENCE: 163
cggccggccc uggguccauc uuccaguaca guguuggaug gucuaauugu gaagcuccua 60
acacugucug guaaagaugg cucccgggug gguuc 95

<210> SEQ ID NO 164
<211> LENGTH: 72
<212> TYPE: RNA
<213> ORGANISM: Homo sapiens

<400> SEQUENCE: 164
ggguccaucu uccaguacag uguuggaugg ucuaauugug aagcuccuaa cacugucugg 60
uaaagauggc cc 72

<210> SEQ ID NO 165
<211> LENGTH: 64
<212> TYPE: RNA
<213> ORGANISM: Homo sapiens

<400> SEQUENCE: 165
acccauaaag uagaaagcac uacuaacagc acuggagggu guaguguuuc cuacuuuaug 60
gaug 64

<210> SEQ ID NO 166
<211> LENGTH: 106
<212> TYPE: RNA
<213> ORGANISM: Homo sapiens

<400> SEQUENCE: 166
gcgcagcgcc cugucuccca gccugaggug cagugcugca ucucugguca guugggaguc 60
ugagaugaag cacuguagcu caggaagaga gaaguuguuc ugcagc 106

<210> SEQ ID NO 167
<211> LENGTH: 63
<212> TYPE: RNA
<213> ORGANISM: Homo sapiens

<400> SEQUENCE: 167
ccugaggugc agugcugcau cucuggucag uugggagucu gagaugaagc acuguagcuc 60
agg 63

<210> SEQ ID NO 168
<211> LENGTH: 86
<212> TYPE: RNA
<213> ORGANISM: Homo sapiens

<400> SEQUENCE: 168
uggggcccug gcugggauau caucauauac uguaaguuug cgaugagaca cuacaguaua 60
gaugauguac uaguccgggc accccc 86

<210> SEQ ID NO 169
<211> LENGTH: 66
<212> TYPE: RNA
<213> ORGANISM: Homo sapiens

<400> SEQUENCE: 169
ggcugggaua ucaucauaua cuguaaguuu gcgaugagac acuacaguau agaugaugua 60
cuaguc 66

<210> SEQ ID NO 170
<211> LENGTH: 88
<212> TYPE: RNA
<213> ORGANISM: Homo sapiens

<400> SEQUENCE: 170
caccuugucc ucacggucca guuuucccag gaaucccuua gaugcuaaga uggggauucc 60
uggaaauacu guucuugagg ucaugguu 88

<210> SEQ ID NO 171
<211> LENGTH: 70
<212> TYPE: RNA
<213> ORGANISM: Homo sapiens

<400> SEQUENCE: 171
cucacggucc aguuuuccca ggaaucccuu agaugcuaag auggggauuc cuggaaauac 60
uguucuugag 70

<210> SEQ ID NO 172
<211> LENGTH: 99
<212> TYPE: RNA
<213> ORGANISM: Homo sapiens

<400> SEQUENCE: 172
ccgaugugua uccucagcuu ugagaacuga auuccauggg uugugucagu gucagaccuc    60
ugaaauucag uucuucagcu gggauaucuc ugucaucgu                          99

<210> SEQ ID NO 173
<211> LENGTH: 65
<212> TYPE: RNA
<213> ORGANISM: Homo sapiens

<400> SEQUENCE: 173
agcuuugaga acugaauucc auggguugug ucagugucag accugugaaa uucaguucuu    60
cagcu                                                               65

<210> SEQ ID NO 174
<211> LENGTH: 72
<212> TYPE: RNA
<213> ORGANISM: Homo sapiens

<400> SEQUENCE: 174
aaucuaaaga caacauuucu gcacacacac cagacuaugg aagccagugu guggaaaugc    60
uucugcuaga uu                                                       72

<210> SEQ ID NO 175
<211> LENGTH: 68
<212> TYPE: RNA
<213> ORGANISM: Homo sapiens

<400> SEQUENCE: 175
gaggcaaagu ucugagacac uccgacucug aguaugauag aagucagugc acuacagaac    60
uuugucuc                                                            68

<210> SEQ ID NO 176
<211> LENGTH: 99
<212> TYPE: RNA
<213> ORGANISM: Homo sapiens

<400> SEQUENCE: 176
caagcacgau uagcauuuga ggugaaguuc uguuauacac ucaggcugug gcucucugaa    60
agucagugca ucacagaacu uugucucgaa agcuuucua                          99

<210> SEQ ID NO 177
<211> LENGTH: 70
<212> TYPE: RNA
<213> ORGANISM: Homo sapiens

<400> SEQUENCE: 177
aagcacgauu agcauuugag gugaaguucu guuauacacu caggcugugg cucucugaaa    60
gucagugcau                                                          70

<210> SEQ ID NO 178
<211> LENGTH: 89
<212> TYPE: RNA
<213> ORGANISM: Homo sapiens

<400> SEQUENCE: 178
gccggcgccc gagcucuggc uccgugucuu cacuccccgug cuuguccgag gagggaggga 60
gggacggggg cugugcuggg gcagcugga 89

<210> SEQ ID NO 179
<211> LENGTH: 53
<212> TYPE: RNA
<213> ORGANISM: Homo sapiens

<400> SEQUENCE: 179
gcucuggcuc cgugucuuca cucccgugcu uguccgagga gggagggagg gac 53

<210> SEQ ID NO 180
<211> LENGTH: 84
<212> TYPE: RNA
<213> ORGANISM: Homo sapiens

<400> SEQUENCE: 180
cuccccaugg cccugucucc caacccuugu accagugcug ggcucagacc cugguacagg 60
ccugggggac agggaccugg ggac 84

<210> SEQ ID NO 181
<211> LENGTH: 64
<212> TYPE: RNA
<213> ORGANISM: Homo sapiens

<400> SEQUENCE: 181
cccugucucc caacccuugu accagugcug ggcucagacc cugguacagg ccugggggac 60
aggg 64

<210> SEQ ID NO 182
<211> LENGTH: 72
<212> TYPE: RNA
<213> ORGANISM: Homo sapiens

<400> SEQUENCE: 182
uuuccugccc ucgaggagcu cacagucuag uaugucucau ccccuacuag acugaagcuc 60
cuugaggaca gg 72

<210> SEQ ID NO 183
<211> LENGTH: 69
<212> TYPE: RNA
<213> ORGANISM: Homo sapiens

<400> SEQUENCE: 183
ccuguccuca aggagcuuca gucuaguagg ggaugagaca uacuagacug ugagcuccuc 60
gagggcagg 69

<210> SEQ ID NO 184
<211> LENGTH: 87
<212> TYPE: RNA
<213> ORGANISM: Homo sapiens

<400> SEQUENCE: 184
uguccccccc ggcccagguu cugugauaca cuccgacucg ggcucuggag cagucagugc 60
augacagaac uugggcccgg aaggacc 87

<210> SEQ ID NO 185
<211> LENGTH: 71
<212> TYPE: RNA

<213> ORGANISM: Homo sapiens

<400> SEQUENCE: 185
ggcccagguu cugugauaca cuccgacucg ggcucuggag cagucagugc augacagaac 60
uugggccccg g 71

<210> SEQ ID NO 186
<211> LENGTH: 90
<212> TYPE: RNA
<213> ORGANISM: Homo sapiens

<400> SEQUENCE: 186
cucacagcug ccagugucau uuuugugauc ugcagcuagu auucucacuc caguugcaua 60
gucacaaaag ugaucauugg caggugugge 90

<210> SEQ ID NO 187
<211> LENGTH: 71
<212> TYPE: RNA
<213> ORGANISM: Homo sapiens

<400> SEQUENCE: 187
ucucucucuc ccucacagcu gccaguguca uugucacaaa agugaucauu ggcaggugug 60
gcugcugcau g 71

<210> SEQ ID NO 188
<211> LENGTH: 87
<212> TYPE: RNA
<213> ORGANISM: Homo sapiens

<400> SEQUENCE: 188
agcgguggcc agugucauuu uugugauguu gcagcuagua auaugagccc aguugcauag 60
ucacaaaagu gaucauugga aacugug 87

<210> SEQ ID NO 189
<211> LENGTH: 69
<212> TYPE: RNA
<213> ORGANISM: Homo sapiens

<400> SEQUENCE: 189
cagugucauu uuugugaugu ugcagcuagu aauaugagcc caguugcaua gucacaaaag 60
ugaucauug 69

<210> SEQ ID NO 190
<211> LENGTH: 84
<212> TYPE: RNA
<213> ORGANISM: Homo sapiens

<400> SEQUENCE: 190
gugguacuug aagauagguu auccguguug ccuucgcuuu auuugugacg aaucauacac 60
gguugaccua uuuuucagua ccaa 84

<210> SEQ ID NO 191
<211> LENGTH: 66
<212> TYPE: RNA
<213> ORGANISM: Homo sapiens

<400> SEQUENCE: 191
gaagauaggu uauccguguu gccuucgcuu uauuugugac gaaucauaca cgguugaccu 60
auuuuu 66

-continued

<210> SEQ ID NO 192
<211> LENGTH: 65
<212> TYPE: RNA
<213> ORGANISM: Homo sapiens

<400> SEQUENCE: 192
cuguuaaugc uaaucgugau aggggguuuuu gccuccaacu gacuccuaca uauuagcauu 60
aacag 65

<210> SEQ ID NO 193
<211> LENGTH: 82
<212> TYPE: RNA
<213> ORGANISM: Homo sapiens

<400> SEQUENCE: 193
ccuaacacug ucugguaaag auggcucccg ggugggguucu cucggcagua accuucaggg 60
agcccugaag accauggagg ac 82

<210> SEQ ID NO 194
<211> LENGTH: 110
<212> TYPE: RNA
<213> ORGANISM: Homo sapiens

<400> SEQUENCE: 194
gccgagaccg agugcacagg gcucugaccu augaauugac agccagugcu cucgucuccc 60
cucuggcugc caauuccaua ggucacaggu auguucgccu caaugccagc 110

<210> SEQ ID NO 195
<211> LENGTH: 80
<212> TYPE: RNA
<213> ORGANISM: Homo sapiens

<400> SEQUENCE: 195
ucccgccccc uguaacagca acuccaugug gaagugccca cugguuccag uggggcugcu 60
guuaucuggg gcgagggcca 80

<210> SEQ ID NO 196
<211> LENGTH: 70
<212> TYPE: RNA
<213> ORGANISM: Homo sapiens

<400> SEQUENCE: 196
aaagcugggu ugagagggcg aaaaaggaug aggugacugg ucugggcuac gcuaugcugc 60
ggcgcucggg 70

<210> SEQ ID NO 197
<211> LENGTH: 64
<212> TYPE: RNA
<213> ORGANISM: Homo sapiens

<400> SEQUENCE: 197
cauuggccuc cuaagccagg gauugugggu ucgaguccca cccggggguaa agaaaggccg 60 aauu 64

<210> SEQ ID NO 198
<211> LENGTH: 70
<212> TYPE: RNA
<213> ORGANISM: Homo sapiens

<400> SEQUENCE: 198
ccuaagccag ggauuguggg uucgaguccc accuggggua gaggugaaag uuccuuuuac 60
ggaauuuuuu 70

<210> SEQ ID NO 199
<211> LENGTH: 108
<212> TYPE: RNA
<213> ORGANISM: Homo sapiens

<400> SEQUENCE: 199
caaugucagc agugccuuag cagcacguaa auauuggcgu uaagauucua aaauuaucuc 60
caguauuaac ugugcugcug aaguaagguu gaccauacuc uacaguug 108

<210> SEQ ID NO 200
<211> LENGTH: 81
<212> TYPE: RNA
<213> ORGANISM: Homo sapiens

<400> SEQUENCE: 200
gggcuuucaa gucacuagug guuccguuua guagaugauu gugcauuguu ucaaaauggu 60
gcccuaguga cuacaaagcc c 81

<210> SEQ ID NO 201
<211> LENGTH: 70
<212> TYPE: RNA
<213> ORGANISM: Homo sapiens

<400> SEQUENCE: 201
acgcaagugu ccuaagguga gcucagggag cacagaaacc uccaguggaa cagaagggca 60
aaagcucauu 70

<210> SEQ ID NO 202
<211> LENGTH: 70
<212> TYPE: RNA
<213> ORGANISM: Homo sapiens

<400> SEQUENCE: 202
caugugucac uuucaggugg aguuucaaga gucccuuccu gguucaccgu cuccuuugcu 60
cuuccacaac 70

<210> SEQ ID NO 203
<211> LENGTH: 110
<212> TYPE: RNA
<213> ORGANISM: Homo sapiens

<400> SEQUENCE: 203
agaagggcua ucaggccagc cuucagagga cuccaaggaa cauucaacgc ugucggugag 60
uuugggauuu gaaaaaacca cugaccguug acuguaccuu ggggguccuua 110

<210> SEQ ID NO 204
<211> LENGTH: 110
<212> TYPE: RNA
<213> ORGANISM: Homo sapiens

<400> SEQUENCE: 204
ccugugcaga gauuauuuuu uaaaagguca caaucaacau ucauugcugu cggugggguug 60 aacugugugg acaagcucac ugaacaauga augcaacugu ggccccgcuu 110

```
<210> SEQ ID NO 205
<211> LENGTH: 89
<212> TYPE: RNA
<213> ORGANISM: Homo sapiens

<400> SEQUENCE: 205

cugauggcug cacucaacau ucauugcugu cggugggüuu gagucugaau caacucacug    60

aucaaugaau gcaaacugcg gaccaaaca                                     89

<210> SEQ ID NO 206
<211> LENGTH: 110
<212> TYPE: RNA
<213> ORGANISM: Homo sapiens

<400> SEQUENCE: 206

cggaaaauuu gccaaggguu uggggggaaca uucaaccugu cggugaguuu gggcagcuca    60

ggcaaaccau cgaccguuga guggacccug aggccuggaa uugccauccu              110

<210> SEQ ID NO 207
<211> LENGTH: 110
<212> TYPE: RNA
<213> ORGANISM: Homo sapiens

<400> SEQUENCE: 207

gagcugcuug ccuccccccg uuuuuggcaa ugguagaacu cacacuggug agguaacagg    60

auccgguggu ucuagacuug ccaacuaugg ggcgaggacu cagccggcac              110

<210> SEQ ID NO 208
<211> LENGTH: 70
<212> TYPE: RNA
<213> ORGANISM: Homo sapiens

<400> SEQUENCE: 208

uuuuuggcaa ugguagaacu cacacuggug agguaacagg auccgguggu ucuagacuug    60

ccaacuaugg                                                          70

<210> SEQ ID NO 209
<211> LENGTH: 110
<212> TYPE: RNA
<213> ORGANISM: Homo sapiens

<400> SEQUENCE: 209

ccgcagagug ugacuccugu ucuguguaug gcacugguag aauucacugu gaacagucuc    60

agucagugaa uuaccgaagg gccauaaaca gagcagagac agauccacga              110

<210> SEQ ID NO 210
<211> LENGTH: 84
<212> TYPE: RNA
<213> ORGANISM: Homo sapiens

<400> SEQUENCE: 210

ccagucacgu ccccuuauca cuuuuccagc ccagcuuugu gacuguaagu guuggacgga    60

gaacugauaa gggüaggüga uuga                                          84

<210> SEQ ID NO 211
<211> LENGTH: 65
<212> TYPE: RNA
<213> ORGANISM: Homo sapiens

<400> SEQUENCE: 211
```

-continued ccuuaucacu uuuccagccc agcuuuguga cuguaagugu uggacggaga acugauaagg 60
guagg 65

<210> SEQ ID NO 212
<211> LENGTH: 82
<212> TYPE: RNA
<213> ORGANISM: Homo sapiens

<400> SEQUENCE: 212
agggggcgag ggauuggaga gaaaggcagu uccugauggu ccccucccca ggggcuggcu 60
uuccucuggu ccuucccucc ca 82

<210> SEQ ID NO 213
<211> LENGTH: 66
<212> TYPE: RNA
<213> ORGANISM: Homo sapiens

<400> SEQUENCE: 213
agggauugga gagaaaggca guuccugaug guccccuccc caggggcugg cuuuccucug 60
guccuu 66

<210> SEQ ID NO 214
<211> LENGTH: 86
<212> TYPE: RNA
<213> ORGANISM: Homo sapiens

<400> SEQUENCE: 214
ugcuuguaac uuuccaaaga auucuccuuu ugggcuuucu gguuuuauuu uaagcccaaa 60
ggugaauuuu uugggaaguu ugagcu 86

<210> SEQ ID NO 215
<211> LENGTH: 71
<212> TYPE: RNA
<213> ORGANISM: Homo sapiens

<400> SEQUENCE: 215
acuuuccaaa gaauucuccu uuugggcuuu cugguuuuau uuuaagccca aaggugaauu 60
uuuugggaag u 71

<210> SEQ ID NO 216
<211> LENGTH: 109
<212> TYPE: RNA
<213> ORGANISM: Homo sapiens

<400> SEQUENCE: 216
ggucgggcuc accaugacac agugugagac ucgggcuaca acacaggacc cggggcgcug 60
cucugacccc ucgugucuug uguugcagcc ggagggacgc agguccgca 109

<210> SEQ ID NO 217
<211> LENGTH: 86
<212> TYPE: RNA
<213> ORGANISM: Homo sapiens

<400> SEQUENCE: 217
ugcucccucu cucacauccc uugcauggug gagggugagc uuucugaaaa ccccucccac 60 augcagggu ugcaggaugg cgagcc 86

<210> SEQ ID NO 218
<211> LENGTH: 68

<212> TYPE: RNA
<213> ORGANISM: Homo sapiens

<400> SEQUENCE: 218
ucucacaucc cuugcauggu ggagggugag cuuucugaaa accccuccca caugcagggu 60
uugcagga 68

<210> SEQ ID NO 219
<211> LENGTH: 102
<212> TYPE: RNA
<213> ORGANISM: Homo sapiens

<400> SEQUENCE: 219
cugucgauug gacccgcccu ccggugccua cugagcugau aucaguucuc auuuuacaca 60
cuggcucagu ucagcaggaa caggagucga gcccuugagc aa 102

<210> SEQ ID NO 220
<211> LENGTH: 68
<212> TYPE: RNA
<213> ORGANISM: Homo sapiens

<400> SEQUENCE: 220
cuccggugcc uacugagcug auaucaguuc ucauuuuaca cacuggcuca guucagcagg 60
aacaggag 68

<210> SEQ ID NO 221
<211> LENGTH: 85
<212> TYPE: RNA
<213> ORGANISM: Homo sapiens

<400> SEQUENCE: 221
ugcaggccuc ugugugauau guuugauaua uuagguuguu auuuaaucca acuauauauc 60
aaacauauuc cuacaguguc uugcc 85

<210> SEQ ID NO 222
<211> LENGTH: 67
<212> TYPE: RNA
<213> ORGANISM: Homo sapiens

<400> SEQUENCE: 222
cugugugaua uguuugauau auuagguugu uauuuaaucc aacuauauau caaacauauu 60
ccuacag 67

<210> SEQ ID NO 223
<211> LENGTH: 92
<212> TYPE: RNA
<213> ORGANISM: Homo sapiens

<400> SEQUENCE: 223
cggcuggaca gcgggcaacg gaaucccaaa agcagcuguu gucuccagag cauuccagcu 60
gcgcuuggau uucgucccu gcucuccugc cu 92

<210> SEQ ID NO 224
<211> LENGTH: 74
<212> TYPE: RNA
<213> ORGANISM: Homo sapiens

<400> SEQUENCE: 224
agcgggcaac ggaaucccaa aagcagcugu ugucuccaga gcauuccagc ugcgcuugga 60

-continued uuucgucccc ugcu 74

<210> SEQ ID NO 225
<211> LENGTH: 108
<212> TYPE: RNA
<213> ORGANISM: Homo sapiens

<400> SEQUENCE: 225
ccgagaccga gugcacaggg cucugaccua ugaauugaca gccagugcuc ucgucucccc 60
ucuggcugcc aauuccauag gucacaggua uguucgccuc aaugccag 108

<210> SEQ ID NO 226
<211> LENGTH: 110
<212> TYPE: RNA
<213> ORGANISM: Homo sapiens

<400> SEQUENCE: 226
gccgagaccg agugcacagg gcucugaccu augaauugac agccagugcu cucgucuccc 60
cucuggcugc caauuccaua ggucacaggu auguucgccu caaugccagc 110

<210> SEQ ID NO 227
<211> LENGTH: 88
<212> TYPE: RNA
<213> ORGANISM: Homo sapiens

<400> SEQUENCE: 227
cgaggauggg agcugagggc ugggucuuug cgggcgagau gagggugucg gaucaacugg 60
ccuacaaagu cccaguucuc ggcccccg 88

<210> SEQ ID NO 228
<211> LENGTH: 58
<212> TYPE: RNA
<213> ORGANISM: Homo sapiens

<400> SEQUENCE: 228
gcugggucuu ugcgggcgag augagggugu cggaucaacu ggccuacaaa gucccagu 58

<210> SEQ ID NO 229
<211> LENGTH: 85
<212> TYPE: RNA
<213> ORGANISM: Homo sapiens

<400> SEQUENCE: 229
augguguuau caaguguaac agcaacucca uguggacugu guaccaauuu ccaguggaga 60
ugcuguuacu uuugaugguu accaa 85

<210> SEQ ID NO 230
<211> LENGTH: 63
<212> TYPE: RNA
<213> ORGANISM: Homo sapiens

<400> SEQUENCE: 230
guguaacagc aacuccaugu ggacugugua ccaauuucca guggagaugc uguuacuuuu 60
gau 63

<210> SEQ ID NO 231
<211> LENGTH: 87
<212> TYPE: RNA
<213> ORGANISM: Homo sapiens

<400> SEQUENCE: 231
agcuucccug gcucuagcag cacagaaaua uuggcacagg gaagcgaguc ugccaauauu 60
ggcugugcug cuccaggcag gguggug 87

<210> SEQ ID NO 232
<211> LENGTH: 58
<212> TYPE: RNA
<213> ORGANISM: Homo sapiens

<400> SEQUENCE: 232
uagcagcaca gaaauauugg cacagggaag cgagucugcc aauauuggcu gugcugcu 58

<210> SEQ ID NO 233
<211> LENGTH: 110
<212> TYPE: RNA
<213> ORGANISM: Homo sapiens

<400> SEQUENCE: 233
cuagagcuug aauuggaacu gcugagugaa uuagguaguu ucauguuguu gggccugggu 60
uucugaacac aacaacauua aaccacccga uucacggcag uuacugcucc 110

<210> SEQ ID NO 234
<211> LENGTH: 70
<212> TYPE: RNA
<213> ORGANISM: Homo sapiens

<400> SEQUENCE: 234
gugaauuagg uaguuucaug uuguugggcc uggguuucug aacacaacaa cauuaaacca 60
cccgauucac 70

<210> SEQ ID NO 235
<211> LENGTH: 110
<212> TYPE: RNA
<213> ORGANISM: Homo sapiens

<400> SEQUENCE: 235
ugcucgcuca gcugaucugu ggcuuaggua guuucauguu guugggauug aguuuugaac 60
ucggcaacaa gaaacugccu gaguuacauc agucgguuuu cgucgagggc 110

<210> SEQ ID NO 236
<211> LENGTH: 70
<212> TYPE: RNA
<213> ORGANISM: Homo sapiens

<400> SEQUENCE: 236
gugaauuagg uaguuucaug uuguugggcc uggguuucug aacacaacaa cauuaaacca 60
cccgauucac 70

<210> SEQ ID NO 237
<211> LENGTH: 84
<212> TYPE: RNA
<213> ORGANISM: Homo sapiens

<400> SEQUENCE: 237
acuggucggu gauuuaggua guuuccuguu guugggaucc accuuucucu cgacagcacg 60
acacugccuu cauuacuuca guug 84

<210> SEQ ID NO 238
<211> LENGTH: 75
<212> TYPE: RNA

```
<213> ORGANISM: Homo sapiens

<400> SEQUENCE: 238

ggcugugccg gguagagagg gcagugggag guaagagcuc uucacccuuc accaccuucu    60

ccacccagca uggcc                                                     75

<210> SEQ ID NO 239
<211> LENGTH: 60
<212> TYPE: RNA
<213> ORGANISM: Homo sapiens

<400> SEQUENCE: 239

gugcaugugu auguaugugu gcaugugcau guguaugugu augagugcau gcgugugugc    60

<210> SEQ ID NO 240
<211> LENGTH: 62
<212> TYPE: RNA
<213> ORGANISM: Homo sapiens

<400> SEQUENCE: 240

ucauuggucc agaggggaga uagguuccug ugauuuuucc uucuucucua uagaauaaau    60

ga                                                                   62

<210> SEQ ID NO 241
<211> LENGTH: 71
<212> TYPE: RNA
<213> ORGANISM: Homo sapiens

<400> SEQUENCE: 241

gccaacccag uguucagacu accuguucag gaggcucuca auguguacag uagucugcac    60

auugguuagg c                                                         71

<210> SEQ ID NO 242
<211> LENGTH: 110
<212> TYPE: RNA
<213> ORGANISM: Homo sapiens

<400> SEQUENCE: 242

aggaagcuuc uggagauccu gcuccgucgc cccaguguuc agacuaccug uucaggacaa    60

ugccguugua caguagucug cacauugguu agacugggca agggagagca               110

<210> SEQ ID NO 243
<211> LENGTH: 110
<212> TYPE: RNA
<213> ORGANISM: Homo sapiens

<400> SEQUENCE: 243

ccagaggaca ccuccacucc gucuacccag uguuuagacu aucuguucag gacucccaaa    60

uuguacagua gucugcacau ugguuaggcu gggcuggguu agacccucgg               110

<210> SEQ ID NO 244
<211> LENGTH: 71
<212> TYPE: RNA
<213> ORGANISM: Homo sapiens

<400> SEQUENCE: 244

gccaacccag uguucagacu accuguucag gaggcucuca auguguacag uagucugcac    60

auugguuagg c                                                         71
```

<210> SEQ ID NO 245
<211> LENGTH: 70
<212> TYPE: RNA
<213> ORGANISM: Homo sapiens

<400> SEQUENCE: 245
gccguggcca ucuuacuggg cagcauugga uggagucagg ucucuaauac ugccugguaa 60
ugaugacggc 70

<210> SEQ ID NO 246
<211> LENGTH: 95
<212> TYPE: RNA
<213> ORGANISM: Homo sapiens

<400> SEQUENCE: 246
ccagcucggg cagccguggc caucuuacug ggcagcauug gauggaguca ggucucuaau 60
acugccuggu aaugaugacg gcggagcccu gcacg 95

<210> SEQ ID NO 247
<211> LENGTH: 68
<212> TYPE: RNA
<213> ORGANISM: Homo sapiens

<400> SEQUENCE: 247
cccucgucuu acccagcagu guuugggugc gguugggagu cucuaauacu gccggguaau 60
gauggagg 68

<210> SEQ ID NO 248
<211> LENGTH: 72
<212> TYPE: RNA
<213> ORGANISM: Homo sapiens

<400> SEQUENCE: 248
guuccuuuuu ccuaugcaua uacuucuuug aggaucuggc cuaaagaggu auagggcaug 60
ggaagaugga gc 72

<210> SEQ ID NO 249
<211> LENGTH: 110
<212> TYPE: RNA
<213> ORGANISM: Homo sapiens

<400> SEQUENCE: 249
guguugggga cucgcgcgcu ggguccagug guucuuaaca guucaacagu ucuguagcgc 60
aauugugaaa uguuuaggac cacuagaccc ggcgggcgcg gcgacagcga 110

<210> SEQ ID NO 250
<211> LENGTH: 110
<212> TYPE: RNA
<213> ORGANISM: Homo sapiens

<400> SEQUENCE: 250
ggcuacaguc uuucuucaug ugacucgugg acuucccuuu gucauccuau gccugagaau 60
auaugaagga ggcugggaag gcaaagggac guucaauugu caucacuggc 110

<210> SEQ ID NO 251
<211> LENGTH: 110
<212> TYPE: RNA
<213> ORGANISM: Homo sapiens

<400> SEQUENCE: 251

-continued

```
aaagauccuc agacaaucca ugugcuucuc uuguccuuca uuccaccgga gucugucuca     60

uacccaacca gauuucagug gagugaaguu caggaggcau ggagcugaca               110


<210> SEQ ID NO 252
<211> LENGTH: 86
<212> TYPE: RNA
<213> ORGANISM: Homo sapiens

<400> SEQUENCE: 252

ugcuucccga ggccacaugc uucuuuauau ccccauaugg auuacuuugc uauggaaugu     60

aaggaagugu gugguuucgg caagug                                          86


<210> SEQ ID NO 253
<211> LENGTH: 69
<212> TYPE: RNA
<213> ORGANISM: Homo sapiens

<400> SEQUENCE: 253

aggccacaug cuucuuuaua uccccauaug gauuacuuug cuauggaaug uaaggaagug     60

ugugguuuu                                                             69


<210> SEQ ID NO 254
<211> LENGTH: 71
<212> TYPE: RNA
<213> ORGANISM: Homo sapiens

<400> SEQUENCE: 254

ugacgggcga gcuuuuggcc cggguuauac cugaugcuca cguauaagac gagcaaaaag     60

cuuguugguc a                                                          71


<210> SEQ ID NO 255
<211> LENGTH: 110
<212> TYPE: RNA
<213> ORGANISM: Homo sapiens

<400> SEQUENCE: 255

acccggcagu gccuccaggc gcagggcagc cccugcccac cgcacacugc gcugccccag     60

acccacugug cgugugacag cggcugaucu gugccugggc agcgcgaccc               110


<210> SEQ ID NO 256
<211> LENGTH: 110
<212> TYPE: RNA
<213> ORGANISM: Homo sapiens

<400> SEQUENCE: 256

ucaccuggcc augugacuug ugggcuuccc uuugucaucc uucgccuagg gcucugagca     60

gggcagggac agcaaagggg ugcucaguug ucacuuccca cagcacggag               110


<210> SEQ ID NO 257
<211> LENGTH: 110
<212> TYPE: RNA
<213> ORGANISM: Homo sapiens

<400> SEQUENCE: 257

cggggcaccc cgcccggaca gcgcgccggc accuuggcuc uagacugcuu acugcccggg     60

ccgcccucag uaacagucuc cagucacggc caccgacgcc uggccccgcc               110


<210> SEQ ID NO 258
<211> LENGTH: 110
```

<212> TYPE: RNA
<213> ORGANISM: Homo sapiens

<400> SEQUENCE: 258
ccugugcaga gauuauuuuu uaaaagguca caaucaacau ucauugcugu cgguggguug 60
aacugugugg acaagcucac ugaacaauga augcaacugu ggccccgcuu 110

<210> SEQ ID NO 259
<211> LENGTH: 108
<212> TYPE: RNA
<213> ORGANISM: Homo sapiens

<400> SEQUENCE: 259 gaguuugag guugcuucag ugaacauuca acgcugucgg ugaguuugga auuaaaauca 60
aaaccaucga ccguugauug uacccuaugg cuaaccauca ucuacucc 108

<210> SEQ ID NO 260
<211> LENGTH: 110
<212> TYPE: RNA
<213> ORGANISM: Homo sapiens

<400> SEQUENCE: 260
ggccuggcug gacagaguug ucaugugucu gccugucuac acuugcugug cagaacaucc 60
gcucaccugu acagcaggca cagacaggca gucacaugac aacccagccu 110

<210> SEQ ID NO 261
<211> LENGTH: 110
<212> TYPE: RNA
<213> ORGANISM: Homo sapiens

<400> SEQUENCE: 261
aucauucaga aaugguauac aggaaaauga ccuaugaauu gacagacaau auagcugagu 60
uugucuguca uuucuuuagg ccaauauucu guaugacugu gcuacuucaa 110

<210> SEQ ID NO 262
<211> LENGTH: 110
<212> TYPE: RNA
<213> ORGANISM: Homo sapiens

<400> SEQUENCE: 262
gauggcugug aguuggcuua aucucagcug gcaacuguga gauguucaua caaucccuca 60
caguggucuc ugggauuaug cuaaacagag caauuuccua gcccucacga 110

<210> SEQ ID NO 263
<211> LENGTH: 110
<212> TYPE: RNA
<213> ORGANISM: Homo sapiens

<400> SEQUENCE: 263
aguauaauua uuacauaguu uuugaugucg cagauacugc aucaggaacu gauuggauaa 60
gaaucaguca ccaucaguuc cuaaugcauu gccuucagca ucuaaacaag 110

<210> SEQ ID NO 264
<211> LENGTH: 110
<212> TYPE: RNA
<213> ORGANISM: Homo sapiens

<400> SEQUENCE: 264
gugauaaugu agcgagauuu ucuguugugc uugaucuaac caugugguug cgagguauga 60

-continued

```
guaaaacaug guuccgucaa gcaccaugga acgucacgca gcuuucuaca              110


<210> SEQ ID NO 265
<211> LENGTH: 110
<212> TYPE: RNA
<213> ORGANISM: Homo sapiens

<400> SEQUENCE: 265

gaccagucgc ugcggggcuu uccuuugugc uugaucuaac cauguggugg aacgauggaa    60

acggaacaug guucugucaa gcaccgcgga aagcaccgug cucuccugca              110


<210> SEQ ID NO 266
<211> LENGTH: 110
<212> TYPE: RNA
<213> ORGANISM: Homo sapiens

<400> SEQUENCE: 266

ccgccccggg ccgcggcucc ugauugucca aacgcaauuc ucgagucuau ggcuccggcc    60

gagaguugag ucuggacguc ccgagccgcc gcccccaaac cucgagcggg              110


<210> SEQ ID NO 267
<211> LENGTH: 110
<212> TYPE: RNA
<213> ORGANISM: Homo sapiens

<400> SEQUENCE: 267

ccgccccggg ccgcggcucc ugauugucca aacgcaauuc ucgagucuau ggcuccggcc    60

gagaguugag ucuggacguc ccgagccgcc gcccccaaac cucgagcggg              110


<210> SEQ ID NO 268
<211> LENGTH: 97
<212> TYPE: RNA
<213> ORGANISM: Homo sapiens

<400> SEQUENCE: 268

acucaggggc uucgccacug auuguccaaa cgcaauucuu guacgagucu gcggccaacc    60

gagaauugug gcuggacauc uguggcugag cuccggg                             97


<210> SEQ ID NO 269
<211> LENGTH: 110
<212> TYPE: RNA
<213> ORGANISM: Homo sapiens

<400> SEQUENCE: 269

gacaguguggg cauuguaggg cuccacaccg uaucugacac uuugggcgag ggcaccaugc    60

ugaagguguu caugaugcgg ucugggaacu ccucacggau cuuacugaug              110


<210> SEQ ID NO 270
<211> LENGTH: 110
<212> TYPE: RNA
<213> ORGANISM: Homo sapiens

<400> SEQUENCE: 270

ugaacaucca ggucuggggc augaaccugg cauacaaugu agauuucugu guucguuagg    60

caacagcuac auugucugcu ggguuucagg cuaccuggaa acauguucuc              110


<210> SEQ ID NO 271
<211> LENGTH: 110
<212> TYPE: RNA
<213> ORGANISM: Homo sapiens
```

<400> SEQUENCE: 271
gcugcuggaa gguguaggua cccucaaugg cucaguagcc aguguagauc cugucuuucg 60
uaaucagcag cuacaucugg cuacuggguc ucugauggca ucuucuagcu 110

<210> SEQ ID NO 272
<211> LENGTH: 110
<212> TYPE: RNA
<213> ORGANISM: Homo sapiens

<400> SEQUENCE: 272
ccuggccucc ugcagugcca cgcuccgugu auuugacaag cugaguugga cacuccaugu 60
gguagagugu caguuuguca aauaccccaa gugcggcaca ugcuuaccag 110

<210> SEQ ID NO 273
<211> LENGTH: 81
<212> TYPE: RNA
<213> ORGANISM: Homo sapiens

<400> SEQUENCE: 273
gggcuuucaa gucacuagug guuccguuua guagaugauu gugcauuguu ucaaaauggu 60
gcccuaguga cuacaaagcc c 81

<210> SEQ ID NO 274
<211> LENGTH: 60
<212> TYPE: RNA
<213> ORGANISM: Homo sapiens

<400> SEQUENCE: 274
caaucuuccu uuaucauggu auugauuuuu cagugcuucc cuuuugugug agagaagaua 60

<210> SEQ ID NO 275
<211> LENGTH: 80
<212> TYPE: RNA
<213> ORGANISM: Homo sapiens

<400> SEQUENCE: 275
aggacccuuc cagagggccc cccucaauc cuguugugcc uaauucagag gguugggugg 60
aggcucuccu gaagggcucu 80

<210> SEQ ID NO 276
<211> LENGTH: 63
<212> TYPE: RNA
<213> ORGANISM: Homo sapiens

<400> SEQUENCE: 276
aagaaauggu uuaccguccc acauacauuu ugaauaugua ugugggaugg uaaaccgcuu 60
cuu 63

<210> SEQ ID NO 277
<211> LENGTH: 86
<212> TYPE: RNA
<213> ORGANISM: Homo sapiens

<400> SEQUENCE: 277
acugcuaacg aaugcucuga cuuuauugca cuacuguacu uuacagcuag cagugcaaua 60
guauugucaa agcaucugaa agcagg 86

<210> SEQ ID NO 278

<211> LENGTH: 69
<212> TYPE: RNA
<213> ORGANISM: Homo sapiens

<400> SEQUENCE: 278
ccaccacuua aacguggaug uacuugcuuu gaaacuaaag aaguaagugc uuccauguuu 60
uggugaugg 69

<210> SEQ ID NO 279
<211> LENGTH: 73
<212> TYPE: RNA
<213> ORGANISM: Homo sapiens

<400> SEQUENCE: 279
gcucccuuca acuuuaacau ggaagugcuu ucugugacuu uaaaaguaag ugcuuccaug 60
uuuuaguagg agu 73

<210> SEQ ID NO 280
<211> LENGTH: 68
<212> TYPE: RNA
<213> ORGANISM: Homo sapiens

<400> SEQUENCE: 280
ccuuugcuuu aacaugggggg uaccugcugu gugaaacaaa aguaagugcu uccauguuuc 60
aguggagg 68

<210> SEQ ID NO 281
<211> LENGTH: 68
<212> TYPE: RNA
<213> ORGANISM: Homo sapiens

<400> SEQUENCE: 281
ccucuacuuu aacauggagg cacuugcugu gacaugacaa aaauaagugc uuccauguuu 60
gagugugg 68

<210> SEQ ID NO 282
<211> LENGTH: 82
<212> TYPE: RNA
<213> ORGANISM: Homo sapiens

<400> SEQUENCE: 282
gcuucgcucc ccuccgccuu cucuucccgg uucuucccgg agucgggaaa agcuggguug 60
agagggcgaa aaaggaugag gu 82

<210> SEQ ID NO 283
<211> LENGTH: 59
<212> TYPE: RNA
<213> ORGANISM: Homo sapiens

<400> SEQUENCE: 283
uuggccuccu aagccaggga uugugggguuc gagucccacc cgggguaaag aaaggccga 59

<210> SEQ ID NO 284
<211> LENGTH: 86
<212> TYPE: RNA
<213> ORGANISM: Homo sapiens

<400> SEQUENCE: 284
uugguacuug gagagaggug guccguggcg cguucgcuuu auuuauggcg cacauuacac 60
ggucgaccuc uuugcaguau cuaauc 86

<210> SEQ ID NO 285
<211> LENGTH: 83
<212> TYPE: RNA
<213> ORGANISM: Homo sapiens

<400> SEQUENCE: 285
cugacuaugc cucccccgcau ccccuagggc auugguguaa agcuggagac ccacugcccc 60
aggugcugcu gggggguugua guc 83

<210> SEQ ID NO 286
<211> LENGTH: 98
<212> TYPE: RNA
<213> ORGANISM: Homo sapiens

<400> SEQUENCE: 286
auacagugcu ugguuccuag uaggugucca guaaguguuu gugacauaau uuguuuauug 60
aggaccuccu aucaaucaag cacugugcua ggcucugg 98

<210> SEQ ID NO 287
<211> LENGTH: 95
<212> TYPE: RNA
<213> ORGANISM: Homo sapiens

<400> SEQUENCE: 287
cucaucuguc uguugggcug gaggcagggc cuuugugaag gcggguggug cucagaucgc 60
cucugggccc uuccuccagc cccgaggcgg auuca 95

<210> SEQ ID NO 288
<211> LENGTH: 75
<212> TYPE: RNA
<213> ORGANISM: Homo sapiens

<400> SEQUENCE: 288 uggaguggggg gggcaggagg ggcucaggga gaaagugcau acagccccug gcccucucug 60
cccuuccguc cccug 75

<210> SEQ ID NO 289
<211> LENGTH: 94
<212> TYPE: RNA
<213> ORGANISM: Homo sapiens

<400> SEQUENCE: 289
cuuuggcgau cacugccucu cugggccugu gucuuaggcu cugcaagauc aaccgagcaa 60
agcacacggc cugcagagag gcagcgcucu gccc 94

<210> SEQ ID NO 290
<211> LENGTH: 94
<212> TYPE: RNA
<213> ORGANISM: Homo sapiens

<400> SEQUENCE: 290
gaguuugguu uuguuugggu uuguucuagg uaugguccca gggaucccag aucaaaccag 60
gccccugggc cuauccuaga accaaccuaa gcuc 94

<210> SEQ ID NO 291
<211> LENGTH: 94
<212> TYPE: RNA
<213> ORGANISM: Homo sapiens

<400> SEQUENCE: 291
uguuuugagc gggggucaag agcaauaacg aaaaauguuu gucauaaacc guuuuucauu 60
auugcuccug accuccucuc auuugcuaua uuca 94

<210> SEQ ID NO 292
<211> LENGTH: 93
<212> TYPE: RNA
<213> ORGANISM: Homo sapiens

<400> SEQUENCE: 292
guagucagua guuggggggu gggaacggcu ucauacagga guugaugcac aguuauccag 60
cuccuauaug augccuuucu ucauccccuu caa 93

<210> SEQ ID NO 293
<211> LENGTH: 67
<212> TYPE: RNA
<213> ORGANISM: Homo sapiens

<400> SEQUENCE: 293
ucuccaacaa uauccuggug cugagugaug acucaggcga cuccagcauc agugauuuug 60
uugaaga 67

<210> SEQ ID NO 294
<211> LENGTH: 94
<212> TYPE: RNA
<213> ORGANISM: Homo sapiens

<400> SEQUENCE: 294
cggggcggcc gcucucccug uccuccagga gcucacgugu gccugccugu gagcgccucg 60
acgacagagc cggcgccugc cccagugucu gcgc 94

<210> SEQ ID NO 295
<211> LENGTH: 95
<212> TYPE: RNA
<213> ORGANISM: Homo sapiens

<400> SEQUENCE: 295
uuguaccugg ugugauuaua aagcaaugag acugauuguc auaugucguu ugugggaucc 60
gucucaguua cuuuauagcc auaccuggua ucuua 95

<210> SEQ ID NO 296
<211> LENGTH: 99
<212> TYPE: RNA
<213> ORGANISM: Homo sapiens

<400> SEQUENCE: 296
gaaacugggc ucaaggugag ggugcuauc ugugauugag ggacaugguu aauggaauug 60
ucucacacag aaaucgcacc cgucaccuug gccuacuua 99

<210> SEQ ID NO 297
<211> LENGTH: 98
<212> TYPE: RNA
<213> ORGANISM: Homo sapiens

<400> SEQUENCE: 297
acccaaaccc uaggucugcu gacuccuagu ccagggcucg ugauggcugg ugggcccuga 60 acgaggggguc uggaggccug gguuugaaua ucgacagc 98

<210> SEQ ID NO 298
<211> LENGTH: 86
<212> TYPE: RNA
<213> ORGANISM: Homo sapiens

<400> SEQUENCE: 298
gucugucugc ccgcaugccu gccucucugu ugcucugaag gaggcagggg cugggccugc 60
agcugccugg gcagagcggc uccugc 86

<210> SEQ ID NO 299
<211> LENGTH: 68
<212> TYPE: RNA
<213> ORGANISM: Homo sapiens

<400> SEQUENCE: 299
ccauuacugu ugcuaauaug caacucuguu gaauauaaau uggaauugca cuuuagcaau 60
ggugaugg 68

<210> SEQ ID NO 300
<211> LENGTH: 66
<212> TYPE: RNA
<213> ORGANISM: Homo sapiens

<400> SEQUENCE: 300
aaaaggugga uauuccuucu auguuuaugu uauuuauggu uaaacauaga ggaaauucca 60
cguuuu 66

<210> SEQ ID NO 301
<211> LENGTH: 70
<212> TYPE: RNA
<213> ORGANISM: Homo sapiens

<400> SEQUENCE: 301
uugaagggag aucgaccgug uuauauucgc uuuauugacu ucgaauaaua caugguugau 60
cuuuucucag 70

<210> SEQ ID NO 302
<211> LENGTH: 75
<212> TYPE: RNA
<213> ORGANISM: Homo sapiens

<400> SEQUENCE: 302
agacagagaa gccaggucac gucucugcag uuacacagcu cacgagugcc ugcuggggug 60
gaaccugguc ugucu 75

<210> SEQ ID NO 303
<211> LENGTH: 67
<212> TYPE: RNA
<213> ORGANISM: Homo sapiens

<400> SEQUENCE: 303
guggcacuca aacugugggg gcacuuucug cucucuggug aaagugccgc caucuuuuga 60
guguuac 67

<210> SEQ ID NO 304
<211> LENGTH: 67
<212> TYPE: RNA
<213> ORGANISM: Homo sapiens

<400> SEQUENCE: 304
gugggccuca aauguggagc acuauucuga uguccaagug gaaagugcug cgacauuuga 60
gcgucac 67

<210> SEQ ID NO 305
<211> LENGTH: 69
<212> TYPE: RNA
<213> ORGANISM: Homo sapiens

<400> SEQUENCE: 305
gggauacuca aaaugggggc gcuuuccuuu uugucuguac ugggaagugc uucgauuuug 60
gggugUccc 69

<210> SEQ ID NO 306
<211> LENGTH: 72
<212> TYPE: RNA
<213> ORGANISM: Homo sapiens

<400> SEQUENCE: 306
uacaucggcc auuauaauac aaccugauaa guguuauagc acuuaucaga uuguauugua 60
auugucugug ua 72

<210> SEQ ID NO 307
<211> LENGTH: 102
<212> TYPE: RNA
<213> ORGANISM: Homo sapiens

<400> SEQUENCE: 307
auggagcugc ucacccugug ggccucaaau guggaggaac uauucugaug uccaagugga 60
aagugcugcg acauuugagc gucaccggug acgcccauau ca 102

<210> SEQ ID NO 308
<211> LENGTH: 101
<212> TYPE: RNA
<213> ORGANISM: Homo sapiens

<400> SEQUENCE: 308
gcauccccuc agccuguggc acucaaacug ugggggcacu uucugcucuc uggugaaagu 60
gccgccaucu uuugaguguu accgcuugag aagacucaac c 101

<210> SEQ ID NO 309
<211> LENGTH: 102
<212> TYPE: RNA
<213> ORGANISM: Homo sapiens

<400> SEQUENCE: 309
cgaggagcuc auacugggau acucaaaaug gggggcgcuuu ccuuuuuguc uguuacuggg 60
aagugcuucg auuuuggggu gucccuguuu gaguagggca uc 102

<210> SEQ ID NO 310
<211> LENGTH: 22
<212> TYPE: RNA
<213> ORGANISM: Homo sapiens

<400> SEQUENCE: 310
ugagguagua gguuguauag uu 22

<210> SEQ ID NO 311
<211> LENGTH: 22
<212> TYPE: RNA
<213> ORGANISM: Homo sapiens

<400> SEQUENCE: 311
ugagguagua gguugugugg uu 22

<210> SEQ ID NO 312
<211> LENGTH: 22
<212> TYPE: RNA
<213> ORGANISM: Homo sapiens

<400> SEQUENCE: 312
ugagguagua gguuguaugg uu 22

<210> SEQ ID NO 313
<211> LENGTH: 21
<212> TYPE: RNA
<213> ORGANISM: Homo sapiens

<400> SEQUENCE: 313
agagguagua gguugcauag u 21

<210> SEQ ID NO 314
<211> LENGTH: 21
<212> TYPE: RNA
<213> ORGANISM: Homo sapiens

<400> SEQUENCE: 314
ugagguagga gguuguauag u 21

<210> SEQ ID NO 315
<211> LENGTH: 22
<212> TYPE: RNA
<213> ORGANISM: Homo sapiens

<400> SEQUENCE: 315
ugagguagua gauuguauag uu 22

<210> SEQ ID NO 316
<211> LENGTH: 21
<212> TYPE: RNA
<213> ORGANISM: Homo sapiens

<400> SEQUENCE: 316
ugagguagua guuuguacag u 21

<210> SEQ ID NO 317
<211> LENGTH: 19
<212> TYPE: RNA
<213> ORGANISM: Homo sapiens

<400> SEQUENCE: 317
ugagguagua guuugugcu 19

<210> SEQ ID NO 318
<211> LENGTH: 21
<212> TYPE: RNA
<213> ORGANISM: Homo sapiens

<400> SEQUENCE: 318
uggaauguaa agaaguaugu a 21

<210> SEQ ID NO 319
<211> LENGTH: 21
<212> TYPE: RNA

<213> ORGANISM: Homo sapiens

<400> SEQUENCE: 319
uggaagacua gugauuuugu u 21

<210> SEQ ID NO 320
<211> LENGTH: 23
<212> TYPE: RNA
<213> ORGANISM: Homo sapiens

<400> SEQUENCE: 320
ucuuugguua ucuagcugua uga 23

<210> SEQ ID NO 321
<211> LENGTH: 21
<212> TYPE: RNA
<213> ORGANISM: Homo sapiens

<400> SEQUENCE: 321
uaaagcuaga uaaccgaaag u 21

<210> SEQ ID NO 322
<211> LENGTH: 23
<212> TYPE: RNA
<213> ORGANISM: Homo sapiens

<400> SEQUENCE: 322
uacccuguag auccgaauuu gug 23

<210> SEQ ID NO 323
<211> LENGTH: 22
<212> TYPE: RNA
<213> ORGANISM: Homo sapiens

<400> SEQUENCE: 323
uacccuguag aaccgaauuu gu 22

<210> SEQ ID NO 324
<211> LENGTH: 22
<212> TYPE: RNA
<213> ORGANISM: Homo sapiens

<400> SEQUENCE: 324
uagcagcaca uaaugguuug ug 22

<210> SEQ ID NO 325
<211> LENGTH: 22
<212> TYPE: RNA
<213> ORGANISM: Homo sapiens

<400> SEQUENCE: 325
uagcagcaca ucaugguuua ca 22

<210> SEQ ID NO 326
<211> LENGTH: 22
<212> TYPE: RNA
<213> ORGANISM: Homo sapiens

<400> SEQUENCE: 326
uagcagcacg uaaauauugg cg 22

<210> SEQ ID NO 327
<211> LENGTH: 24

<212> TYPE: RNA
<213> ORGANISM: Homo sapiens

<400> SEQUENCE: 327
caaagugcuu acagugcagg uagu 24

<210> SEQ ID NO 328
<211> LENGTH: 20
<212> TYPE: RNA
<213> ORGANISM: Homo sapiens

<400> SEQUENCE: 328
acugcaguga aggcacuugu 20

<210> SEQ ID NO 329
<211> LENGTH: 22
<212> TYPE: RNA
<213> ORGANISM: Homo sapiens

<400> SEQUENCE: 329
uaaggugcau cuagugcaga ua 22

<210> SEQ ID NO 330
<211> LENGTH: 23
<212> TYPE: RNA
<213> ORGANISM: Homo sapiens

<400> SEQUENCE: 330
ugugcaaauc uaugcaaaac uga 23

<210> SEQ ID NO 331
<211> LENGTH: 23
<212> TYPE: RNA
<213> ORGANISM: Homo sapiens

<400> SEQUENCE: 331
ugugcaaauc caugcaaaac uga 23

<210> SEQ ID NO 332
<211> LENGTH: 22
<212> TYPE: RNA
<213> ORGANISM: Homo sapiens

<400> SEQUENCE: 332
uaaagugcuu auagugcagg ua 22

<210> SEQ ID NO 333
<211> LENGTH: 22
<212> TYPE: RNA
<213> ORGANISM: Homo sapiens

<400> SEQUENCE: 333
uagcuuauca gacugauguu ga 22

<210> SEQ ID NO 334
<211> LENGTH: 22
<212> TYPE: RNA
<213> ORGANISM: Homo sapiens

<400> SEQUENCE: 334
aagcugccag uugaagaacu gu 22

<210> SEQ ID NO 335

<211> LENGTH: 21
<212> TYPE: RNA
<213> ORGANISM: Homo sapiens

<400> SEQUENCE: 335
aucacauugc cagggauuuc c 21

<210> SEQ ID NO 336
<211> LENGTH: 23
<212> TYPE: RNA
<213> ORGANISM: Homo sapiens

<400> SEQUENCE: 336
aucacauugc cagggauuac cac 23

<210> SEQ ID NO 337
<211> LENGTH: 22
<212> TYPE: RNA
<213> ORGANISM: Homo sapiens

<400> SEQUENCE: 337
uggcucaguu cagcaggaac ag 22

<210> SEQ ID NO 338
<211> LENGTH: 22
<212> TYPE: RNA
<213> ORGANISM: Homo sapiens

<400> SEQUENCE: 338
cauugcacuu gucucggucu ga 22

<210> SEQ ID NO 339
<211> LENGTH: 22
<212> TYPE: RNA
<213> ORGANISM: Homo sapiens

<400> SEQUENCE: 339
uucaaguaau ccaggauagg cu 22

<210> SEQ ID NO 340
<211> LENGTH: 21
<212> TYPE: RNA
<213> ORGANISM: Homo sapiens

<400> SEQUENCE: 340
uucaaguaau ucaggauagg u 21

<210> SEQ ID NO 341
<211> LENGTH: 22
<212> TYPE: RNA
<213> ORGANISM: Homo sapiens

<400> SEQUENCE: 341
uucacagugg cuaaguuccg cc 22

<210> SEQ ID NO 342
<211> LENGTH: 20
<212> TYPE: RNA
<213> ORGANISM: Homo sapiens

<400> SEQUENCE: 342
uucacagugg cuaaguucug 20

<210> SEQ ID NO 343
<211> LENGTH: 22
<212> TYPE: RNA
<213> ORGANISM: Homo sapiens

<400> SEQUENCE: 343
aaggagcuca cagucuauug ag 22

<210> SEQ ID NO 344
<211> LENGTH: 22
<212> TYPE: RNA
<213> ORGANISM: Homo sapiens

<400> SEQUENCE: 344
cuagcaccau cugaaaucgg uu 22

<210> SEQ ID NO 345
<211> LENGTH: 20
<212> TYPE: RNA
<213> ORGANISM: Homo sapiens

<400> SEQUENCE: 345
uagcaccauu ugaaaucagu 20

<210> SEQ ID NO 346
<211> LENGTH: 22
<212> TYPE: RNA
<213> ORGANISM: Homo sapiens

<400> SEQUENCE: 346
uagcaccauu ugaaaucggu ua 22

<210> SEQ ID NO 347
<211> LENGTH: 23
<212> TYPE: RNA
<213> ORGANISM: Homo sapiens

<400> SEQUENCE: 347
uguaaacauc cucgacugga agc 23

<210> SEQ ID NO 348
<211> LENGTH: 22
<212> TYPE: RNA
<213> ORGANISM: Homo sapiens

<400> SEQUENCE: 348
cuuucagucg gauguuugca gc 22

<210> SEQ ID NO 349
<211> LENGTH: 21
<212> TYPE: RNA
<213> ORGANISM: Homo sapiens

<400> SEQUENCE: 349
uguaaacauc cuacacucag c 21

<210> SEQ ID NO 350
<211> LENGTH: 23
<212> TYPE: RNA
<213> ORGANISM: Homo sapiens

<400> SEQUENCE: 350
uguaaacauc cuacacucuc agc 23

<210> SEQ ID NO 351
<211> LENGTH: 22
<212> TYPE: RNA
<213> ORGANISM: Homo sapiens

<400> SEQUENCE: 351
uguaaacauc cccgacugga ag 22

<210> SEQ ID NO 352
<211> LENGTH: 20
<212> TYPE: RNA
<213> ORGANISM: Homo sapiens

<400> SEQUENCE: 352
uguaaacauc cuugacugga 20

<210> SEQ ID NO 353
<211> LENGTH: 21
<212> TYPE: RNA
<213> ORGANISM: Homo sapiens

<400> SEQUENCE: 353
ggcaagaugc uggcauagcu g 21

<210> SEQ ID NO 354
<211> LENGTH: 21
<212> TYPE: RNA
<213> ORGANISM: Homo sapiens

<400> SEQUENCE: 354
uauugcacau uacuaaguug c 21

<210> SEQ ID NO 355
<211> LENGTH: 19
<212> TYPE: RNA
<213> ORGANISM: Homo sapiens

<400> SEQUENCE: 355
gugcauugua guugcauug 19

<210> SEQ ID NO 356
<211> LENGTH: 22
<212> TYPE: RNA
<213> ORGANISM: Homo sapiens

<400> SEQUENCE: 356
uggcaguguc uuagcugguu gu 22

<210> SEQ ID NO 357
<211> LENGTH: 22
<212> TYPE: RNA
<213> ORGANISM: Homo sapiens

<400> SEQUENCE: 357
aggcaguguc auuagcugau ug 22

<210> SEQ ID NO 358
<211> LENGTH: 22
<212> TYPE: RNA
<213> ORGANISM: Homo sapiens

<400> SEQUENCE: 358
aggcagugua guuagcugau ug 22

<210> SEQ ID NO 359
<211> LENGTH: 22
<212> TYPE: RNA
<213> ORGANISM: Homo sapiens

<400> SEQUENCE: 359
uauugcacuu gucccggccu gu 22

<210> SEQ ID NO 360
<211> LENGTH: 22
<212> TYPE: RNA
<213> ORGANISM: Homo sapiens

<400> SEQUENCE: 360
aaagugcugu ucgugcaggu ag 22

<210> SEQ ID NO 361
<211> LENGTH: 22
<212> TYPE: RNA
<213> ORGANISM: Homo sapiens

<400> SEQUENCE: 361
uucaacgggu auuuauugag ca 22

<210> SEQ ID NO 362
<211> LENGTH: 22
<212> TYPE: RNA
<213> ORGANISM: Homo sapiens

<400> SEQUENCE: 362
uuuggcacua gcacauuuuu gc 22

<210> SEQ ID NO 363
<211> LENGTH: 22
<212> TYPE: RNA
<213> ORGANISM: Homo sapiens

<400> SEQUENCE: 363
ugagguagua aguuguauug uu 22

<210> SEQ ID NO 364
<211> LENGTH: 22
<212> TYPE: RNA
<213> ORGANISM: Homo sapiens

<400> SEQUENCE: 364
aacccguaga uccgaucuug ug 22

<210> SEQ ID NO 365
<211> LENGTH: 22
<212> TYPE: RNA
<213> ORGANISM: Homo sapiens

<400> SEQUENCE: 365
cacccguaga accgaccuug cg 22

<210> SEQ ID NO 366
<211> LENGTH: 22
<212> TYPE: RNA
<213> ORGANISM: Homo sapiens

<400> SEQUENCE: 366
uacaguacug ugauaacuga ag 22

<210> SEQ ID NO 367
<211> LENGTH: 22
<212> TYPE: RNA
<213> ORGANISM: Homo sapiens

<400> SEQUENCE: 367
uacaguacug ugauaacuga ag 22

<210> SEQ ID NO 368
<211> LENGTH: 23
<212> TYPE: RNA
<213> ORGANISM: Homo sapiens

<400> SEQUENCE: 368
agcagcauug uacagggcua uga 23

<210> SEQ ID NO 369
<211> LENGTH: 20
<212> TYPE: RNA
<213> ORGANISM: Homo sapiens

<400> SEQUENCE: 369
ucaaaugcuc agacuccugu 20

<210> SEQ ID NO 370
<211> LENGTH: 24
<212> TYPE: RNA
<213> ORGANISM: Homo sapiens

<400> SEQUENCE: 370
aaaagugcuu acagugcagg uagc 24

<210> SEQ ID NO 371
<211> LENGTH: 21
<212> TYPE: RNA
<213> ORGANISM: Homo sapiens

<400> SEQUENCE: 371
uaaagugcug acagugcaga u 21

<210> SEQ ID NO 372
<211> LENGTH: 23
<212> TYPE: RNA
<213> ORGANISM: Homo sapiens

<400> SEQUENCE: 372
agcagcauug uacagggcua uca 23

<210> SEQ ID NO 373
<211> LENGTH: 23
<212> TYPE: RNA
<213> ORGANISM: Homo sapiens

<400> SEQUENCE: 373
uggaguguga caaugguguu ugu 23

<210> SEQ ID NO 374
<211> LENGTH: 22
<212> TYPE: RNA
<213> ORGANISM: Homo sapiens

<400> SEQUENCE: 374
uuaaggcacg cggugaaugc ca 22

<210> SEQ ID NO 375
<211> LENGTH: 23
<212> TYPE: RNA
<213> ORGANISM: Homo sapiens

<400> SEQUENCE: 375
ucccugagac ccuuuaaccu gug 23

<210> SEQ ID NO 376
<211> LENGTH: 22
<212> TYPE: RNA
<213> ORGANISM: Homo sapiens

<400> SEQUENCE: 376
ucccugagac ccuaacuugu ga 22

<210> SEQ ID NO 377
<211> LENGTH: 21
<212> TYPE: RNA
<213> ORGANISM: Homo sapiens

<400> SEQUENCE: 377
cauuauuacu uuugguacgc g 21

<210> SEQ ID NO 378
<211> LENGTH: 21
<212> TYPE: RNA
<213> ORGANISM: Homo sapiens

<400> SEQUENCE: 378
ucguaccgug aguaauaaug c 21

<210> SEQ ID NO 379
<211> LENGTH: 22
<212> TYPE: RNA
<213> ORGANISM: Homo sapiens

<400> SEQUENCE: 379
ucggauccgu cugagcuugg cu 22

<210> SEQ ID NO 380
<211> LENGTH: 22
<212> TYPE: RNA
<213> ORGANISM: Homo sapiens

<400> SEQUENCE: 380
ucacagugaa ccggucucuu uu 22

<210> SEQ ID NO 381
<211> LENGTH: 22
<212> TYPE: RNA
<213> ORGANISM: Homo sapiens

<400> SEQUENCE: 381
ucacagugaa ccggucucuu uc 22

<210> SEQ ID NO 382
<211> LENGTH: 21
<212> TYPE: RNA
<213> ORGANISM: Homo sapiens

<400> SEQUENCE: 382
cuuuuugcgg ucugggcuug c 21

<210> SEQ ID NO 383
<211> LENGTH: 20
<212> TYPE: RNA
<213> ORGANISM: Homo sapiens

<400> SEQUENCE: 383
cagugcaaug uuaaaagggc 20

<210> SEQ ID NO 384
<211> LENGTH: 22
<212> TYPE: RNA
<213> ORGANISM: Homo sapiens

<400> SEQUENCE: 384
cagugcaaug augaaagggc au 22

<210> SEQ ID NO 385
<211> LENGTH: 22
<212> TYPE: RNA
<213> ORGANISM: Homo sapiens

<400> SEQUENCE: 385
uaacagucua cagccauggu cg 22

<210> SEQ ID NO 386
<211> LENGTH: 22
<212> TYPE: RNA
<213> ORGANISM: Homo sapiens

<400> SEQUENCE: 386
uugguccccu ucaaccagcu gu 22

<210> SEQ ID NO 387
<211> LENGTH: 21
<212> TYPE: RNA
<213> ORGANISM: Homo sapiens

<400> SEQUENCE: 387
uugguccccu ucaaccagcu a 21

<210> SEQ ID NO 388
<211> LENGTH: 21
<212> TYPE: RNA
<213> ORGANISM: Homo sapiens

<400> SEQUENCE: 388
ugugacuggu ugaccagagg g 21

<210> SEQ ID NO 389
<211> LENGTH: 23
<212> TYPE: RNA
<213> ORGANISM: Homo sapiens

<400> SEQUENCE: 389
uauggcuuuu uauuccuaug uga 23

<210> SEQ ID NO 390
<211> LENGTH: 22
<212> TYPE: RNA
<213> ORGANISM: Homo sapiens

<400> SEQUENCE: 390
uauggcuuuu cauuccuaug ug 22

<210> SEQ ID NO 391
<211> LENGTH: 23
<212> TYPE: RNA
<213> ORGANISM: Homo sapiens

<400> SEQUENCE: 391
acuccauuug uuuugaugau gga 23

<210> SEQ ID NO 392
<211> LENGTH: 22
<212> TYPE: RNA
<213> ORGANISM: Homo sapiens

<400> SEQUENCE: 392
uauugcuuaa gaauacgcgu ag 22

<210> SEQ ID NO 393
<211> LENGTH: 17
<212> TYPE: RNA
<213> ORGANISM: Homo sapiens

<400> SEQUENCE: 393
agcugguguu gugaauc 17

<210> SEQ ID NO 394
<211> LENGTH: 18
<212> TYPE: RNA
<213> ORGANISM: Homo sapiens

<400> SEQUENCE: 394
ucuacagugc acgugucu 18

<210> SEQ ID NO 395
<211> LENGTH: 21
<212> TYPE: RNA
<213> ORGANISM: Homo sapiens

<400> SEQUENCE: 395
agugguuuua cccuauggua g 21

<210> SEQ ID NO 396
<211> LENGTH: 21
<212> TYPE: RNA
<213> ORGANISM: Homo sapiens

<400> SEQUENCE: 396
aacacugucu gguaaagaug g 21

<210> SEQ ID NO 397
<211> LENGTH: 23
<212> TYPE: RNA
<213> ORGANISM: Homo sapiens

<400> SEQUENCE: 397
uguaguguuu ccuacuuuau gga 23

<210> SEQ ID NO 398
<211> LENGTH: 20
<212> TYPE: RNA

<213> ORGANISM: Homo sapiens

<400> SEQUENCE: 398
cauaaaguag aaagcacuac 20

<210> SEQ ID NO 399
<211> LENGTH: 22
<212> TYPE: RNA
<213> ORGANISM: Homo sapiens

<400> SEQUENCE: 399
ugagaugaag cacuguagcu ca 22

<210> SEQ ID NO 400
<211> LENGTH: 22
<212> TYPE: RNA
<213> ORGANISM: Homo sapiens

<400> SEQUENCE: 400
uacaguauag augauguacu ag 22

<210> SEQ ID NO 401
<211> LENGTH: 24
<212> TYPE: RNA
<213> ORGANISM: Homo sapiens

<400> SEQUENCE: 401
guccaguuuu cccaggaauc ccuu 24

<210> SEQ ID NO 402
<211> LENGTH: 22
<212> TYPE: RNA
<213> ORGANISM: Homo sapiens

<400> SEQUENCE: 402
ugagaacuga auuccauggg uu 22

<210> SEQ ID NO 403
<211> LENGTH: 20
<212> TYPE: RNA
<213> ORGANISM: Homo sapiens

<400> SEQUENCE: 403
guguguggaa augcuucugc 20

<210> SEQ ID NO 404
<211> LENGTH: 22
<212> TYPE: RNA
<213> ORGANISM: Homo sapiens

<400> SEQUENCE: 404
ucagugcacu acagaacuuu gu 22

<210> SEQ ID NO 405
<211> LENGTH: 22
<212> TYPE: RNA
<213> ORGANISM: Homo sapiens

<400> SEQUENCE: 405
ucagugcauc acagaacuuu gu 22

<210> SEQ ID NO 406
<211> LENGTH: 22

<212> TYPE: RNA
<213> ORGANISM: Homo sapiens

<400> SEQUENCE: 406
ucuggcuccg ugucuucacu cc 22

<210> SEQ ID NO 407
<211> LENGTH: 22
<212> TYPE: RNA
<213> ORGANISM: Homo sapiens

<400> SEQUENCE: 407
ucucccaacc cuuguaccag ug 22

<210> SEQ ID NO 408
<211> LENGTH: 22
<212> TYPE: RNA
<213> ORGANISM: Homo sapiens

<400> SEQUENCE: 408
acuagacuga agcuccuuga gg 22

<210> SEQ ID NO 409
<211> LENGTH: 21
<212> TYPE: RNA
<213> ORGANISM: Homo sapiens

<400> SEQUENCE: 409
ucagugcaug acagaacuug g 21

<210> SEQ ID NO 410
<211> LENGTH: 20
<212> TYPE: RNA
<213> ORGANISM: Homo sapiens

<400> SEQUENCE: 410
uugcauaguc acaaaaguga 20

<210> SEQ ID NO 411
<211> LENGTH: 22
<212> TYPE: RNA
<213> ORGANISM: Homo sapiens

<400> SEQUENCE: 411
uagguuaucc guguugccuu cg 22

<210> SEQ ID NO 412
<211> LENGTH: 22
<212> TYPE: RNA
<213> ORGANISM: Homo sapiens

<400> SEQUENCE: 412
aaucauacac gguugaccua uu 22

<210> SEQ ID NO 413
<211> LENGTH: 22
<212> TYPE: RNA
<213> ORGANISM: Homo sapiens

<400> SEQUENCE: 413
uuaaugcuaa ucgugauagg gg 22

<210> SEQ ID NO 414

<211> LENGTH: 23
<212> TYPE: RNA
<213> ORGANISM: Homo sapiens

<400> SEQUENCE: 414
aacauucaac gcugucggug agu 23

<210> SEQ ID NO 415
<211> LENGTH: 24
<212> TYPE: RNA
<213> ORGANISM: Homo sapiens

<400> SEQUENCE: 415
aacauucauu gcugucggug gguu 24

<210> SEQ ID NO 416
<211> LENGTH: 22
<212> TYPE: RNA
<213> ORGANISM: Homo sapiens

<400> SEQUENCE: 416
aacauucaac cugucgguga gu 22

<210> SEQ ID NO 417
<211> LENGTH: 22
<212> TYPE: RNA
<213> ORGANISM: Homo sapiens

<400> SEQUENCE: 417
uuuggcaaug guagaacuca ca 22

<210> SEQ ID NO 418
<211> LENGTH: 21
<212> TYPE: RNA
<213> ORGANISM: Homo sapiens

<400> SEQUENCE: 418
ugguucuaga cuugccaacu a 21

<210> SEQ ID NO 419
<211> LENGTH: 23
<212> TYPE: RNA
<213> ORGANISM: Homo sapiens

<400> SEQUENCE: 419
uauggcacug guagaauuca cug 23

<210> SEQ ID NO 420
<211> LENGTH: 22
<212> TYPE: RNA
<213> ORGANISM: Homo sapiens

<400> SEQUENCE: 420
uggacggaga acugauaagg gu 22

<210> SEQ ID NO 421
<211> LENGTH: 18
<212> TYPE: RNA
<213> ORGANISM: Homo sapiens

<400> SEQUENCE: 421
uggagagaaa ggcaguuc 18

<210> SEQ ID NO 422
<211> LENGTH: 23
<212> TYPE: RNA
<213> ORGANISM: Homo sapiens

<400> SEQUENCE: 422
caaagaauuc uccuuuuggg cuu 23

<210> SEQ ID NO 423
<211> LENGTH: 21
<212> TYPE: RNA
<213> ORGANISM: Homo sapiens

<400> SEQUENCE: 423
ucgugucuug uguugcagcc g 21

<210> SEQ ID NO 424
<211> LENGTH: 22
<212> TYPE: RNA
<213> ORGANISM: Homo sapiens

<400> SEQUENCE: 424
caucccuugc augguggagg gu 22

<210> SEQ ID NO 425
<211> LENGTH: 23
<212> TYPE: RNA
<213> ORGANISM: Homo sapiens

<400> SEQUENCE: 425
gugccuacug agcugauauc agu 23

<210> SEQ ID NO 426
<211> LENGTH: 22
<212> TYPE: RNA
<213> ORGANISM: Homo sapiens

<400> SEQUENCE: 426
ugauauguuu gauauauuag gu 22

<210> SEQ ID NO 427
<211> LENGTH: 22
<212> TYPE: RNA
<213> ORGANISM: Homo sapiens

<400> SEQUENCE: 427
caacggaauc ccaaaagcag cu 22

<210> SEQ ID NO 428
<211> LENGTH: 21
<212> TYPE: RNA
<213> ORGANISM: Homo sapiens

<400> SEQUENCE: 428
cugaccuaug aauugacagc c 21

<210> SEQ ID NO 429
<211> LENGTH: 21
<212> TYPE: RNA
<213> ORGANISM: Homo sapiens

<400> SEQUENCE: 429
aacuggccua caaaguccca g 21

<210> SEQ ID NO 430
<211> LENGTH: 22
<212> TYPE: RNA
<213> ORGANISM: Homo sapiens

<400> SEQUENCE: 430
uguaacagca acuccaugug ga 22

<210> SEQ ID NO 431
<211> LENGTH: 21
<212> TYPE: RNA
<213> ORGANISM: Homo sapiens

<400> SEQUENCE: 431
uagcagcaca gaaauauugg c 21

<210> SEQ ID NO 432
<211> LENGTH: 21
<212> TYPE: RNA
<213> ORGANISM: Homo sapiens

<400> SEQUENCE: 432
uagguaguuu cauguuguug g 21

<210> SEQ ID NO 433
<211> LENGTH: 21
<212> TYPE: RNA
<213> ORGANISM: Homo sapiens

<400> SEQUENCE: 433
uagguaguuu ccuguuguug g 21

<210> SEQ ID NO 434
<211> LENGTH: 22
<212> TYPE: RNA
<213> ORGANISM: Homo sapiens

<400> SEQUENCE: 434
uucaccaccu ucuccaccca gc 22

<210> SEQ ID NO 435
<211> LENGTH: 19
<212> TYPE: RNA
<213> ORGANISM: Homo sapiens

<400> SEQUENCE: 435
gguccagagg ggagauagg 19

<210> SEQ ID NO 436
<211> LENGTH: 23
<212> TYPE: RNA
<213> ORGANISM: Homo sapiens

<400> SEQUENCE: 436
cccaguguuc agacuaccug uuc 23

<210> SEQ ID NO 437
<211> LENGTH: 22
<212> TYPE: RNA
<213> ORGANISM: Homo sapiens

<400> SEQUENCE: 437
uacaguaguc ugcacauugg uu 22

<210> SEQ ID NO 438
<211> LENGTH: 23
<212> TYPE: RNA
<213> ORGANISM: Homo sapiens

<400> SEQUENCE: 438
cccaguguuu agacuaucug uuc 23

<210> SEQ ID NO 439
<211> LENGTH: 22
<212> TYPE: RNA
<213> ORGANISM: Homo sapiens

<400> SEQUENCE: 439
uaacacuguc ugguaacgau gu 22

<210> SEQ ID NO 440
<211> LENGTH: 24
<212> TYPE: RNA
<213> ORGANISM: Homo sapiens

<400> SEQUENCE: 440
cucuaauacu gccugguaau gaug 24

<210> SEQ ID NO 441
<211> LENGTH: 22
<212> TYPE: RNA
<213> ORGANISM: Homo sapiens

<400> SEQUENCE: 441
aauacugccg gguaaugaug ga 22

<210> SEQ ID NO 442
<211> LENGTH: 22
<212> TYPE: RNA
<213> ORGANISM: Homo sapiens

<400> SEQUENCE: 442
agagguauag ggcaugggaa ga 22

<210> SEQ ID NO 443
<211> LENGTH: 22
<212> TYPE: RNA
<213> ORGANISM: Homo sapiens

<400> SEQUENCE: 443
gugaaauguu uaggaccacu ag 22

<210> SEQ ID NO 444
<211> LENGTH: 22
<212> TYPE: RNA
<213> ORGANISM: Homo sapiens

<400> SEQUENCE: 444
uucccuuugu cauccuaugc cu 22

<210> SEQ ID NO 445
<211> LENGTH: 22
<212> TYPE: RNA
<213> ORGANISM: Homo sapiens

<400> SEQUENCE: 445
uccuucauuc caccggaguc ug 22

<210> SEQ ID NO 446
<211> LENGTH: 22
<212> TYPE: RNA
<213> ORGANISM: Homo sapiens

<400> SEQUENCE: 446
uggaauguaa ggaagugugu gg 22

<210> SEQ ID NO 447
<211> LENGTH: 22
<212> TYPE: RNA
<213> ORGANISM: Homo sapiens

<400> SEQUENCE: 447
auaagacgag caaaaagcuu gu 22

<210> SEQ ID NO 448
<211> LENGTH: 21
<212> TYPE: RNA
<213> ORGANISM: Homo sapiens

<400> SEQUENCE: 448
cugugcgugu gacagcggcu g 21

<210> SEQ ID NO 449
<211> LENGTH: 22
<212> TYPE: RNA
<213> ORGANISM: Homo sapiens

<400> SEQUENCE: 449
uucccuuugu cauccuucgc cu 22

<210> SEQ ID NO 450
<211> LENGTH: 21
<212> TYPE: RNA
<213> ORGANISM: Homo sapiens

<400> SEQUENCE: 450
uaacagucuc cagucacggc c 21

<210> SEQ ID NO 451
<211> LENGTH: 22
<212> TYPE: RNA
<213> ORGANISM: Homo sapiens

<400> SEQUENCE: 451
accaucgacc guugauugua cc 22

<210> SEQ ID NO 452
<211> LENGTH: 21
<212> TYPE: RNA
<213> ORGANISM: Homo sapiens

<400> SEQUENCE: 452
acagcaggca cagacaggca g 21

<210> SEQ ID NO 453
<211> LENGTH: 21
<212> TYPE: RNA
<213> ORGANISM: Homo sapiens

<400> SEQUENCE: 453
augaccuaug aauugacaga c 21

<210> SEQ ID NO 454
<211> LENGTH: 21
<212> TYPE: RNA
<213> ORGANISM: Homo sapiens

<400> SEQUENCE: 454
uaaucucagc uggcaacugu g 21

<210> SEQ ID NO 455
<211> LENGTH: 24
<212> TYPE: RNA
<213> ORGANISM: Homo sapiens

<400> SEQUENCE: 455
uacugcauca ggaacugauu ggau 24

<210> SEQ ID NO 456
<211> LENGTH: 21
<212> TYPE: RNA
<213> ORGANISM: Homo sapiens

<400> SEQUENCE: 456
uugugcuuga ucuaaccaug u 21

<210> SEQ ID NO 457
<211> LENGTH: 21
<212> TYPE: RNA
<213> ORGANISM: Homo sapiens

<400> SEQUENCE: 457
ugauugucca aacgcaauuc u 21

<210> SEQ ID NO 458
<211> LENGTH: 21
<212> TYPE: RNA
<213> ORGANISM: Homo sapiens

<400> SEQUENCE: 458
ccacaccgua ucugacacuu u 21

<210> SEQ ID NO 459
<211> LENGTH: 23
<212> TYPE: RNA
<213> ORGANISM: Homo sapiens

<400> SEQUENCE: 459
agcuacauug ucugcugggu uuc 23

<210> SEQ ID NO 460
<211> LENGTH: 24
<212> TYPE: RNA
<213> ORGANISM: Homo sapiens

<400> SEQUENCE: 460
agcuacaucu ggcuacuggg ucuc 24

<210> SEQ ID NO 461
<211> LENGTH: 21
<212> TYPE: RNA
<213> ORGANISM: Homo sapiens

<400> SEQUENCE: 461
ugucaguuug ucaaauaccc c 21

<210> SEQ ID NO 462
<211> LENGTH: 23
<212> TYPE: RNA
<213> ORGANISM: Homo sapiens

<400> SEQUENCE: 462
caagucacua gugguuccgu uua 23

<210> SEQ ID NO 463
<211> LENGTH: 21
<212> TYPE: RNA
<213> ORGANISM: Homo sapiens

<400> SEQUENCE: 463
agggcccccc cucaauccug u 21

<210> SEQ ID NO 464
<211> LENGTH: 22
<212> TYPE: RNA
<213> ORGANISM: Homo sapiens

<400> SEQUENCE: 464
ugguuuaccg ucccacauac au 22

<210> SEQ ID NO 465
<211> LENGTH: 23
<212> TYPE: RNA
<213> ORGANISM: Homo sapiens

<400> SEQUENCE: 465
cagugcaaua guauugucaa agc 23

<210> SEQ ID NO 466
<211> LENGTH: 23
<212> TYPE: RNA
<213> ORGANISM: Homo sapiens

<400> SEQUENCE: 466
uaagugcuuc cauguuuugg uga 23

<210> SEQ ID NO 467
<211> LENGTH: 23
<212> TYPE: RNA
<213> ORGANISM: Homo sapiens

<400> SEQUENCE: 467
acuuuaacau ggaagugcuu ucu 23

<210> SEQ ID NO 468
<211> LENGTH: 23
<212> TYPE: RNA
<213> ORGANISM: Homo sapiens

<400> SEQUENCE: 468
uaagugcuuc cauguuuuag uag 23

<210> SEQ ID NO 469
<211> LENGTH: 22
<212> TYPE: RNA
<213> ORGANISM: Homo sapiens

```
<400> SEQUENCE: 469

uuuaacaugg ggguaccugc ug                                          22

<210> SEQ ID NO 470
<211> LENGTH: 23
<212> TYPE: RNA
<213> ORGANISM: Homo sapiens

<400> SEQUENCE: 470

uaagugcuuc cauguuucag ugg                                         23

<210> SEQ ID NO 471
<211> LENGTH: 23
<212> TYPE: RNA
<213> ORGANISM: Homo sapiens

<400> SEQUENCE: 471

uaagugcuuc cauguuugag ugu                                         23

<210> SEQ ID NO 472
<211> LENGTH: 23
<212> TYPE: RNA
<213> ORGANISM: Homo sapiens

<400> SEQUENCE: 472

aaaagcuggg uugagagggc gaa                                         23

<210> SEQ ID NO 473
<211> LENGTH: 21
<212> TYPE: RNA
<213> ORGANISM: Homo sapiens

<400> SEQUENCE: 473

uaagccaggg auuguggguu c                                           21

<210> SEQ ID NO 474
<211> LENGTH: 22
<212> TYPE: RNA
<213> ORGANISM: Homo sapiens

<400> SEQUENCE: 474

gcacauuaca cggucgaccu cu                                          22

<210> SEQ ID NO 475
<211> LENGTH: 23
<212> TYPE: RNA
<213> ORGANISM: Homo sapiens

<400> SEQUENCE: 475

cgcauccccu agggcauugg ugu                                         23

<210> SEQ ID NO 476
<211> LENGTH: 22
<212> TYPE: RNA
<213> ORGANISM: Homo sapiens

<400> SEQUENCE: 476

ccacugcccc aggugcugcu gg                                          22

<210> SEQ ID NO 477
<211> LENGTH: 21
<212> TYPE: RNA
```

<213> ORGANISM: Homo sapiens

<400> SEQUENCE: 477
ccuaguaggu guccaguaag u 21

<210> SEQ ID NO 478
<211> LENGTH: 20
<212> TYPE: RNA
<213> ORGANISM: Homo sapiens

<400> SEQUENCE: 478
ccucugggcc cuuccuccag 20

<210> SEQ ID NO 479
<211> LENGTH: 22
<212> TYPE: RNA
<213> ORGANISM: Homo sapiens

<400> SEQUENCE: 479
cuggcccucu cugcccuucc gu 22

<210> SEQ ID NO 480
<211> LENGTH: 23
<212> TYPE: RNA
<213> ORGANISM: Homo sapiens

<400> SEQUENCE: 480
gcaaagcaca cggccugcag aga 23

<210> SEQ ID NO 481
<211> LENGTH: 21
<212> TYPE: RNA
<213> ORGANISM: Homo sapiens

<400> SEQUENCE: 481
gccccugggc cuauccuaga a 21

<210> SEQ ID NO 482
<211> LENGTH: 23
<212> TYPE: RNA
<213> ORGANISM: Homo sapiens

<400> SEQUENCE: 482
ucaagagcaa uaacgaaaaa ugu 23

<210> SEQ ID NO 483
<211> LENGTH: 23
<212> TYPE: RNA
<213> ORGANISM: Homo sapiens

<400> SEQUENCE: 483
uccagcuccu auaugaugcc uuu 23

<210> SEQ ID NO 484
<211> LENGTH: 23
<212> TYPE: RNA
<213> ORGANISM: Homo sapiens

<400> SEQUENCE: 484
uccagcauca gugauuuugu uga 23

<210> SEQ ID NO 485
<211> LENGTH: 21

<212> TYPE: RNA
<213> ORGANISM: Homo sapiens

<400> SEQUENCE: 485
ucccuguccu ccaggagcuc a 21

<210> SEQ ID NO 486
<211> LENGTH: 23
<212> TYPE: RNA
<213> ORGANISM: Homo sapiens

<400> SEQUENCE: 486
uccgucucag uuacuuuaua gcc 23

<210> SEQ ID NO 487
<211> LENGTH: 24
<212> TYPE: RNA
<213> ORGANISM: Homo sapiens

<400> SEQUENCE: 487
ucucacacag aaaucgcacc cguc 24

<210> SEQ ID NO 488
<211> LENGTH: 21
<212> TYPE: RNA
<213> ORGANISM: Homo sapiens

<400> SEQUENCE: 488
ugcugacucc uaguccaggg c 21

<210> SEQ ID NO 489
<211> LENGTH: 23
<212> TYPE: RNA
<213> ORGANISM: Homo sapiens

<400> SEQUENCE: 489
ugucugcccg caugccugcc ucu 23

<210> SEQ ID NO 490
<211> LENGTH: 22
<212> TYPE: RNA
<213> ORGANISM: Homo sapiens

<400> SEQUENCE: 490
aauugcacuu uagcaauggu ga 22

<210> SEQ ID NO 491
<211> LENGTH: 22
<212> TYPE: RNA
<213> ORGANISM: Homo sapiens

<400> SEQUENCE: 491
acauagagga aauuccacgu uu 22

<210> SEQ ID NO 492
<211> LENGTH: 21
<212> TYPE: RNA
<213> ORGANISM: Homo sapiens

<400> SEQUENCE: 492
aauaauacau gguugaucuu u 21

<210> SEQ ID NO 493

<211> LENGTH: 21
<212> TYPE: RNA
<213> ORGANISM: Homo sapiens

<400> SEQUENCE: 493
gccugcuggg guggaaccug g 21

<210> SEQ ID NO 494
<211> LENGTH: 21
<212> TYPE: RNA
<213> ORGANISM: Homo sapiens

<400> SEQUENCE: 494
gugccgccau cuuuugagug u 21

<210> SEQ ID NO 495
<211> LENGTH: 23
<212> TYPE: RNA
<213> ORGANISM: Homo sapiens

<400> SEQUENCE: 495
aaagugcugc gacauuugag cgu 23

<210> SEQ ID NO 496
<211> LENGTH: 22
<212> TYPE: RNA
<213> ORGANISM: Homo sapiens

<400> SEQUENCE: 496
acucaaaaug ggggcgcuuu cc 22

<210> SEQ ID NO 497
<211> LENGTH: 23
<212> TYPE: RNA
<213> ORGANISM: Homo sapiens

<400> SEQUENCE: 497
gaagugcuuc gauuuugggg ugu 23

<210> SEQ ID NO 498
<211> LENGTH: 22
<212> TYPE: RNA
<213> ORGANISM: Homo sapiens

<400> SEQUENCE: 498
uuauaauaca accugauaag ug 22

<210> SEQ ID NO 499
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 499
aactttgtct tgggggacac 20

<210> SEQ ID NO 500
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 500
gaggggagga tctgttttcc 20

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 501
ccaggagctc aggaagaaga gat 23

<210> SEQ ID NO 502
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 502
ccctctgagg catctgattg ggttt 25

<210> SEQ ID NO 503
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 503
gcatctagag caccccagag gagtgt 26

<210> SEQ ID NO 504
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 504
gcatctagac aagcaccatg cggttc 26

<210> SEQ ID NO 505
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 505
tactctagac caggagctca ggaaga 26

<210> SEQ ID NO 506
<211> LENGTH: 27
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 506
mcattctaga tgaggcatct gattggg 27

<210> SEQ ID NO 507
<211> LENGTH: 31
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 507
cuagaaaugu uuagguuacu aaaacagggu g 31